(12) United States Patent
Bunyan et al.

(10) Patent No.: US 11,814,406 B2
(45) Date of Patent: Nov. 14, 2023

(54) COMPOUNDS AND METHODS FOR TREATMENT OF VIRAL INFECTIONS

(71) Applicant: Gilead Sciences, Inc., Foster City, CA (US)

(72) Inventors: Elaine Bunyan, San Francisco, CA (US); Byoung-Kwon Chun, Pleasanton, CA (US); Kassibla E. Dempah, San Francisco, CA (US); Hon C. Hui, San Mateo, CA (US); Rao V. Kalla, Cupertino, CA (US); Richard L. Mackman, Millbrae, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 18/098,950

(22) Filed: Jan. 19, 2023

(65) Prior Publication Data
US 2023/0151043 A1 May 18, 2023

Related U.S. Application Data

(63) Continuation of application No. 17/458,023, filed on Aug. 26, 2021.

(60) Provisional application No. 63/215,310, filed on Jun. 25, 2021, provisional application No. 63/162,283, filed on Mar. 17, 2021, provisional application No. 63/071,134, filed on Aug. 27, 2020.

(51) Int. Cl.
C07H 7/06 (2006.01)
A61P 31/12 (2006.01)

(52) U.S. Cl.
CPC .............. *C07H 7/06* (2013.01); *A61P 31/12* (2018.01); *C07B 2200/13* (2013.01)

(58) Field of Classification Search
None
See application file for complete search history.

(56) References Cited

U.S. PATENT DOCUMENTS

| | | | |
|---|---|---|---|
| 4,816,570 A | 3/1989 | Farquhar | |
| 4,968,788 A | 11/1990 | Farquhar | |
| 5,663,159 A | 9/1997 | Starrett, Jr. et al. | |
| 5,792,756 A | 8/1998 | Starrett, Jr. et al. | |
| 6,312,662 B1 | 11/2001 | Erion et al. | |
| 6,475,985 B1 | 11/2002 | Wagner et al. | |
| 6,476,030 B1 | 11/2002 | Carling et al. | |
| 6,656,915 B1 | 12/2003 | Bantia et al. | |
| 6,909,011 B2 | 6/2005 | Skranc et al. | |
| 7,078,403 B1 | 7/2006 | Wu et al. | |
| 7,105,493 B2 | 9/2006 | Sommadossi et al. | |
| 7,125,855 B2 | 10/2006 | Bhat et al. | |
| 7,166,604 B2 | 1/2007 | Watson et al. | |
| 7,176,203 B2 | 2/2007 | Chambers et al. | |
| 7,268,119 B2 | 9/2007 | Cook et al. | |
| 7,285,658 B2 | 10/2007 | Cook et al. | |
| 7,368,437 B1 | 5/2008 | Bojack et al. | |
| 7,390,791 B2 | 6/2008 | Becker et al. | |
| 7,429,571 B2 | 9/2008 | Chand et al. | |
| 7,514,410 B2 | 4/2009 | Babu et al. | |
| 7,560,434 B2 | 7/2009 | Babu et al. | |
| 7,598,230 B2 | 10/2009 | Cook et al. | |
| 7,608,597 B2 | 10/2009 | Sommadossi et al. | |
| 7,713,941 B2 | 5/2010 | Cook et al. | |
| 7,803,788 B2 | 9/2010 | Becker et al. | |
| 7,807,653 B2 | 10/2010 | Cook et al. | |
| 7,842,672 B2 | 11/2010 | Boojamra et al. | |
| 7,951,787 B2 | 5/2011 | McGuigan | |
| 7,973,013 B2 | 7/2011 | Cho et al. | |
| 7,994,139 B2 | 8/2011 | Babu et al. | |
| 8,008,264 B2 | 8/2011 | Butler et al. | |
| 8,012,941 B2 | 9/2011 | Cho et al. | |
| 8,012,942 B2 | 9/2011 | Butler et al. | |
| 8,071,568 B2 | 12/2011 | Narjes et al. | |
| 8,119,607 B2 | 2/2012 | Francom et al. | |
| 8,242,085 B2 | 8/2012 | Babu et al. | |
| 8,318,682 B2 | 11/2012 | Butler et al. | |
| 8,415,308 B2 | 4/2013 | Cho et al. | |
| 8,455,451 B2 | 6/2013 | Cho et al. | |
| 8,853,171 B2 | 10/2014 | Butler et al. | |
| 8,871,737 B2 | 10/2014 | Smith et al. | |
| 8,889,159 B2 | 11/2014 | Clearly et al. | |
| 8,980,865 B2 | 3/2015 | Wang | |
| 9,090,642 B2 | 7/2015 | Cho et al. | |
| 9,243,022 B2 | 1/2016 | Beigelman et al. | |

(Continued)

FOREIGN PATENT DOCUMENTS

| CN | 110330540 | 10/2019 |
|---|---|---|
| CN | 110776512 | 2/2020 |

(Continued)

OTHER PUBLICATIONS

Anonymous [online], "University of Alabama & Multi-Center Collaboration Help Develop Remdesivir with Gilead Thanks to $37.5m from NIH," TrialSiteNews.com, retrieved on Mar. 13, 2023, URL <https://www.trialsitenews.com/a/university-of-alabama-multi-center-collaboration-help-develop-remdesivir-with-gilead-thanks-to-37-5m-from-nih>, Mar. 1, 2020, 5 pages.

Joseph [online], "As the coronavirus spreads, a drug that once raised the world's hopes is given a second shot," StatNews.com, retrieved on Mar. 13, 2023, URL <https://www.statnews.com/2020/03/16/remdesivir-surges-ahead-against-coronavirus>, Mar. 16, 2020, 11 pages.

(Continued)

*Primary Examiner* — Traviss C McIntosh, III

(74) *Attorney, Agent, or Firm* — Fish & Richardson P.C.

(57) ABSTRACT

Compounds and methods of using said compounds, singly or in combination with additional agents, and salts, crystalline forms, pharmaceutical compositions of said compounds for the treatment of viral infections are disclosed.

22 Claims, 53 Drawing Sheets

Specification includes a Sequence Listing.

(56) References Cited

U.S. PATENT DOCUMENTS

| | | |
|---|---|---|
| 9,249,174 B2 | 2/2016 | Beigelman et al. |
| 9,278,990 B2 | 3/2016 | Smith et al. |
| 9,388,208 B2 | 7/2016 | Clarke et al. |
| 9,393,256 B2 | 7/2016 | Ray et al. |
| 9,452,154 B2 | 9/2016 | Delaney et al. |
| 9,481,703 B2 | 11/2016 | Kalayanov et al. |
| 9,487,544 B2 | 11/2016 | Cho et al. |
| 9,504,701 B2 | 11/2016 | Casola et al. |
| 9,540,411 B2 | 1/2017 | Kalayanov et al. |
| 9,549,941 B2 | 1/2017 | Cleary et al. |
| 9,605,018 B2 | 3/2017 | Wang et al. |
| 9,616,076 B2 | 4/2017 | Casola et al. |
| 9,701,682 B2 | 7/2017 | Clarke et al. |
| 9,724,360 B2 | 8/2017 | Chun et al. |
| 9,828,408 B2 | 11/2017 | Kalayanov |
| RE46,762 E | 3/2018 | Butler et al. |
| 9,949,994 B2 | 4/2018 | Chun et al. |
| 10,023,600 B2 | 7/2018 | Butler et al. |
| 10,034,893 B2 | 7/2018 | Luly et al. |
| 10,059,716 B2 | 8/2018 | Clarke et al. |
| 10,065,958 B2 | 9/2018 | Mackman et al. |
| 10,251,898 B2 | 4/2019 | Chun et al. |
| 10,251,904 B2 | 4/2019 | Clarke et al. |
| 10,377,761 B2 | 8/2019 | Clarke et al. |
| RE47,589 E | 9/2019 | McGuigan |
| 10,675,296 B2 | 6/2020 | Larson |
| 10,682,368 B2 | 6/2020 | Perron et al. |
| 10,695,357 B2 | 6/2020 | Chun et al. |
| 10,695,361 B2 | 6/2020 | Clarke et al. |
| 10,696,679 B2 | 6/2020 | Mackman et al. |
| 10,836,787 B2 | 11/2020 | Brak et al. |
| 10,988,498 B2 | 4/2021 | Butler et al. |
| 11,007,208 B2 | 5/2021 | Clarke et al. |
| 11,260,070 B2 | 3/2022 | Perron et al. |
| 11,266,666 B2 | 3/2022 | Chun et al. |
| 11,266,681 B2 | 3/2022 | Larson et al. |
| 11,344,565 B2 | 5/2022 | Axt et al. |
| 11,377,456 B2 * | 7/2022 | Souza ................... C07H 7/06 |
| 11,382,926 B2 | 7/2022 | Clarke et al. |
| 11,491,169 B2 | 11/2022 | Cihlar |
| 11,492,353 B2 | 11/2022 | Mackman et al. |
| 11,541,071 B1 | 1/2023 | Liang et al. |
| 11,597,742 B2 | 3/2023 | Brak et al. |
| 11,613,553 B2 | 3/2023 | Badalov et al. |
| 11,660,307 B2 | 5/2023 | Cihlar et al. |
| 2003/0050229 A1 | 3/2003 | Sommadossi et al. |
| 2003/0092775 A1 | 5/2003 | Ernst et al. |
| 2004/0006002 A1 | 1/2004 | Sommadossi et al. |
| 2004/0023901 A1 | 2/2004 | Cook et al. |
| 2004/0063658 A1 | 4/2004 | Roberts et al. |
| 2004/0067901 A1 | 4/2004 | Bhat et al. |
| 2004/0138170 A1 | 7/2004 | Montgomery et al. |
| 2005/0187180 A1 | 8/2005 | Loeb et al. |
| 2005/0209166 A1 | 9/2005 | Eckhardt et al. |
| 2005/0215513 A1 | 9/2005 | Boojamra et al. |
| 2005/0250728 A1 | 11/2005 | Bantia et al. |
| 2006/0058303 A1 | 3/2006 | Chambers et al. |
| 2006/0142238 A1 | 6/2006 | McGuigan |
| 2006/0241064 A1 | 10/2006 | Roberts et al. |
| 2008/0107628 A1 | 5/2008 | Boojamra et al. |
| 2008/0161324 A1 | 7/2008 | Johansen et al. |
| 2008/0280842 A1 | 11/2008 | MacCoss et al. |
| 2009/0004138 A1 | 1/2009 | Francom et al. |
| 2009/0221524 A1 | 9/2009 | Kotra et al. |
| 2009/0233879 A1 | 9/2009 | Reddy et al. |
| 2009/0317361 A1 | 12/2009 | Cho et al. |
| 2010/0015094 A1 | 1/2010 | Babu et al. |
| 2010/0016251 A1 | 1/2010 | Sofia et al. |
| 2010/0021425 A1 | 1/2010 | Butler et al. |
| 2010/0035835 A1 | 2/2010 | Narjes et al. |
| 2010/0035836 A1 | 2/2010 | Francom et al. |
| 2010/0065512 A1 | 3/2010 | Bjorsvik |
| 2010/0203015 A1 | 8/2010 | Butler et al. |
| 2010/0234584 A1 | 9/2010 | Chang |
| 2010/0249068 A1 | 9/2010 | Beigelman et al. |
| 2010/0291031 A2 | 11/2010 | Francom et al. |
| 2010/0298257 A1 | 11/2010 | Ross et al. |
| 2010/0305202 A1 | 12/2010 | Hwang et al. |
| 2011/0070194 A1 | 3/2011 | Cho et al. |
| 2011/0084230 A1 | 4/2011 | Knochel et al. |
| 2011/0230654 A1 | 9/2011 | Butler et al. |
| 2011/0257122 A1 | 10/2011 | Sofia et al. |
| 2011/0293563 A1 | 12/2011 | Butler et al. |
| 2012/0009147 A1 | 1/2012 | Cho et al. |
| 2012/0020921 A1 | 1/2012 | Cho et al. |
| 2012/0027752 A1 | 2/2012 | Mackman et al. |
| 2012/0071434 A1 | 3/2012 | Smith et al. |
| 2012/0107274 A1 | 5/2012 | Clarke et al. |
| 2013/0034521 A1 | 2/2013 | Butler et al. |
| 2013/0143835 A1 | 6/2013 | Eneroth et al. |
| 2013/0281686 A1 | 10/2013 | Cho et al. |
| 2013/0315868 A1 | 11/2013 | Mayes |
| 2013/0344028 A2 | 12/2013 | Butler et al. |
| 2014/0219958 A1 | 8/2014 | Luly et al. |
| 2015/0031687 A1 | 1/2015 | Guo et al. |
| 2015/0111839 A1 | 4/2015 | Mackman et al. |
| 2015/0133395 A1 | 5/2015 | Clarke et al. |
| 2015/0152116 A1 | 6/2015 | Mackman et al. |
| 2015/0210682 A1 | 7/2015 | Han et al. |
| 2015/0252057 A1 | 9/2015 | Guo et al. |
| 2016/0058779 A1 | 3/2016 | Casola et al. |
| 2016/0122344 A1 | 5/2016 | Han et al. |
| 2016/0122356 A1 | 5/2016 | Axt et al. |
| 2016/0122374 A1 | 5/2016 | Chun |
| 2016/0176899 A1 | 6/2016 | Schwitter et al. |
| 2016/0220586 A1 | 8/2016 | Andre et al. |
| 2016/0237090 A1 | 8/2016 | Hu et al. |
| 2017/0071964 A1 | 3/2017 | Clark et al. |
| 2018/0346504 A1 | 12/2018 | Brak et al. |
| 2019/0083525 A1 | 3/2019 | Larson |
| 2020/0197422 A1 | 6/2020 | Axt et al. |
| 2020/0360420 A1 | 11/2020 | Larson |
| 2020/0376014 A1 | 12/2020 | Perron et al. |
| 2021/0052613 A1 | 2/2021 | Chun et al. |
| 2021/0061806 A1 | 3/2021 | Mackman et al. |
| 2021/0283150 A1 | 9/2021 | Cihlar et al. |
| 2021/0309689 A1 | 10/2021 | Badalov et al. |
| 2021/0330685 A1 | 10/2021 | Ellis et al. |
| 2021/0393653 A1 | 12/2021 | Cihlar et al. |
| 2021/0393659 A1 | 12/2021 | Clarke et al. |
| 2021/0403497 A1 | 12/2021 | Butler et al. |
| 2022/0081462 A1 | 3/2022 | Chun et al. |
| 2022/0175805 A1 | 6/2022 | Cihlar |
| 2022/0280549 A1 | 9/2022 | Larson et al. |
| 2022/0354873 A1 | 11/2022 | Axt et al. |
| 2022/0356196 A1 | 11/2022 | Byun et al. |
| 2023/0027727 A1 | 1/2023 | Clarke et al. |
| 2023/0040586 A1 | 2/2023 | Byun et al. |
| 2023/0125751 A1 | 4/2023 | Mackman et al. |

FOREIGN PATENT DOCUMENTS

| | | |
|---|---|---|
| CN | 111171078 | 5/2020 |
| CN | 111205294 | 5/2020 |
| CN | 111205327 | 5/2020 |
| CN | 111233869 | 6/2020 |
| CN | 111265532 | 6/2020 |
| CN | 111440176 | 7/2020 |
| CN | 111548384 | 8/2020 |
| CN | 111961057 | 11/2020 |
| CN | 202011613943.3 | 12/2020 |
| CN | 112778310 | 5/2021 |
| CN | 202110562244.9 | 5/2021 |
| CN | 113754665 | 6/2021 |
| CN | 113185519 | 7/2021 |
| CN | 113292565 | 8/2021 |
| CN | 113387954 | 9/2021 |
| CN | 113735862 | 9/2021 |
| CN | 113698405 | 11/2021 |
| CN | 113698405 A * | 11/2021 |
| CN | 114292272 | 12/2021 |
| CN | 114437159 | 5/2022 |
| IN | 202121023147 | 5/2021 |
| IN | 202134041493 | 9/2021 |

(56) References Cited

FOREIGN PATENT DOCUMENTS

| | | |
|---|---|---|
| IN | 202011021676 | 11/2021 |
| JP | 2005185235 | 7/2005 |
| JP | 2005187428 | 7/2005 |
| WO | WO1991019721 | 12/1991 |
| WO | WO1999045029 | 9/1999 |
| WO | WO2000056734 | 9/2000 |
| WO | WO2000075157 | 12/2000 |
| WO | WO2001032153 | 5/2001 |
| WO | WO2001060315 | 8/2001 |
| WO | WO2001090121 | 11/2001 |
| WO | WO2001091737 | 12/2001 |
| WO | WO2001092282 | 12/2001 |
| WO | WO2002008241 | 1/2002 |
| WO | WO2002018404 | 3/2002 |
| WO | WO2002032920 | 4/2002 |
| WO | WO2002057287 | 7/2002 |
| WO | WO2002057425 | 7/2002 |
| WO | WO2003093272 | 11/2003 |
| WO | WO2003093273 | 11/2003 |
| WO | WO2003100009 | 12/2003 |
| WO | WO2004046159 | 6/2004 |
| WO | WO2004046331 | 6/2004 |
| WO | WO2004112687 | 12/2004 |
| WO | WO2005009418 | 2/2005 |
| WO | WO2005092877 | 10/2005 |
| WO | WO2005123087 | 12/2005 |
| WO | WO2006031725 | 3/2006 |
| WO | WO2006050161 | 5/2006 |
| WO | WO2006064033 | 6/2006 |
| WO | WO2006065335 | 6/2006 |
| WO | WO2006121820 | 11/2006 |
| WO | WO2006135978 | 12/2006 |
| WO | WO2007027248 | 3/2007 |
| WO | WO2007056170 | 5/2007 |
| WO | WO2007062542 | 6/2007 |
| WO | WO2007064883 | 6/2007 |
| WO | WO2007064931 | 6/2007 |
| WO | WO2007065289 | 6/2007 |
| WO | WO2007065829 | 6/2007 |
| WO | WO2007095269 | 8/2007 |
| WO | WO2007097991 | 8/2007 |
| WO | WO2007113294 | 10/2007 |
| WO | WO2007135134 | 11/2007 |
| WO | WO2008005542 | 1/2008 |
| WO | WO2008011406 | 1/2008 |
| WO | WO2008055870 | 5/2008 |
| WO | WO2008079206 | 7/2008 |
| WO | WO2008082601 | 7/2008 |
| WO | WO2008085508 | 7/2008 |
| WO | WO2008089105 | 7/2008 |
| WO | WO2008116064 | 9/2008 |
| WO | WO2008121634 | 10/2008 |
| WO | WO2008141079 | 11/2008 |
| WO | WO2009009951 | 1/2009 |
| WO | WO2009018609 | 2/2009 |
| WO | WO2009131926 | 10/2009 |
| WO | WO2009132123 | 10/2009 |
| WO | WO2009132135 | 10/2009 |
| WO | WO2010002877 | 1/2010 |
| WO | WO2010036407 | 4/2010 |
| WO | WO2010039548 | 4/2010 |
| WO | WO2010093608 | 8/2010 |
| WO | WO2010099458 | 9/2010 |
| WO | WO2010108140 | 9/2010 |
| WO | WO2010135569 | 11/2010 |
| WO | WO2011011303 | 1/2011 |
| WO | WO2010111381 | 3/2011 |
| WO | WO2011035231 | 3/2011 |
| WO | WO2011035250 | 3/2011 |
| WO | WO2011080568 | 7/2011 |
| WO | WO2011100131 | 8/2011 |
| WO | WO2011123645 | 10/2011 |
| WO | WO2011123668 | 10/2011 |
| WO | WO2011123672 | 10/2011 |
| WO | WO2011150288 | 12/2011 |
| WO | WO2012012465 | 1/2012 |
| WO | WO2012012776 | 1/2012 |
| WO | WO2012039787 | 3/2012 |
| WO | WO2012039791 | 3/2012 |
| WO | WO2012051570 | 4/2012 |
| WO | WO2012040127 | 5/2012 |
| WO | WO2012121764 | 9/2012 |
| WO | WO2012142523 | 10/2012 |
| WO | WO2012158643 | 11/2012 |
| WO | WO2013084165 | 6/2013 |
| WO | WO2014033617 | 3/2014 |
| WO | WO2014042433 | 3/2014 |
| WO | WO2014078463 | 5/2014 |
| WO | WO2014078778 | 5/2014 |
| WO | WO2014116755 | 7/2014 |
| WO | WO2014169280 | 10/2014 |
| WO | WO2014209979 | 12/2014 |
| WO | WO2016107833 | 12/2014 |
| WO | WO2015054465 | 4/2015 |
| WO | WO2015069939 | 5/2015 |
| WO | WO2015173164 | 11/2015 |
| WO | WO2015200205 | 12/2015 |
| WO | WO2015200219 | 12/2015 |
| WO | WO2016012470 | 1/2016 |
| WO | WO2016023877 | 2/2016 |
| WO | WO2016069825 | 5/2016 |
| WO | WO2016069826 | 5/2016 |
| WO | WO2016069827 | 5/2016 |
| WO | WO2016102438 | 6/2016 |
| WO | WO2016107832 | 7/2016 |
| WO | WO2016120186 | 8/2016 |
| WO | WO2016128335 | 8/2016 |
| WO | WO2017165489 | 9/2017 |
| WO | WO2017184668 | 10/2017 |
| WO | WO2018085307 | 5/2018 |
| WO | WO2018121678 | 7/2018 |
| WO | WO2018145148 | 8/2018 |
| WO | WO2018204198 | 11/2018 |
| WO | WO2019014247 | 1/2019 |
| WO | WO2019053696 | 3/2019 |
| WO | WO2022098371 | 11/2020 |
| WO | WO2021021717 | 2/2021 |
| WO | WO2021040356 | 3/2021 |
| WO | WO2021050961 | 3/2021 |
| WO | WO2021147236 | 7/2021 |
| WO | WO2021175296 | 9/2021 |
| WO | WO2021195661 | 9/2021 |
| WO | WO2022142477 | 9/2021 |
| WO | WO2021202907 | 10/2021 |
| WO | WO2021207049 | 10/2021 |
| WO | WO2021213288 | 10/2021 |
| WO | WO2021222807 | 11/2021 |
| WO | WO2022143473 | 12/2021 |
| WO | WO2022029704 | 2/2022 |
| WO | WO2022047065 | 3/2022 |
| WO | WO2022047441 | 3/2022 |
| WO | WO2022165386 | 8/2022 |
| WO | WO2022174194 | 8/2022 |
| WO | WO2022217153 | 10/2022 |
| WO | WO2022217154 | 10/2022 |
| WO | WO2022217155 | 10/2022 |
| WO | WO2022218274 | 10/2022 |
| WO | WO2022251663 | 12/2022 |
| WO | WO2022265964 | 12/2022 |

OTHER PUBLICATIONS

Koplon [online], "$37.5 million grant will address research of high-priority infections," UAB News, retrieved on Mar. 13, 2023, URL <https://www.uab.edu/news/health/item/10307-37-5-million-grant-will-address-research-of-high-priority-infections>, Mar. 20, 2019, 1 page.

Remington's Pharmaceutical Science, 17th ed., Gennaro (ed)., 1985, Chapter 68, 58 pages.

Yan et al., "Advantages of the Parent Nucleoside GS-441524 over Remdesivir for Covid-19 Treatment," ACS Medicinal Chemistry Letters, Jun. 30, 2020, 11(7):1361-1366.

(56) References Cited

OTHER PUBLICATIONS

Yan et al., "Gilead should ditch remdesivir and focus on its simpler and safer ancestor," STAT Health Care News, May 14, 2020, 6 pages.
Yan et al., "Pharmacokinetics of 1 Orally Administered GS-441524 in Dogs," bioRxiv Preprint, May 31, 2021, 18 pages.
Adlington et al., "Synthesis of novel C-nucleosides with potential applications in combination and parallel synthesis," Tetrahedron Letters, 2000, 41:575-578.
Agostini et al., "Coronavirus Susceptibility to the Antiviral Remdesivir (GS5734) Is Mediated by the Viral Polymerase and the Proofreading Exoribonuclease", MBIO, Mar. 6, 2018, 9(2):1-15.
Alessandrini, et al., Synthesis of Differently Protected 1-C-methyl-ribofuranoses Intermediates for the Preparation of Biologically Active 1'-C-methyl-ribonucleosides, Journal of Carbohydrate Chemistry, 2008, pp. 332-344, vol. 27, No. 5.
Ali, et al., Quantitative structure-activity relationships (QSAR) of two series of O-aryl or N-acyl O-ethyl phosphoramidate and phosphorodiamidate fungicides incorporating amino acid ethyl esters, Bulletin of Environmental Contamination and Toxicology, 2000, pp. 415-420, vol. 65, No. 4.
Anonymous, "Gillings research on broad-spectrum antiviral could aid public health response to coronavirus outbreaks",—UNC Gillings School of Global Public Health, Jan. 10, 2020, retrieved on May 13, 2021, retrieved from URL <"https://sph.unc.edu/sph-news/gillings-research-on-broad-spectrum-antiviral-could-aid-public-health-response-to-coronavirus-outbreaks/">, 5 pages.
Arimilli, et al., Synthesis, In Vitro Biological Evaluation and Oral Bioavailability of 9-[2-(phosphonomethoxy)propyl]adenine (PMPA) Prodrugs, Antiviral Chemistry & Chemotherapy, 1997, pp. 557-564, vol. 8, No. 6.
Asbun, et al., Synthesis of 5-substituted Pyrimidines. II, Journal of Organic Chemistry, 1968, pp. 140-142, vol. 31.
Ballini, et al., Enantioselective Synthesis of the Lactone Moiety of the Mevinic Acids using D-Xylose as a Chiral Precursor, Journal of the Chemical Society, Perkin Transactions 1, 1991, pp. 490-491.
Balzarini, et al., Inhibition of Feline (FIPV) and Human (SARS) Coronavirus by Semisynthetic Derivatives of Glycopeptide Antibiotics, Antiviral Research, 2006, pp. 20-33, vol. 72.
Bandini, et al., Indium tribromide: a highly effective catalyst for the addition of trimethylsilyl cyanide to α-hetero-substituted ketone, Tetrahedron Letters, 2001, pp. 3041-3043, vol. 42.
Barker, et al., 2,3,5-Tri-O-benzyl-D-ribosyl and -L-arabinosyl Bromides, Journal of Organic Chemistry, 1961, pp. 4605-4609, vol. 26, No. 11.
Barl, et al., The halogen/magnesium-exchange using iPrMgCl·LiCl and related exchange reagents, Heterocycles, Jan. 2014, pp. 827-844, vol. 88, No. 2.
Beer et al., "Characteristics of Filoviridae: Marburg and Ebola Viruses," Naturwissenschaften, 1999, 86:8-17.
Behzadi et al., "Overview of Current Therapeutics and Novel Candidates Against Influenza Respiratory Syncytial Virus, and Middle East Respiratory Syndrome Coronavirus Infections," Frontiers in Microbiology, Jun. 2019, 10:1327, pp. 1-16.
Belokon et al., "Optimized catalysts for the asymmetric addition of trimethylsilyl cyanide to aldehydes and ketones," Tetrahedron, 2001, 57: 771-779.
Benksim et al., "A Novel Stereospecific Synthesis of Glycosyl Cyanides from 1,2-O-sulfinyl Derivatives," Organic Letters, 2004, 6(22): 3913-3915.
Benzaria et al., "Synthesis, In Vitro Antiviral Evaluation, and Stability Studies of Bis(S-acyl-2-thioethyl) Ester Derivatives of 9-[2-(phosphonomethoxy)ethyl]adenine (PMEA) as Potential PMEA prodrugs with Improved Oral Bioavailability," J. Med. Chem., 1996, 39(25): 4958-4965.
Bio et al., "Practical Synthesis of a Potent Hepatitis C Virus RNA Replication Inhibitor," J. Org. Chem., 2004, 69(19): 6257-6266.
Bobeck et al., "Advances in Nucleoside Monophosphate Prodrugs as Anti-HCV Agents," Antiviral Therapy, 2010, 15: 935-950.

Bobrowski et al., "Synergistic and Antagonistic Drug Combinations against SARS-CoV-2", Molecular Therapy, Feb. 2021, 29(2):873-885.
Bojack, et al., Design and Synthesis of Inhibitors of Adenosine and AMP Deaminases, Organic Letters, 2001, pp. 839-842, vol. 3, No. 6.
Bowie et al., "RIG-I: tri-ing to discriminate between self and non-self RNA," Trends in Immmology, Apr. 2007, 28(4): 147-150.
Boyer, et al., Pathogenesis, diagnosis and management of hepatitis C, Journal of Hepatology, 2000, pp. 98-112, vol. 32.
Bozza, Zika Outbreak, Brazil 2015, ISARIC, 2015, 28 pages.
Bradley et al., "The Management of Community-Acquired Pneumonia in Infants and Children Older Than 3 Months of Age: Clinical Practice Guidelines by the Pediatric Infectious Diseases Society and the Infectious Diseases Society of America", Pediatric Community Pneumonia Guidelines, Clinical Infectious Diseases, Oct. 2011, 53(7):e25-e76.
Brands et al., "Crystallization-Induced Diastereomer Transformations," Chem. Rev., 2006, 106(7): 2711-2733.
Brittain, Polymorphism in Pharmaceutical Solids, 2nd Edition, 2009, pp. 183-226, Informa Healthcare USA, Inc.
Brotschi et al., "Bipyridyl and biphenyl DNA: A recognition motif based on interstrand aromatic stacking," Chemistry—A European Journal, 2005, 11(6):1911-1923.
Brown et al., "Broad spectrum antiviral remdesivir inhibits human endemic and zoonotic deltacoronaviruses with a highly divergent RNA dependent RNA polymerase", Antiviral Research, Jun. 21, 2019, 169:1-31.
Brown, "Progress towards improving antiviral therapy for hepatitis C virus polymerase inhibitors", Part O: Nucleoside analogues, 2009, 18: 709-725.
Bullard-Feibelman et al., "The FDA-approved drug Sofosbuvir inhibits Zika Virus infection," Antiviral Res., Jan. 1, 2018, 137: 134-140.
Burns, "A Glimmer of Hope for Fatal Feline Disease," JAVMAnews, Dec. 15, 2017, 5 pages.
Butora et al., "Synthesis and HCV inhibitory properties of 9-deaza- and 7,9-dideaza-7-oxa-2'-C-methyladenosine," Bioorganic & Medicinal Chemistry, 2007, 15(15): 5219-5229.
Cabirol et al., Robust and Efficient, yet Uncatalyzed, Synthesis of Triarylsilyl-protected Cyanohydrins from Ketones, 2008, pp. 2446-2449, vol. 73.
Caira, "Crystalline Polymorphism of Organic Compounds," Topics in Current Chemistry, 1998, 198: 163-208.
Cales et al., "Treatment of liver fibrosis: clinical aspects," Gastroentérologie Clinique et Biologique, 2009, 33(10-11): 958-966.
Calisher et al., "Antigenic Relationships between Flaviviruses as Determined by Cross-neutralization Tests with Polyclonal Antisera," Journal of General Virology, 1989, 70: 37-43.
Camps, "Studies on Structurally Simple-αβ-butenolides-II," Tetrahedron, 1982, 38(15): 2395-2402.
Carey et al., "Addition, Condensation and Substitution Reactions of Carbonyl Compounds," Advanced Organic Chemistry: Part B: Reaction and Synthesis, Springer Science & Business Media, 2007, pp. 629-711.
Carroll, "Robust Antiviral Efficacy upon Administration of a Nucleoside Analog to Hepatitis C Virus-Infected Chimpanzees," Antimicrobial Agents and Chemotherapy, 2009, 53(3): 926-934.
Carryer et al., "The effect of cortisone on bronchial asthma and hay fever occurring in subjects sensitive to ragweed pollen", Journal of Allergy, Jul. 1950, 21(4): 282-287.
CAS No. 1476-52-4, "Desethyl Chloroquine", ChemSRc, retrieved on Jul. 29, 2021, retrieved from URL <"https://www.chemsrc.com/en/cas/1476-52-4_1032909.html">, 5 pages.
CAS No. 4298-15-1, "2-[4-[(7-chloroquinolin-4-yl)amino]pentylamino]ethanol", ChemSRc, retrieved on Jul. 29, 2021, retrieved from URL <"https://www.chemsrc.com/en/cas/4298-15-1_589766.html">, 4 pages.
CAS No. 54-05-7, "Chloroquine", ChemSRc, retrieved on Jul. 29, 2021, retrieved from URL <"https://www.chemsrc.com/en/cas/54-05-7_419322.html">, 16 pages.

(56) References Cited

OTHER PUBLICATIONS

CAS Registry No. 1809249-37-3, "L-Alanine, N-[(S)-hydroxyphenoxyphosphinyl]-, 2-ethylbutyl ester, 6-ester with 2-C-(4-aminopyrrolo[2,1-f][1,2,4]triazin-7-yl)-2,5-anhydro-D-altrononitrile", American Cemical Society, retrieved on Jul. 27, 2021, retrieved from URL <"https://commonchemistry.cas.org/detail?cas_rn=1809249-37-3">, 3 pages.

Chapman et al., "RSV604, a Novel Inhibitor of Respiratory Syncytial Virus Replication," Antimicrobial Agents and Chemotherapy, 2007, 51(9): 3346-3353.

Cho et al., "Discovery of the First C-Nucleoside HCV Polymerase Inhibitor (GS-6620) with Demonstrated Antiviral Response in HCV Infected Patients," J. Med. Chem., 2014, 57(5): 1812-1825.

Cho et al., "Synthesis and antiviral Activity of a Series of 1'-Substituted 4-aza-7,9-dideazaadenosine C-Nucleosides", Bioorganic & Medicinal Chemistry Letters, 2012, 22(8):2705-2707.

Cihlar et al., "Design and Profiling of GS-9148, a Novel Nucleotide Analog Active against Nucleoside-resistant Variants of Human Immunodeficiency Virus Type 1, and Its Orally Bioavailable Phosphonoamidate Prodrug, GS-9131," Antimicrobial Agents and Chemotherapy, 2008, 52(2): 655-665.

Clark et al., "Design, Synthesis, and Antiviral Activity of 2'-Deoxy-2'-fluoro-2'-C-methylcytidine, a Potent Inhibitor of Hepatitis C Virus Replication," Journal of Medicinal Chemistry, 2005, 48(17): 5504-5508.

Clarke et al., "Discovery of beta-D-2'-Deoxy-2'-alpha-Fluoro-4'-alpha-Cyano-5-aza-7,9-Dideaza Adenosine as a Potent Nucleoside Inhibitor of Respiratory Syncytial Virus with Excellent Selectivity Over Mitochondrial RNA and DNA Polymerases," Bioorganic & Medicinal Chemistry Letters, Apr. 29, 2015, 25: 2484-2487.

Colacino et al., "Synthesis and Biological Evaluation of Some 5-Nitro- and 5-Amino Derivatives of 2'-Deoxycytidine, 2',3'-Dideoxyuridine, and 2',3'-Dideoxycytidine," Nucleoside, Nucleotides & Nucleic Acids, 2003, 22(11): 2013-2026.

Cox et al., "Therapeutically administered ribonucleoside analogue MK-4482/EIDD-2801 blocks SARS-CoV-2 transmission in ferrets," Nature Microbiology, 2020, 6(1): 11-18.

Dai et al., "Synthesis of 2'-C-β-Fluoromethyluridine," Organic Letters, 2003, 5(6): 807-810.

Damont et al., "Synthesis of 1'-C-Fluoromethyladenosine," Nucleosides, Nucleotides , and Nucleic Acids, 2007, 26:1431-1434.

De Clercq, "Antiviral Drugs: Current State of the Art," J. Clin. Virol., 2001, 22(1): 73-89.

De Clercq, "Molecular Targets for Antiviral Agents," The Journal of Pharmacology and Experimental Therapeutics, 2001, 297(1): 1-10.

De Francesco et al., "Approaching a New Era for Hepatitis C Virus Therapy: Inhibitors of the NS3-4A Serine Protease and the NS5B RNA-Dependent RNA Polymerase," Antiviral Research, 2003, 58(1): 1-16.

De Las Heras, "Synthesis of Ribosyl and Arabinosyl Cyanides by Reaction of 1-O-Acyl Sugars with Trimethylsilyl Cyanide," Journal of the Chemical Society, Perkin Transactions 1, 1982, pp. 903-907.

De Lombaert et al., "N-Phosphonomethyl Dipeptides and Their Phosphonate Prodrugs, a New Generation of Neutral Endopeptidase (NEP, EC 3.4.24.11) Inhibitors," J. Med. Chem., 1994, 37(4): 498-511.

Di Bisceglie et al., "The Unmet Challenges of Hepatitis C," Scientific American, Oct. 1999, pp. 80-85.

Dinnon et al., "A mouse-adapted model of SARS-CoV-2 to test COVID-19 countermeasures," Nature, Aug. 2020, 586: 560-566.

Dolzhenko et al., "Pyrazolo[1,5-a][1,3,5]Triazines(5-Aza-9-Deazapurines): Synthesis and Biological Activity," Heterocycles, 2008, 75(7): 1575-1622.

Domingo et al., "The quasispecies (extremely heterogeneous) nature of viral RNA genome populations: biological relevance—a review," Gene, 1985, 40: 1-8.

Dondoni et al., "Thiazole-Based Synthesis of Formyl C-Glycosides," Journal of Organic Chemistry, 1994, 59: 6404-6414.

Dudfield et al., "Synthesis of C-ribosyl imidazo[2,1-f][1,2,4]triazines as inhibitors of adenosine and AMP deaminases," J. Chem. Soc, Perkin Trans I, 1999, pp. 2929-2936.

Dudfield et al., "Synthesis of C-ribosyl 1,2,4-triazolo[3,4-f][1,2,4]triazines as Inhibitors of Adenosine and AMP Deaminasses," J. Chem. Soc., Perkin Trans. 1, 1999, pp. 2937-2942.

Durcan et al., "Hydroxychloroquine Blood Levels in Systemic Lupus Erythematosus: Clarifying Dosing Controversies and Improving Adherence", Journal of Rheumatology, 2015, 42(11):2092-2097.

Dymock et al., "Novel approaches to the treatment of hepatitis C virus infection," Antiviral Chemistry & Chemotherapy, 2000, 11(2): 79-96.

El Safadi et al., "5-Modified-2'-dU and 2'-dC as Mutagenic Anti HIV-1 Proliferation Agents: Synthesis and Activity," Journal of Medicinal Chemistry, 2010, 53(4): 1534-1545.

Farquhar et al., "Biologically Reversible Phosphate-Protective Groups," Journal of Pharmaceutical Sciences, 1983, 72(3): 324-325.

Fauquet et al., "Abbreviations for vertebrate virus species names", Archives of Virology, Dec. 31, 1999, pp. 1865-1880.

fda.gov [online], "Remdesivir by Gilead Sciences: FDA Warns of Newly Discovered Potential Drug Interaction That May Reduce Effectiveness of Treatment," Jun. 15, 2020, retrieved on Sep. 2, 2022, retrieved from URL <https://www.fda.gov/safety/medical-product-safety-information/remdesivir-gilead-sciences-fda-warns-newly-discovered-potential-drug-interaction-may-reduce>, 2 pages.

Flint et al., "Functional analysis of cell surface-expressed hepatitis C virus E2 glycoprotein," J. Virol., Aug. 1999, 73(8): 6782-6790.

Foster et al., "Deuterium isotope effects in studies of drug metabolism," Trends in Pharmacological Sciences, Jan. 1984, 5:524-527.

Franchetti et al., "Antitumor Activity of C-Methyl-β-D-ribofuranosyladenine Nuceoside Ribonuceotide Reductase Inhibitors," J. Med. Chem. 2005, 48: 4983-4989.

Freeman et al., "3 Prodrug Design for Phosphates and Phosphonates," Progress in Medicinal Chemistry, 1997, 34: 111-147.

Fukumoto et al., "Viral Dynamics of Hepatitis C: Early After Orthotopic Liver Transplantation: Evidence for Rapid Turnover of Serum Virions," Hepatology, 1996, 24: 1351-1354.

Garcia et al., "Synthesis of (2,3,4,6-tetra-O-acetyl-alpha-D-glycopyranosyl)thiophene derivatives as new C-nucleoside analogues," J. Carbohydrate Chemistry, 2001, 20(7/8): 681-687.

Gardelli et al., "Phosphoramidate Prodrugs of 2'-C-Methylcytidine for Therapy of Hepatitis C Virus Infection," Journal of Medicinal Chemistry, 2009, 52(17): 5394-5407.

George et al., "Preparation of silyl- and germylmetallic compounds," Journal of the American Chemical Society, Jan. 1960, 82(2):403-6.

Gleeson et al., "Prediction of the Potency of Inhibitors of Adenosine Deaminase by QM/MM Calculations," Chem. Commun., 2003, pp. 2180-2181.

Gordon et al., "Remdesivir is a direct-acting antiviral that inhibits RNA-dependent RNA polymerase from severe acute respiratory syndrome coronavirus 2 with high potency," J. Biol. Chem., 2020, 295(20):6785-6797.

Gordon et al., "The antiviral compound remdesivir potently inhibits RNA-dependent RNA polymerase from Middle East respiratory syndrome coronavirus," Journal of Biol. Chemistry, 2020, 295(15):4773-4779.

Gordon et al., Control of Hepatitis C: A Medicinal Chemistry Perspective, J. Med. Chem., 2005, pp. 1-20, vol. 48, No. 1.

Greene et al., "Protective Groups in Organic Synthesis," John Wiley & Sons., 1991, pp. 118-142.

Greene et al., "Protective Groups in Organic Synthesis," published by John Wiley & Sons, v Inc., 1991, pp. 1-4, 10-14, 47-53 and 100-103.

Grein et al., "Compassionate Use of Remdesivir for Patients with Severe Covid-19", The New England Journal of Medicine, Apr. 2020, 382(24): 2327-2336.

Gudmundsson et al., "Synthesis of imidazo[1,2-a]pyridine C-Nucleosides with an Unexpected Site of Ribosylation," Journal of Organic Chemistry, 1997, 62: 3453-3459.

(56) References Cited

OTHER PUBLICATIONS

Gudmundsson et al., "The Condensation of 2,6-dichloroimidazo[1,2-a]pyridine C-nucleoside with an Unexpected Site of Ribosylation," Tetrahedron Letters, 1996, 7(14): 2365-2368.

Gunic et al., "Cyclic monophosphate prodrugs of base-modified 2'-C-methyl ribonucleosides as potent inhibitors of hepatitis C virus RNA replication," Bioorganic & Medicinal Chemistry Letters, 2007, 17: 2452-2455.

Hamann et al., "Synthesis and antiviral evaluation of 7,9-dideaza-8-thiapurine C-nucleoside derivatives," Collection Symposium Series, 2008, 10: 347-349.

Hamann et al., "Synthesis and antiviral evaluation of thieno[3,4-d]pyrimidine C-nucleoside analogues of 2',3'-dideoxy- and 2',3'-dideoxy-2',3'-didehydro-adenosine and -inosine," Bioorganic & Medicinal Chemistry, 2009, 17: 2321-2326.

Han et al., "Synthesis of 1-Chloroacetyl-1-dehydroxy-2,3,5-tri-O-benzoyl-β-D-ribofuranose. A Potentially Versatile Intermediate for the Synthesis of C-Nucleosides," Synthetic Communications, 1992, 22(19): 2815-2822.

Haraguchi et al., "Stereoselective Synthesis of 1'-C-Branched Uracil Nucleosides From Uridine," Nucleosides & Nucleotides, 1995, 14(3-5): 417-420.

Harcourt et al., "Molecular Characterization of the Polymerase Gene and Genomic Termini of Nipah Virus," Virology, 2001, 287: 192-201.

Harki et al., "Synthesis and Antiviral Activity of 5-Substituted Cytidine Analogues: Identification of Potent Inhibitor of Viral RNA-Dependent RNA Polymerases," Journal of Medicinal Chemistry, 2006, 49(21): 6166-6169.

Hayashi et al., "C-Nucleosides, A Synthesis of 2-Substituted 7-(b-D-Ribofuranosyl)-Pyrrolo[2,1-f]-1,2,4-Triazines. A New Type of "Purine Like" C-Nucleoside," Heterocycles, 1992, 34(3): 569-574.

Hecker et al., "Liver Targeted Prodrugs of 2'-C-Methyladenosine for Therapy of Hepatitis C Virus Infection," J. Med. Chem., 2007, 50(16): 3891-3896.

Hoffmann et al., "When, in the context of drug design, can a fluorine atom successfully substitute a hydroxyl group?," International Journal of Quantum Chemistry, 2002, 89: 419-427.

Holshue et al., "First Case of 2019 Novel Coronavirus in the United States", The New England Journal of Medicine, Jan. 2020, 9 pages.

Huang et al., "Recent development of therapeutics for chronic HCV infection," Antiviral Research, Sep. 2006, 71(2-3): 351-362.

Itoh et al., "Divergent and Stereocontrolled Approach to the Synthesis of Uracil Nucleosides Branched at the Anomeric Position," J. Org. Chem, 1995, 60: 656-662.

Jasko et al., "5'-Phosphonates of Ribonucleosides and 2'-Deoxyribonucleosides: Synthesis and Antiviral Activity," Nucleosides & Nucleotides, 1993, 12(8): 879-893.

Jonckers et al., "2'Deoxy-2'-spirocyclopropylcytidine Revisited: A New and Selective Inhibitor of the Hepatitis C Virus NS5B Polymerase," Journal of Medicinal Chemistry, Nov. 2010, 53(22)8150-60.

Jones et al., "Di- and Triester Prodrugs of the Varicella-Zoster Antiviral Agent 6-Methoxypurine Arabinoside," Journal of Medicinal Chemistry, Jan. 1992, 35(1):56-63.

Kabat et al., "Nucleosides, CXLVIII, Synthesis of 6-(β-D-Ribofuranosyl)picolinamide: A Novel C-Nucleoside from D-Ribonolactone", Chemical & Pharmaceutical Bulletin, 1988, pp. 634-640, vol. 36, No. 2.

Kaewkhao et al., "High sensitivity methods to quantify chloroquine and its metabolite in human blood samples using LC-MS/MS", Bioanalysis, Mar. 2019, 11(5):333-347.

Kalil et al., "Baricitinib plus Remdesivir for hospitalized adults with Covid-19," New England Journal of Medicine, Dec. 11, 2020, 13 pages.

Khamnei et al., "Neighboring Group Catalysis in the Design of Nucleotide Prodrugs," J. Med. Chem., 1996, 39(20): 4109-4115.

Khan et al., "Coronaviruses disease 2019 (COVID-19): Causative agent, mental health concerns, and potential management options," Journal of Infection and Public Health, Dec. 2020, 13(12):1840-1844.

Kim et al., "Reversal of the Progression of Fatal Coronavirus Infection in Cats by a Broad-Spectrum Coronavirus Protease Inhibitor," PLOS Pathogens, Mar. 30, 2016, 18 pages.

Kim et al., "Synthesis and Evaluation of 2-Amino-6-fluoro-9-(4-hydroxy-3-hydroxymethylbut-1-yl)purine Mono- and Diesters as Potential Prodrugs of Penciclovir," Bioorganic & Medicinal Chemistry, Mar. 1999, 7(3):565-70.

Kim et al., "Synthesis and Evaluation of 2-Amino-9-(1,3-dihydroxy-2-propoxymethyl)-6-fluoropurine Mono- and Diesters as Potential Prodrugs of Ganciclovir," Journal of Medicinal Chemistry, Jan. 1999, 42(2):324-28.

Klumpp et al., "Chapter 20: Discovery and Clinical Evaluation of the Nucleoside Analog Balapiravir (R1626) for the Treatment of HCV Infection," Antiviral Drugs: From Basic Discovery through Clinical Trials, Jun. 20, 2011, pp. 287-304.

Klumpp et al., "The Novel Nucleoside Analog R1479 (4'-Azidocytidine) is a Potent Inhibitor of NS5B-dependent RNA Synthesis and Hepatitis C virus Replication in Cell Culture," Journal of Biological Chemistry, 2006, 281(7): 3793-3799.

Knaggs et al., A QSAR Study Investigating the Effect of L-Alanine Ester Variation on the Anti-HIV Activity of Some Phosphoramidate Derivatives of d4T, Bioorganic & Medicinal Chemistry Letters, 2000, 10: 2075-2078.

Knutsen et al., "Synthesis of Imidazo-fused Bridgehead-nitrogen C-Nucleosides : Coupling-Elimination Reactions of 2,5-Anhydro-3,4,6-tri-O-benzoyl-D-allonic Acid," J. Chem. Soc. Perkin Trans I, 1985, pp. 621-630.

Knutsen et al., "Synthesis of Imidazo-fused Bridgehead-nitrogen C-Nucleosides via Dehydrative Coupling Reactions of 2,5-Anhydro-3,4,6-tri-O-benzoyl-D-allonic Acid," J. Chem. Soc. Perkin Trans I, 1984, pp. 229-238.

Kobe et al., "Use of Distance Geometry Approach for the In Vitro Antiviral Activity Evaluation of N-bridgehead C-nucleosides," European J. Med. Chem., 1992, 27(3): 259-266.

Kulli, "K Banhatti Polynomials of Remdesivir, Chloroquine, Hydroxychloroquine: Research Advances for the Prevention and Treatment of COVID-19," SSRG International Journal of Applied Chemistry, May-Aug. 2020, 7(2):48-55.

Kushner et al., "Pharmacological uses and perspectives of heavy water and deuterated compounds," Canadian Journal of Physiology and Pharmacology, Feb. 1999, 77(2):79-88.

Kuzik et al., "Nebulized Hypertonic Saline in the Treatment of Viral Bronchiolitis in Infants", The Journal of Pediatrics, Sep. 2007, 151(3):266-270.e1.

Lefebvre et al., "Mononucleoside Phosphotriester Derivatives with S-Acyl-2-thioethyl Bioreversible Phosphate-Protecting Groups: Intracellular Delivery of 3'-Azido-2',3'-dideoxythymidine 5'-Monophosphate," Journal of Medicinal Chemistry, 1995, 38(20): 3941-3950.

Lefebvre et al., "Synthesis, Decomposition Pathways and 'In Vitro' Evaluation of Bioreversible Phosphotriesters of Azt, Nucleosides," Nucleotides & Nucleic Acids, 1995, 14(3-5): 763-766.

Leyssen et al., "Molecular strategies to inhibit the replication of RNA Viruses," Antiviral Research, 2008, 78:9-25.

Lindell et al., "Synthesis and Biochemical Testing of 3-(Carboxyphenylethyl)imidazo[2,1-f][1,2,4]triazines as Inhibitors of AMP Deaminase," ACS Medicinal Chemistry Letters, 2010, 1(6): 286-289.

Liu et al., "Hydroxychloroquine, a less toxic derivative of chloroquine, is effective in inhibiting SARS-CoV-2 infection in vitro," Cell Discovery, Mar. 18, 2020, 6:16, 4 pages.

Lo et al., "GS-5734 and its parent nucleoside analog inhibit Filo-, Pneumo-, and Paramyxoviruses," Scientific Reports, 2017, 7(43395):1-7.

Lovelette, "1,2,4-Triazines. Synthesis of selected members of the s-triazolo[3,4-f][1,2,4]triazine and tetrazolo[1,5-f][1,2,4]triazine ring systems," Journal of Heterocyclic Chemistry, 1979, 16: 555-560.

Lu, Chengping, Veterinary Microbiology 5th edition, Jan. 31, 2013, p. 431, China Agriculure Press (No English Translation available).

(56) References Cited

OTHER PUBLICATIONS

Martell et al., "Hepatitis C Virus (HCV) Circulates as a Population of Different but Closely Related Genomes: Quasispecies Nature of HCV Genome Distribution," Journal of Virology, 1992, 6695: 3225-3229.
Martin et al., "Hint2, A Mitochondrial Apoptotic Sensitizer Down-Regulated in Hepatocellular Carcinoma," Gastroenterology, Jun. 2006, 130(7):2179-2188.
Mason et al., "Polyadenylation-dependent screening assay for respiratory syncytial virus RNA transcriptase activity and identification of an inhibitor," Nucleic Acids Research, 2004, 32(16): 4758-4767.
Matulic-Adamic et al., "Synthesis of 3-(β-D-Ribofuranosyl)-2-Fluoropyridine and 3-(β-D-Ribofuranosyl)-Pyridin-2-one," Tetrahedron Letters, 1997, 38(2): 203-206.
Matulic-Adamic et al., "Synthesis of 5-(β-D-Ribofuranosyl)-Pyridin-2-one: a 'Deletion-Modified' Analogue of Uridine," Tetrahedron Letters, 1997, 38(10): 1669-1672.
McGuigan et al. "Application of Phosphoramidate ProTide Technology Significantly Improves Antiviral Potency of Carbocyclic Adenosine Derivatives," J. Med. Chem., 2006, 49: 7215-7226.
McGuigan et al., "Aryl Phosphoramidate Derivatives of d4T Have Improved Anti-HIV Efficacy in Tissue Culture and May Act by the Generation of a Novel Intracellular Metabolite," J. Med. Chem., 1996, 39: 1748-1753.
McGuigan et al., "Design, synthesis and biological evaluation of phosphorodiamidate prodrugs of antiviral and anticancer nucleosides," European Journal of Medical Chemistry, 2013, 70:326-340.
McGuigan et al., "Intracellular Delivery of Bioactive AZT Nucleotides by Aryl Phosphate Derivatives of AZT," J. Med. Chem., 1993, 36(8): 1048-1052.
Mehellou et al., ""Aryloxy Phosphoramidate Triesters: a Technology for Delivering Monophosphorylated Nucleosides and Sugars into Cells,"" ChemMedChem, 2009, 4:1779-1791.
Meppen et al., "Cyclic phosphoramidates as prodrugs of 2'-C-methylcytidine," European Journal of Medicinal Chemistry, 2009, 49(9): 3765-3770.
Meppen et al., "Medi-404—A Prodrug Approach for the Treatment of HCV Infection," Abstracts of papers, 236th ACS National Meeting, Philadelphia, PA, United States, Aug. 17-21, 2008, 1 page.
Metobo et al., "Practical synthesis of 1'-substituted Tubercidin C-nucleoside analogs," Tetrahedron Letters, Feb. 2012, 53(5): 484-486.
Migliaccio et al., "Characterization of Resistance to Non-obligate Chain-terminating Ribonucleoside Analogs That Inhibit Hepatitis C Virus Replication in vitro," The Journal of Biological Chemistry, 2003, 278(49): 49164-49170.
Mitchell et al., "Bioreversible Protection for the Phospho Group: Bioactivation of the Di(4-acyloxybenzyl) and Mono(4-acyloxybenzyl) Phosphoesters of Methylphosphonate and Phosphonoacetate," J. Chem. Soc., Perkin Trans. 1, 1992, pp. 2345-2353.
Mitchell et al., "Synthesis of C-Nucleoside Isosteres of 9-(2-Hydroxyethoxymethyl)guanine (Acyclovir)," J. Het. Chem., 1984, 21(3): 697-699.
Moennig et al., "The Pestiviruses", Advances in Virus Research, 1992, 41: 53-98.
Moorman et al., "5'-ester prodrugs of the varicella-zoster antiviral agent, 6-methoxypurine arabinoside," Antiviral Chemistry & Chemotherapy, Jun. 1992, 3(3):141-46.
Moradpour et al., "Replication of hepatitis C virus," Nature Reviews Microbiology, 2007, 5(6): 453-463.
Morris, "Mechanisms of action and therapeutic role of corticosteroids in asthma", J. Allergy Clin. Immunol., Jan. 1985, 75(1 Pt):1-13.
Moscow et al., "Reduced Folate Carrier Gene (RFC1) Expression and Anti-Folate Resistance in Transfected and Non-Selected Cell Lines," International Journal of Cancer, 1997, 72: 184-190.
Mossel et al., "Exogenous ACE2 expression allows refractory cell lines to support severe acute respiratory syndrome coronavirus replication," Journal of Virology, Mar. 15, 2005, 79(6):3846-50.
Munster et al., "Hydroxychloroquine concentration-response relationships in patients with rheumatoid arthritis", Arthritis Rheumatology, Jun. 2002, 46(6):1460-1469.
Murakami et al., "Mechanism of Activation of Beta-D-2'-Fluoro-2'-C-Methylcytidine and Inhibition of Hepatitis C Virus NS5B RNA Polymerase", Antimicrob Agents Chemother., Feb. 2007, 51(2):503-509.
Murakami et al., "Mechanism of Activation of PSI-7851 and Its Diastereoisomer PSI-7977", The Journal of Biological Chemistry, 2010, 285(45):34337-34347.
Murphy et al., "The Nucleoside Analog GS-441524 Strongly Inhibits Feline Infectious Peritonisitis (FIP) Virus in Tissue Culture and Experimental Cat Infection Studies", Veterinary Microbiology, 2018, 219:226-233.
Neumann et al., "Hepatitis C Viral Dynamics in Vivo and the Antiviral Efficacy of Interferon-α Therapy", Science, 1998, 282:103-107.
Nilsson et al., "Discovery of 4'-azido-2'-deoxy-2'-C-methyl cytidine and prodrugs thereof: A potent inhibitor of Hepatitis C virus replication," Bioorganic & Medicinal Chemistry Letters, May 2012, 22(9):3265-68.
Nishimura et al., "Synthesis of pyrrolo[2,1-f][1,2,4]triazine C-nucleosides. Isosteres of sangivamycin, tubercidin, and toyocamycin," Carbohydrate Research, 2001, 331: 77-82.
Ogura et al., "Reaction of Ethynyl Compounds with Lactones," Journal of Organic Chemistry, 1972, 37(1): 72-75.
Olsen et al., "A 7-Deaza-Adenosine Analog Is a Potent and Selective Inhibitor of Hepatitis C Virus Replication with Excellent Pharmacokinetic Properties," Antimicrobial agents and Chemotherapy, 2004, 3944-3953.
Otter et al., "Conformational Properties of Purine-Like C-Nucleosides," Nucleosides & Nucleotides, 1996, 15(1-3): 793-807.
Owusu et al., "A Comparison Analysis on Remdesivir, Favipiravir, Hydroxychloroquine, Chloroquine and Azithromycin in the Treatment of Corona Virus Disease 2019 (COVID-19)—A Review," World Journal of Pharmacy and Pharmaceutical Sciences, May 2020, 9(5):121-133.
Pankiewicz et al., "C-Nucleoside Analogues of Nicotinamide Mononucleotide (NMN)," Nucleosides and Nucleotides, 1988, 7(5 &6): 589-593.
Pankiewicz et al., "Efficient Synthesis of 5-(β-D-Ribofuranosyl)nicotinamide and its α-Isomer," Journal of Organic Chemistry, 1988, 53: 3473-3479.
Patani et al., "Bioisosterism: a rational approach in drug design," Chem. Rev., 1996, 96:3147-3176.
Patil et al., "4-Aza-7,9-Dideazaadenosine, a New Cytotoxic Synthetic C-Nucleoside Analogue of Adenosine," Tetrahedron Letters, 1994, 35(30): 5339-5342.
Patil et al., "C-Glycosylation of Substituted Heterocycles under Friedel-Crafts Conditions (II): Robosylation of Multi-Functionalized Thiophenes and Furans for the Synthesis of Purine-Like C-Nucleosides," Nucleosides & Nucleotides, 1990, 9(7): 937-956.
Patil et al., "Synthesis of Pyrrolo[2,1-f][1,2,4]triazine Congeners of Nucleic Acid Purines via the N-Amination of 2-Substituted Pyrroles," J. Het. Chem., 1994, 31: 781-786.
Patil et al., "Synthesis of some new thieno[3,4-d]pyrimidines and their C-nucleosides," Journal of Heterocyclic Chemistry, 1993, 30(2): 509-515.
PCT International Search Report and Written Opinion in International Application No. PCT/US2021/047800, dated Jan. 18, 2022, 21 pages.
PCT Invitation to Pay Additional Fees in International Application No. PCT/US2021/047800, dated Dec. 3, 2021, 14 pages.
Pelet et al., "High throughput screening assay for negative single stranded RNA virus polymerase inhibitors," J. Virol. Methods, Sep. 2005, 128(1-2): 29-36.
Perrone et al., "Application of the Phosphoramidate ProTide Approach to 4'-Azidouridine Confers Sub-micromolar Potency versus Hepatitis C Virus on an Inactive Nucleoside", Journal of Medicinal Chemistry, 2007, 50(8):1840-1849.
Perrone et al., "First Example of Phosphoramidate Approach Applied to a 4'-Substituted Purine Nucleoside (4'-Azidoadenosine): Conver-

(56) References Cited

OTHER PUBLICATIONS sion of an Inactive Nucleoside to a Submicromolar Compound versus Hepatitis C Virus," Journal of Medicinal Chemistry, Oct. 2007, 50(22): 5463-5470.
Peterson et al., "Prodrug approaches to improving the oral absorption of antiviral nucleotide analogues," Expert Opinion, Drug Deliv., 2009, 6(4): 405-420.
Piccirilli et al., "A Direct Route to 3-(D-Ribofuranosyl)pyridine Nucleosides," Helvetica Chimica Acta, 1991, 74: 397-406.
Pierra et al., "Synthesis and Pharmacokinetics of Valopicitabine (NM283), and Efficient Prodrug of the Potent Anti-HCV Agent 2'-C-Methylcytidine," Journal of Medicinal Chemistry, 2006, 49(22): 6614-6620.
Pizzorno et al., "In vitro evaluation of antiviral activity of single and combined repurposable drugs against SARS-CoV-2," Antiviral Research, Sep. 2020, 181:104878.
Poduch et al., "Design of Inhibitors of Orotidine Monophosphate Decarboxylase Using Bioisosteric Replacement and Determination of Inhibition Kinetics," Journal of Medicinal Chemistry, 2006, 49(16): 4937-4945.
Porter et al., "Zika virus, drug discovery, and student projects," ScienceBlogs, Mar. 9, 2016, 7 pages.
Pruijssers et al., "Remdesivir Inhibits SARS-CoV-2 in Human Lung Cells and Chimeric SARS-CoV Expressing the SARS-CoV-2 RNA Polymerase in Mice," Cell Reports, 2020, 32(107940):1-16.
Puech et al., "Intracellular Delivery of Nucleoside Monophosphates through a Reductase-mediated Activation Process," Antiviral Research, 1993, 22(4): 155-174.
Ramasamy et al., "Synthesis and Antitumor Activity of Certain 3-B-D-Ribofuranosyl-1,2,4-triazolo[3,4-f]-1,2,4-triazines Related to Formycin Prepared via Ring Closure of a 1,2,4-Triazine Precursor," J. Med. Chem., 1986, 29(11): 2231-2235.
Rao et al., "C-Glycosylation of Substituted Heterocycles under Friedel-Crafts Conditions (I): A Two-Step Synthesis of the Thieno[3,4-d]Pyrimidine C-Nucleoside Analog of Inosine," Tetrahedron Letters, 1988, 29(29): 3537-3540.
Rebeaud et al., "SARS-CoV-2 and the Use of Chloroquine as an Antiviral Treatment," Frontiers in Medicine, Apr. 24, 2020, 7:184, 6 pages.
Reddy et al., "Stereoselective Synthesis of Nucleoside Monophosphate HepDirectTM Prodrugs," Tet. Lett., 2005, 46: 4321-4324.
Ross et al., "Synthesis of Diastereomerically Pure Nucleotide and Phosphoramidates," J. Org. Chem., 2011, 76: 8311-8319.
Sacramento et al., "The clinically approved antiviral drug Sofosbuvir inhibits Zika Virus replication," Nature, Jan. 18, 2017, 7: 40920, 12 pages.
Sahakijpijarn et al., "Development of Remdesivir as a Dry Powder for Inhalation by Thin Film Freezing," Pharmaceutics, Oct. 2020, 12(11):1002, 27 pages.
Schnirring, "China releases genetic data on new coronavirus, now deadly," CIDRAP News, Jan. 2020, retrieved on Mar. 15, 2022, retrieved from URL <https://www.cidrap.umn.edu/news-perspective/2020/01/china-releases-genetic-data-new-coronavirus-now-deadly>, 3 pages.
Schul et al., "A Dengue Fever Viremia Model in Mice Shows Reduction in Viral Replication and Suppression of the Inflammatory Response after Treatment with Antiviral Drugs," Journal of Infectious Diseases, 2007, 195: 665-674.
Schultz, "Prodrugs of Biologically Active Phosphate Esters," Bioorganic & Medicinal Chemistry, 2003, 11: 885-898.
Scott et al., "Interferon-a-2b Plus Ribavirin: A Review of its Use in the Management of Chronic Hepatitis C," Drugs, 2002, 62(3): 507-556.
Sheahan et al., "Broad-spectrum antiviral GS-5734 inhibits both epidemic and zoonotic coronaviruses", Science Translational Medicine, Jun. 2017, 9(396):eaal3653, 11 pages.
Sheahan et al., "Comparative therapeutic efficacy of remdesivir and combination lopinavir, ritonavir, and interferon beta against MER-CoV," Nature Communications, 2020, 11(222):1-14.
Sheahan, "Preparing for future pandemics, today with broad-spectrum antivirals", Nature Portfolio Microbiology Community, Jan. 10, 2020, retrieved on May 13, 2021, retrieved from URL <"https://naturemicrobiologycommunity.nature.com/posts/58125-preparing-for-future-pandemics-today-with-broad-spectrum-antivirals", 13 pages.
Shekunov et al., "Crystallization processes in pharmaceutical technology and drug delivery design," Journal of Crystal Growth, 2000, 211: 122-136.
Shi et al., "Synthesis and anti-viral activity of a series of d- and 1-2'-deoxy-2'-fluororibonucleosides in the subgenomic HCV replicon system," Bioorganic & Medicinal Chemistry, Mar. 2005, 13(5):1641-1652.
Siegel et al., "Discovery and Synthesis of a Phosphoramidate Prodrug of a Pyrrolo[2,1-f][triazin-4-amino] Adenine C-Nucleoside (GS-5734) for the Treatment of Ebola and Emerging Viruses," J. Med. Chem., 2017, 60, 5, 1648-1661 Supplementary Material.
Siegel et al., "Discovery and Synthesis of a Phosphoramidate Prodrug of a Pyrrolo[2,1-f][triazin-4-amino] Adenine C-Nucleoside(GS-5734) for the Treatment of Ebola and Emerging Viruses", Journal of Medicinal Chemistry, 2017, 60(5): 1648-1661.
Silverman et al., "The Organic Chemistry of Drug Design and Drug Action," Elsevier Science, 1992, pp. 19-23.
Silverman, "The Organic Chemistry of Drug Design and Drug Action," Elsevier Science, 2nd Ed., 2004, pp. 29-34.
Sofia et al., "Discovery of a β-d-2'-Deoxy-2'-α-fluoro-2'-β-C-methyluridine Nucleotide Prodrug (PSI-7977) for the Treatment of Hepatitis C Virus," Journal of Medicinal Chemistry, Sep. 2010, 53(19):7202-7218.
Srivastav et al., "Antiviral Activity of Various 1-(2'-Deoxy-β-D-lyxofuranosyl), 1-(2'-Fluoro-β-D-xylofuranosyl), 1-(3'-Fluor-β-D-arabinofuranosyl), and 2'-Fluoro-2',3'-didehydro-2',3'-dideoxyribose Pyrimidine Nucleoside Analogues against Duck Hepatitis B Virus (DHBV) and Human Hepatitis B Virus (HBV) Replication," Journal of Medicinal Chemistry, 2010, 53(19): 7156-7166.
Stein et al., "Phosphorylation of Nucleoside Analog Antiretrovirals: A Review for Clinicians," Pharmacotherapy, Jan. 2001, 21(1):11-34.
Stella et al., "Cyclodextrins," Toxicologic Pathology, 2008, 36(1):30-42.
Streetman, "Drug Interaction Concerns for COVID-19 Treatments", Wolters Kluwer, Apr. 15, 2020, retrieved on Sep. 7, 2021, retrieved from URL <"https://www.wolterskluwer.com/en/expert-insights/drug-interaction-concerns-for-covid-19-treatments">, 10 pages.
Sun, "Remdesivir for Treatment of COVID-19: Combination of Pulmonary and IV Administration May Offer Additional Benefit", The AAPS Journal, 2020, 22(77):1-6.
Szente et al., "Sulfobutylether-beta-cyclodextrin-enabled antiviral remdesivir: Characterization of electrospun- and lyophilized formulations," Carbohydrate Polymers, 2021, 264:118011, 8 pages.
Taiwanese Office Action in TW Appln. No. 110131732, dated Jun. 7, 2022, 12 pages (with English translation).
Tan et al., "Combination Treatment With Remdesivir and Ivermectin Exerts Highly Synergistic and Potent Antiviral Activity Against Murine Coronavirus Infection," Frontiers in Cellular and Infection Microbiology, Jul. 30, 2021, 11(700502):1-10.
Tapia et al., "Combination of a Mutagenic Agent with a Reverse Transcriptase Inhibitor Results n Systematic Inhibition of HIV-1 Infection," Virology, 2005, 338: 1-8.
Totura et al., "Broad-spectrum coronavirus antiviral drug discovery", Expert Opinion on Drug Discovery, Mar. 2019, 17 pages.
Towner et al., "Newly Discovered Ebola Virus Associated with Hemorrhagic Fever Outbreak in Uganda," PLoS Pathogens, 2008, 4(11): e1000212, 6 pages.
Tschesnokov et al., "Template-dependent inhibition of coronavirus RNA-dependent RNA polymerase by remdesivir reveals a second mechanism of action," J. Biol. Chem., 2020, 295(47):16156-16165.
Uchiyama et al., "O-selective Phosphorylation of Nucleosides without N-protection," J. Org. Chem., Jan. 1, 1993, 58(2): 373-379.
Vaghefi et al., "Synthesis and Antiviral Activity of Certain Nucleoside 5'-Phosphonoformate Derivatives," Journal of Medicinal Chemistry, 1986, 29(8): 1389-1393.

(56) References Cited

OTHER PUBLICATIONS

Venkatachalam et al., "Effect of change in nucleoside structure on the activation and antiviral activity of phosphoramidate derivatives," Bioorganic & Medicinal Chemistry, 2005, 13: 5408-5423.

Vieira et al., "Development of a Large-Scale Cyanation Process Using Continuous Flow Chemistry En Route to the Synthesis of Remdesivir," Organic Process Research & Development, May 2020, 24(10):2113-2121.

Walker et al., "Plasma chloroquine and desethylchloroquine concentrations in children during and after chloroquine treatment for malaria.", British Journal Clinical Pharmacology, Dec. 1983, 16(6):701-705.

Wang et al., "ANNOVAR: functional annotation of genetic variants from high-throughput sequencing data," Nucleic Acids Research, 2010, 38(16): e164, 7 pages.

Wang et al., "Remdesivir and chloroquine effectively inhibit the recently emerged novel coronavirus (2019-nCoV) in vitro", Cell Research, 2020, 30:269-271.

Wang et al., "Remdesivir in adults with severe COVID-19: a randomised, double-blind, placebo-controlled, multicentre trial," Lancet, Apr. 29, 2020, 395:1569-1578.

Warren et al., "Protection against filovirus diseases by a novel broad-spectrum nucleoside analogue BCX4430", Nature, Apr. 2014, 508(7496):402-405.

Warren et al., "Therapeutic efficacy of the small molecules GS-5734 against EBOLA virus in rhesus monkeys", Nature, Mar. 17, 2016, 531(7594): 381-385.

Wolfel et al., "Virological assessment of hospitalized patients with COVID-2019," Nature, Apr. 2020, 581: 465-470.

Wu et al., "Synthetic Methodologies for C-Nucleosides," Synthesis, 2004, 10: 1533-1553.

Xie et al., "A nanoluciferase SARS-CoV-2 for rapid neutralization testing and screening of anti-infective drugs for COVID-19," Nature Communications, Oct. 15, 2020, 11(1):1-11.

Xie et al., "Weinreb Amide Approach to the Practical Synthesis of a Key Remdesivir Intermediate," The Journal of Organic Chemistry, 2021, 86:5065-5072.

Xu et al., "Off-Target In Vitro Profiling Demonstrates that Remdesivir Is a Highly Selective Antiviral Agent," Antimicrobial Agents and Chemotherapy, Jan. 20, 2021, 65(2), 14 pages.

Yamanaka et al., "Metabolic Studies on BMS-200475, a New Antiviral Compound Active against Hepatitis B Virus," Antimicrobial Agents and Chemotherapy, 1999, p. 43(1): 190.

Yang et al., "Lewis acid catalyzed direct cyanation of indoles and pyrroles with N-cyano-N-phenyl-p-toluenesulfonamide (NCTS)," Organic Letters, 2011, 13(20): 5608-5611.

Yates et al., "The evolution of antiviral nucleoside analogues: A review for chemists and non-chemists. Part II: Complex modifications to the nucleoside scaffold", Antiviral Research, Dec. 8, 2018, 162:5-21.

Yoon et al., "High-throughput screening-based identification of paramyxovirus inhibitors," J. Biomol. Screen., Aug. 2008, 13(7): 591-608.

Yoshimura et al., "Synthesis and Biological Evaluation of 1'-C-Cyano-Pyrimidine Nucleosides," Nucleosides & Nucleotides, 1996, 15(1-3): 305-324.

Zhang et al., "A Practical Synthesis of (2R)-3,5-di-O-benzoyl-2-fluoro-2-C-methyl-D-ribono-y-lactone", Tetrahedron: Asymmetry, 2009, 20:305-312.

Zhu et al., "A novel coronavirus from patients with pneumonia in China, 2019," New England Journal of Medicine, Jan. 24, 2020, 14 pages.

Beigel et al., "Remdesivir for the Treatment of Covid-19—Final Report," New England Journal of Medicine, Nov. 5, 2020, 383(19): 1813-1826.

Coppock et al., "COVID-19 treatment combinations and associations with mortality in a large multi-site healthcare system," PloS one, Jun. 11, 2021, 16(6): 13 pages.

Douafer et al., "Scope and limitations on aerosol drug delivery for the treatment of infectious respiratory diseases," Journal of Controlled Release, Sep. 2020, 325: 276-292.

Humeniuk et al., "Pharmacokinetic, Pharmacodynamic, and Drug-Interaction Profile of Remdesivir, a SARS-CoV-2 Replication Inhibitor," Clinical pharmacokinetics, May 2021, 60(2021): 569-583.

Pilcer et al., "Formulation strategy and use of excipients in pulmonary drug delivery," International Journal of Pharmaceutics, Jun. 2010, 392(1-2): 1-19.

Spinner et al., "Effect of Remdesivir vs Standard Care on Clinical Status at 11 Days in Patients With Moderate COVID-19: A Randomized Clinical Trial," Jama, Sep. 2020, 324(11): 1048-1057.

Taylor, "Aulton's Pharmaceutics: The Design and Manufacture of Medicines; Chapter 37: Pulmonary Drug Delivery," 5th ed., Aulton et al (ed), 2018: 653-670.

Taiwanese Office Action in TW Appln. No. 110131732, dated Feb. 15, 2023, 9 pages (with English translation).

Xie et al., "Engineering SARS-CoV-2 using a reverse genetic system," Nature protocols, Jan. 29, 2021, 16(3): 1761-1784.

U.S. Appl. No. 17/458,023, filed Aug. 26, 2021, Byoung-Kwon Chun.

Wei et al., "Potency and Pharmacokinetics of GS-441524 Derivatives Against SARS-CoV-2," Bioorganic & Medicinal Chemistry, Sep. 2021, 46: 12 pages.

U.S. Appl. No. 13/189,373, filed Jul. 22, 2011, Richard L. Mackman.

U.S. Appl. No. 14/613,719, filed Feb. 4, 2015, Richard L. Mackman.

U.S. Appl. No. 14/579,348, filed Dec. 22, 2014, Richard L. Mackman.

U.S. Appl. No. 16/042,085, filed Jul. 23, 2018, Richard L. Mackman.

U.S. Appl. No. 16/879,491, filed May 20, 2020, Richard L. Mackman.

U.S. Appl. No. 17/854,818, filed Jun. 30, 2022, Richard L. Mackman.

U.S. Appl. No. 17/333,389, filed May 28, 2021, Tomas Cihlar.

U.S. Appl. No. 17/676,920, filed Feb. 22, 2022, Tomas Cihlar.

U.S. Appl. No. 18/128,850, filed Mar. 30, 2023, Tomas Cihlar.

U.S. Appl. No. 17/222,125, filed Apr. 5, 2021, Scott Ellis.

U.S. Appl. No. 18/202,751, filed May 26, 2023, Scott Ellis.

U.S. Appl. No. 17/158,391, filed Jan. 26, 2021, Tomas Cihlar.

U.S. Appl. No. 18/131,106, filed Apr. 5, 2023, Tomas Cihlar.

U.S. Appl. No. 17/198,829, filed Mar. 11, 2021, Pavel R. Badalov.

U.S. Appl. No. 18/108,480, filed Feb. 10, 2023, Pavel R. Badalov.

U.S. Appl. No. 16/031,620, filed Jul. 10, 2018, Nate Larson.

U.S. Appl. No. 16/865,209, filed May 1, 2020, Nate Larson.

U.S. Appl. No. 17/585,651, filed Jan. 27, 2022, Nate Larson.

U.S. Appl. No. 15/919,750, filed Mar. 13, 2018, Michel Joseph Perron.

U.S. Appl. No. 16/852,102, filed Apr. 17, 2020, Michel Joseph Perron.

U.S. Appl. No. 17/578,682, filed Jan. 19, 2022, Michel Joseph Perron.

U.S. Appl. No. 17/895,123, filed Aug. 25, 2022, Michel Joseph Perron.

U.S. Appl. No. 18/133,612, filed Apr. 12, 2023, Michel Joseph Perron.

U.S. Appl. No. 15/964,597, filed Apr. 27, 2018, Katrien Brak.

U.S. Appl. No. 17/069,248, filed Oct. 13, 2020, Katrien Brak.

U.S. Appl. No. 18/099,477, filed Jan. 20, 2023, Katrien Brak.

U.S. Appl. No. 15/267,433, filed Sep. 16, 2016, Michael O'Neil Hanrahan Clarke.

U.S. Appl. No. 16/265,016, filed Feb. 1, 2019, Michael O'Neil Hanrahan Clarke.

U.S. Appl. No. 16/863,566, filed Apr. 30, 2020, Michael O'Neil Hanrahan Clarke.

U.S. Appl. No. 17/222,066, filed Apr. 5, 2021, Michael O'Neil Hanrahan Clarke.

U.S. Appl. No. 17/748,400, filed May 19, 2022, Michael O'Neil Hanrahan Clarke.

U.S. Appl. No. 14/926,063, filed Oct. 29, 2015, Steven Donald Axt.

U.S. Appl. No. 16/692,966, filed Nov. 22, 2019, Steven Axt.

(56) References Cited

OTHER PUBLICATIONS

U.S. Appl. No. 17/665,724, filed Feb. 7, 2022, Steven Donald Axt.
U.S. Appl. No. 14/926,062, filed Oct. 29, 2015, Byoung Chun.
U.S. Appl. No. 15/246,240, filed Aug. 24, 2016, Byoung Chun.
U.S. Appl. No. 15/902,690, filed Feb. 22, 2018, Byoung Chun.
U.S. Appl. No. 16/274,049, filed Feb. 12, 2019, Byoung Chun.
U.S. Appl. No. 16/881,419, filed May 22, 2020, Byoung-Kwon Chun.
U.S. Appl. No. 17/579,650, filed Jan. 20, 2022, Byoung Kwon Chun.
U.S. Appl. No. 17/897,380, filed Aug. 29, 2022, Byoung Kwon Chun.
U.S. Appl. No. 18/134,792, filed Apr. 14, 2023, Byoung Kwon Chun.
U.S. Appl. No. 14/746,430, filed Jun. 22, 2015, Aesop Cho.
U.S. Appl. No. 13/813,886, filed Jun. 25, 2013, Aesop Cho.
U.S. Appl. No. 12/886,248, filed Sep. 20, 2010, Thomas Butler.
U.S. Appl. No. 16/011,055, filed Jun. 18, 2018, Thomas Butler.
U.S. Appl. No. 16/988,250, filed Aug. 7, 2020, Thomas Butler.
U.S. Appl. No. 17/209,639, filed Mar. 23, 2021, Thomas Butler.
U.S. Appl. No. 12/428,176, filed Apr. 22, 2009, Thomas Butler.
U.S. Appl. No. 13/196,117, filed Aug. 2, 2011, Thomas Butler.
U.S. Appl. No. 13/649,511, filed Oct. 11, 2012, Thomas Butler.
U.S. Appl. No. 17/458,023, filed Aug. 26, 2021, Elaine Bunyan.
U.S. Appl. No. 18/115,895, filed Mar. 1, 2023, Rao V. Kalla.
U.S. Appl. No. 18/115,955, filed Mar. 1, 2023, Mark J. Bartlett.
U.S. Appl. No. 18/117,858, filed Mar. 6, 2023, Mark J. Bartlett.
U.S. Appl. No. 18/117,878, filed Mar. 6, 2023, Mark J. Bartlett.
U.S. Appl. No. 18/117,913, filed Mar. 6, 2023, Mark J. Bartlett.
U.S. Appl. No. 17/355,813, filed Jun. 23, 2021, Daniel H. Byun.
U.S. Appl. No. 18/205,745, filed Jun. 5, 2023, Roy Maxim Bannister.
European Office Action in EP Appln. No. 21770403.0, dated Jul. 5, 2023, 5 pages.

* cited by examiner

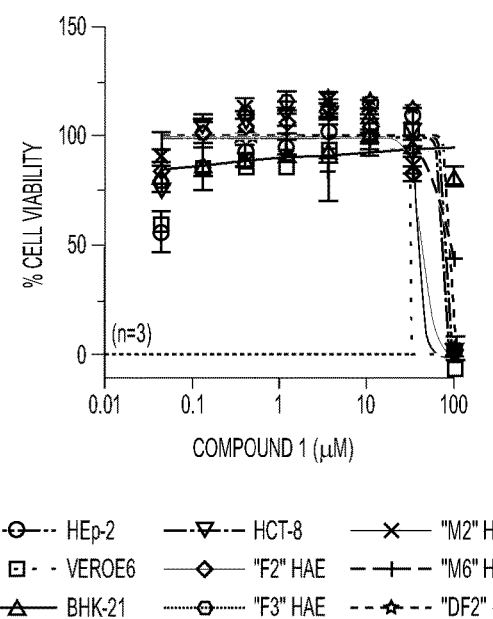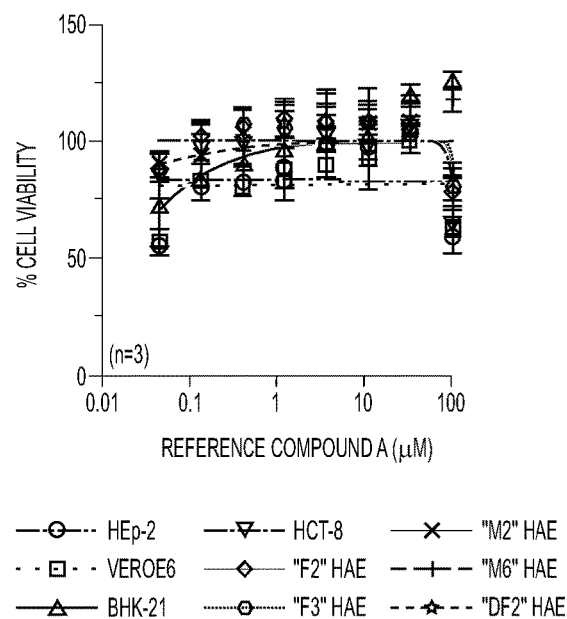
FIG. 1c  FIG. 1d

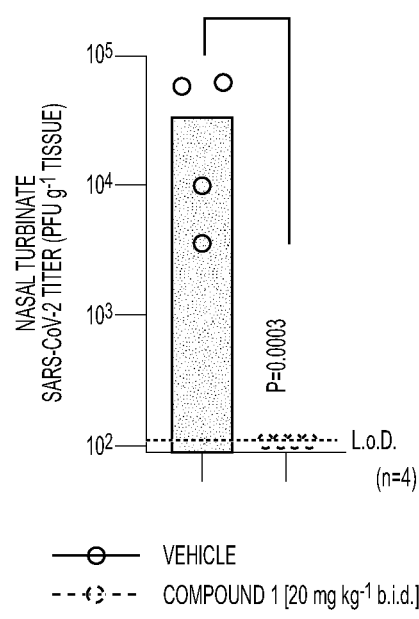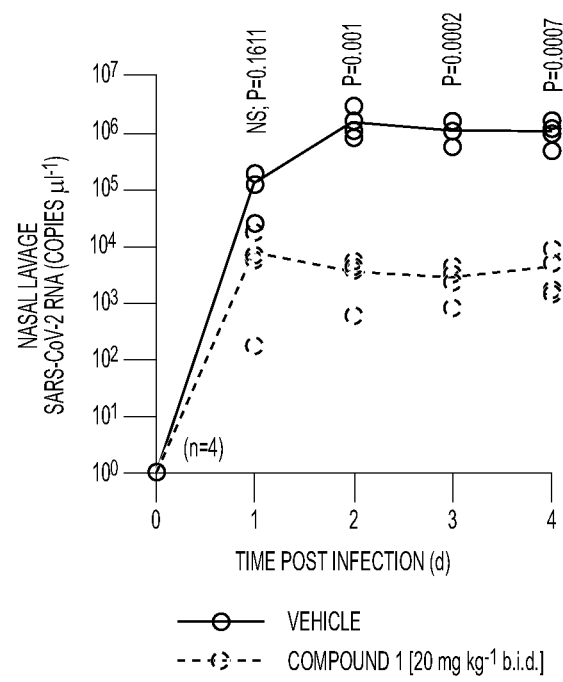
FIG. 2e
FIG. 2f

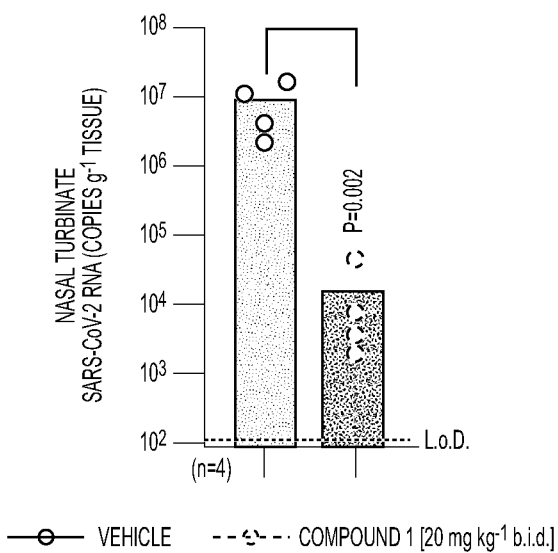
FIG. 2g
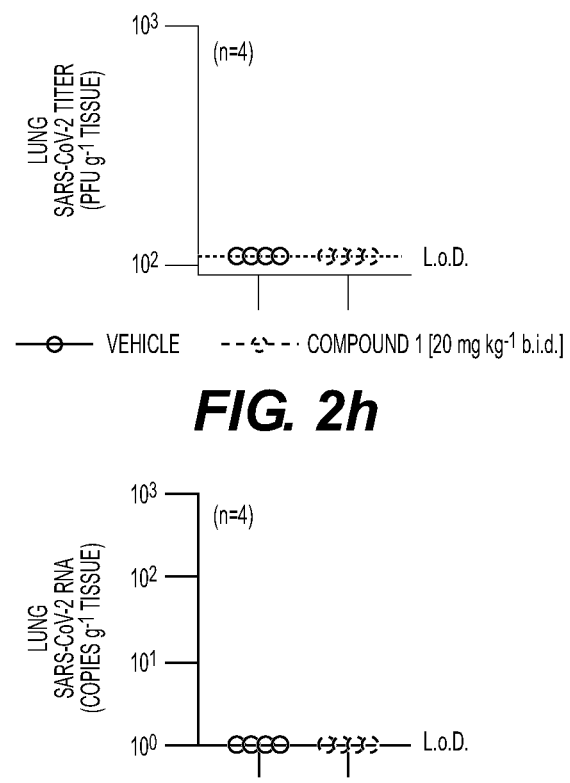
FIG. 2h
FIG. 2i

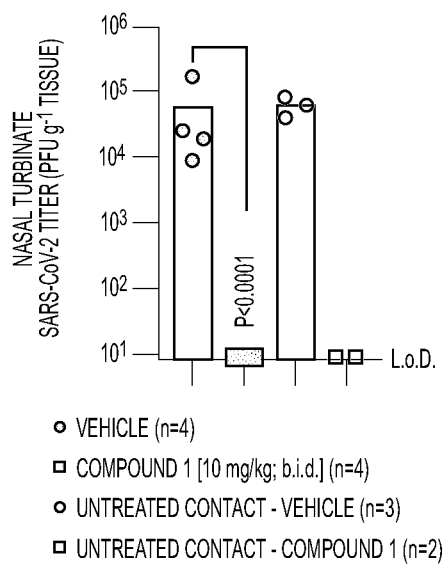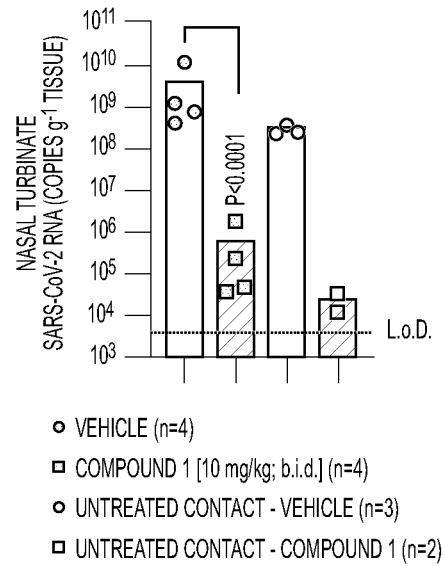
FIG. 4d
FIG. 4e

TGA thermogram of Compound 15 xinafoate Material A

TGA thermogram of Compound 15 HCl salt Material A

COMPOUNDS AND METHODS FOR TREATMENT OF VIRAL INFECTIONS

CROSS REFERENCE

This application is a Continuation of U.S. patent application Ser. No. 17/458,023 filed Aug. 26, 2021 which claims priority to U.S. Provisional Application No. 63/071,134, filed Aug. 27, 2020, U.S. Provisional Application. No. 63/162,283, filed Mar. 17, 2021, and U.S. Provisional Application No. 63/215,310, filed Jun. 25, 2021, each of which application is incorporated herein in its entirety for all purposes.

SEQUENCE LISTING

This application contains a Sequence Listing that has been submitted electronically as an XML file named "35648-0125002_SL_ST26.XML." The XML file, created on Jul. 11, 2023, is 3,671 bytes in size. The material in the XML file is hereby incorporated by reference in its entirety.

BACKGROUND

There is a need for compounds and methods for treating viral infections, for example paramyxoviridae, pneumoviridae, picornaviridae, flaviviridae, filoviridae, arenaviridae, orthomyxovirus, and coronaviridae infections. The present disclosure addresses these and other needs.

SUMMARY

The instant disclosure provides a compound of Formula I:

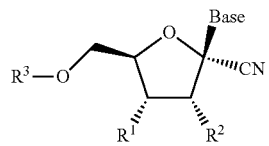

Formula I or a pharmaceutically acceptable salt thereof, wherein:
$R^1$ is OH, OCOR$^4$, or OC(O)OR$^4$; $R^2$ is OH, OCOR$^5$, or OC(O)OR$^5$; or
$R^1$ and $R^2$ are taken together to form —OC(O)O— or —OCHR$^6$O—; wherein
$R^6$ is H, $C_1$-$C_6$ alkyl or $C_6$-$C_{10}$ aryl;
$R^3$ is H, COR$^7$ or COOR$^7$;
$R^4$, $R^5$, and $R^7$ are each independently $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S;
wherein $R^4$, $R^5$, and $R^7$ are each, independently, optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl; and
each $R^8$ is independently H, $C_1$-$C_6$ alkyl, $C_1$-$C_6$ haloalkyl, and $C_3$-$C_6$ cycloalkyl;
each $R^9$ is independently H, $C_1$-$C_6$ alkyl, $C_1$-$C_6$ haloalkyl, and $C_3$-$C_6$ cycloalkyl;
each $R^{10}$ is independently H, $C_1$-$C_6$ alkyl, $C_1$-$C_6$ haloalkyl, and $C_3$-$C_6$ cycloalkyl; and Base is

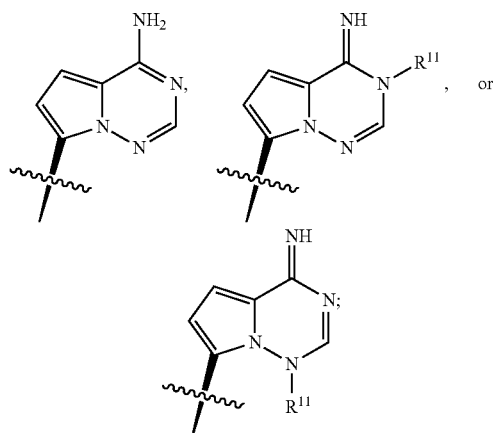

wherein
$R^{11}$ is $C_1$-$C_6$ alkyl substituted with —OP(O)(OH)$_2$;
provided that when $R^3$ is H then
$R^1$ is OCOR$^4$ or OC(O)OR$^4$; or
$R^2$ is OCOR$^5$ or OC(O)OR$^5$; or
$R^1$ and $R^2$ are taken together to form —OC(O)O— or —OCHR$^6$O—.

Also provided herein are pharmaceutical compositions comprising a compound disclosed herein, or a pharmaceutically acceptable salt thereof.

The disclosure further provides methods of treating or preventing a viral infection in a human in need thereof, wherein the method comprises administering to the human a compound of the disclosure, or a pharmaceutically acceptable salt thereof.

Also provided herein are methods for manufacturing a medicament for treating or preventing a viral infection in a human in need thereof, characterized in that a compound of the disclosure, or a pharmaceutically acceptable salt thereof, is used.

The disclosure also provides use of a compound of the disclosure, or a pharmaceutically acceptable salt thereof, for the manufacture of a medicament for the treatment or prevention of a viral infection in a human in need thereof.

DETAILED DESCRIPTION OF THE INVENTION

I. General

Figure 1A:
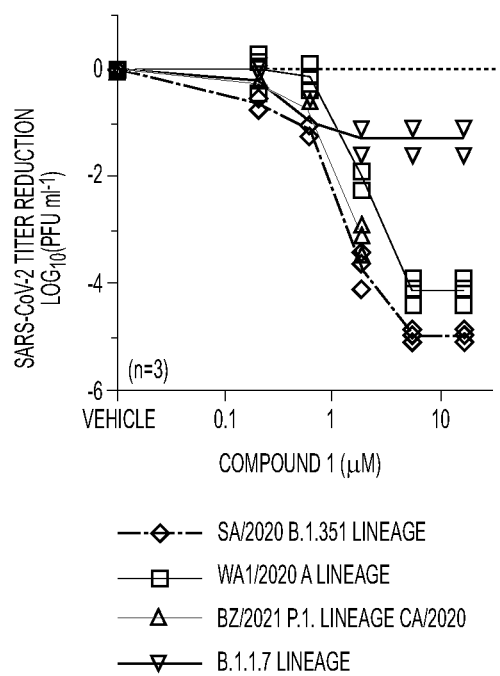
FIG. 1: Shows antiviral potency of Compound 1. 1a-b: Virus yield reduction of SARS-CoV-2 clinical isolates WA1/2020, SA/2020, CA/2020, and BZ/2021 representing the A, B.1.351, B.1.1.7 and P.1 lineages, respectively, by Compound 1 (a) and Reference Compound A (b) and on VeroE6 cells. EC$_{50}$ concentrations are specified. 1c-d: In vitro cytotoxicity profiles of Compound 1 (c) and Reference Compound A (d) on VeroE6, HEp-2, BHK-21, HCT-8 and a panel of primary HAE cells from independent donors ("F2", "F3", "M2", "M6", "DF2"). In (a-d), symbols represent individual biological repeats (n=3), error bars show standard deviations, lines depict non-linear regression models. 1e: In vitro cytotoxicity profile of remdesivir on VeroE6, HEp-2, BHK-21, HCT-8 and the panel of primary HAE cells ("F2", "F3", "M2", "M6", "DF2"). Symbols represent individual biological repeats (n=3), error bars show standard deviations, lines depict non-linear regression models.

The invention relates generally to methods and compounds for treating or preventing viral infections, for example paramyxoviridae, pneumoviridae, picornaviridae, flaviviridae, filoviridae, arenaviridae, orthomyxovirus, and coronaviridae infections.

II. Definitions

Unless stated otherwise, the following terms and phrases as used herein are intended to have the following meanings:

"Alkyl" refers to an unbranched or branched saturated hydrocarbon chain. For example, an alkyl group can have 1 to 20 carbon atoms (i.e., $C_1$-$C_{20}$ alkyl), 1 to 8 carbon atoms (i.e., $C_1$-$C_8$ alkyl), 1 to 6 carbon atoms (i.e., $C_1$-$C_6$ alkyl), or 1 to 3 carbon atoms (i.e., $C_1$-$C_3$ alkyl). Examples of suitable alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), and 3,3-dimethyl-2-butyl (—$CH(CH_3)C(CH_3)_3$).

"Alkenyl" refers to an aliphatic group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an aliphatic group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Haloalkyl" is an alkyl group, as defined above, in which one or more hydrogen atoms of the alkyl group is replaced with a halogen atom. The alkyl portion of a haloalkyl group can have 1 to 20 carbon atoms (i.e., $C_1$-$C_{20}$ haloalkyl), 1 to 12 carbon atoms (i.e., $C_1$-$C_{12}$ haloalkyl), 1 to 8 carbon atoms (i.e., $C_1$-$C_8$ haloalkyl), 1 to 6 carbon atoms (i.e., $C_1$-$C_6$ alkyl) or 1 to 3 carbon atoms (i.e., $C_1$-$C_3$ alkyl). Examples of suitable haloalkyl groups include, but are not limited to, —$CF_3$, —$CHF_2$, —$CFH_2$, —$CH_2CF_3$, and the like.

"Aryl" means an aromatic hydrocarbon radical derived by the removal of one hydrogen atom from a single carbon atom of a parent aromatic ring system. For example, an aryl group can have 6 to 20 carbon atoms, 6 to 14 carbon atoms, or 6 to 10 carbon atoms. Typical aryl groups include, but are not limited to, radicals derived from benzene (e.g., phenyl), substituted benzene, naphthalene, anthracene, biphenyl, and the like.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring atoms (i.e., 1 to 20 membered heteroaryl), 3 to 12 ring atoms (i.e., 3 to 12 membered heteroaryl) or 3 to 8 carbon ring atoms (3 to 8 membered heteroaryl) or 5 to 6 ring atoms (5 to 6 membered heteroaryl). Examples of heteroaryl groups include pyrimidinyl, purinyl, pyridyl, pyridazinyl, benzothiazolyl, and pyrazolyl. Heteroaryl does not encompass or overlap with aryl as defined above.

"Carbocyclyl" or "carbocyclic ring" refers to a non-aromatic hydrocarbon ring consisting of carbon and hydrogen atoms, having from three to twenty carbon atoms, in certain embodiments having from three to fifteen carbon atoms, in certain embodiments having from three to ten carbon atoms, from three to eight carbon atoms, from three to seven carbon atoms, or from 3 to 6 carbon atoms and which is saturated or partially unsaturated and attached to the rest of the molecule by a single bond. Carbocyclic rings include, for example, cyclopropane, cyclobutane, cyclopentane, cyclopentene, cyclohexane, cyclohexene, 1,3-cyclohexadiene, 1,4-cyclohexadiene, cycloheptane, cycloheptene, and cyclooctane.

"Cycloalkyl" refers to a saturated cyclic alkyl group having a single ring or multiple rings including fused, bridged, and spiro ring systems. As used herein, cycloalkyl has from 3 to 20 ring carbon atoms (i.e., $C_3$-20 cycloalkyl), 3 to 12 ring carbon atoms (i.e., $C_3$-12 cycloalkyl), 3 to 10 ring carbon atoms (i.e., $C_3$-10 cycloalkyl), 3 to 8 ring carbon atoms (i.e., $C_3$-8 cycloalkyl), or 3 to 6 ring carbon atoms (i.e., $C_3$-6 cycloalkyl). Examples of cycloalkyl groups include cyclopropyl, cyclobutyl, cyclopentyl, cyclohexyl, cycloheptyl, and cyclooctyl.

The term "optionally substituted" in reference to a particular moiety of the compound of Formula I (e.g., an optionally substituted aryl group) refers to a moiety wherein all substituents are hydrogen or wherein one or more of the hydrogens of the moiety may be replaced by the listed substituents.

Unless otherwise specified, the carbon atoms of the compounds of Formula I are intended to have a valence of four. If in some chemical structure representations, carbon atoms do not have a sufficient number of variables attached to produce a valence of four, the remaining carbon substituents needed to provide a valence of four should be assumed to be hydrogen.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

"Prevention" or "preventing" means any treatment of a disease or condition that causes the clinical symptoms of the disease or condition not to develop. The compounds and compositions disclosed herein may, in some embodiments, be administered to a subject (including a human) who is at risk of having the disease or condition. As used herein, the terms "preventing" and "prevention" encompass the administration of a compound, composition, or pharmaceutically acceptable salt according to the embodiments disclosed herein pre- or post-exposure of the individual to a virus, but before the appearance of symptoms of the viral infection, and/or prior to the detection of the virus in the blood. The terms also refer to prevention of the appearance of symptoms of the disease and/or to prevent the virus from reaching detectible levels in the blood. The terms include both pre-exposure prophylaxis (PrEP), as well as post-exposure prophylaxis (PEP) and event driven or "on demand" prophylaxis. The terms also refer to prevention of perinatal transmission of a virus from mother to baby, by administration to the mother before giving birth and to the child within the first days of life. The terms also refer to prevention of transmission of a virus through blood transfusion.

The term "therapeutically effective amount", as used herein, is the amount of compound of Formula I present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the particular compound of Formula I, the specific activity of the composition, the delivery device employed, the physical characteristics of the composition, its intended use, as well as patient considerations such as severity of the disease state, patient cooperation, etc., and can readily be determined by one skilled in the art based upon the information provided herein.

"DSC" refers to differential scanning calorimetry.

""XRPD" refers to the X-ray powder diffraction pattern of a solid form.

"TGA" refers to thermogravimetric analysis.

The term "substantially as shown in" when referring, for example, to an XRPD pattern, a DSC thermogram, or a TGA graph includes a pattern, thermogram or graph that may not be necessarily identical to those depicted herein, but that falls within the limits of experimental error or deviations when considered by one of ordinary skill in the art.

"Protecting group" refers to a moiety of a compound that masks or alters the properties of a functional group or the properties of the compound as a whole. The chemical substructure of a protecting group varies widely. One function of a protecting group is to serve as an intermediate in the synthesis of the parental drug substance. Chemical protecting groups and strategies for protection/deprotection are well known in the art. See: "Protective Groups in Organic Chemistry", Theodora W. Greene (John Wiley & Sons, Inc., New York, 1991. See also *Protective Groups in Organic Chemistry*, Peter G. M. Wuts and Theodora W. Greene, 4th Ed., 2006. Protecting groups are often utilized to mask the reactivity of certain functional groups, to assist in the efficiency of desired chemical reactions, e.g., making and breaking chemical bonds in an ordered and planned fashion. Protection of functional groups of a compound alters other physical properties besides the reactivity of the protected functional group, such as the polarity, lipophilicity (hydrophobicity), and other properties which can be measured by common analytical tools. Chemically protected intermediates may themselves be biologically active or inactive.

"Hydroxy protecting groups" refers to those protecting groups useful for protecting hydroxy groups (—OH).

"Deprotection agent" refers to any agent capable of removing a protecting group. The deprotection agent will depend on the type of protecting group used. Representative deprotection agents are known in the art and can be found in *Protective Groups in Organic Chemistry*, Peter G. M. Wuts and Theodora W. Greene, 4th Ed., 2006.

III. Compounds

Any reference to the compounds of the invention described herein also includes a reference to a pharmaceutically acceptable salt thereof. Examples of pharmaceutically acceptable salts of the compounds of the invention include salts derived from an appropriate base, such as an alkali metal or an alkaline earth (for example, $Na^+$, $Li^+$, $K^+$, $Ca^{+2}$ and $Mg^{+2}$), ammonium and $NR_4^+$ (wherein R is defined herein). Pharmaceutically acceptable salts of a nitrogen atom or an amino group include (a) acid addition salts formed with inorganic acids, for example, hydrochloric acid, hydrobromic acid, sulfuric acid, sulfamic acids, phosphoric acid, nitric acid and the like; (b) salts formed with organic acids such as, for example, acetic acid, oxalic acid, tartaric acid, succinic acid, maleic acid, fumaric acid, gluconic acid, citric acid, malic acid, ascorbic acid, benzoic acid, isethionic acid, lactobionic acid, tannic acid, palmitic acid, alginic acid, polyglutamic acid, naphthalenesulfonic acid, methanesulfonic acid, p-toluenesulfonic acid, benzenesulfonic acid, naphthalenedisulfonic acid, polygalacturonic acid, malonic acid, sulfosalicylic acid, glycolic acid, 2-hydroxy-3-naphthoate, pamoate, salicylic acid, stearic acid, phthalic acid, mandelic acid, lactic acid, ethanesulfonic acid, lysine, arginine, glutamic acid, glycine, serine, threonine, alanine, isoleucine, leucine and the like; and (c) salts formed from elemental anions for example, chlorine, bromine, and iodine. Pharmaceutically acceptable salts of a compound of a hydroxy group include the anion of said compound in combination with a suitable cation such as $Na^+$ and $NR_4^+$.

The compounds disclosed herein (e.g., compounds of Formula I, II, III, IV, V, Va, Vb, VI, VIa, and VIb) and its pharmaceutically acceptable salts may exist as different polymorphs or pseudopolymorphs. As used herein, crystalline polymorphism means the ability of a crystalline compound to exist in different crystal structures. The crystalline polymorphism may result from differences in crystal packing (packing polymorphism) or differences in packing between different conformers of the same molecule (conformational polymorphism). As used herein, crystalline pseudopolymorphism means the ability of a hydrate or solvate of a compound to exist in different crystal structures. The pseudopolymorphs of the instant invention may exist due to differences in crystal packing (packing pseudopolymorphism) or due to differences in packing between different conformers of the same molecule (conformational pseudopolymorphism). The instant invention comprises all polymorphs and pseudopolymorphs of the compounds of Formula I, Ia, Ib, II, IIa, IIb, III, IIIa, IIIb, or IIIc, and their pharmaceutically acceptable salts.

The compounds disclosed herein (e.g., compounds of Formula I, II, III, IV, V, Va, Vb, VI, VIa, and VIb) and its pharmaceutically acceptable salts may also exist as an amorphous solid. As used herein, an amorphous solid is a solid in which there is no long-range order of the positions of the atoms in the solid. This definition applies as well when the crystal size is two nanometers or less. Additives, including solvents, may be used to create the amorphous forms of the instant invention. The instant invention comprises all amorphous forms of the compounds of Formula I, II, III, IV, V, V a. Vb, VI, VIa, and VIb, and their pharmaceutically acceptable salts.

For therapeutic use, salts of active ingredients of the compounds of the invention will be pharmaceutically acceptable, i.e., they will be salts derived from a pharmaceutically acceptable acid or base. However, salts of acids or bases which are not pharmaceutically acceptable may also find use, for example, in the preparation or purification of a pharmaceutically acceptable compound. All salts, whether or not derived form a pharmaceutically acceptable acid or base, are within the scope of the present invention.

It is also to be understood that the compositions herein comprise compounds of the invention in their un-ionized, as well as zwitterionic form, and combinations with stoichiometric amounts of water as in hydrates.

It is to be noted that all enantiomers, diastereomers, and racemic mixtures, tautomers, polymorphs, pseudopolymorphs of compounds within the scope of Formula I, II, III, IV, V, Va, Vb, VI, VIa, or VIb and pharmaceutically acceptable salts thereof are embraced by the present invention. All mixtures of such enantiomers and diastereomers are within the scope of the present invention.

The compounds of the invention, exemplified by Formula I, II, III, IV, V, Va, Vb, VI, VIa, or VIb may have chiral centers, e.g., chiral carbon or phosphorus atoms. The compounds of the invention thus include racemic mixtures of all stereoisomers, including enantiomers, diastereomers, and atropisomers. In addition, the compounds of the invention include enriched or resolved optical isomers at any or all asymmetric, chiral atoms. In other words, the chiral centers apparent from the depictions are provided as the chiral isomers or racemic mixtures.

Both racemic and diastereomeric mixtures, as well as the individual optical isomers isolated or synthesized, substantially free of their enantiomeric or diastereomeric partners, are all within the scope of the invention. The racemic mixtures are separated into their individual, substantially optically pure isomers through appropriate techniques such as, for example, the separation of diastereomeric salts formed with optically active adjuncts, e.g., acids or bases followed by conversion back to the optically active substances. In most instances, the desired optical isomer is synthesized by means of stereospecific reactions, beginning with the appropriate stereoisomer of the desired starting material.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l, D and L, or (+) and (−) are employed to designate the sign of rotation of plane-polarized light by the compound, with S, (−), or l meaning that the compound is levorotatory while a compound prefixed with R, (+), or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The compounds of the invention may also exist as tautomeric isomers in certain cases. Although only one delocalized resonance structure may be depicted, all such forms are contemplated within the scope of the invention. For example, ene-amine tautomers can exist for purine, pyrimidine, imidazole, guanidine, amidine, and tetrazole systems and all their possible tautomeric forms are within the scope of the invention.

Any formula or structure given herein, including Formula I, II, III, IV, V, Va, Vb, VI, VIa, and VIb compounds, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl and $^{125}$I. Various isotopically labeled compounds of the present disclosure, for example those into which radioactive isotopes such as $^3$H, $^{13}$C and $^{14}$C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes compounds of Formula I in which from 1 to x hydrogens attached to a carbon atom is/are replaced by deuterium, in which x is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism", Trends Pharmacol. Sci. 5(12):524-527 (1984). In view of the present disclosure, such compounds are synthesized by means known in the art, for example by employing starting materials in which one or more hydrogens have been replaced by deuterium.

Deuterium labeled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

Whenever a compound described herein is substituted with more than one of the same designated group, e.g., "R" or "R'", then it will be understood that the groups may be the same or different, i.e., each group is independently selected.

Wavy lines, ∿∿∿, indicate the site of covalent bond attachments to the adjoining substructures, groups, moieties, or atoms.

IV. Compounds

In certain embodiments, provided herein is a compound of Formula I:

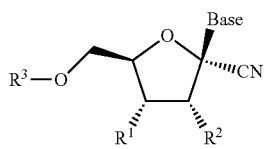

Formula I or a pharmaceutically acceptable salt thereof, wherein:
$R^1$ is OH, $OCOR^4$, or $OC(O)OR^4$;
$R^2$ is OH, $OCOR^5$, or $OC(O)OR^5$; or
$R^1$ and $R^2$ are taken together to form —OC(O)O— or —OCHR$^6$O—; wherein
$R^6$ is H, $C_1$-$C_6$ alkyl or $C_6$-$C_1$a aryl;
$R^3$ is H, $COR^7$ or $COOR^7$;
$R^4$, $R^5$, and $R^7$ are each independently $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S;
wherein $R^4$, $R^5$, and $R^7$ are each, independently, optionally substituted with one, two or three substituents independently selected from the group consisting of halogen, cyano, —N$_3$, —OR$^9$, —NR$^9$R$^{10}$, and phenyl optionally substituted with one, two or three substituents independently selected from halo, cyano, and $C_1$-$C_6$ alkyl; and
each $R^{11}$ is independently H, $C_1$-$C_6$ alkyl, $C_1$-$C_6$ haloalkyl, and $C_3$-$C_6$ cycloalkyl;
each $R^9$ is independently H, $C_1$-$C_6$ alkyl, $C_1$-$C_6$ haloalkyl, and $C_3$-$C_6$ cycloalkyl;
each $R^{10}$ is independently H, $C_1$-$C_6$ alkyl, $C_1$-$C_6$ haloalkyl, and $C_3$-$C_6$ cycloalkyl; and
Base is

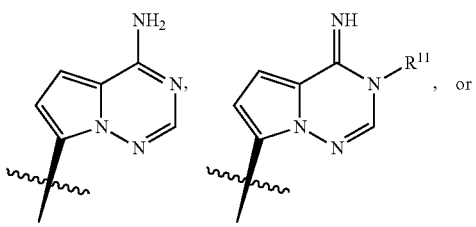

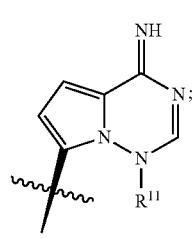

wherein
$R^{11}$ is $C_1$-$C_6$ alkyl substituted with —OP(O)(OH)$_2$;
provided that when $R^3$ is H then
$R^1$ is $OCOR^4$ or $OC(O)OR^4$; or
$R^2$ is $OCOR^5$ or $OC(O)OR^5$; or
$R^1$ and $R^2$ are taken together to form —OC(O)O— or —OCHR$^6$O—.

In some embodiments of the compound of Formula I, or a pharmaceutically acceptable salt thereof, Base is

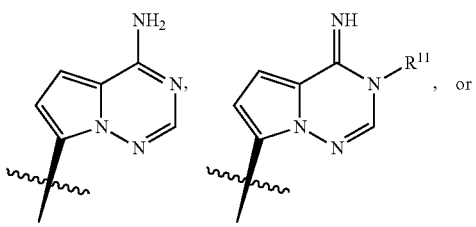

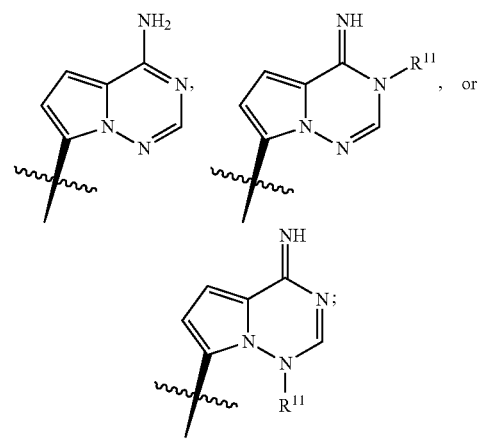

wherein $R^1$ is —CH$_2$OP(O)(OH)$_2$. In some embodiments, Base is

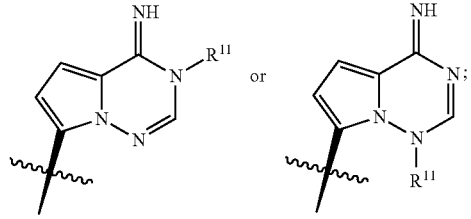

wherein $R^{11}$ $C_1$-$C_6$ alkyl substituted with —OP(O)(OH)$_2$. In some embodiments, Base is

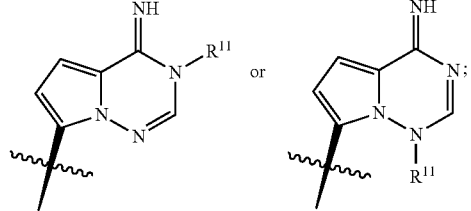

wherein $R^{11}$ is —CH$_2$OP(O)(OH)$_2$. In some embodiments, Base is

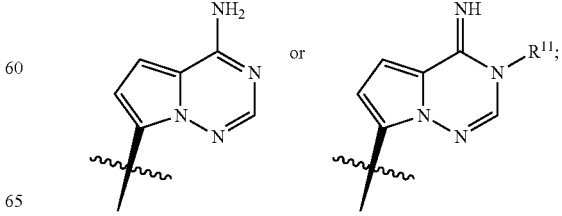

wherein $R^{11}$ $C_1$-$C_6$ alkyl substituted with —OP(O)(OH)$_2$. In some embodiments, Base is

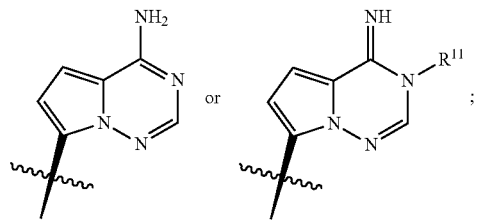

wherein $R^{11}$ is —CH$_2$OP(O)(OH)$_2$.

In some embodiments of the compound of Formula I, or a pharmaceutically acceptable salt thereof, Base is

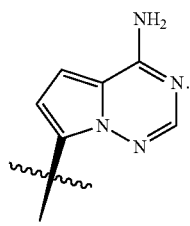

In some embodiments, the Formula I is a compound of Formula Ia:

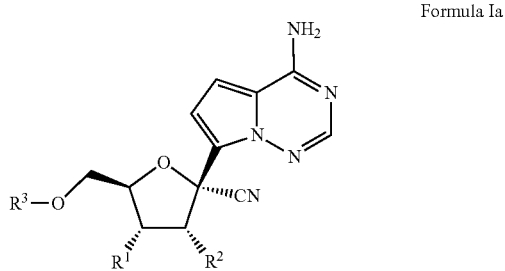

Formula Ia

In some embodiments of the compound of Formula I or Ia, or a pharmaceutically acceptable salt thereof, $R^3$ is COR$^7$ or COOR$^7$; wherein R$^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl or $C_3$-$C_8$ carbocyclyl; and wherein the R$^7$ group is optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_4$ alkyl optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and $C_1$-$C_6$ alkyl. In some embodiments, R$^9$ and R$^{10}$ are both H.

In some embodiments of the compound of Formula I or Ia, or a pharmaceutically acceptable salt thereof, R$^3$ is COR$^7$ or COOR$^7$; wherein R$^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of —NR$^9$R$^{10}$ and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of —NR$^9$R$^{10}$ and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl or $C_3$-$C_8$ carbocyclyl: and wherein the R$^7$ group is optionally substituted with one, two or three substituents independently selected from the group consisting of —NR$^9$R$^{10}$ and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_8$ alkyl optionally substituted with one, two or three substituents independently selected from the group consisting of —NR$^9$R$^{10}$ and phenyl optionally substituted with one, two or three substituents independently selected from halo, cyano, and $C_1$-$C_6$ alkyl. In some embodiments, R$^3$ is COR$^7$ or COOR$^7$; wherein R$^7$ is $C_1$-$C_4$ alkyl optionally substituted with one, two or three substituents independently selected from the group consisting of —NR$^9$R$^{10}$ and phenyl optionally substituted with one, two or three substituents independently selected from halo, cyano, and $C_1$-$C_6$ alkyl. In some embodiments, R$^9$ and R$^{10}$ are both H.

In some embodiments of the compound of Formula I or Ia, or a pharmaceutically acceptable salt thereof, R$^3$ is COR$^7$ or COOR$^7$; wherein R$^7$ is $C_1$—C alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected from N, O, and S; and wherein the R$^7$ group is optionally substituted with one, two or three substituents independently selected from the group consisting of —NR$^9$R$^{10}$ and phenyl. In some embodiments, R$^3$ is COR$^7$ or COOR$^7$; wherein R$^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of —NR$^9$R$^{10}$ and phenyl. In some embodiments, R$^3$ is COR$^7$ or COOR$^7$; wherein R$^7$ is $C_1$-$C_8$ alkyl or $C_3$-$C_8$ carbocyclyl; and wherein the R$^7$ group is optionally substituted with one, two or three substituents independently selected from the group consisting of —NR⁹R¹⁰ and phenyl. In some embodiments, R³ is COR⁷ or COOR⁷; wherein R⁷ is $C_1$-$C_8$ alkyl optionally substituted with one, two or three substituents independently selected from the group consisting of —NR⁹R¹⁰ and phenyl. In some embodiments, R³ is COR⁷ or COOR⁷; wherein R⁷ is $C_1$-$C_4$ alkyl optionally substituted with one, two or three substituents independently selected from the group consisting of —NR⁹R¹⁰ and phenyl. In some embodiments, R⁹ and R¹⁰ are both H.

In some embodiments of the compound of Formula I or Ia, or a pharmaceutically acceptable salt thereof, R³ is COR⁷ or COOR⁷; wherein R⁷ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, R³ is COR⁷ or COOR⁷; wherein R⁷ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, R³ is COR⁷ or COOR⁷; wherein R⁷ is $C_1$-$C_8$ alkyl or $C_3$-$C_8$ carbocyclyl. In some embodiments, R³ is COR⁷ or COOR⁷; wherein R⁷ is $C_1$-$C_8$ alkyl. In some embodiments, R³ is COR⁷ or COOR⁷; wherein R⁷ is $C_1$-$C_4$ alkyl.

In some embodiments of the compounds of Formula I or Ia, or a pharmaceutically acceptable salt thereof, R³ is COR⁷ or COOR⁷, wherein R⁷ is selected from the group consisting of —CH₃, —CH₂CH₃,

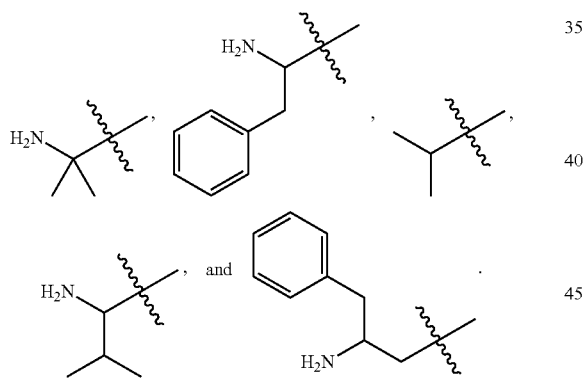

In some embodiments, R³ is COR⁷ or COOR⁷, wherein R⁷ is selected from the group consisting of —CH₃, —CH₂CH₃,

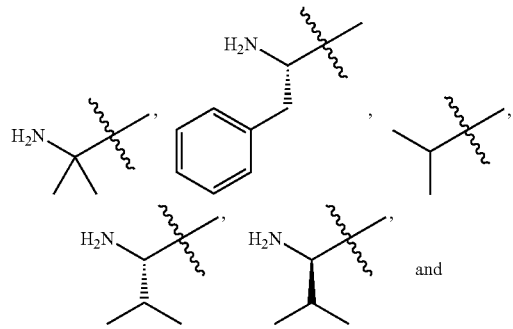

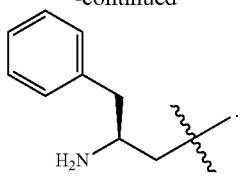

In some embodiments, R³ is COR⁷ or COOR⁷, wherein R⁷ is selected from the group consisting of —CH₃, —CH₂CH₃,

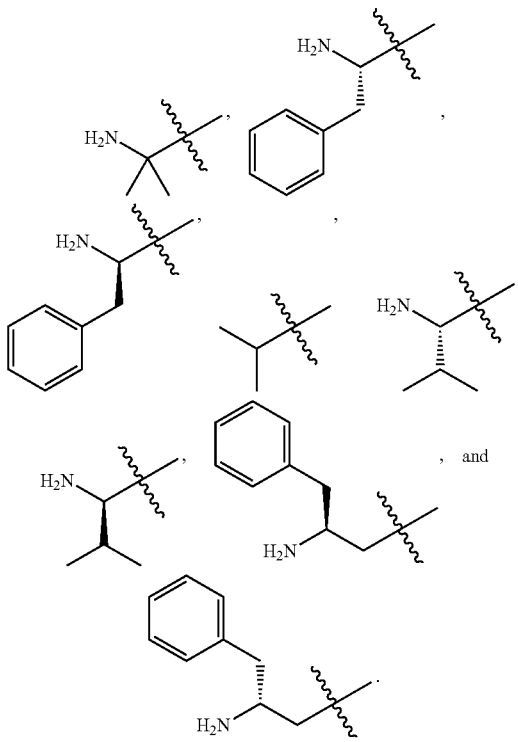

In some embodiments of the compound of Formula I or Ia, or a pharmaceutically acceptable salt thereof, R³ is COR⁷; wherein R⁷ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S: and wherein the R⁷ group is optionally substituted with one, two or three substituents independently selected from the group consisting of halogen, cyano, —N₃, —OR⁸, —NR⁹R¹⁰, and phenyl optionally substituted with one, two or three substituents independently selected from halo, cyano, and $C_1$-$C_6$ alkyl. In some embodiments, R³ is COR⁷; wherein R⁷ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the R⁷ group is optionally substituted with one, two or three substituents independently selected from the group consisting of halogen, cyano, —N₃, —OR⁸, —NR⁹R¹⁰, and phenyl optionally substituted with one, two or three substituents independently selected from halo, cyano, and $C_1$-$C_6$ alkyl. In some embodiments, R³ is COR⁷; wherein R⁷ is $C_1$-$C_8$ alkyl or $C_3$-$C_8$ carbocyclyl; and wherein the R⁷ group is optionally substituted with one, two or three substituents independently selected from the group consisting of halogen, cyano, —N₃, —OR$^B$, —NR⁹R¹⁰, and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_8$ alkyl optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_4$ alkyl optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^9$ and $R^{10}$ are both H.

In some embodiments of the compound of Formula I or Ia, or a pharmaceutically acceptable salt thereof, $R^3$ is $COR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S: and wherein the $R^7$ group is optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_8$ alkyl or $C_3$-$C_8$ carbocyclyl; and wherein the $R^7$ group is optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_8$ alkyl optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COR^7$; wherein $R^7$ is $C_1$-$C_4$ alkyl optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^9$ and $R^{10}$ are both H.

In some embodiments of the compound of Formula I or Ia, or a pharmaceutically acceptable salt thereof, $R^3$ is $COR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl. In some embodiments, $R^3$ is $COR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl. In some embodiments, $R^3$ is $COR^7$; wherein $R^7$ is $C_1$-$C_8$ alkyl optionally substituted with one, two or three substituents independently selected from the group consisting of —$NR^9R^{10}$ and phenyl. In some embodiments, $R^3$ is $COR^7$; wherein $R^7$ is $C_1$-$C_4$ alkyl optionally substituted with one, two or three substituents independently selected from the group consisting of —$NR^9R^{10}$ and phenyl. In some embodiments, $R^9$ and $R^{10}$ are both H.

In some embodiments of the compound of Formula I or Ia, or a pharmaceutically acceptable salt thereof, $R^3$ is $COR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, $R^3$ is $COR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, $R^3$ is $COR^7$; wherein $R^7$ is $C_1$-$C_8$ alkyl or $C_3$-$C_8$ carbocyclyl. In some embodiments, $R^3$ is $COR^7$; wherein $R^7$ is $C_1$-$C_8$ alkyl. In some embodiments, $R^3$ is $COR^7$; wherein $R^7$ is $C_1$-$C_4$ alkyl.

In some embodiments of the compound of Formula I or Ia, or a pharmaceutically acceptable salt thereof, $R^3$ is $COR^7$, wherein $R^7$ is selected from the group consisting of —$CH_3$, —$CH_2CH_3$,

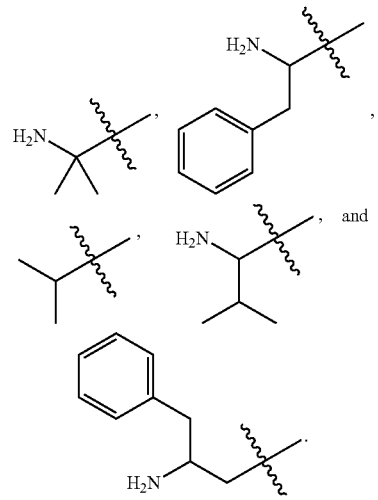

In some embodiments, $R^3$ is $COR^7$, wherein $R^7$ is selected from the group consisting of —$CH_3$, —$CH_2CH_3$,

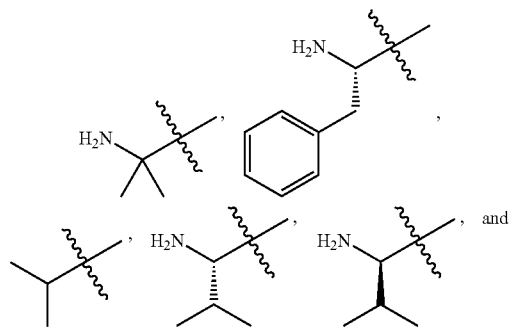

-continued

[Structure: H2N-substituted phenylpropyl group]

In some embodiments of the compound of Formula I or Ia, or a pharmaceutically acceptable salt thereof, $R^3$ is $COOR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_8$ alkyl or $C_3$-$C_8$ carbocyclyl; and wherein the $R^7$ group is optionally substituted with one, two or three substituents independently selected from the group consisting of halogen, cyano, —$N_3$, —$OR^B$, —$NR^9R^{10}$, and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_8$ alkyl optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_4$ alkyl optionally substituted with one, two or three substituents independently selected from the group consisting of halogen, cyano, —$N_3$, —$OR^8$, —$NR^9R^{10}$, and phenyl optionally substituted with one, two or three substituents independently selected from halo, cyano, and $C_1$-$C_6$ alkyl. In some embodiments, $R^9$ and $R^{10}$ are both H.

In some embodiments of the compound of Formula I or Ia, or a pharmaceutically acceptable salt thereof, $R^3$ is $COOR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_8$ alkyl optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^3$ is $COOR^7$; wherein $R^7$ is $C_1$-$C_4$ alkyl optionally substituted with one, two or three substituents independently selected from the group consisting of —$NR^9R^{10}$ and phenyl optionally substituted with one, two or three substituents independently selected from halo, cyano, and $C_1$-$C_6$ alkyl. In some embodiments, $R^9$ and $R^{10}$ are both H.

In some embodiment of the compound of Formula I or Ia, or a pharmaceutically acceptable salt thereof, $R^3$ is $COOR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl. In some embodiments, $R^3$ is $COOR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S; and wherein the $R^7$ group is optionally substituted with one, two or three substituents independently selected from the group consisting of —$NR^9R^{10}$ and phenyl. In some embodiments, $R^3$ is $COOR^7$; wherein $R^7$ is $C_1$-$C_8$ alkyl or $C_3$-$C_8$ carbocyclyl; and wherein the $R^7$ group is optionally substituted with one, two or three substituents independently selected from the group consisting of —$NR^9R^{10}$ and phenyl. In some embodiments, $R^3$ is $COOR^7$; wherein $R^7$ is $C_1$-$C_8$ alkyl optionally substituted with one, two or three substituents independently selected from the group consisting of —$NR^9R^{10}$ and phenyl. In some embodiments, $R^3$ is $COOR^7$; wherein $R^7$ is $C_1$-$C_4$ alkyl optionally substituted with one, two or three substituents independently selected from the group consisting of —$NR^9R^{10}$ and phenyl. In some embodiments, $R^9$ and $R^{10}$ are both H.

In some embodiments of the compound of Formula I or Ia, or a pharmaceutically acceptable salt thereof, $R^3$ is $COOR^7$; wherein $R^7$ is $C_1$-$C_8$ alkyl, $C_2$-$C_8$ alkenyl, $C_2$-$C_8$ alkynyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, $R^3$ is $COOR^7$; wherein $R^7$ is $C_1$-$C_8$ alkyl, $C_3$-$C_8$ carbocyclyl, $C_6$-$C_{10}$ aryl, or 5 to 6 membered heteroaryl containing 1, 2, or 3 heteroatoms selected form N, O, and S. In some embodiments, $R^3$ is $COOR^7$; wherein $R^7$ is $C_1$-$C_8$ alkyl or $C_3$-$C_8$ carbocyclyl. In some embodiments, $R^3$ is $COOR^7$ wherein $R^7$ is $C_1$-$C_8$ alkyl. In some embodiments, $R^3$ is $COOR^7$ wherein $R^7$ is $C_1$-$C_4$ alkyl.

In some embodiments of the compound of Formula I or Ia, or a pharmaceutically acceptable salt thereof, $R^3$ is $COOR^7$, wherein $R^7$ is selected from the group consisting of —$CH_3$, —$CH_2CH_3$,

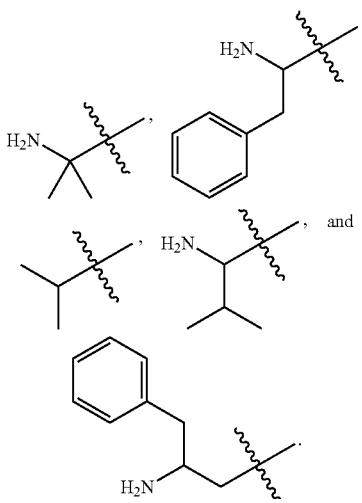

In some embodiments, $R^3$ is $COOR^7$, wherein $R^7$ is selected from the group consisting of —$CH_3$, —$CH_2CH_3$,

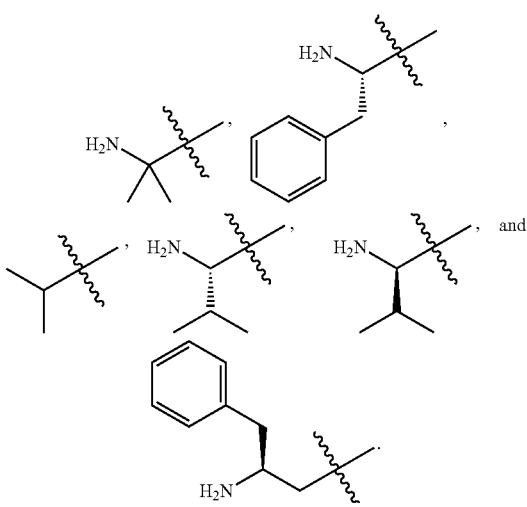

In some embodiments of the compound of Formula I or Ia, or a pharmaceutically acceptable salt thereof, $R^1$ is OH, $OCOR^4$, or $OC(O)OR^4$ and $R^2$ is OH, $OCOR^5$, or $OC(O)OR^5$. In some embodiments, $R^1$ is OH and $R^2$ is OH, $OCOR^5$, or $OC(O)OR^5$. In some embodiments, $R^1$ is OH and $R^2$ is $OCOR^5$ or $OC(O)OR^5$. In some embodiments, $R^1$ is OH and $R^2$ is $OCOR^5$. In some embodiments, $R^1$ is OH and $R^2$ is $OC(O)OR^5$.

In some embodiments, of the compound of Formula I or Ia, or a pharmaceutically acceptable salt thereof, $R^1$ is OH, $OCOR^4$, or $OC(O)OR^4$ and $R^2$ is OH. In some embodiments, $R^1$ is $OCOR^4$, or $OC(O)OR^4$ and $R^2$ is OH. In some embodiments, $R^1$ is $OCOR^4$ and $R^2$ is OH.

In some embodiments, $R^1$ is $OC(O)OR^4$ and $R^2$ is OH.

In some embodiments of the compound of Formula I or Ia, or a pharmaceutically acceptable salt thereof, $R^1$ is $OCOR^4$ or $OC(O)OR^4$ and $R^2$ is $OCOR^5$ or $OC(O)OR^5$. In some embodiments, $R^1$ is $OCOR^4$ and $R^2$ is $OCOR^5$ or $OC(O)OR^5$. In some embodiments, $R^1$ is $OC(O)OR^4$ and $R^2$ is $OCOR^5$ or $OC(O)OR^5$.

In some embodiments of the compound of Formula I or Ia, or a pharmaceutically acceptable salt thereof, $R^1$ is $OCOR^4$ or $OC(O)OR^4$ and $R^2$ is $OCOR^5$. In some embodiments, $R^1$ is $OCOR^4$ or $OC(O)OR^4$ and R is $OC(O)OR^5$.

In some embodiments of the compound of Formula I or Ia, or a pharmaceutically acceptable salt thereof, $R^1$ is $OCOR^4$ and $R^2$ is $OCOR^5$. In some embodiments, $R^1$ is $OCOR^4$ and $R^2$ is $OC(O)OR^5$.

In some embodiments of the compound of Formula I or Ia, or a pharmaceutically acceptable salt thereof, $R^1$ is $OC(O)OR^4$ and $R^2$ is $OCOR^5$. In some embodiments, $R^1$ is $OC(O)OR^4$ and $R^2$ is $OC(O)OR^5$.

In some embodiments of the compound of Formula I or Ia, or a pharmaceutically acceptable salt thereof, $R^4$ and $R^5$ are each independently a $C_1$-$C_8$ alkyl. In some embodiments, $R^4$ and $R^5$ are each independently a $C_1$-$C_6$ alkyl. In some embodiments, $R^4$ and $R^5$ are each independently a $C_1$-$C_3$ alkyl. In some embodiments, $R^4$ and $R^5$ are each independently methyl, ethyl, or isopropyl.

In some embodiments of the compound of Formula I or Ia, or a pharmaceutically acceptable salt thereof, $R^1$ is OH, $OCOR^4$, or $OC(O)OR^4$ and $R^2$ is OH, $OCOR^5$, or $OC(O)OR^5$; wherein $R^4$ and $R^5$ are each independently a $C_1$-$C_8$ alkyl. In some embodiments, $R^1$ is OH, $OCOR^4$, or $OC(O)OR^4$ and $R^1$ is OH, $OCOR^5$, or $OC(O)OR^5$; wherein $R^4$ and $R^5$ are each independently a $C_1$-$C_6$ alkyl. In some embodiments, $R^1$ is OH, $OCOR^4$, or $OC(O)OR^4$ and $R^2$ is OH, $OCOR^5$, or $OC(O)OR^5$; wherein $R^4$ and $R^5$ are each independently a $C_1$-$C_3$ alkyl. In some embodiments, $R^1$ is OH, $OCOR^4$, or $OC(O)OR^4$ and $R^2$ is OH, $OCOR^5$, or $OC(O)OR^5$; wherein $R^4$ and $R^5$ are each independently methyl, ethyl, or isopropyl.

In some embodiments, $R^1$ is OH and $R^2$ is OH, $OCOR^5$, or $OC(O)OR^5$; wherein $R^5$ is a $C_1$-$C_8$ alkyl. In some embodiments, $R^1$ is OH and $R^2$ is OH, $OCOR^5$, or $OC(O)OR^5$; wherein $R^5$ is a $C_1$-$C_6$ alkyl. In some embodiments, $R^1$ is OH and $R^2$ is OH, $OCOR^5$, or $OC(O)OR^5$; wherein $R^5$ is a $C_1$-$C_3$ alkyl. In some embodiments, $R^1$ is OH and $R^2$ is OH, $OCOR^5$, or $OC(O)OR^5$; wherein $R^5$ is methyl, ethyl, or isopropyl.

In some embodiments, $R^1$ is OH and $R^2$ is $OCOR^5$ or $OC(O)OR^5$; wherein $R^5$ is a $C_1$-$C_8$ alkyl. In some embodiments, $R^1$ is OH and $R^2$ is $OCOR^5$ or $OC(O)OR^5$; wherein $R^5$ is a $C_1$-$C_6$ alkyl. In some embodiments, $R^1$ is OH and $R^2$ is $OCOR^5$ or $OC(O)OR^5$; wherein $R^5$ is a $C_1$-$C_3$ alkyl. In some embodiments, $R^1$ is OH and $R^2$ is $OCOR^5$ or $OC(O)OR^5$; wherein $R^5$ is methyl, ethyl, or isopropyl.

In some embodiments, of the compounds of Formula I or Ia, or a pharmaceutically acceptable salt thereof, $R^1$ is OH, $OCOR^4$, or $OC(O)OR^4$ and $R^2$ is OH; wherein $R^4$ is $C_1$-$C_8$ alkyl. In some embodiments, $R^1$ is OH, $OCOR^4$, or $OC(O)OR^4$ and $R^2$ is OH; wherein $R^4$ is $C_1$-$C_6$ alkyl. In some embodiments, $R^1$ is OH, $OCOR^4$, or $OC(O)OR^4$ and $R^2$ is OH; wherein $R^4$ is $C_1$-$C_3$ alkyl. In some embodiments, $R^1$ is OH, $OCOR^4$, or $OC(O)OR^4$ and $R^2$ is OH; wherein $R^4$ is methyl, ethyl, or isopropyl.

In some embodiments, $R^1$ is $OCOR^4$, or $OC(O)OR^4$ and $R^2$ is OH; wherein $R^4$ is $C_1$-$C_8$ alkyl. In some embodiments, $R^1$ is $OCOR^4$, or $OC(O)OR^4$ and $R^2$ is OH; wherein $R^4$ is $C_1$-$C_6$ alkyl. In some embodiments, $R^1$ is $OCOR^4$, or $OC(O)OR^4$ and $R^2$ is OH; wherein $R^4$ is $C_1$-$C_3$ alkyl. In some embodiments, $R^1$ is $OCOR^4$, or $OC(O)OR^4$ and $R^2$ is OH; wherein $R^4$ is methyl, ethyl, or isopropyl.

In some embodiments, $R^1$ is $OCOR^4$ and $R^2$ is OH; wherein $R^4$ is $C_1$-$C_8$ alkyl. In some embodiments, $R^1$ is $OCOR^4$ and $R^2$ is OH; wherein $R^4$ is $C_1$-$C_6$ alkyl. In some embodiments, $R^1$ is $OCOR^4$ and $R^2$ is OH; wherein $R^4$ is $C_1$-$C_3$ alkyl. In some embodiments, $R^1$ is $OCOR^4$ and $R^2$ is OH; wherein $R^4$ is methyl, ethyl, or isopropyl.

In some embodiments, $R^1$ is OC(O)OR$^4$ and $R^2$ is OH; wherein $R^4$ is $C_1$-$C_8$ alkyl. In some embodiments, $R^1$ is OC(O)OR$^4$ and $R^2$ is OH; wherein $R^4$ is $C_1$-$C_6$ alkyl. In some embodiments, $R^1$ is OC(O)OR$^4$ and $R^2$ is OH; wherein $R^4$ is $C_1$-$C_3$ alkyl. In some embodiments, $R^1$ is OC(O)OR$^4$ and $R^2$ is OH; wherein $R^4$ is methyl, ethyl, or isopropyl.

In some embodiments of the compounds of Formula I or Ia, $R^1$ is OCOR$^4$ or OC(O)OR$^4$ and $R^2$ is OCOR$^5$ or OC(O)OR$^5$; wherein $R^4$ and $R^5$ are each independently $C_1$-$C_8$ alkyl. In some embodiments, $R^1$ is OCOR$^4$ or OC(O)OR$^4$ and $R^2$ is OCOR$^5$ or OC(O)OR$^5$; wherein $R^4$ and $R^5$ are each independently $C_1$-$C_6$ alkyl. In some embodiments, $R^1$ is OCOR$^4$ or OC(O)OR$^4$ and $R^2$ is OCOR$^5$ or OC(O)OR$^5$; wherein $R^4$ and $R^5$ are each independently $C_1$-$C_3$ alkyl. $R^1$ is OCOR$^4$ or OC(O)OR$^4$ and $R^2$ is OCOR$^1$ or OC(O)OR$^5$; wherein $R^4$ and $R^5$ are each independently methyl, ethyl, or isopropyl.

In some embodiments, $R^1$ is OCOR$^4$ and $R^2$ is OCOR$^5$ or OC(O)OR$^5$; wherein $R^4$ and $R^5$ are each independently $C_1$-$C_8$ alkyl. In some embodiments, $R^1$ is OCOR$^4$ and $R^2$ is OCOR$^5$ or OC(O)OR$^5$; wherein $R^4$ and $R^5$ are each independently $C_1$-$C_6$ alkyl. In some embodiments, $R^1$ is OCOR$^4$ and $R^2$ is OCOR$^5$ or OC(O)OR$^5$; wherein $R^4$ and $R^5$ are each independently $C_1$-$C_3$ alkyl. In some embodiments, $R^1$ is OCOR$^4$ and $R^2$ is OCOR$^5$ or OC(O)OR$^5$; wherein $R^4$ and $R^5$ are each independently methyl, ethyl, or isopropyl.

In some embodiments, $R^1$ is OC(O)OR$^4$ and $R^2$ is OCOR$^5$ or OC(O)OR$^5$; wherein $R^4$ and $R^5$ are each independently $C_1$-$C_8$ alkyl. In some embodiments, $R^1$ is OC(O)OR$^4$ and $R^2$ is OCOR$^5$ or OC(O)OR$^5$; wherein $R^4$ and R are each independently $C_1$-$C_6$ alkyl. In some embodiments, $R^1$ is OC(O)OR$^4$ and $R^2$ are OCOR$^5$ or OC(O)OR$^5$; wherein $R^4$ and $R^5$ are each independently $C_1$-$C_3$ alkyl. In some embodiments, $R^1$ is OC(O)OR$^4$ and $R^2$ is OCOR$^5$ or OC(O)OR$^5$; wherein $R^4$ and $R^5$ are each independently methyl, ethyl, or isopropyl.

In some embodiments, of the compounds of Formula I or Ia, or a pharmaceutically acceptable salt thereof, $R^1$ is OCOR$^4$ or OC(O)OR$^4$ and $R^2$ is OCOR$^5$; wherein $R^4$ and $R^5$ are each independently $C_1$-$C_8$ alkyl. In some embodiments, $R^1$ is OCOR$^4$ or OC(O)OR$^4$ and $R^2$ is OCOR$^5$; wherein $R^4$ and $R^5$ are each independently $C_1$-$C_6$ alkyl. In some embodiments, $R^1$ is OCOR$^4$ or OC(O)OR$^4$ and $R^2$ is OCOR$^5$; wherein $R^4$ and $R^5$ are each independently $C_1$-$C_3$ alkyl. In some embodiments, $R^1$ is OCOR$^4$ or OC(O)OR$^4$ and $R^2$ is OCOR$^5$; wherein $R^4$ and $R^5$ are each independently methyl, ethyl, or isopropyl.

In some embodiments, $R^1$ is OCOR$^4$ or OC(O)OR$^4$ and $R^2$ is OC(O)OR$^5$; wherein $R^4$ and $R^5$ are each independently $C_1$-$C_8$ alkyl. In some embodiments, $R^1$ is OCOR$^4$ or OC(O)OR$^4$ and $R^2$ is OC(O)OR$^5$; wherein $R^4$ and $R^5$ are each independently $C_1$-$C_6$ alkyl. In some embodiments, $R^1$ is OCOR$^4$ or OC(O)OR$^4$ and $R^2$ is OC(O)OR$^5$; wherein $R^4$ and $R^5$ are each independently $C_1$-$C_3$ alkyl. In some embodiments, $R^1$ is OCOR$^4$ or OC(O)OR$^4$ and $R^2$ is OC(O)OR$^5$; wherein $R^4$ and $R^5$ are each independently methyl, ethyl, or isopropyl.

In some embodiments, of the compounds of Formula I or Ia, or a pharmaceutically acceptable salt thereof, $R^1$ is OCOR$^4$ and $R^2$ is OCOR$^5$; wherein $R^4$ and $R^5$ are each independently $C_1$-$C_8$ alkyl. In some embodiments, $R^1$ is OCOR$^4$ and $R^2$ is OCOR$^5$; wherein $R^4$ and $R^5$ are each independently $C_1$-$C_6$ alkyl. In some embodiments, $R^1$ is OCOR$^4$ and $R^2$ is OCOR$^5$; wherein $R^4$ and $R^5$ are each independently $C_1$-$C_3$ alkyl. In some embodiments, $R^1$ is OCOR$^4$ and $R^2$ is OCOR$^5$; wherein $R^4$ and $R^5$ are each independently methyl, ethyl, or isopropyl.

In some embodiments, $R^1$ is OCOR$^4$ and $R^2$ is OC(O)OR$^5$; wherein $R^4$ and $R^5$ are each independently $C_1$-$C_8$ alkyl. In some embodiments, $R^1$ is OCOR$^4$ and $R^2$ is OC(O)OR$^5$; wherein $R^4$ and $R^5$ are each independently $C_1$-$C_6$ alkyl. In some embodiments, $R^1$ is OCOR$^4$ and $R^2$ is OC(O)OR$^5$; wherein $R^4$ and $R^5$ are each independently $C_1$-$C_3$ alkyl. In some embodiments, $R^1$ is OCOR$^4$ and $R^2$ is OC(O)OR$^5$; wherein $R^4$ and $R^5$ are each independently methyl, ethyl, or isopropyl.

In some embodiments, of the compounds of Formula I or Ia, or a pharmaceutically acceptable salt thereof, $R^1$ is OC(O)OR$^4$ and $R^2$ is OCOR$^5$; wherein $R^4$ and $R^5$ are each independently $C_1$-$C_8$ alkyl. In some embodiments, $R^1$ is OC(O)OR$^4$ and $R^2$ is OCOR$^5$; wherein $R^4$ and $R^5$ are each independently $C_1$-$C_6$ alkyl. In some embodiments, $R^1$ is OC(O)OR$^4$ and $R^2$ is OCOR$^5$; wherein $R^4$ and $R^5$ are each independently $C_1$-$C_3$alkyl. In some embodiments, $R^1$ is OC(O)OR$^4$ and $R^2$ is OCOR$^5$; wherein $R^4$ and $R^5$ are each independently methyl, ethyl, or isopropyl.

In some embodiments, $R^1$ is OC(O)OR$^4$ and $R^2$ is OC(O)OR$^5$; wherein $R^4$ and $R^5$ are each independently $C_1$-$C_8$ alkyl. In some embodiments, $R^1$ is OC(O)OR$^4$ and $R^2$ is OC(O)OR$^5$; wherein $R^4$ and $R^5$ are each independently $C_1$-$C_6$ alkyl. In some embodiments, $R^1$ is OC(O)OR$^4$ and $R^2$ is OC(O)OR$^5$; wherein $R^4$ and $R^5$ are each independently $C_1$-$C_3$ alkyl. In some embodiments, $R^1$ is OC(O)OR$^4$ and $R^2$ is OC(O)OR$^5$; wherein $R^4$ and $R^5$ are each independently methyl, ethyl, or isopropyl.

In some embodiments of the compounds of Formula I or Ia, $R^6$ is H, $C_1$-$C_3$ alkyl or $C_6$-$C_{10}$ aryl. In some embodiments, $R^6$ is H, $C_1$-$C_6$ alkyl or phenyl. In some embodiments, $R^6$ is H, $C_1$-$C_3$ alkyl or phenyl. In some embodiments, $R^6$ is $C_6$-$C_{10}$ aryl. In some embodiments, $R^6$ is phenyl.

In some embodiments of the compounds of Formula I or Ia, $R^1$ and $R^2$ are taken together to form —OC(O)O— or —OCHR$^6$O—; wherein $R^6$ is H, $C_1$-$C_6$ alkyl or $C_6$-$C_{10}$ aryl. In some embodiments, $R^1$ and $R^2$ are taken together to form —OC(O)O— or —OCHR$^6$O—; wherein $R^6$ is H, $C_1$-$C_3$ alkyl or $C_6$-$C_{10}$ aryl. In some embodiments, $R^1$ and $R^2$ are taken together to form —OC(O)O— or —OCHR$^6$O—; wherein $R^6$ is H, $C_1$-$C_6$ alkyl or phenyl. In some embodiments, $R^1$ and $R^2$ are taken together to form —OC(O)O— or —OCHR$^6$O—; wherein $R^6$ is H, $C_1$-$C_3$ alkyl or phenyl. In some embodiments, $R^1$ and $R^2$ are taken together to form —OC(O)O— or —OCHR$^6$O—; wherein $R^6$ is $C_6$-$C_{10}$ aryl. In some embodiments, $R^1$ and $R^2$ are taken together to form —OC(O)O— or —OCHR$^6$O—; wherein $R^6$ is phenyl.

In some embodiments of the compounds of Formula I or Ia, $R^1$ and $R^2$ are taken together to form —OCHR$^6$O—; wherein $R^6$ is H, $C_1$-$C_6$ alkyl or $C_6$-$C_{10}$ aryl. In some embodiments, $R^1$ and $R^2$ are taken together to form —OCHR$^6$O—; wherein $R^6$ is H, $C_1$-$C_3$ alkyl or $C_6$-$C_{10}$ aryl. In some embodiments, $R^1$ and $R^2$ are taken together to form —OCHR$^6$O—; wherein $R^6$ is $C_6$-$C_{10}$ aryl. In some embodiments, $R^1$ and $R^2$ are taken together to form —OCHR$^6$O—; wherein $R^6$ is phenyl.

In some embodiments of the compounds of Formula I or Ia, $R^1$ and $R^2$ are taken together to form —OC(O)O—.

In some embodiments of the compound of Formula I or Ia, or a pharmaceutically acceptable salt thereof, wherein, $R^3$ is H and R is OCOR$^4$, or OC(O)OR$^4$. In some embodiments, $R^3$ is H and $R^2$ is OCOR$^5$, or OC(O)OR$^5$. In some embodiments, $R^3$ is H and $R^1$ and $R^2$ are taken together to form —OC(O)O— or —OCHR$^6$O—. In some embodiments, $R^3$ is H and $R^1$ and $R^2$ are taken together to form —OC(O)O—. In some embodiments, $R^3$ is H and $R^1$ and $R^2$ are taken together to form —OCHR⁶O—; wherein $R^6$ is H, $C_1$-$C_6$ alkyl or $C_6$-$C_{10}$ aryl. In some embodiments, $R^3$ is H and $R^1$ and $R^2$ are taken together to form —OCHR⁶O—; wherein $R^6$ is H, $C_1$-$C_3$ alkyl or $C_6$-$C_{10}$ aryl. In some embodiments, $R^3$ is H and $R^1$ and $R^2$ are taken together to form —OCHR⁶O—; wherein $R^6$ is H, $C_1$-$C_6$ alkyl or phenyl. In some embodiments, $R^3$ is H and $R^1$ and $R^2$ are taken together to form —OCHR⁶O—; wherein $R^6$ is H, $C_1$-$C_3$ alkyl or phenyl. In some embodiments, $R^3$ is H and $R^1$ and $R^2$ are taken together to form —OCHR⁶O—; wherein $R^6$ is $C_6$-$C_{10}$ aryl. In some embodiments, $R^3$ is H and $R^1$ and $R^2$ are taken together to form —OCHR⁶O—; wherein $R^6$ is phenyl.

In some embodiments of the compound of Formula I or Ia, or a pharmaceutically acceptable salt thereof, each $R^8$ is independently H, $C_1$-$C_6$ alkyl, or $C_3$-$C_6$ cycloalkyl. In some embodiments, each $R^8$ is independently H or $C_1$-$C_6$ alkyl. In some embodiments, each $R^5$ is independently H or $C_1$-$C_3$ alkyl. In some embodiments, each $R^8$ is H.

In some embodiments of the compound of Formula I or Ia, or a pharmaceutically acceptable salt thereof, each $R^9$ is independently H, $C_1$-$C_6$ alkyl, or $C_3$-$C_6$ cycloalkyl. In some embodiments, each $R^9$ is independently H or $C_1$-$C_6$ alkyl. In some embodiments, each $R^9$ is independently H or $C_1$-$C_3$ alkyl. In some embodiments, each $R^9$ is H.

In some embodiments of the compound of Formula I or Ia, or a pharmaceutically acceptable salt thereof, each $R^{10}$ is independently H, $C_1$-$C_6$ alkyl, or $C_3$-$C_6$ cycloalkyl. In some embodiments, each $R^{10}$ is independently H or $C_1$-$C_6$ alkyl. In some embodiments, each $R^{10}$ is independently H or $C_1$-$C_3$ alkyl. In some embodiments, each $R^{10}$ is H.

In some embodiments of the compound of Formula I or Ia, or a pharmaceutically acceptable salt thereof, each $R^8$, $R^9$ and $R^{10}$ is H.

In some embodiments of the compound of Formula I or Ia, or a pharmaceutically acceptable salt thereof, the compound is selected form the group consisting of:

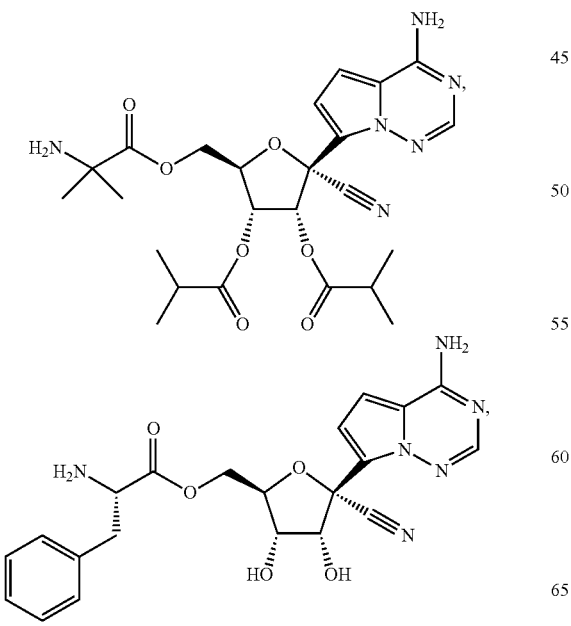

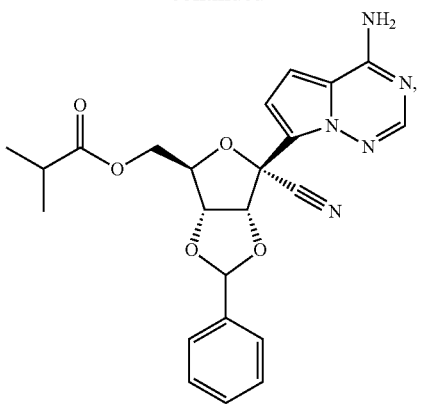

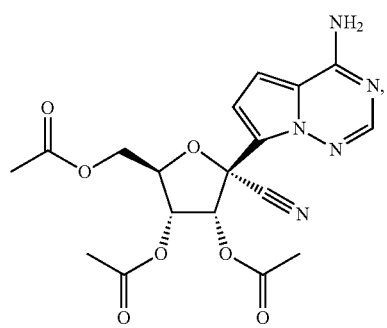

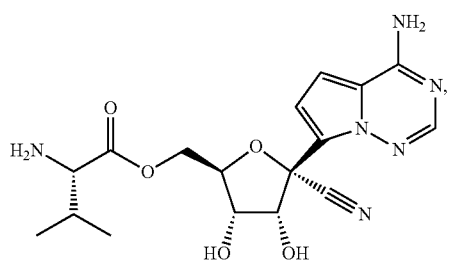

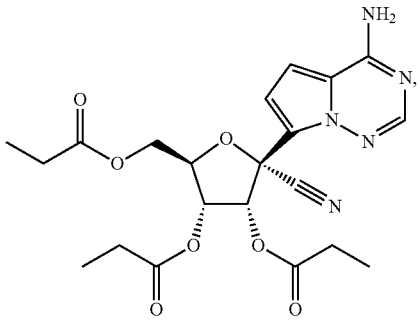

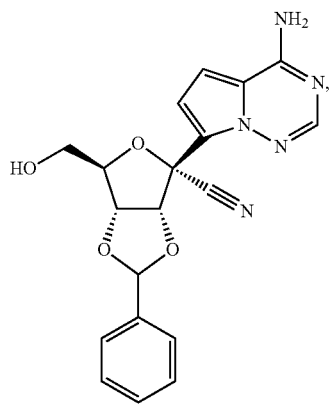

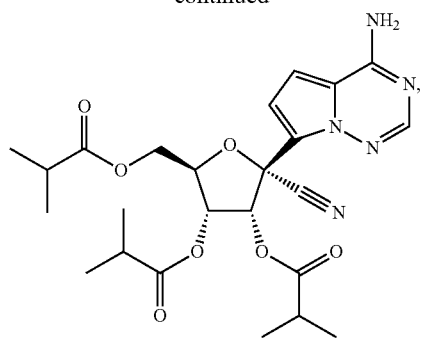
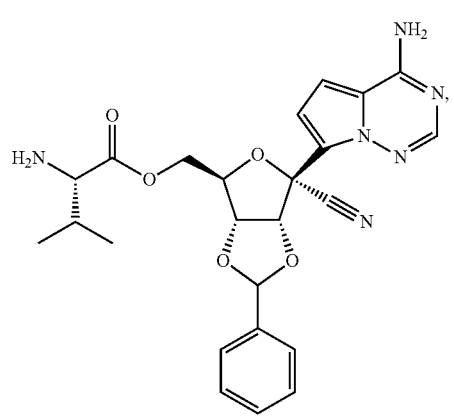
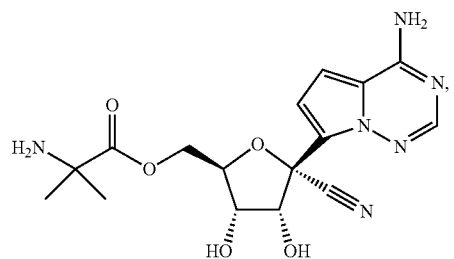
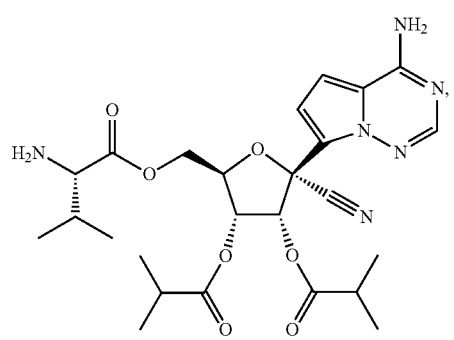
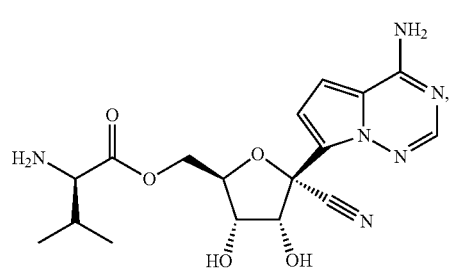
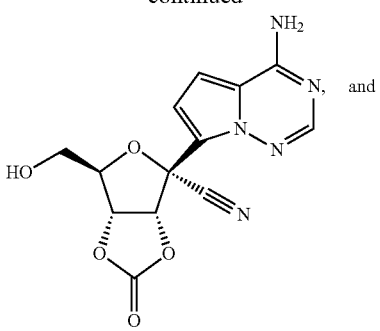
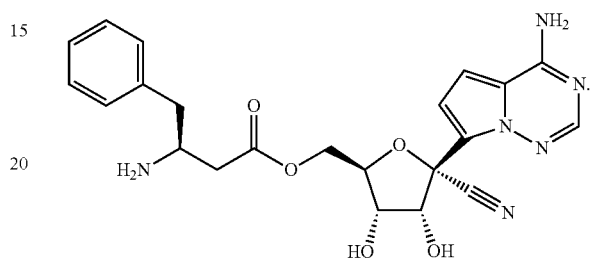
In some embodiments of the compound of Formula I or Ia, or a pharmaceutically acceptable salt thereof, wherein the compound is
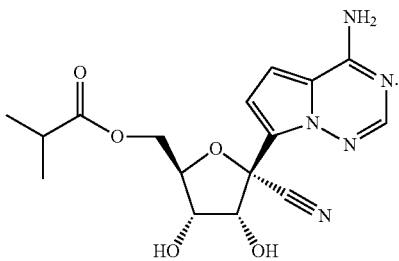 [SMILES: CC(C)C(=O)OC[C@H]1O[C@@](C#N)(c2ccc3c(N)ncnn23)[C@H](O)[C@@H]1O]
In some embodiments of the compound of Formula I and Ia, or a pharmaceutically acceptable salt thereof, wherein the compound is selected from the group consisting of:
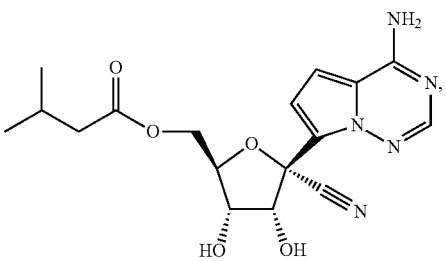
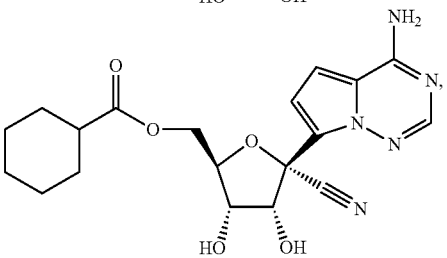

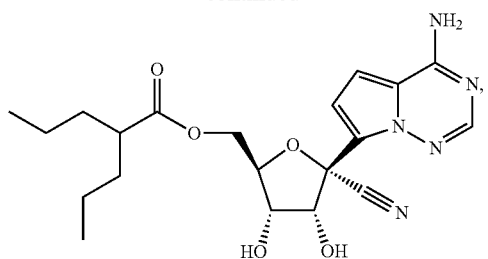
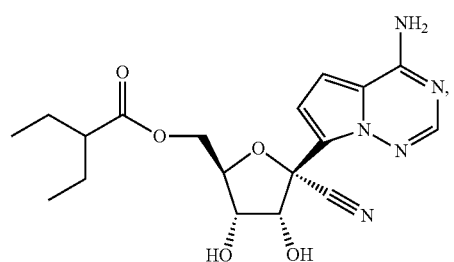
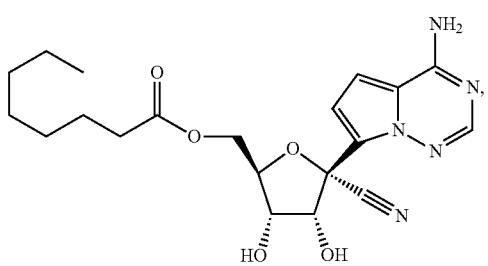
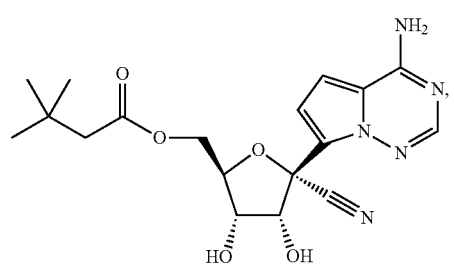
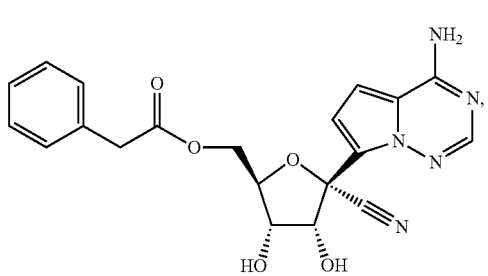
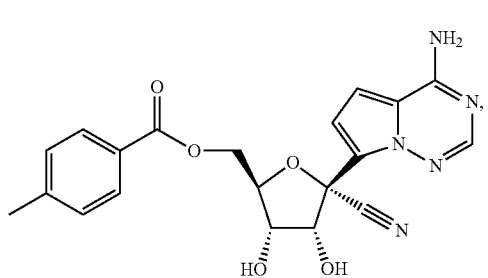
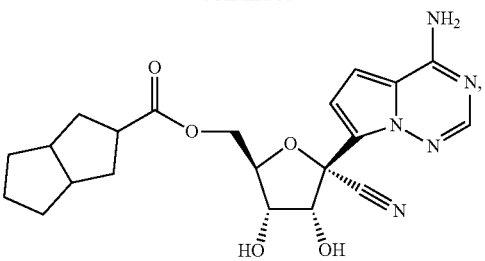
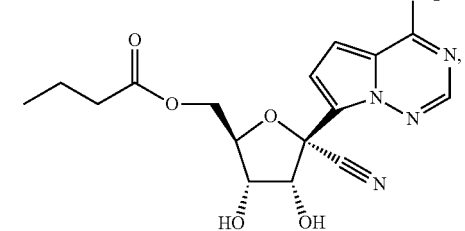
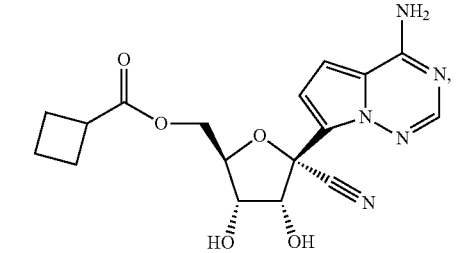
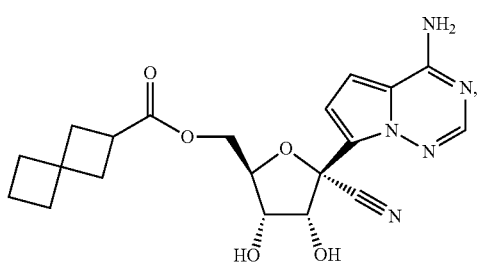
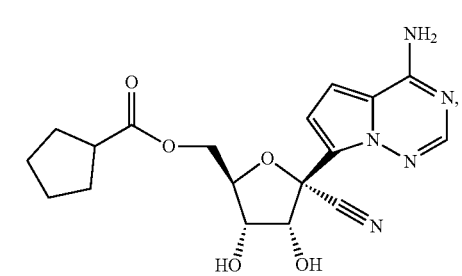
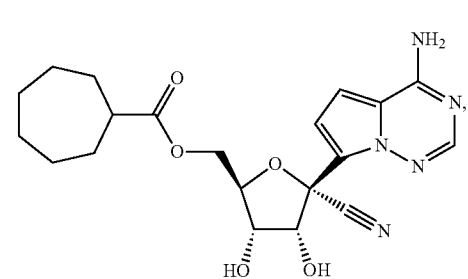

-continued

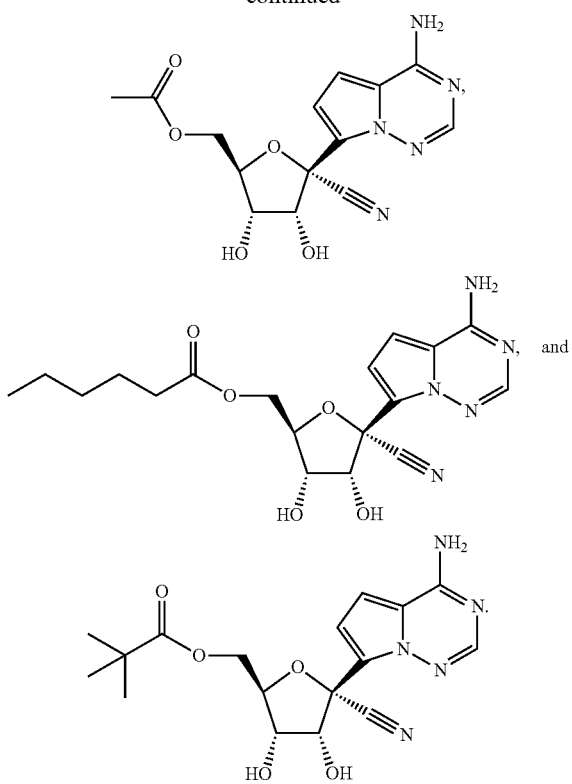

In some embodiments, the compounds of Formula I or Ia disclosed herein can be considered as prodrugs of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (herein after "Reference Compound A") (Compound 13 in WO2009132135; Compound 4 in *J. Med. Chem.* 2017, 60, 1648-1661). While not intending to be bound by any particular theory of operation, it is believed that the compounds of Formula I and Ia are metabolized in vivo to the Reference Compound A. In some embodiments, the compounds of Formula I or Ia provide increased bioavailability of the Reference Compound A when administered orally. In some embodiments, the compounds of Formula I or Ia provide at least 2 times, at least 3 times, at least 4 times, at least 5 times, at least 6 times, at least 8 times, at least 10 times, at least 12 times, at least 14 times, at least 16 times, at least 18 times, at least 20 times, at least 25 times, or at least 30 times increased bioavailability of the Reference Compound A when administered orally.

Reference Compound A

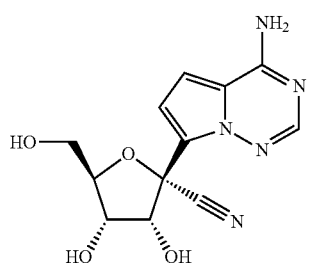

V. Pharmaceutical Formulations

The compounds disclosed herein may be formulated with conventional carriers and excipients. For example, tablets will contain excipients, glidants, fillers, binders and the like. Aqueous formulations are prepared in sterile form, and when intended for delivery by other than oral administration generally will be isotonic. All formulations may optionally contain excipients such as those set forth in the "Handbook of Pharmaceutical Excipients" (1986). Excipients include ascorbic acid and other antioxidants, chelating agents such as EDTA, carbohydrates such as dextran, hydroxyalkylcellulose, hydroxyalkylmethylcellulose, stearic acid and the like. The pH of the formulations ranges from about 3 to about 11, but is ordinarily about 7 to 10. In some embodiments, the pH of the formulations ranges from about 2 to about 5, but is ordinarily about 3 to 4.

While it is possible for the compounds of the disclosure ("the active ingredients") to be administered alone it may be preferable to present them as pharmaceutical formulations. The formulations, both for veterinary and for human use, of the invention comprise at least one active ingredient, as above defined, together with one or more acceptable carriers therefor and optionally other therapeutic ingredients, particularly those additional therapeutic ingredients as discussed herein. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any appropriate method known in the art of pharmacy. Techniques and formulations generally are found in Remington's Pharmaceutical Sciences (Mack Publishing Co., Easton, PA). Such methods include the step of bringing into association the active ingredient with the carrier which constitutes one or more accessory ingredients. In general, the formulations are prepared by uniformly and intimately bringing into association the active ingredient with liquid carriers or finely divided solid carriers or both, and then, if necessary, shaping the product.

In some embodiments the compound of Formula I or Ia, or the pharmaceutically acceptable salt thereof, described herein have optimized/improved pharmacokinetic properties and are amenable to oral administration. For example, the compounds of Formula I or Ia, have improved bioavailability and can therefore be administered by oral administration.

In some embodiments, the formulations of the present invention are suitable for oral administration may be presented as discrete units such as capsules, cachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be administered as a bolus, electuary or paste.

In some embodiments, the tablet is made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent. The tablets may optionally be coated or scored and optionally are formulated so as to provide slow or controlled release of the active ingredient therefrom.

For infections of the eye or other external tissues, e.g., mouth and skin, the formulations are applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc.), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base.

If desired, the aqueous phase of the cream base may include, for example, at least 30% w/w of a polyhydric alcohol, i.e., an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulphoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

Emulgents and emulsion stabilizers suitable for use in the formulation of the invention include Tween® 60, Span® 80, cetostearyl alcohol, benzyl alcohol, myristyl alcohol, glyceryl mono-stearate and sodium lauryl sulfate. Further emulgents and emulsion stabilizers suitable for use in the formulation of the invention include Tween® 80.

The choice of suitable oils or fats for the formulation is based on achieving the desired cosmetic properties. The cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils are used.

Pharmaceutical formulations according to the present invention comprise a compound according to the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, calcium or sodium phosphate; granulating and disintegrating agents, such as maize starch, or alginic acid; binding agents, such as starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

Formulations for oral use may be also presented as hard gelatin capsules where the active ingredient is mixed with an inert solid diluent, for example calcium phosphate or kaolin, or as soft gelatin capsules wherein the active ingredient is mixed with water or an oil medium, such as peanut oil, liquid paraffin or olive oil.

Aqueous suspensions of the invention contain the active materials in admixture with excipients suitable for the manufacture of aqueous suspensions. Such excipients include a suspending agent, such as sodium carboxymethylcellulose, methylcellulose, hydroxypropyl methylcellulose, sodium alginate, polyvinylpyrrolidone, gum tragacanth and gum acacia, and dispersing or wetting agents such as a naturally-occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin. Further non-limiting examples of suspending agents include Cyclodextrin. In some examples, the suspending agent is Sulfobutyl ether beta-cyclodextrin (SEB-beta-CD), for example Captisol®.

Oil suspensions may be formulated by suspending the active ingredient in a vegetable oil, such as arachis oil, olive oil, sesame oil or coconut oil, or in a mineral oil such as liquid paraffin. The oral suspensions may contain a thickening agent, such as beeswax, hard paraffin or cetyl alcohol. Sweetening agents, such as those set forth above, and flavoring agents may be added to provide a palatable oral preparation. These compositions may be preserved by the addition of an antioxidant such as ascorbic acid.

Dispersible powders and granules of the invention suitable for preparation of an aqueous suspension by the addition of water provide the active ingredient in admixture with a dispersing or wetting agent, a suspending agent, and one or more preservatives. Suitable dispersing or wetting agents and suspending agents are exemplified by those disclosed above. Additional excipients, for example sweetening, flavoring and coloring agents, may also be present.

The pharmaceutical compositions of the invention may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth, naturally-occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

The pharmaceutical compositions of the invention may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose, any bland fixed oil may be employed including synthetic mono- or diglycerides. In addition, fatty acids such as oleic acid may likewise be used in the preparation of injectables. Among the acceptable vehicles and solvents that may be employed are water, Ringer's solution isotonic sodium chloride solution, and hypertonic sodium chloride solution.

The amount of active ingredient that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 μg of the active ingredient per milliliter of solution in order that infusion of a suitable volume at a rate of about 30 mL/hr can occur.

Formulations suitable for topical administration to the eye also include eye drops wherein the active ingredient is dissolved or suspended in a suitable carrier, especially an aqueous solvent for the active ingredient. The active ingredient is preferably present in such formulations in a concentration of 0.5 to 20%, advantageously 0.5 to 10%, and particularly about 1.5% w/w.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate.

In some embodiments, the compounds disclosed herein are administered by inhalation. In some embodiments, formulations suitable for intrapulmonary or nasal administration have a particle size for example in the range of 0.1 to 500 microns, such as 0.5, 1, 30, 35 etc., which is administered by rapid inhalation through the nasal passage or by inhalation through the mouth so as to reach the alveolar sacs. Suitable formulations include aqueous or oily solutions of the active ingredient. Formulations suitable for aerosol or dry powder administration may be prepared according to conventional methods and may be delivered with other therapeutic agents. In some embodiments, the compounds used herein are formulated and dosed as dry powder. In some embodiments, the compounds used herein are formulated and dosed as a nebulized formulation. In some embodiments, the compounds used herein are formulated for delivery by a face mask. In some embodiments, the compounds used herein are formulated for delivery by a face tent.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations are presented in unit-dose or multi-dose containers, for example sealed ampoules and vials, and may be stored in a freeze-dried (lyophilized) condition requiring only the addition of the sterile liquid carrier, for example water for injection, immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

It should be understood that in addition to the ingredients particularly mentioned above the formulations of this invention may include other agents conventional in the art having regard to the type of formulation in question, for example those suitable for oral administration may include flavoring agents.

The invention further provides veterinary compositions comprising at least one active ingredient as above defined together with a veterinary carrier therefor.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Compounds of the invention are used to provide controlled release pharmaceutical formulations containing as active ingredient one or more compounds of the invention ("controlled release formulations") in which the release of the active ingredient are controlled and regulated to allow less frequency dosing or to improve the pharmacokinetic or toxicity profile of a given active ingredient.

VI. Kits

Also provided herein are kits that includes a compound disclosed herein, a pharmaceutically acceptable salt, stereoisomer, mixture of stereoisomers or tautomer thereof. In some embodiments the kits described herein may comprise a label and/or instructions for use of the compound in the treatment of a disease or condition in a subject (e.g., human) in need thereof. In some embodiments, the disease or condition is viral infection.

In some embodiments, the kit may also comprise one or more additional therapeutic agents and/or instructions for use of additional therapeutic agents in combination with the compound of Formula I in the treatment of the disease or condition in a subject (e.g., human) in need thereof.

In some embodiments, the kits provided herein comprises individual dose units of a compound as described herein, or a pharmaceutically acceptable salt, racemate, enantiomer, diastereomer, tautomer, polymorph, pseudopolymorph, amorphous form, hydrate or solvate thereof. Examples of individual dosage units may include pills, tablets, capsules, prefilled syringes or syringe cartridges, IV bags, inhalers, nebulizers etc., each comprising a therapeutically effective amount of the compound in question, or a pharmaceutically acceptable salt, racemate, enantiomer, diastereomer, tautomer, polymorph, pseudopolymorph, amorphous form, hydrate or solvate thereof. In some embodiments, the kit may contain a single dosage unit and in others multiple dosage units are present, such as the number of dosage units required for a specified regimen or period.

Also provided are articles of manufacture that include a compound of Formula I, or a pharmaceutically acceptable salt, stereoisomer, mixture of stereoisomers or tautomer thereof; and a container. In some embodiments, the container of the article of manufacture is a vial, jar, ampoule, preloaded syringe, blister package, tin, can, bottle, box, an intravenous bag, an inhaler, or a nebulizer.

VII. Administration

One or more compounds of the invention are administered by any route appropriate to the condition to be treated. Suitable routes include oral, rectal, inhalation, pulmonary, topical (including buccal and sublingual), vaginal and parenteral (including subcutaneous, intramuscular, intravenous, intradermal, intrathecal and epidural), and the like. In some embodiments, the compounds disclosed herein are administered by inhalation or intravenously. It will be appreciated that the preferred route may vary with for example the condition of the recipient.

In the methods of the present invention for the treatment of a viral infection, the compounds of the present invention can be administered at any time to a human who may come into contact with the virus or is already suffering from the viral infection. In some embodiments, the compounds of the present invention can be administered prophylactically to humans coming into contact with humans suffering from the viral infection or at risk of coming into contact with humans suffering from the viral infection, e.g., healthcare providers. In some embodiments, administration of the compounds of the present invention can be to humans testing positive for the viral infection but not yet showing symptoms of the viral infection. In some embodiments, administration of the compounds of the present invention can be to humans upon commencement of symptoms of the viral infection.

In some embodiments, the methods disclosed herein comprise event driven administration of the compound of Formula I, or a pharmaceutically acceptable salt thereof, to the subject.

As used herein, the terms "event driven" or "event driven administration" refer to administration of the compound of Formula I, or a pharmaceutically acceptable salt thereof, (1) prior to an event (e.g., 2 hours, 1 day, 2 days, 5 day, or 7 or more days prior to the event) that would expose the individual to the virus (or that would otherwise increase the individual's risk of acquiring the viral infection); and/or (2) during an event (or more than one recurring event) that would expose the individual to the virus (or that would otherwise increase the individual's risk of acquiring the viral infection); and/or (3) after an event (or after the final event in a series of recurring events) that would expose the individual to the virus (or that would otherwise increase the individual's risk of acquiring the viral infection). In some embodiments, the event driven administration is performed pre-exposure of the subject to the virus. In some embodiments, the event driven administration is performed post-exposure of the subject to the virus. In some embodiments, the event driven administration is performed pre-exposure of the subject to the virus and post-exposure of the subject to the virus.

In certain embodiments, the methods disclosed herein involve administration prior to and/or after an event that would expose the individual to the virus or that would otherwise increase the individual's risk of acquiring the viral infection, e.g., as pre-exposure prophylaxis (PrEP) and/or as post-exposure prophylaxis (PEP). In some embodiments, the methods disclosed herein comprise pre-exposure prophylaxis (PrEP). In some embodiments, methods disclosed herein comprise post-exposure prophylaxis (PEP).

In some embodiments, the compound of Formula I, or a pharmaceutically acceptable salt thereof, is administered before exposure of the subject to the virus.

In some embodiments, the compound of Formula I, or a pharmaceutically acceptable salt thereof, is administered before and after exposure of the subject to the virus.

In some embodiments, the compound of Formula I, or a pharmaceutically acceptable salt thereof, is administered after exposure of the subject to the virus.

An example of event driven dosing regimen includes administration of the compound of Formula I, or a pharmaceutically acceptable salt thereof, within 24 to 2 hours prior to the virus, followed by administration of the compound of Formula I, or a pharmaceutically acceptable salt, every 24 hours during the period of exposure, followed by a further administration of the compound of Formula I, or a pharmaceutically acceptable salt thereof, after the last exposure, and one last administration of the compound of Formula I, or a pharmaceutically acceptable salt thereof, 24 hours later.

A further example of an event driven dosing regimen includes administration of the compound of Formula I, or a pharmaceutically acceptable salt thereof, within 24 hours before the viral exposure, then daily administration during the period of exposure, followed by a last administration approximately 24 hours later after the last exposure (which may be an increased dose, such as a double dose).

The specific dose level of a compound of the present disclosure for any particular subject will depend upon a variety of factors including the activity of the specific compound employed, the age, body weight, general health, sex, diet, time of administration, route of administration, and rate of excretion, drug combination and the severity of the particular disease in the subject undergoing therapy. For example, a dosage may be expressed as a number of milligrams of a compound described herein per kilogram of the subject's body weight (mg/kg). Dosages of between about 0.1 and 150 mg/kg may be appropriate. In some embodiments, about 0.1 and 100 mg/kg may be appropriate. In other embodiments a dosage of between 0.5 and 60 mg/kg may be appropriate. Normalizing according to the subject's body weight is particularly useful when adjusting dosages between subjects of widely disparate size, such as occurs when using the drug in both children and adult humans or when converting an effective dosage in a non-human subject such as dog to a dosage suitable for a human subject.

The daily dosage may also be described as a total amount of a compound described herein administered per dose or per day. Daily dosage of a compound of Formula I, or a pharmaceutically acceptable salt thereof, may be between about 1 mg and 4,000 mg, between about 2,000 to 4,000 mg/day, between about 1 to 2,000 mg/day, between about 1 to 1,000 mg/day, between about 10 to 500 mg/day, between about 20 to 500 mg/day, between about 50 to 300 mg/day, between about 75 to 200 mg/day, or between about 15 to 150 mg/day.

The dosage or dosing frequency of a compound of the present disclosure may be adjusted over the course of the treatment, based on the judgment of the administering physician.

The compounds of the present disclosure may be administered to an individual (e.g., a human) in a therapeutically effective amount. In some embodiments, the compound is administered once daily.

The compounds provided herein can be administered by any useful route and means, such as by oral or parenteral (e.g., intravenous) administration. Therapeutically effective amounts of the compound may include from about 0.00001 mg/kg body weight per day to about 10 mg/kg body weight per day, such as from about 0.0001 mg/kg body weight per day to about 10 mg/kg body weight per day, or such as from about 0.001 mg/kg body weight per day to about 1 mg/kg body weight per day, or such as from about 0.01 mg/kg body weight per day to about 1 mg/kg body weight per day, or such as from about 0.05 mg/kg body weight per day to about 0.5 mg/kg body weight per day. In some embodiments, a therapeutically effective amount of the compounds provided herein include from about 0.3 mg to about 30 mg per day, or from about 30 mg to about 300 mg per day, or from about 0.3 µg to about 30 mg per day, or from about 30 µg to about 300 µg per day.

A compound of the present disclosure may be combined with one or more additional therapeutic agents in any dosage amount of the compound of the present disclosure (e.g., from 1 mg to 1000 mg of compound). Therapeutically effective amounts may include from about 0.1 mg per dose to about 1000 mg per dose, such as from about 50 mg per dose to about 500 mg per dose, or such as from about 100 mg per dose to about 400 mg per dose, or such as from about 150 mg per dose to about 350 mg per dose, or such as from about 200 mg per dose to about 300 mg per dose, or such as from about 0.01 mg per dose to about 1000 mg per dose, or such as from about 0.01 mg per dose to about 100 mg per dose, or such as from about 0.1 mg per dose to about 100 mg per dose, or such as from about 1 mg per dose to about 100 mg per dose, or such as from about 1 mg per dose to about 10 mg per dose, or such as from about 1 mg per dose to about 1000 mg per dose. Other therapeutically effective amounts of the compound of Formula I are about 1 mg per dose, or about 2, 3, 4, 5, 6, 7, 8, 9, 10, 15, 20, 25, 30, 35, 40, 45, 50, 55, 60, 65, 70, 75, 80, 85, 90, 95, or about 100 mg per dose. Other therapeutically effective amounts of the compound of the present disclosure are about 100, 125, 150, 175, 200, 225, 250, 275, 300, 325, 350, 375, 400, 425, 450, 475, 500, 525, 550, 575, 600, 625, 650, 675, 700, 725, 750, 775, 800, 825, 850, 875, 900, 925, 950, 975, or about 1000 mg per dose.

In some embodiments, the methods described herein comprise administering to the subject an initial daily dose of about 1 to 500 mg of a compound provided herein and increasing the dose by increments until clinical efficacy is achieved. Increments of about 5, 10, 25, 50, or 100 mg can be used to increase the dose. The dosage can be increased daily, every other day, twice per week, once per week, once every two weeks, once every three weeks, or once a month.

When administered orally, the total daily dosage for a human subject may be between about 1-4,000 mg/day, between about 1-3,000 mg/day, between 1-2,000 mg/day, about 1-1,000 mg/day, between about 10-500 mg/day, between about 50-300 mg/day, between about 75-200 mg/day, or between about 100-150 mg/day. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000 mg/day administered in a single dose. In some embodiments, the total daily dosage for a human subject may be about 200, 300, 400, 500, 600, 700, or 800 mg/day administered in a single dose. In some embodiments, the total daily dosage for a human subject may be about 300, 400, 500, or 600 mg/day administered in a single dose. In some embodiments, the total daily dosage for a human subject may be about 100, 200, 300, 400, 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, 3500, 3600, 3700, 3800, 3900, or 4000 mg/day. In some embodiments, the total daily dosage for a human subject may be about 100-200, 100-300, 100-400, 100-500, 100-600, 100-700, 100-800, 100-900, 100-1000, 500-1100, 500-1200, 500-1300, 500-1400, 500-1500, 500-1600, 500-1700, 500-1800, 500-1900, 500-2000, 1500-2100, 1500-2200, 1500-2300, 1500-2400, 1500-2500, 2000-2600, 2000-2700, 2000-2800, 2000-2900, 2000-3000, 2500-3100, 2500-3200, 2500-3300, 2500-3400, 2500-3500, 3000-3600, 3000-3700, 3000-3800, 3000-3900, or 3000-4000 mg/day.

In some embodiments, the total daily dosage for a human subject may be about 100 mg/day administered in a single dose. In some embodiments, the total daily dosage for a human subject may be about 150 mg/day administered in a single dose. In some embodiments, the total daily dosage for a human subject may be about 200 mg/day administered in a single dose. In some embodiments, the total daily dosage for a human subject may be about 250 mg/day administered in a single dose. In some embodiments, the total daily dosage for a human subject may be about 300 mg/day administered in a single dose. In some embodiments, the total daily dosage for a human subject may be about 350 mg/day administered in a single dose. In some embodiments, the total daily dosage for a human subject may be about 400 mg/day administered in a single dose. In some embodiments, the total daily dosage for a human subject may be about 450 mg/day administered in a single dose. In some embodiments, the total daily dosage for a human subject may be about 500 mg/day administered in a single dose. In some embodiments, the total daily dosage for a human subject may be about 550 mg/day administered in a single dose. In some embodiments, the total daily dosage for a human subject may be about 600 mg/day administered in a single dose. In some embodiments, the total daily dosage for a human subject may be about 650 mg/day administered in a single dose. In some embodiments, the total daily dosage for a human subject may be about 700 mg/day administered in a single dose. In some embodiments, the total daily dosage for a human subject may be about 750 mg/day administered in a single dose. In some embodiments, the total daily dosage for a human subject may be about 800 mg/day administered in a single dose. In some embodiments, the total daily dosage for a human subject may be about 850 mg/day administered in a single dose. In some embodiments, the total daily dosage for a human subject may be about 900 mg/day administered in a single dose. In some embodiments, the total daily dosage for a human subject may be about 950 mg/day administered in a single dose. In some embodiments, the total daily dosage for a human subject may be about 1000 mg/day administered in a single dose. In some embodiments, the total daily dosage for a human subject may be about 1500 mg/day administered in a single dose. In some embodiments, the total daily dosage for a human subject may be about 2000 mg/day administered in a single dose. In some embodiments, the total daily dosage for a human subject may be about 2500 mg/day administered in a single dose. In some embodiments, the total daily dosage for a human subject may be about 3000 mg/day administered in a single dose. In some embodiments, the total daily dosage for a human subject may be about 4000 mg/day administered in a single dose.

A single dose can be administered hourly, daily, weekly, or monthly. For example, a single dose can be administered once every 1 hour, 2, 3, 4, 6, 8, 12, 16 or once every 24 hours. A single dose can also be administered once every 1 day, 2, 3, 4, 5, 6, or once every 7 days. A single dose can also be administered once every 1 week, 2, 3, or once every 4 weeks. In certain embodiments, a single dose can be administered once every week. A single dose can also be administered once every month. In some embodiments, a compound disclosed herein is administered once daily in a method disclosed herein. In some embodiments, a compound disclosed herein is administered twice daily in a method disclosed herein. In some embodiments, a compound disclosed herein is administered three times daily in a method disclosed herein.

In some embodiments, a compound disclosed herein is administered once daily in the total daily dose of 100-4000 mg/day. In some embodiments, a compound disclosed herein is administered twice daily in the total daily dose of 100-4000 mg/day. In some embodiments, a compound disclosed herein is administered three times daily in the total daily dose of 100-4000 mg/day.

The frequency of dosage of the compound of the present disclosure will be determined by the needs of the individual patient and can be, for example, once per day or twice, or more times, per day. Administration of the compound continues for as long as necessary to treat the viral infection. For example, a compound can be administered to a human being infected with the virus for a period of from 20 days to 180 days or, for example, for a period of from 20 days to 90 days or, for example, for a period of from 30 days to 60 days.

Administration can be intermittent, with a period of several or more days during which a patient receives a daily dose of the compound of the present disclosure followed by a period of several or more days during which a patient does not receive a daily dose of the compound. For example, a patient can receive a dose of the compound every other day, or three times per week. Again by way of example, a patient can receive a dose of the compound each day for a period of from 1 to 14 days, followed by a period of 7 to 21 days during which the patient does not receive a dose of the compound, followed by a subsequent period (e.g., from 1 to 14 days) during which the patient again receives a daily dose of the compound. Alternating periods of administration of the compound, followed by non-administration of the compound, can be repeated as clinically required to treat the patient.

The compounds of the present disclosure or the pharmaceutical compositions thereof may be administered once, twice, three, or four times daily, using any suitable mode described above. Also, administration or treatment with the compounds may be continued for a number of days; for example, commonly treatment would continue for at least 7 days, 14 days, or 28 days, for one cycle of treatment. Treatment cycles are well known in cancer chemotherapy, and are frequently alternated with resting periods of about 1 to 28 days, commonly about 7 days or about 14 days, between cycles. The treatment cycles, in other embodiments, may also be continuous.

VIII. Methods of Use

The present disclosure also provides a method of treating or preventing a viral infection in a subject (e.g., human) in need thereof, the method comprising administering to the subject a compound described herein.

In some embodiments, the present disclosure provides a method of treating a viral infection in a subject (e.g., human) in need thereof, the method comprising administering to a subject in need thereof a compound described herein.

In some embodiments, the present disclosure provides for methods of treating or preventing a viral infection in a subject (e.g., human) in need thereof, the method comprising administering to the subject a compound disclosed herein and at least one additional active therapeutic agent.

In some embodiments, the present disclosure provides for methods of treating a viral infection in a subject (e.g., human) in need thereof, the method comprising administering to the subject a compound disclosed herein, and at least one additional active therapeutic agent.

In one embodiment, the present disclosure provides for methods of inhibiting a viral polymerase in a cell, the methods comprising contacting the cell infected a virus with a compound disclosed herein, whereby the viral polymerase is inhibited.

In one embodiment, the present disclosure provides for methods of inhibiting a viral polymerase in a cell, the methods comprising contacting the cell infected a virus with a compound disclosed herein, and at least one additional active therapeutic agent, whereby the viral polymerase is inhibited.

Also provided here are the uses of the compounds disclosed herein for use in treating or preventing a viral infection in a subject in need thereof. For example, provided herein are uses of the compounds disclosed herein for use in treating a viral infection in a subject in need thereof.

In some embodiments, the viral infection is a paramyxoviridae virus infection. As such, in some embodiments, the present disclosure provides methods for treating a paramyxoviridae infection in a subject (e.g., a human) in need thereof, the method comprising administering to the subject a compound disclosed herein. Paramyxoviridae viruses include, but are not limited to Nipah virus, Hendra virus, measles, mumps, and parainfluenze virus.

In some embodiments, the viral infection is a pneumoviridae virus infection. As such, in some embodiments, the present disclosure provides a method of treating a pneumoviridae virus infection in a human in need thereof, the method comprising administering to the human a compound provided herein. Pneumoviridae viruses include, but are not limited to, respiratory snycytial virus and human metapneumovirus. In some embodiments, the pneumoviridae virus infection is a respiratory syncytial virus infection. In some embodiments, the pneumoviridae virus infection is human metapneumovirus infection.

In some embodiments, the present disclosure provides a compound disclosed herein, for use in the treatment of a pneumoviridae virus infection in a human in need thereof. In some embodiments, the pneumoviridae virus infection is a respiratory syncytial virus infection. In some embodiments, the pneumoviridae virus infection is human metapneumovirus infection.

In some embodiments, the present disclosure provides methods for treating a RSV infection in a human in need thereof, the method comprising administering to the human a compound provided herein. In some embodiments, the human is suffering from a chronic respiratory syncytial viral infection. In some embodiments, the human is acutely infected with RSV.

In some embodiments, a method of inhibiting RSV replication is provided, wherein the method comprises administering to a human in need thereof, a compound disclosed herein, wherein the administration is by inhalation.

In some embodiments, the present disclosure provides a method for reducing the viral load associated with RSV infection, wherein the method comprises administering to a human infected with RSV a compound disclosed herein.

In some embodiments, the viral infection is a picornaviridae virus infection. As such, in some embodiments, the present disclosure provides a method of treating a picornaviridae virus infection in a human in need thereof, the method comprising administering to the human a compound of the present disclosure. Picornaviridae viruses are eneteroviruses causing a heterogeneous group of infections including herpangina, aseptic meningitis, a common-cold-like syndrome (human rhinovirus infection), a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis. In some embodiments, the Picornaviridae virus infection is human rhinovirus infection (HRV). In some embodiments, the Picornaviridae virus infection is HRV-A, HRV-B, or HRV-C infection.

In some embodiments, the present disclosure provides a compound, for use in the treatment of a picornaviridae virus infection in a human in need thereof. In some embodiments, the picornaviridae virus infection is human rhinovirus infection.

In some embodiments, the viral infection is a flaviviridae virus infection. As such, in some embodiments, the present disclosure provides a method of treating a flaviviridae virus infection in a human in need thereof, the method comprising administering to a human a compound described herein. Representative flaviviridae viruses include, but are not limited to, dengue, Yellow fever, West Nile, Zika, Japanese encephalitis virus, and Hepatitis C (HCV). In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a Japanese ensephalitis virus infection. In some embodiments, the flaviviridae virus infection is a hepatitis C virus infection.

In some embodiments, the present disclosure provides use of a compound disclosed herein for treatment of a flaviviridae virus infection in a human in need thereof. In some embodiments, the flaviviridae virus infection is a dengue virus infection. In some embodiments, the flaviviridae virus infection is a yellow fever virus infection. In some embodiments, the flaviviridae virus infection is a West Nile virus infection. In some embodiments, the flaviviridae virus infection is a zika virus infection. In some embodiments, the flaviviridae virus infection is a hepatitis C virus infection.

In some embodiments, the viral infection is a filoviridae virus infection. As such, in some embodiments, provided herein is a method of treating a filoviridae virus infection in a human in need thereof, the method comprising administering to the human a compound disclosed herein. Representative filoviridae viruses include, but are not limited to, ebola (variants Zaire, Bundibugio, Sudan, Tai forest, or Reston) and marburg. In some embodiments, the filoviridae virus infection is an ebola virus infection. In some embodiments, the filoviridae virus infection is a marburg virus infection.

In some embodiments, the present disclosure provides a compound for use in the treatment of a filoviridae virus infection in a human in need thereof. In some embodiments, the filoviridae virus infection is an ebola virus infection. In some embodiments, the filoviridae virus infection is a marburg virus infection.

In some embodiments, the viral infection is a coronavirus infection. As such, in some embodiments, provided herein is a method of treating a coronavirus infection in a human in need thereof, wherein the method comprises administering to the human a compound provided herein. In some embodiments, the coronavirus infection is a Severe Acute Respiratory Syndrome (SARS-CoV) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection. In some embodiments, the viral infection is a zoonotic coronavirus infection, In some embodiments, the viral infection is caused by a virus having at least 70% sequence homology to a viral polymerase selected from the group consisting of SARS-CoV polymerase, MERS-CoV polymerase and SARS-CoV-2. In some embodiments, the viral infection is caused by a virus having at least 80% sequence homology to a viral polymerase selected from the group consisting of SARS-CoV polymerase, MERS-CoV polymerase and SARS-CoV-2. In some embodiments, the viral infection is caused by a virus having at least 90% sequence homology to a viral polymerase selected from the group consisting of SARS-CoV polymerase, MERS-CoV polymerase and SARS-CoV-2. In some embodiments, the viral infection is caused by a virus having at least 95% sequence homology to a viral polymerase selected from the group consisting of SARS-CoV polymerase, MERS-CoV polymerase and SARS-CoV-2.

In some embodiments, the viral infection is caused by a variant of SARS-CoV-2, for example by the B.1.1.7 variant (the UK variant), B.1.351 variant (the South African variant), P.1 variant (the Brazil variant), B.1.1.7 with E484K variant, B.1.1.207 variant, B.1.1.317 variant, B.1.1.318 variant, B.1.429 variant, B.1.525 variant, or P.3 variant. In some embodiments, the viral infection is caused by the B.1.1.7 variant of SARS-CoV-2. In some embodiments, the viral infection is caused by the B.1.351 variant of SARS-CoV-2. In some embodiments, the viral infection is caused by the P.1 variant of SARS-CoV-2.

In some embodiments, the present disclosure provides a compound for use in the treatment of a coronavirus virus infection in a human in need thereof. In some embodiments, the coronavirus infection is a Severe Acute Respiratory Syndrome (SARS) infection, Middle Eastern Respiratory Syndrome (MERS) infection, SARS-CoV-2 infection, other human coronavirus (229E, NL63, OC43, HKU1, or WIV1) infections, zoonotic coronavirus (PEDV or HKU CoV isolates such as HKU3, HKU5, or HKU9) infections. In some embodiments, the viral infection is a Severe Acute Respiratory Syndrome (SARS) infection. In some embodiments, the viral infection is a Middle Eastern Respiratory Syndrome (MERS) infection. In some embodiments, the viral infection is SARS-CoV-2 infection (COVID19).

In some embodiments, the viral infection is an arenaviridae virus infection. As such, in some embodiments, the disclosure provides a method of treating an arenaviridae virus infection in a human in need thereof, the method comprising administering to the human a compound disclosed herein. In some embodiments, the arenaviridae virus infection is a Lassa infection or a Junin infection.

In some embodiments, the present disclosure provides a compound for use in the treatment of an arenaviridae virus infection in a human in need thereof. In some embodiments, the arenaviridae virus infection is a Lassa infection or a Junin infection.

In some embodiments, the viral infection is an orthomyxovirus infection, for example, an influenza virus infection. In some embodiments, the viral infection is an influenza virus A, influenza virus B, or influenza virus C infection.

As described more fully herein, the compounds described herein can be administered with one or more additional therapeutic agent(s) to an individual (e.g., a human) infected with a viral infection. The additional therapeutic agent(s) can be administered to the infected individual at the same time as the compound of the present disclosure or before or after administration of the compound of the present disclosure.

IX. Combination Therapy

The compounds described herein can also be used in combination with one or more additional therapeutic agents. As such, also provided herein are methods of treatment of a viral infection in a subject in need thereof, wherein the methods comprise administering to the subject a compound disclosed therein and a therapeutically effective amount of one or more additional therapeutic agents.

In some embodiments, the additional therapeutic agent is an antiviral agent. Any suitable antiviral agent can be used in the methods described herein. In some embodiments, the antiviral agent is selected from the group consisting of 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, HCV NS5A/NS5B inhibitors, influenza virus inhibitors, interferons, immunostimulators, oligonucleotides, antimitotic inhibitors, and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, β-D-N4-hydroxycytidine or a combination thereof.

In some embodiments, the additional therapeutic agent is a pyrophosphate analogue. For example, in some embodiments, the additional therapeutic agent is foscarnet or phosphonoacetic acid. In some embodiments, the additional therapeutic agent is foscarnet.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is a protease inhibitor. In some embodiments, the protease inhibitor is a HIV protease inhibitor. For example, in some embodiments, the antiviral agent is selected from the group consisting of saquinavir, ritonavir, indinavir, nelfinavir, amprenavir, lopinavir, atazanavir, fosamprenavir, darunavir, tipranavir, cobicistat, and combinations thereof. In some embodiments, the antiviral agent is selected from the group consisting of saquinavir, ritonavir, indinavir, nelfinavir, amprenavir, lopinavir, atazanavir, fosamprenavir, darunavir, tipranavir, and combinations thereof. In some embodiments, the protease inhibitor is a HCV NS3/4A protease inhibitor. For example, in some embodiments, the additional therapeutic agent is selected from the group consisting of voxilaprevir, asunaprevir, boceprevir, paritaprevir, simeprevir, telaprevir, vaniprevir, grazoprevir, ribavirin, danoprevir, faldaprevir, vedroprevir, sovaprevir, deldeprevir, narlaprevir and combinations thereof. In some embodiments, the additional therapeutic agent is selected from the group consisting of voxilaprevir, asunaprevir, boceprevir, paritaprevir, simeprevir, telaprevir, vaniprevir, grazoprevir, and combinations thereof.

In some embodiments, the additional therapeutic agent is an integrase inhibitor. For example, in some embodiments, the additional therapeutic agent is selected from the group consisting of raltegravir, dolutegravir, elvitegravir, abacavir, lamivudine, and combinations thereof. In some embodiments, the additional therapeutic agent is selected from the group consisting of bictegravir, raltegravir, dolutegravir, cabotegravir, elvitegravir, and combinations thereof. In some embodiments, the additional therapeutic agent is selected from the group consisting of bictegravir, dolutegravir, and cabotegravir, and combinations thereof. In some embodiments, the additional therapeutic agent is bictegravir.

In some embodiments, the additional therapeutic agent is an entry inhibitor. For example, in some embodiments, the additional therapeutic agent is selected from the group consisting of docosanol, enfuvirtide, maraviroc, ibalizumab, fostemsavir, leronlimab, ibalizumab, fostemsavir, leronlimab, palivizumab, respiratory syncytial virus immune globulin, intravenous [RSV-IGIV], varicella-zoster immunoglobulin [VariZIG], varicella-zoster immune globulin [VZIG]), and combinations thereof.

In some embodiments, the additional therapeutic agent is an acyclic guanosine analogue. For example, in some embodiments, the additional therapeutic agent is selected from the group consisting of acyclovir, ganciclovir, valacyclovir (also known as valaciclovir), valganciclovir, penciclovir, famciclovir, and combinations thereof.

In some embodiments, the additional therapeutic agent is an acyclic nucleoside phosphonate analogues. For example, in some embodiments, the additional therapeutic agent is selected from a group consisting of cidofovir, adefovir, adefovir dipivoxil, tenofovir, TDF, emtricitabine, efavirenz, rilpivirine, elvitegravir, and combinations thereof. In some embodiment, the additional therapeutic agent is selected from the group consisting of cidofovir, adefovir, adefovir dipivoxil, tenofovir, TDF, and combinations thereof. In some embodiment, the additional therapeutic agent is selected from the group consisting of cidofovir, adefovir dipivoxil, TDF, and combinations thereof.

In some embodiments, the additional therapeutic agent is a HCV NS5A/NS5B inhibitor. In some embodiments, the additional therapeutic agent is a NS3/4A protease inhibitor. In some embodiments, the additional therapeutic agent is a NS5A protein inhibitor. In some embodiments, the additional therapeutic agent is a NS5B polymerase inhibitor of the nucleoside/nucleotide type. In some embodiments, the additional therapeutic agent is a NS5B polymerase inhibitor of the nonnucleoside type. In some embodiments, the additional therapeutic agent is selected from the group consisting of daclatasvir, ledipasvir, velpatasvir, ombitasvir, elbasvir, sofosbuvir, dasabuvir, ribavirin, asunaprevir, simeprevir, paritaprevir, ritonavir, elbasvir, grazoprevir, AT-527, and combinations thereof. In some embodiments, the additional therapeutic agent is selected from the group consisting of daclatasvir, ledipasvir, velpatasvir, ombitasvir, elbasvir, sofosbuvir, dasabuvir, and combinations thereof.

In some embodiments, the additional therapeutic agent is an influenza virus inhibitor. In some embodiments, the additional therapeutic agent is a matrix 2 inhibitor. For example, in some embodiments, the additional therapeutic agent is selected from the group consisting of amantadine, rimantadine, and combinations thereof. In some embodiments, the additional therapeutic agent is a neuraminidase inhibitor. For example, in some embodiments, the additional therapeutic agent is selected from the group consisting of zanamivir, oseltamivir, peramivir, laninamivir octanoate, and combinations thereof. In some embodiments, the additional therapeutic agent is a polymerase inhibitor. For example, in some embodiments, the additional therapeutic agent is selected from the group consisting of ribavirin, favipiravir, and combinations thereof. In some embodiments, the additional therapeutic agent is selected from the group consisting of amantadine, rimantadine, arbidol (umifenovir), baloxavir marboxil, oseltamivir, peramivir, ingavirin, laninamivir octanoate, zanamivir, favipiravir, ribavirin, and combinations thereof. In some embodiments, the additional therapeutic agent is selected from the group consisting of amantadine, rimantadine, zanamivir, oseltamivir, peramivir, laninamivir octanoate, ribavirin, favipiravir, and combinations thereof.

In some embodiments, the additional therapeutic agent is an interferon. In some embodiments, the additional therapeutic agent is selected from the group consisting of interferon alfacon 1, interferon alfa 1b, interferon alfa 2a, interferon alfa 2b, pegylated interferon alfacon 1, pegylated interferon alfa 1b, pegylated interferon alfa 2a (PegIFNα-2a), and PegIFNα-2b. e embodiments, the additional therapeutic agent is selected from the group consisting of interferon alfacon 1, interferon alfa 1b, interferon alfa 2a, interferon alfa 2b, pegylated interferon alfa 2a (PegIFNα-2a), and PegIFNα-2b. In some embodiments, the additional therapeutic agent is selected from the group consisting of interferon alfacon 1, pegylated interferon alfa 2a (PegIFNα-2a), PegIFNα-2b, and ribavirin. In some embodiments, the additional therapeutic agent is pegylated interferon alfa-2a, pegylated interferon alfa-2b, or a combination thereof.

In some embodiments, the additional therapeutic agent is an immunostimulatory agent. In some embodiments, the additional therapeutic agent is an oligonucleotide. In some embodiments, the additional therapeutic agent is an antimitotic inhibitor. For example, in some embodiments, the additional therapeutic agent is selected from the group consisting of fomivirsen, podofilox, imiquimod, sinecatechins, and combinations thereof.

In some embodiments, the additional therapeutic agent is selected from the group consisting of besifovir, nitazoxanide, REGN2222, doravirine, sofosbuvir, velpatasvir, daclatasvir, asunaprevir, beclabuvir, FV100, and letermovir, and combinations thereof.

In some embodiments, the additional therapeutic agent is an agent for treatment of RSV. For example, in some embodiments, the antiviral agent is ribavirin, ALS-8112 or presatovir. For example, in some embodiments, the antiviral agent is ALS-8112 or presatovir.

In some embodiments, the additional therapeutic agent is an agent for treatment of picornavirus. In some embodiments, the additional therapeutic agent is selected from the group consisting of hydantoin, guanidine hydrochloride, L-buthionine sulfoximine, Py-11, and combinations thereof. In some embodiments, the additional therapeutic agent is a picomavirus polymerase inhibitor. In some embodiments, the additional therapeutic agent is rupintrivir.

In some embodiments, the additional therapeutic agent is an agent for treatment of malaria. In some embodiments, the additional therapeutic agent is chloroquine.

In some embodiments, the additional therapeutic agent is selected from the group consisting of hydroxychloroquine, chloroquine, artemether, lumefantrine, atovaquone, proguanil, tafenoquine, pyronaridine, artesunate, artenimol, piperaquine, artesunate, amodiaquine, pyronaridine, artesunate, halofantrine, quinine sulfate, mefloquine, solithromycin, pyrimethamine, MMV-390048, ferroquine, artefenomel mesylate, ganaplacide, DSM-265, cipargamin, artemisone, and combinations thereof.

In some embodiments, the additional therapeutic agent is an agent for treatment of coronavirus. In some embodiments, the additional therapeutic agent is selected from a group consisting of IFX-1, FM-201, CYNK-001, DPP4-Fc, ranpimase, nafamostat, LB-2, AM-1, anti-viroporins, and combinations thereof.

In some embodiments, the additional therapeutic agent is an agent for treatment of ebola virus. For example, in some embodiments, the additional therapeutic agent is selected from the group consisting of ribavirin, palivizumab, motavizumab, RSV-IGIV (RespiGam®), MEDI-557, A-60444, MDT-637, BMS-433771, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), favipiravir (also known as T-705 or Avigan), T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), JK-05, TKM-Ebola, ZMapp, rNAPc2, VRC-EBOADC076-00-VP, OS-2966, MVA-BN filo, brincidofovir, Vaxart adenovirus vector 5-based ebola vaccine, Ad26-ZEBOV, FiloVax vaccine, GOVX-E301, GOVX-E302, ebola virus entry inhibitors (NPC1 inhibitors), rVSV-EBOV, and combinations thereof. In some embodiments, the additional therapeutic agent is ZMapp, mAB114, REGEN-EB3, and combinations thereof.

In some embodiments, the additional therapeutic agent is an agent for treatment of HCV. In some embodiments, the additional therapeutic agent is a HCV polymerase inhibitor. For example, in some embodiments, the additional therapeutic agent is selected from the group consisting of sofosbuvir, GS-6620, PSI-938, ribavirin, tegobuvir, radalbuvir, MK-0608, and combinations thereof. In some embodiments, the additional therapeutic agent is a HCV protease inhibitor. For example, in some embodiments, the additional therapeutic agent is selected from the group consisting of such as GS-9256, vedroprevir, voxilaprevir, and combinations thereof.

In some embodiments, the additional therapeutic agent is a NS5A inhibitor. For example, in some embodiments, the additional therapeutic agent is selected from the group consisting of ledipasvir, velpatasvir, and combinations thereof.

In some embodiments, the additional therapeutic agent is an anti HBV agent. For example, in some embodiments, the additional therapeutic agent is tenofovir disoproxil fumarate and emtricitabine, or a combination thereof. Examples of additional anti HBV agents include but are not limited to alpha-hydroxytropolones, amdoxovir, antroquinonol, beta-hydroxycytosine nucleosides, ARB-199, CCC-0975, ccc-R08, elvucitabine, ezetimibe, cyclosporin A, gentiopicrin (gentiopicroside), HH-003, hepalatide, JNJ-56136379, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbama, IBPB-006IA, Hepuyinfen, DasKloster 0014-01, ISA-204, Jiangantai (Ganxikang), MIV-210, OB-AI-004, PF-06, picroside, DasKloster-0039, hepulantai, IMB-2613, TCM-800B, reduced glutathione, RO-6864018, RG-7834, QL-007sofosbuvir, ledipasvir, UB-551, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche). In some embodiments, the additional therapeutic agent is a HBV polymerase inhibitor. Examples of HBV DNA polymerase inhibitors include, but are not limited to, adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovir disoproxil aspartate, tenofovir disoproxil orotate, and HS-10234. In some embodiments, the additional therapeutic agent is a HBV capsid inhibitor.

In some embodiments, the additional therapeutic agent is an agent for treatment of HIV. In some embodiments, the additional therapeutic agent is selected from the group consisting of HIV protease inhibitors, HIV integrase inhibitors, entry inhibitors, HIV nucleoside reverse transcriptase inhibitors, HIV nonnucleoside reverse transcriptase inhibitors, acyclic nucleoside phosphonate analogues, and combinations thereof.

In some embodiments, the additional therapeutic agent is selected from the group consisting of HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, immunomodulators, immunotherapeutic agents, antibody-drug conjugates, gene modifiers, gene editors (such as CRISPR/Cas9, zinc finger nucleases, homing nucleases, synthetic nucleases, TALENs), and cell therapies (such as chimeric antigen receptor T-cell, CAR-T, and engineered T cell receptors, TCR-T, autologous T cell therapies).

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, capsid inhibitors, immune-based therapies, PI3K inhibitors, HIV antibodies, and bispecific antibodies, and "antibody-like" therapeutic proteins, and combinations thereof.

In some embodiments, the additional therapeutic agent is a HIV combination drug. Examples of the HIV combination drugs include, but are not limited to ATRIPLA® (efavirenz, tenofovir disoproxil fumarate, and emtricitabine); BIKTARVY® (bictegravir, emtricitabine, and tenofovir alafenamide); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); SYMTUZA® (darunavir, tenofovir alafenamide hemifumarate, emtricitabine, and cobicistat); SYMFI™ (efavirenz, lamivudine, and tenofovir disoproxil fumarate); CIMDU™ (lamivudine and tenofovir disoproxil fumarate); tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); TRIZ- IVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dapivirine+levonorgestrel, dolutegravir+lamivudine, dolutegravir+emtricitabine+tenofovir alafenamide, elsulfavirine+emtricitabine+tenofovir disoproxil, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine.

In some embodiments, the additional therapeutic agent is a HIV protease inhibitor. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat, ASC-09, AEBL-2, MK-8718, GS-9500, GS-1156, and combinations thereof. For example, in some embodiments the additional therapeutic agent is selected from the group consisting of saquinavir, ritonavir, indinavir, nelfinavir, amprenavir, lopinavir, atazanavir, fosamprenavir, darunavir, tipranavir, cobicistat. In some embodiments, the additional therapeutic agent is selected from the group consisting of amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, DG-17, TMB-657 (PPL-100), T-169, BL-008, MK-8122, TMB-607, TMC-310911, and combinations thereof.

In some embodiments, the additional therapeutic agent is a HIV integrase inhibitor. For example, in some embodiment, the additional therapeutic agent is selected from the group consisting of raltegravir, elvitegravir, dolutegravir, abacavir, lamivudine, bictegravir and combinations thereof. In some embodiment, the additional therapeutic agent is bictegravir. In some embodiments, the additional therapeutic agent is selected from a group consisting of bictegravir, elvitegravir, curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, dolutegravir, JTK-351, bictegravir, AVX-15567, BMS-986197, cabotegravir (long-acting injectable), diketo quinolin-4-1 derivatives, integrase-LEDGF inhibitor, ledgins, M-522, M-532, NSC-310217, NSC-371056, NSC-48240, NSC-642710, NSC-699171, NSC-699172, NSC-699173, NSC-699174, stilbenedisulfonic acid, T-169, VM-3500, cabotegravir, and combinations thereof.

In some embodiments, the additional therapeutic agent is a HIV entry inhibitor. For example, in some embodiments, the additional therapeutic agent is selected from the group consisting of enfuvirtide, maraviroc, and combinations thereof. Further examples of HIV entry inhibitors include, but are not limited to, cenicriviroc, CCR5 inhibitors, gp41 inhibitors, CD4 attachment inhibitors, DS-003 (BMS-599793), gp120 inhibitors, and CXCR4 inhibitors. Examples of CCR5 inhibitors include aplaviroc, vicriviroc, maraviroc, cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, and vMIP (Haimipu). Examples of CXCR4 inhibitors include plerixafor, ALT-1188, N15 peptide, and vMIP (Haimipu).

In some embodiments, the additional therapeutic agent is a HIV nucleoside reverse transcriptase inhibitors. In some embodiments, the additional therapeutic agent is a HIV nonnucleoside reverse transcriptase inhibitors. In some embodiments, the additional therapeutic agent is an acyclic nucleoside phosphonate analogue. In some embodiments, the additional therapeutic agent is a HIV capsid inhibitor.

In some embodiments, the additional therapeutic agent is a HIV nucleoside or nucleotide inhibitor of reverse transcriptase. For example, the additional therapeutic agent is selected from the group consisting of adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, islatravir, lamivudine, phosphazid, stavudine, zalcitabine, zidovudine, rovafovir etalafenamide (GS-9131), GS-9148, MK-8504, MK-8591, MK-858, VM-2500, KP-1461, and combinations thereof.

In some embodiments, the additional therapeutic agent is a HIV non-nucleoside or non-nucleotide inhibitor of reverse transcriptase. For example, the additional agent is selected from the group consisting of dapivirine, delavirdine, delavirdine mesylate, doravirine, efavirenz, etravirine, lentinan, MK-8583, nevirapine, rilpivirine, TMC-278LA, ACC-007, AIC-292, KM-023, PC-1005, elsulfavirine rilp (VM-1500), combinations thereof.

In some embodiments, the additional therapeutic agents are selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

In some embodiments, the additional therapeutic agent is selected from the group consisting of colistin, valrubicin, icatibant, bepotastine, epirubicin, epoprosetnol, vapreotide, aprepitant, caspofungin, perphenazine, atazanavir, efavirenz, ritonavir, acyclovir, ganciclovir, penciclovir, prulifloxacin, bictegravir, nelfinavir, tegobuvi, nelfinavir, praziquantel, pitavastatin, perampanel, eszopiclone, and zopiclone.

In some embodiments, the additional therapeutic agent is an inhibitor of Bruton tyrosine kinase (BTK, AGMX1, AT, ATK, BPK, IGHD3, IMDI, PSCTK1, XLA; NCBI Gene ID: 695). For example, in some embodiments, the additional therapeutic agent is selected from the group consisting of (S)-6-amino-9-(1-(but-2-ynoyl)pyrrolidin-3-yl)-7-(4-phenoxyphenyl)-7H-purin-8(9H)-one, acalabrutinib (ACP-196), BGB-3111, CB988, HM71224, ibrutinib (Imbruvica), M-2951 (evobrutinib), M7583, tirabrutinib (ONO-4059), PRN-1008, spebrutinib (CC-292), TAK-020, vecabrutinib, ARQ-531, SHR-1459, DTRMWXHS-12, TAS-5315, AZD6738, calquence, danvatirsen, and combinations thereof. In some embodiments, the additional therapeutic agent is selected from a group consisting of tirabrutinib, ibrutinib, acalabrutinib, and combinations thereof. In some embodiments, the additional therapeutic agent is selected from a group consisting of tirabrutinib, ibrutinib, and combinations thereof. In some embodiments, the additional therapeutic agent is tyrphostin A9 (A9).

In some embodiments, the additional therapeutic agent is a KRAS inhibitor. For example, in some embodiments, the additional therapeutic agent is selected from the group consisting of AMG-510, COTI-219, MRTX-1257, ARS-3248, ARS-853, WDB-178, BI-3406, BI-1701963, ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-NH2), KRpep-2d (Ac-RRRRCPLYISYDPVCRRRR-NH2), and combinations thereof.

In some embodiments, the additional therapeutic agent is a proteasome inhibitor. For example, in some embodiments, the additional therapeutic agent is selected from a group consisting of ixazomib, carfilzomib, marizomib, bortezomib, and combinations thereof. in some embodiments, the additional therapeutic agent is carfilzomib.

In some embodiments, the additional therapeutic agent is a vaccine. For example, in some embodiments, the additional therapeutic agent is a DNA vaccine, RNA vaccine, live-attenuated vaccine, therapeutic vaccine, prophylactic vaccine, protein based vaccine, or a combination thereof. In some embodiments, the additional therapeutic agent is mRNA-1273. In some embodiments, the additional therapeutic agent is INO-4800 or INO-4700. In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a HBV vaccine, for example pediarix, engerix-B, and recombivax HB. In some embodiments, the additional therapeutic agent is a VZV vaccine, for example zostavax and varivax. In some embodiments, the additional therapeutic agent is a HPV vaccine, for example cervarix, gardasil 9, and gardasil. In some embodiments, the additional therapeutic agent is an influenza virus vaccine. For example, a (i) monovalent vaccine for influenza A (e.g., influenza A [H5N1] virus monovalent vaccine and influenza A [H1N1] 2009 virus monovalent vaccines), (ii) trivalent vaccine for influenza A and B viruses (e.g., Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g., Adenovirus Type 4 and Type 7 Vaccine, Live, Oral). In some embodiments, the additional therapeutic agent is a rotavirus vaccine (e.g., Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g., Havrix and Vaqta). In some embodiments, the additional therapeutic agent is poliovirus vaccines (e.g., Kinrix, Quadracel, and Ipol). In some embodiments, the additional therapeutic agent is a yellow fever virus vaccine (e.g., YF-Vax). In some embodiments, the additional therapeutic agent is a Japanese encephalitis virus vaccines (e.g., Ixiaro and JE-Vax). In some embodiments, the additional therapeutic agent is a measles vaccine (e.g., M-M-R II and ProQuad). In some embodiments, the additional therapeutic agent is a mumps vaccine (e.g., M-M-R II and ProQuad). In some embodiments, the additional therapeutic agent is a rubella vaccine (e.g., M-M-R II and ProQuad). In some embodiments, the additional therapeutic agent is a varicella vaccine (e.g., ProQuad). In some embodiments, the additional therapeutic agent is a rabies vaccine (e.g., Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g., HEV239). In some embodiments, the additional therapeutic agent is a 2019-nCov vaccine.

In some embodiments, the additional therapeutic agent is an antibody, for example a monoclonal antibody. For example, the additional therapeutic agent is an antibody against 2019-nCov selected from the group consisting of the Regeneron antibodies, the Wuxi Antibodies, the Vir Biotechnology Antibodies, antibodies that target the SARS-CoV-2 spike protein, antibodies that can neutralize SARS-CoV-2 (SARS-CoV-2 neutralizing antibodies), and combinations thereof. In some embodiments, the additional therapeutic agent is anti-SARS-CoV antibody CR-3022. In some embodiments, the additional therapeutic agent is a PD-1 antibody.

In some embodiments, the additional therapeutic agent is recombinant cytokine gene-derived protein injection.

In some embodiments, the additional therapeutic agent is a polymerase inhibitor. In some embodiments, the additional therapeutic agent is a DNA polymerase inhibitor. For example, in some embodiments, the additional therapeutic agent is cidofovir. In some embodiments, the additional therapeutic agent is a RNA polymerase inhibitor. For example, in some embodiments, the additional therapeutic agent is selected from the group consisting of ribavirin, favipiravir, lamivudine, pimodivir and combination thereof.

In some embodiments, the additional therapeutic agent is selected from the group consisting of lopinavir, ritonavir, interferon-alpha-2b, ritonavir, arbidol, hydroxychloroquine, darunavir and cobicistat, abidol hydrochloride, oseltamivir, litonavir, emtricitabine, tenofovir alafenamide fumarate, baloxavir marboxil, ruxolitinib, and combinations thereof.

In some embodiments, the additional therapeutic agent is selected from the group consisting of 6'-fluorinated aristeromycin analogues, acyclovir fleximer analogues, disulfiram, thiopurine analogues, ASC09F, GC376, GC813, phenyliso-serine derivatives, neuroiminidase inhibitor analogues, pyrithiobac derivatives, bananins and 5-hydroxychromone derivatives, SSYA10-001, griffithsin, HR2P-M1, HR2P-M2, P21S10, Dihydrotanshinone E-64-C and E-64-D, OC43-HR2P, MERS-5HB, 229E-HR1P, 229E-HR2P, resveratrol, 1-thia-4-azaspiro[4.5]decan-3-one derivatives, gemcitabine hydrochloride, loperamide, recombinant interferons, cyclosporine A, alisporivir, imatinib mesylate, dasatinib, selumetinib, trametinib, rapamycin, saracatinib, chlorpromazine, triflupromazine, fluphenazine, thiethylperazine, promethazine, cyclophilin inhibitors, K11777, camostat, k22, teicoplanin derivatives, benzo-heterocyclic amine derivatives N30, mycophenolic acid, silvestrol, and combinations thereof.

In some embodiments, the additional therapeutic agent is an antibody. In some embodiments, the additional therapeutic agent is an antibody that binds to a coronavirus, for example an antibody that binds to SARS-CoV or MERS-CoV. In some embodiments, the additional therapeutic agent is a of 2019-nCoV virus antibody.

Compositions of the invention are also used in combination with other active ingredients. For the treatment of 2019-nCoV virus infections, preferably, the other active therapeutic agent is active against coronavirus infections, for example 2019-nCoV virus infections. The compounds and compositions of the present invention are also intended for use with general care provided patients with 2019-nCoV viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen or steroids), corticosteroids such as methylprednisolone, immonumodulatory medications (e.g., interferon), other small molecule or biologics antiviral agents targeting 2019-nCoV (such as but not limited to lopinavir/ritonavir, EIDD-1931, favipiravir, ribavirine, neutralizing antibodies, etc.), vaccines, pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis. In some embodiments, the additional therapeutic agent is dihydroartemisinin/piperaquine. In some embodiments, the additional therapeutic agent is EIDD-2801 (MH-4482, Molnupiravir).

In some embodiments, the additional therapeutic agent is an immunomodulator. Examples of immune-based therapies include toll-like receptors modulators such as tlr1, tlr2, tlr3, tlr4, tlr5, tlr6, tlr7, tlr8, tlr9, tlr10, tlr11, tlr12, and tlr13; programmed cell death protein 1 (Pd-1) modulators; programmed death-ligand 1 (Pd-L1) modulators; IL-15 modulators; DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, interleukin-15/Fc fusion protein, AM-0015, ALT-803, NIZ-985, NKTR-255, NKTR-262, NKTR-214, normferon, peginterferon alfa-2a, peginterferon alfa-2b, recombinant interleukin-15, Xmab-24306, RPI-MN, STING modulators, RIG-I modulators, NOD2 modulators, SB-9200, and IR-103. In some embodiments, the additional therapeutic agent is fingolimod, leflunomide, or a combination thereof. In some embodiments, the additional therapeutic agent is thalidomide.

In some embodiments, the additional therapeutic agent is an IL-6 inhibitor, for example tocilizumab, sarilumab, or a combination thereof.

In some embodiments, the additional therapeutic agent is an anti-TNF inhibitor. For example, the additional therapeutic agent is adalimumab, etanercept, golimumab, infliximab, or a combination thereof.

In some embodiments, the additional therapeutic agent is a JAK inhibitor, for example the additional therapeutic agent is baricitinib, filgotinib, olumiant, or a combination thereof.

In some embodiments, the additional therapeutic agent is an inflammation inhibitor, for example pirfenidone.

In some embodiments, the additional therapeutic agent is an antibiotic for secondary bacterial pneumonia. For example, the additional therapeutic agent is macrolide antibiotics (e.g., azithromycin, clarithromycin, and *Mycoplasma pneumoniae*), fluoroquinolones (e.g., ciprofloxacin and levofloxacin), tetracyclines (e.g., doxycycline and tetracycline), or a combination thereof.

In some embodiments, the compounds disclosed herein are used in combination with pneumonia standard of care (see e.g., Pediatric Community Pneumonia Guidelines, CID 2011:53 (1 October)). Treatment for pneumonia generally involves curing the infection and preventing complications. Specific treatment will depend on several factors, including the type and severity of pneumonia, age and overall health of the individuals. The options include: (i) antibiotics, (ii) cough medicine, and (iii) fever reducers/pain relievers (for e.g., aspirin, ibuprofen (Advil, Motrin IB, others) and acetaminophen (Tylenol, others)). In some embodiments, the additional therapeutic agent is bromhexine anti-cough.

In some embodiments, the compounds disclosed herein are used in combination with immunoglobulin from cured COVID-19 patients. In some embodiments, the compounds disclosed herein are used in combination with plasma transfusion. In some embodiments, the compounds disclosed herein are used in combination with stem cells.

In some embodiments, the additional therapeutic agent is an TLR agonist. Examples of TLR agonists include, but are not limited to, vesatolimod (GS-9620), GS-986, IR-103, lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.RO-7020531.

In some embodiments, the additional therapeutic agent is selected from the group consisting of bortezomid, flurazepam, ponatinib, sorafenib, paramethasone, clocortolone, flucloxacillin, sertindole, clevidipine, atorvastatin, cinolazepam, clofazimine, fosaprepitant, and combinations thereof.

In some embodiments, the additional therapeutic agent is carrimycin, suramin, triazavirin, dipyridamole, bevacizumab, meplazumab, GD31 (rhizobium), NLRP inflammasome inhibitor, or α-ketoamine. In some embodiments, the additional therapeutic agent is recombinant human angiotensin-converting enzyme 2 (rhACE2). In some embodiments, the additional therapeutic agent is viral macrophage inflammatory protein (vMIP).

In some embodiments, the additional therapeutic agent is an anti-viroporin therapeutic. For example, the additional therapeutic agent is BIT-314 or BIT-225. In some embodiments, the additional therapeutic agent is coronavirus E protein inhibitor. For example, the additional therapeutic agent is BIT-009. Further examples of additional therapeutic agents include those described in WO-2004112687, WO-2006135978, WO-2018145148, and WO-2009018609.

It is also possible to combine any compound of the invention with one or more additional active therapeutic agents in a unitary dosage form for simultaneous or sequential administration to a patient. The combination therapy may be administered as a simultaneous or sequential regimen. When administered sequentially, the combination may be administered in two or more administrations.

Co-administration of a compound of the invention with one or more other active therapeutic agents generally refers to simultaneous or sequential administration of a compound of the invention and one or more other active therapeutic agents, such that therapeutically effective amounts of the compound of the invention and one or more other active therapeutic agents are both present in the body of the patient.

Co-administration includes administration of unit dosages of the compounds of the invention before or after administration of unit dosages of one or more other active therapeutic agents, for example, administration of the compounds of the invention within seconds, minutes, or hours of the administration of one or more other active therapeutic agents. For example, a unit dose of a compound of the invention can be administered first, followed within seconds or minutes by administration of a unit dose of one or more other active therapeutic agents. Alternatively, a unit dose of one or more other therapeutic agents can be administered first, followed by administration of a unit dose of a compound of the invention within seconds or minutes. In some cases, it may be desirable to administer a unit dose of a compound of the invention first, followed, after a period of hours (e.g., 1-12 hours), by administration of a unit dose of one or more other active therapeutic agents. In other cases, it may be desirable to administer a unit dose of one or more other active therapeutic agents first, followed, after a period of hours (e.g., 1-12 hours), by administration of a unit dose of a compound of the invention.

The combination therapy may provide "synergy" and "synergistic", i.e., the effect achieved when the active ingredients used together is greater than the sum of the effects that results from using the compounds separately. A synergistic effect may be attained when the active ingredients are: (1) co-formulated and administered or delivered simultaneously in a combined formulation; (2) delivered by alternation or in parallel as separate formulations; or (3) by some other regimen. When delivered in alternation therapy, a synergistic effect may be attained when the compounds are administered or delivered sequentially, e.g., in separate tablets, pills or capsules, or by different injections in separate syringes. In general, during alternation therapy, an effective dosage of each active ingredient is administered sequentially, i.e., serially, whereas in combination therapy, effective dosages of two or more active ingredients are administered together. A synergistic anti-viral effect denotes an antiviral effect which is greater than the predicted purely additive effects of the individual compounds of the combination.

1. Combination Therapy for the Treatment of Pneumoviridae

The compounds provided herein are also used in combination with other active therapeutic agents. For the treatment of Pneumoviridae virus infections, preferably, the other active therapeutic agent is active against Pneumoviridae virus infections, particularly respiratory syncytial virus infections and/or metapneumovirus infections. Non-limiting examples of these other active therapeutic agents active against RSV are ribavirin, palivizumab, motavizumab, RSV-IGIV (RespiGam®), MEDI-557, A-60444 (also known as RSV604), MDT-637, BMS-433771, ALN-RSV0, ALX-0171 and mixtures thereof. Other non-limiting examples of other active therapeutic agents active against respiratory syncytial virus infections include respiratory syncytial virus protein F inhibitors, such as AK-0529; RV-521, ALX-0171, JNJ-53718678, BTA-585, and presatovir; RNA polymerase inhibitors, such as lumicitabine and ALS-8112; anti-RSV G protein antibodies, such as anti-G-protein mAb; viral replication inhibitors, such as nitazoxanide.

In some embodiments, the other active therapeutic agent may be a vaccine for the treatment or prevention of RSV, including but not limited to MVA-BN RSV, RSV-F, MEDI-8897, JNJ-64400141, DPX-RSV, SynGEM, GSK-3389245A, GSK-300389-1A, RSV-MEDI deltaM2-2 vaccine, VRC-RSVRGP084-00VP, Ad35-RSV-FA2, Ad26-RSV-FA2, and RSV fusion glycoprotein subunit vaccine.

Non-limiting examples of other active therapeutic agents active against metapneumovirus infections include sialidase modulators such as DAS-181; RNA polymerase inhibitors, such as ALS-8112; and antibodies for the treatment of Metapneumovirus infections, such as EV-046113.

In some embodiments, the other active therapeutic agent may be a vaccine for the treatment or prevention of metapneumovirus infections, including but not limited to mRNA-1653 and rHMPV-Pa vaccine.

2. Combination Therapy for the Treatment of Picornaviridae

The compounds provided herein are also used in combination with other active therapeutic agents. For the treatment of Picornaviridae virus infections, preferably, the other active therapeutic agent is active against Picornaviridae virus infections, particularly Enterovirus infections. Non-limiting examples of these other active therapeutic agents are capsid binding inhibitors such as pleconaril, BTA-798 (vapendavir) and other compounds disclosed by Wu, et al. (U.S. Pat. No. 7,078,403) and Watson (U.S. Pat. No. 7,166,604); fusion sialidase protein such as DAS-181; a capsid protein VP1 inhibitor such as VVX-003 and AZN-001; a viral protease inhibitor such as CW-33; a phosphatidylinositol 4 kinase beta inhibitor such as GSK-480 and GSK-533; anti-EV71 antibody.

In some embodiments, the other active therapeutic agent may be a vaccine for the treatment or prevention of Picornaviridae virus infections, including but not limited to EV71 vaccines, TAK-021, and EV-D68 adenovector-based vaccine.

3. Combination Therapy for Respiratory Infections

Many of the infections of the Pneumoviridae, Picornaviridae, and Coronaviridae viruses are respiratory infections. Therefore, additional active therapeutics used to treat respiratory symptoms and sequelae of infection may be used in combination with the compounds provided herein. The additional agents are preferably administered orally or by direct inhalation. For example, other preferred additional therapeutic agents in combination with the compounds provided herein for the treatment of viral respiratory infections include, but are not limited to, bronchodilators and corticosteroids.

Glucocorticoids

Glucocorticoids, which were first introduced as an asthma therapy in 1950 (Carryer, Journal of Allergy, 21, 282-287, 1950), remain the most potent and consistently effective therapy for this disease, although their mechanism of action is not yet fully understood (Morris, J. Allergy Clin. Immunol., 75 (1 Pt) 1-13, 1985). Unfortunately, oral glucocorticoid therapies are associated with profound undesirable side effects such as truncal obesity, hypertension, glaucoma, glucose intolerance, acceleration of cataract formation, bone mineral loss, and psychological effects, all of which limit their use as long-term therapeutic agents (Goodman and Gilman, 10th edition, 2001). A solution to systemic side effects is to deliver steroid drugs directly to the site of inflammation. Inhaled corticosteroids (ICS) have been developed to mitigate the severe adverse effects of oral steroids. Non-limiting examples of corticosteroids that may be used in combinations with the compounds provided herein are dexamethasone, dexamethasone sodium phosphate, fluorometholone, fluorometholone acetate, loteprednol, loteprednol etabonate, hydrocortisone, prednisolone, fludrocortisones, triamcinolone, triamcinolone acetonide, betamethasone, beclomethasone diproprionate, methylprednisolone, fluocinolone, fluocinolone acetonide, flunisolide, fluocortin-21-butylate, flumethasone, flumetasone pivalate, budesonide, halobetasol propionate, mometasone furoate, fluticasone, AZD-7594, ciclesonide; or a pharmaceutically acceptable salts thereof.

Anti-Inflammatory Agents

Other anti-inflammatory agents working through anti-inflammatory cascade mechanisms are also useful as additional therapeutic agents in combination with the compounds provided herein for the treatment of viral respiratory infections. Applying "anti-inflammatory signal transduction modulators" (referred to in this text as AIS™), like phosphodiesterase inhibitors (e.g., PDE-4, PDE-5, or PDE-7 specific), transcription factor inhibitors (e.g., blocking NFκB through IKK inhibition), or kinase inhibitors (e.g., blocking P38 MAP, JNK, PI3K, EGFR or Syk) is a logical approach to switching off inflammation as these small molecules target a limited number of common intracellular pathways—those signal transduction pathways that are critical points for the anti-inflammatory therapeutic intervention (see review by P. J. Barnes, 2006). These non-limiting additional therapeutic agents include: 5-(2,4-Difluoro-phenoxy)-1-isobutyl-1H-indazole-6-carboxylic acid (2-dimethylamino-ethyl)-amide (P38 Map kinase inhibitor ARRY-797); 3-Cyclopropylmethoxy-N-(3,5-dichloro-pyridin-4-yl)-4-difluorormethoxy-benzamide (PDE-4 inhibitor Roflumilast); 4-[2-(3-cyclopentyloxy-4-methoxyphenyl)-2-phenyl-ethyl]-pyridine (PDE-4 inhibitor CDP-840); N-(3,5-dichloro-4-pyridinyl)-4-(difluoromethoxy)-8-[(methylsulfonyl)amino]-1-dibenzofurancarboxamide (PDE-4 inhibitor Oglemilast); N-(3,5-Dichloro-pyridin-4-yl)-2-[1-(4-fluorobenzyl)-5-hydroxy-1H-indol-3-yl]-2-oxo-acetamide (PDE-4 inhibitor AWD 12-281); 8-Methoxy-2-trifluoromethyl-quinoline-5-carboxylic acid (3,5-dichloro-1-oxy-pyridin-4-yl)-amide (PDE-4 inhibitor Sch 351591); 4-[5-(4-Fluorophenyl)-2-(4-methanesulfinyl-phenyl)-1H-imidazol-4-yl]-pyridine (P38 inhibitor SB-203850); 4-[4-(4-Fluoro-phenyl)-1-(3-phenyl-propyl)-5-pyridin-4-yl-1H-imidazol-2-yl]-but-3-yn-1-ol (P38 inhibitor RWJ-67657); 4-Cyano-4-(3-cyclopentyloxy-4-methoxy-phenyl)-cyclohexanecarboxylic acid 2-diethylamino-ethyl ester (2-diethyl-ethyl ester prodrug of Cilomilast, PDE-4 inhibitor); (3-Chloro-4-fluorophenyl)-[7-methoxy-6-(3-morpholin-4-yl-propoxy)-quinazolin-4-yl]-amine (Gefitinib, EGFR inhibitor); and 4-(4-Methyl-piperazin-1-ylmethyl)-N-[4-methyl-3-(4-pyridin-3-yl-pyrimidin-2-ylamino)-phenyl]-benzamide (Imatinib, EGFR inhibitor).

β2-Adrenoreceptor Agonist Bronchodilators

Combinations comprising inhaled β2-adrenoreceptor agonist bronchodilators such as formoterol, albuterol or salmeterol with the compounds provided herein are also suitable, but non-limiting, combinations useful for the treatment of respiratory viral infections.

Combinations of inhaled β2-adrenoreceptor agonist bronchodilators such as formoterol or salmeterol with ICS's are also used to treat both the bronchoconstriction and the inflammation (Symbicort® and Advair®, respectively). The combinations comprising these ICS and β2-adrenoreceptor agonist combinations along with the compounds provided herein are also suitable, but non-limiting, combinations useful for the treatment of respiratory viral infections.

Other examples of Beta 2 adrenoceptor agonists are bedoradrine, vilanterol, indacaterol, olodaterol, tulobuterol, formoterol, abediterol, salbutamol, arformoterol, levalbuterol, fenoterol, and TD-5471.

Anticholinergics

For the treatment or prophylaxis of pulmonary bronchoconstriction, anticholinergics are of potential use and, therefore, useful as an additional therapeutic agent in combination with the compounds provided herein for the treatment of viral respiratory infections. These anticholinergics include, but are not limited to, antagonists of the muscarinic receptor (particularly of the M3 subtype) which have shown therapeutic efficacy in man for the control of cholinergic tone in COPD (Witek, 1999); 1-{4-Hydroxy-1-[3,3,3-tris-(4-fluoro-phenyl)-propionyl]-pyrrolidine-2-carbonyl}-pyrrolidine-2-carboxylic acid (1-methyl-piperidin-4-ylmethyl)-amide; 3-[3-(2-Diethylamino-acetoxy)-2-phenyl-propionyloxy]-8-isopropyl-8-methyl-8-azonia-bicyclo [3.2.1]octane (Ipratropium-N,N-diethylglycinate); 1-Cyclohexyl-3,4-dihydro-1H-isoquinoline-2-carboxylic acid 1-aza-bicyclo[2.2.2]oct-3-yl ester (Solifenacin); 2-Hydroxymethyl-4-methanesulfinyl-2-phenyl-butyric acid 1-aza-bicyclo[2.2.2]oct-3-yl ester (Revatropate); 2-{1-[2-(2,3-Dihydro-benzofuran-5-yl)-ethyl]-pyrrolidin-3-yl}-2,2-diphenyl-acetamide (Darifenacin); 4-Azepan-1-yl-2,2-diphenyl-butyramide (Buzepide); 7-[3-(2-Diethylamino-acetoxy)-2-phenyl-propionyloxy]-9-ethyl-9-methyl-3-oxa-9-azonia-tricyclo[3.3.1.02,4]nonane (Oxitropium-N,N-diethylglycinate); 7-[2-(2-Diethylamino-acetoxy)-2,2-di-thiophen-2-yl-acetoxy]-9,9-dimethyl-3-oxa-9-azonia-tricyclo[3.3.1.02,4]nonane (Tiotropium-N,N-diethylglycinate); Dimethylamino-acetic acid 2-(3-diisopropylamino-1-phenyl-propyl)-4-methyl-phenyl ester (Tolterodine-N,N-dimethylglycinate); 3-[4,4-Bis-(4-fluoro-phenyl)-2-oxo-imidazolidin-1-yl]-1-methyl-1-(2-oxo-2-pyridin-2-yl-ethyl)-pyrrolidinium; 1-[1-(3-Fluoro-benzyl)-piperidin-4-yl]-4,4-bis-(4-fluoro-phenyl)-imidazolidin-2-one; 1-Cyclooctyl-3-(3-methoxy-1-aza-bicyclo[2.2.2]oct-3-yl)-1-phenyl-prop-2-yn-1-ol; 3-[2-(2-Diethylamino-acetoxy)-2,2-di-thiophen-2-yl-acetoxy]-1-(3-phenoxy-propyl)-1-azonia-bicyclo[2.2.2]octane (Aclidinium-N,N-diethylglycinate); or (2-Diethylamino-acetoxy)-di-thiophen-2-yl-acetic acid 1-methyl-1-(2-phenoxy-ethyl)-piperidin-4-yl ester; revefenacin, glycopyrronium bromide, umeclidinium bromide, tiotropium bromide, aclidinium bromide, bencycloquidium bromide.

Mucolytic Agents

The compounds provided herein may also be combined with mucolytic agents to treat both the infection and symptoms of respiratory infections. A non-limiting example of a mucolytic agent is ambroxol. Similarly, the compounds may be combined with expectorants to treat both the infection and symptoms of respiratory infections. A non-limiting example of an expectorant is guaifenesin.

Nebulized hypertonic saline is used to improve immediate and long-term clearance of small airways in patients with lung diseases (Kuzik, *J. Pediatrics* 2007, 266). Thus, the compounds provided herein may also be combined with nebulized hypertonic saline particularly when the virus infection is complicated with bronchiolitis. The combination of the compound provided herein with hypertonic saline may also comprise any of the additional agents discussed above. In one embodiment, nebulized about 3% hypertonic saline is used.

4. Combination Therapy for the Treatment of Flaviviridae Virus Infections

The compounds and compositions provided herein are also used in combination with other active therapeutic agents. For the treatment of Flaviviridae virus infections, preferably, the other active therapeutic agent is active against Flaviviridae virus infections.

For treatment of the dengue virus infection, non-limiting examples of the other active therapeutic agents are host cell factor modulators, such as GBV-006; fenretinide ABX-220, BRM-211; alpha-glucosidase 1 inhibitors, such as celgosivir; platelet activating factor receptor (PAFR) antagonists, such as modipafant; cadherin-5/Factor Ia modulators, such as FX-06; NS4B inhibitors, such as JNJ-8359; viral RNA splicing modulators, such as ABX-202; a NS5 polymerase inhibitor; a NS3 protease inhibitor; and a TLR modulator.

In some embodiments, the other active therapeutic agent may be a vaccine for the treatment or prevention of dengue, including but not limited to TetraVax-DV, Dengvaxia®, DPIV-001, TAK-003, live attenuated dengue vaccine, tetravalent dengue fever vaccine, tetravalent DNA vaccine, rDEN2delta30-7169; and DENV-1 PIV.

5. Combination Therapy for the Treatment of Filoviridae Virus Infections

The compounds provided herein are also used in combination with other active therapeutic agents. For the treatment of Filoviridae virus infections, preferably, the other active therapeutic agent is active against Filoviridae virus infections, particularly Marburg virus, Ebola virus and Cueva virus infections. Non-limiting examples of these other active therapeutic agents are: ribavirin, amiodarone, dronedarone, verapamil, Ebola Convalescent Plasma (ECP), TKM-100201, BCX4430 ((2S,3S,4R,5R)-2-(4-amino-5H-pyrrolo[3,2-d]pyrimidin-7-yl)-5-(hydroxymethyl)pyrrolidine-3,4-diol), TKM-Ebola, T-705 monophosphate, T-705 diphosphate, T-705 triphosphate, FGI-106 (1-N,7-N-bis[3-(dimethylamino)propyl]-3,9-dimethylquinolino[8,7-h]quinolone-1,7-diamine), rNAPc2, OS-2966, brincidofovir, remdesivir; RNA polymerase inhibitors, such as galidesivir, favipiravir (also known as T-705 or Avigan), JK-05; host cell factor modulators, such as GMV-006; cadherin-5/factor Ia modulators, such as FX-06; and antibodies for the treatment of Ebola, such as REGN-3470-3471-3479 and ZMapp.

Other non-limiting active therapeutic agents active against Ebola include an alpha-glucosidase 1 inhibitor, a cathepsin B inhibitor, a CD29 antagonist, a dendritic ICAM-3 grabbing nonintegrin 1 inhibitor, an estrogen receptor antagonist, a factor VII antagonist HLA class II antigen modulator, a host cell factor modulator, a Interferon alpha ligand, a neutral alpha glucosidase AB inhibitor, a niemann-Pick C1 protein inhibitor, a nucleoprotein inhibitor, a polymerase cofactor VP35 inhibitor, a Serine protease inhibitor, a tissue factor inhibitor, a TLR-3 agonist, a viral envelope glycoprotein inhibitor, and an Ebola virus entry inhibitors (NPC1 inhibitors).

In some embodiments, the other active therapeutic agent may be a vaccine for the treatment or prevention of Ebola, including but not limited to VRC-EBOADC076-00-VP, adenovirus-based Ebola vaccine, rVSV-EBOV, rVSVN4CT1-EBOVGP, MVA-BN Filo+Ad26-ZEBOV regimen, INO-4212, VRC-EBODNA023-00-VP, VRC-EBOADC069-00-VP, GamEvac-combi vaccine, SRC VB Vector, HPIV3/EboGP vaccine, MVA-EBOZ, Ebola recombinant glycoprotein vaccine, Vaxart adenovirus vector 5-based Ebola vaccine, FiloVax vaccine, GOVX-E301, and GOVX-E302.

The compounds provided herein may also be used in combination with phosphoramidate morpholino oligomers (PMOs), which are synthetic antisense oligonucleotide analogs designed to interfere with translational processes by forming base-pair duplexes with specific RNA sequences. Examples of PMOs include but are not limited to AVI-7287, AVI-7288, AVI-7537, AVI-7539, AVI-6002, and AVI-6003.

The compounds provided herein are also intended for use with general care provided to patients with Filoviridae viral infections, including parenteral fluids (including dextrose saline and Ringer's lactate) and nutrition, antibiotic (including metronidazole and cephalosporin antibiotics, such as ceftriaxone and cefuroxime) and/or antifungal prophylaxis, fever and pain medication, antiemetic (such as metoclopramide) and/or antidiarrheal agents, vitamin and mineral supplements (including Vitamin K and zinc sulfate), anti-inflammatory agents (such as ibuprofen), pain medications, and medications for other common diseases in the patient population, such anti-malarial agents (including artemether and artesunate-lumefantrine combination therapy), typhoid (including quinolone antibiotics, such as ciprofloxacin, macrolide antibiotics, such as azithromycin, cephalosporin antibiotics, such as ceftriaxone, or aminopenicillins, such as ampicillin), or shigellosis.

X. Compound Preparation

In some embodiments, the present disclosure provides processes and intermediates useful for preparing the compounds provided herein or pharmaceutically acceptable salts thereof.

Compounds described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography.

During any of the processes for preparation of the compounds provided herein, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Skilled artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups.

The methods of the present disclosure generally provide a specific enantiomer or diastereomer as the desired product, although the stereochemistry of the enantiomer or diastereomer was not determined in all cases. When the stereochemistry of the specific stereocenter in the enantiomer or diastereomer is not determined, the compound is drawn without showing any stereochemistry at that specific stereocenter even though the compound can be substantially enantiomerically or disatereomerically pure.

Representative syntheses of compounds of the present disclosure are described in the schemes below, and the particular examples that follow.

The compounds of the present disclosure may be prepared using the methods disclosed herein and routine modifications thereof, which will be apparent to a skilled artisan given the disclosure herein and methods well known in the art. Conventional and well-known synthetic methods may be used in addition to the teachings herein. The synthesis of typical compounds described herein may be accomplished as described in the following examples. If available, reagents may be purchased commercially, e.g., from Sigma Aldrich or other chemical suppliers. In general, compounds described herein are typically stable and isolatable at room temperature and pressure. The compounds prepared herein can be purified using the methods known to the person of ordinary skill in the art, including those described herein. A skilled artisan will appreciate that when acids (e.g., TFA) are present in purification solvents, then the final product may be isolated as a salt (for e.g., TFA salt).

Method of Preparing Compounds of Formula Ib

In some embodiments, the disclosure provides method of making a compound of Formula Ib:

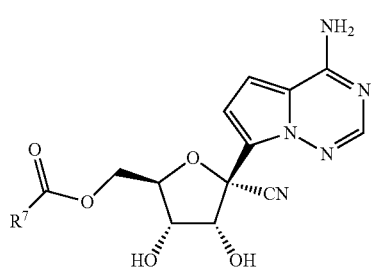

Formula Ib wherein:
R$^7$ is C$_1$-C$_8$ alkyl, C$_2$-C$_8$ alkenyl, C$_2$-C$_8$ alkynyl, C$_3$-C$_5$ carbocyclyl, C$_6$-C$_{10}$ aryl, or 5 to 6 membered heteroaryl containing 1, 2, or 3 heteroatoms selected form N, O, and S; and wherein the R$^7$ group is optionally substituted with one, two or three substituents independently selected from the group consisting of halogen, cyano, —N$_3$, —OR$^8$, —NR$^9$R$^{10}$, and phenyl optionally substituted with one, two or three substituents independently selected from halo, cyano, and C$_1$-C$_6$ alkyl;
each R is independently H, C$_1$-C$_6$ alkyl, C$_1$-C$_6$ haloalkyl, and C$_3$-C$_6$ cycloalkyl;
each R$^9$ is independently H, C$_1$-C$_6$ alkyl, C$_1$-C$_6$ haloalkyl, and C$_3$-C$_6$ cycloalkyl; and
each R$^{10}$ is independently H, C$_1$-C$_6$ alkyl, C$_1$-C$_6$ haloalkyl, and C$_3$-C$_6$ cycloalkyl;
the method comprising coupling a compound of Formula A:

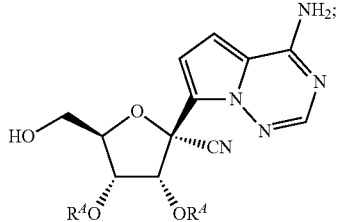

Formula A wherein each R$^A$ is independently a hydroxy protecting group or two R$^A$ groups on are joined to form a —C(R$^B$)$_2$— group, wherein R$^B$ is H, C$_1$-C$_8$ alkyl, phenyl or substituted phenyl;
with a coupling partner of Formula B:

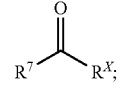

Formula B wherein R$^X$ is chloro, hydroxy, —OCOR$^Y$;
R$^Y$ is C$_1$-C$_8$ alkyl, C$_2$-C$_8$ alkenyl, C$_2$-C$_8$ alkynyl, C$_3$-C$_8$ carbocyclyl, C$_6$-C$_{10}$ aryl, or 5 to 6 membered heteroaryl containing 1, 2, or 3 heteroatoms selected form N, O, and S; and wherein the R$^Y$ group is optionally substituted with one, two or three substituents independently selected from the group consisting of halogen, cyano, —N$_3$, —OR$^{8'}$, —NR$^{9'}$R$^{10'}$, and phenyl optionally substituted with one, two or three substituents independently selected from halo, cyano, and C$_1$-C$_6$ alkyl;
each R$^{8'}$ is independently H, C$_1$-C$_6$ alkyl, C$_1$-C$_6$ haloalkyl, and C$_3$-C$_6$ cycloalkyl;
each R$^{9'}$ is independently H, C$_1$-C$_6$ alkyl, C$_1$-C$_6$ haloalkyl, and C$_3$-C$_6$ cycloalkyl; and
each R$^{10'}$ is independently H, C$_1$-C$_6$ alkyl, C$_1$-C$_6$ haloalkyl, and C$_3$-C$_6$ cycloalkyl.

In some embodiments, the disclosure provides methods of making the compound of Formula Ib:

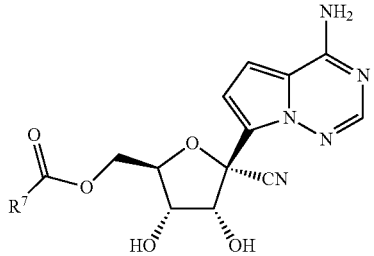

Formula Ib wherein R$^7$ is C$_1$-C$_8$ alkyl;

the method comprising coupling the compound of Formula A is:

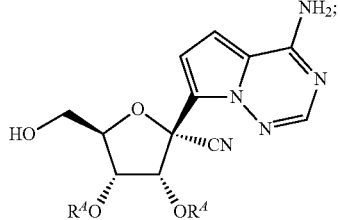

Formula A wherein each $R^A$ is independently a hydroxy protecting group or two $R^A$ groups on are joined to form a —$C(R^B)_2$— group, wherein $R^B$ is H, or $C_1$-$C_8$ alkyl;
with a coupling partner of Formula B is:

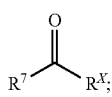

Formula B wherein $R^X$ is chloro, hydroxy, —$OCOR^Y$;
$R^Y$ is $C_1$-$C_8$ alkyl or $C_6$-$C_{10}$ aryl; and wherein the $R^Y$ group is optionally substituted with one, two or three substituents independently selected from the group consisting of halogen.

In some embodiments the disclosure provides methods of making the compound of Formula Ib:

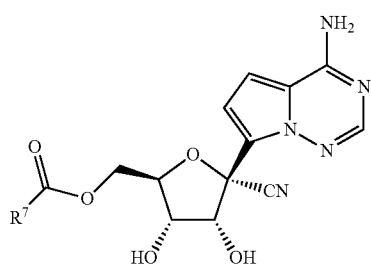

Formula Ib wherein $R^7$ is $C_1$-$C_3$ alkyl;
the method comprising coupling the compound of Formula A is:

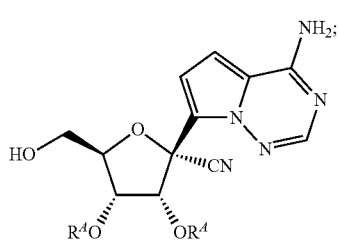

Formula A wherein each $R^A$ is independently a hydroxy protecting group or two $R^A$ groups on are joined to form a —$C(R^B)_2$— group, wherein $R^B$ is H, or $C_1$-$C_8$ alkyl;
with a coupling partner of Formula B is:

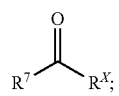

Formula B wherein $R^X$ is chloro, hydroxy, —$OCOR^Y$;
$R^Y$ is $C_1$-$C_3$ alkyl or phenyl; and wherein the phenyl is optionally substituted with one, two or three substituents independently selected from the group consisting of halogen.

In some embodiments the disclosure provides methods of making the compound of Formula Ib:

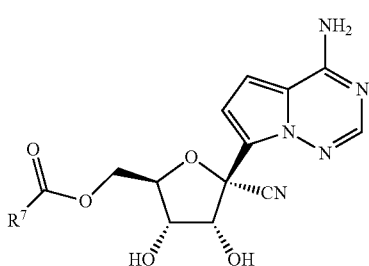

Formula Ib wherein $R^7$ is $C_3$ alkyl;
the method comprising coupling the compound of Formula A is:

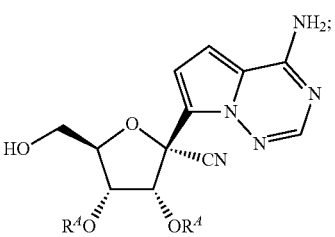

Formula A wherein each $R^A$ is independently a hydroxy protecting group or two $R^A$ groups on are joined to form a —$C(R^B)_2$— group, wherein $R^B$ is H, or $C_1$-$C_8$ alkyl;
with a coupling partner of Formula B is:

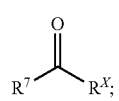

Formula B wherein $R^X$ is chloro, hydroxy, —$OCOR^Y$;
$R^Y$ is $C_3$ alkyl or phenyl; and wherein the phenyl is optionally substituted with one, two or three substituents independently selected from the group consisting of halogen.

In some embodiments the disclosure provides methods of making the compound of Formula Ib:

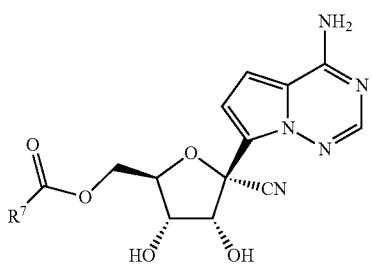

Formula Ib wherein $R^7$ is isopropyl;
the method comprising coupling the compound of Formula A is:

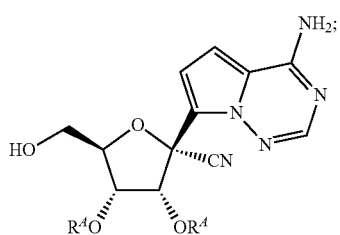

Formula A wherein the two $R^A$ groups on are joined to form a —$C(R^B)_2$— group, wherein $R^B$ is H or $C_1$-$C_3$ alkyl;
with a coupling partner of Formula B is:

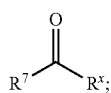

Formula B wherein $R^X$ is chloro, hydroxy, —$OCOR^Y$;
$R^Y$ is isopropyl or phenyl; and wherein the phenyl is optionally substituted with one, two or three substituents independently selected from the group consisting of halogen.

In some embodiments the disclosure provides methods of making the compound of Formula Ib:

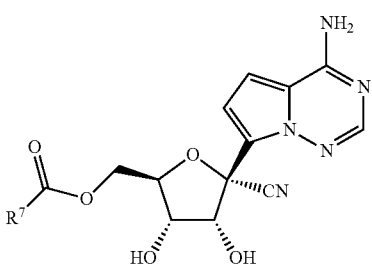

Formula Ib wherein $R^7$ is isopropyl, the method comprising coupling the compound of Formula A is:

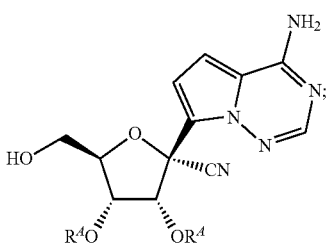

Formula A wherein the two $R^A$ groups on are joined to form a —$C(R^B)_2$— group, wherein $R^B$ is H or methyl;
with a coupling partner of Formula B is:

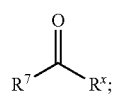

Formula B wherein $R^X$ is chloro, hydroxy, —$OCOR^Y$;
$R^Y$ is isopropyl or phenyl; and wherein the phenyl is optionally substituted with one, two or three chloro groups.

In some embodiments, coupling of the compound of Formula A with the coupling partner of Formula B, results in a compound of Formula C:

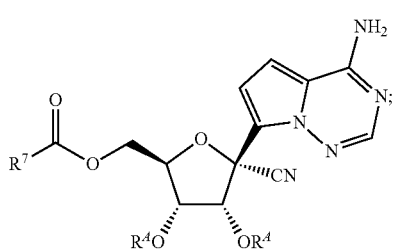

Formula C wherein $R^A$ and $R^7$ are each as defined herein for various embodiments of the method of making the compounds of Formula Ib.

In some embodiments, the method of making the compound of Formula Ib, further comprises deprotecting the compound of Formula C to obtain the compound of Formula Ib. In some embodiments, deprotection of the compound of Formula C comprises use of an acid. In some embodiments, use of an acid of general structure HX (where X is the conjugate base) for deprotection of the compound of Formula C results in a salt of the compound of Formula Ib (Formula Ib-HX). When the deprotected compound is obtained as a salt, optionally a free basing step may be performed. In some embodiments, the free basing step comprises treatment with a base.

Coupling Reaction of Formula A and Formula B

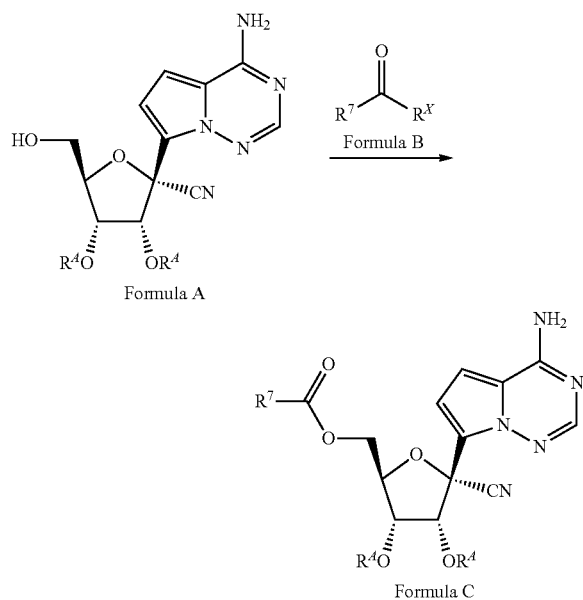

Formula A

Formula B

Formula C

The method of making the compound of Formula Ib provided herein comprise coupling the compound of Formula A with the coupling partner of Formula B.

In some embodiments, of the coupling partner of Formula B, $R^X$ is chloro. In some embodiments, $R^X$ is hydroxy. In some embodiments, $R^X$ is —$OCOR^Y$. In some embodiments, $R^X$ is —$OCOR^Y$; wherein $R^Y$ is same as $R^7$ or $R^Y$ is $C_6$-$C_{10}$ aryl optionally substituted with one, two or three substituents independently selected from the group consisting of halogen, cyano, —$N_3$, —$OR^{8'}$, —$NR^{9'}R^{10'}$, and phenyl optionally substituted with one, two or three substituents independently selected from halo, cyano, and $C_1$-$C_6$ alkyl. In some embodiments, $R^X$ is —$OCOR^Y$; wherein $R^Y$ is same as $R^7$ or R is $C_6$-$C_{10}$ aryl optionally substituted with one, two or three substituents; wherein each substituent is independently a halogen. In some embodiments, $R^X$ is —$OCOR^Y$; wherein $R^Y$ is same as $R^7$ or $R^Y$ is phenyl optionally substituted with one, two or three substituents; wherein each substituent is independently a halogen. In some embodiments, $R^X$ is —$OCOR^Y$; wherein $R^Y$ is same as $R^7$. In some embodiments, $R^X$ is —$OCOR^Y$; wherein $R^Y$ is phenyl optionally substituted with one, two or three substituents; wherein each substituent is independently a halogen. In some embodiments, $R^X$ is —$OCOR^Y$; wherein $R^Y$ is same as $R^7$ or R is phenyl optionally substituted with one, two or three chloro groups.

The coupling partner of Formula B can be used in any suitable amount. In some embodiments, the amount of Formula B is at least 1.0 eq. (mol/mol) with respect to the compound of Formula A. In some embodiments, the amount of Formula B is 0.1-10.0 eq. (mol/mol) with respect to the compound of Formula A. In some embodiments, the amount of Formula B is 0.5-5.0 eq. (mol/mol) with respect to the compound of Formula A. In some embodiments, the amount of Formula B is 1.0-2.0 eq. (mol/mol) with respect to the compound of Formula A. In some embodiments, the amount of Formula B is 1.0-1.5 eq. (mol/mol) with respect to the compound of Formula A. In some embodiments, the amount of Formula B is 1.2 eq. (mol/mol) with respect to the compound of Formula A.

In some embodiments, the coupling of the Formula A with the coupling partner of Formula B is done in presence of a catalyst. Any suitable catalyst can be used. In some embodiments, the catalyst is a nitrogenated heterocycle, azodicarboxylate, guanidinium and uronium-type coupling reagent, triphenylphosphine, tri-n-butylphosphine, or S,S-Bis(4,6-dimethyl-2-pyrimidinyl) carbodithioate.

In some embodiments, the coupling of the Formula A with the coupling partner of Formula B is done in presence of a catalyst; wherein the catalyst is a nitrogenated heterocycle. In some embodiments, the catalyst is 4-dimethylaminopyridine (DMAP), 1-methylimidazole, imidazole or pyridine. In some embodiments, the catalyst is 1-methylimidazole. In some embodiments, the catalyst is imidazole. In some embodiments, the catalyst is pyridine. In some embodiments, the catalyst is DMAP.

In some embodiments, the coupling of the Formula A with the coupling partner of Formula B is done in presence of a catalyst; wherein the catalyst is an azodicarboxylate. In some embodiments, the catalyst is 1-ethyl-3-(3-dimethylaminopropyl)carbodiimide, dicyclohexylcarbodiimide, diethyl azodicarboxylate, or diisopropyl azodicarboxylate. In some embodiments, the catalyst is 1-ethyl-3-(3-dimethylaminopropyl)carbodiimide. In some embodiments, the catalyst is dicyclohexylcarbodiimide. In some embodiments, the catalyst is diethyl azodicarboxylate. In some embodiments, the catalyst is diisopropyl azodicarboxylate.

In some embodiments, the coupling of the Formula A with the coupling partner of Formula B is done in presence of a catalyst; wherein the catalyst is a guanidinium and uronium-type coupling reagent. In some embodiments, the catalyst is N-[dimethylamino)-1H-1,2,3-triazolo[4,5-b]-pyridin-1-ylmethylene]-N-methylmethanaminium hexafluorophosphate N-oxide (HATU), N-[(1H-benzotriazol-1-yl)-(dimethylamino)-methylene]-N-methylmethanaminium hexafluorophosphate N-oxide (HBTU), N-[(1H-benzotriazol-1-yl)-(dimethylamino)-methylene]-N-methylmethanaminium tetrafluoroborate N-oxide (TBTU), 2-(2-oxo-1(2H)-pyridyl-1,1,3,3-tetramethyluronium tetrafluoroborate (TPTU), 0-[(cyano(ethoxycarbonyl)methyleneamino]-N,N,N',N'-tetramethyluronium tetrafluoroborate (TOTU), or (1-cyano-2-ethoxy-2-oxoethylidenaminooxy)dimethylamino-morpholino-carbenium hexafluorophosphate (COMU). In some embodiments, the catalyst is N-[dimethylamino)-1H-1,2,3-triazolo[4,5-b]-pyridin-1-ylmethylene]-N-methylmethanaminium hexafluorophosphate N-oxide (HATU). In some embodiments, the catalyst is HBTU. In some embodiments, the catalyst is TBTU. In some embodiments, the catalyst is TPTU. In some embodiments, the catalyst is TOTU. In some embodiments, the catalyst is COMU.

In some embodiments, the coupling of the Formula A with the coupling partner of Formula B is done in presence of a catalyst; wherein the catalyst is triphenylphosphine, tri-n-butylphosphine, or S,S-Bis(4,6-dimethyl-2-pyrimidinyl) carbodithioate. In some embodiments, the catalyst is triphenylphosphine. In some embodiments, the catalyst is tri-n-butylphosphine. In some embodiments, the catalyst is S,S-Bis(4,6-dimethyl-2-pyrimidinyl) carbodithioate.

The catalyst can be used in any suitable amount. In some embodiments the amount of catalyst is 1-100 mol % with respect to the compound of Formula A. In some embodiments the amount of catalyst is 1-50 mol % with respect to the compound of Formula A. In some embodiments the amount of catalyst is 1-10 mol % with respect to the compound of Formula A. In some embodiments the amount of catalyst is 1-5 mol % with respect to the compound of Formula A. In some embodiments the amount of catalyst is 3 mol % with respect to the compound of Formula A. In some embodiments, no catalyst is used.

In some embodiments, 1-10 mol % of DMAP is used as the catalyst for coupling of Formula A with Formula B. In some embodiments, 1-5 mol % of DMAP is used as the catalyst for coupling of Formula A with Formula B. In some embodiments, 3 mol % of DMAP is used as the catalyst for coupling of Formula A with Formula B.

In some embodiments, the coupling of the Formula A with the coupling partner of Formula B is done further in presence of a base. Any suitable base can be used. In some embodiments, the base used is an inorganic base. In some examples, the base is a carbonate, bicarbonate, metal dibasic phosphate, metal tribasic phosphate, or a nitrogen containing base.

In some embodiments, the base is a bicarbonate. In some embodiments, the base is lithium bicarbonate, sodium bicarbonate, potassium bicarbonate or a combination thereof. In some embodiments, the base is sodium bicarbonate, potassium bicarbonate or a combination thereof. In some embodiments, the base is lithium bicarbonate. In some embodiments, the base is sodium bicarbonate. In some example the base is potassium bicarbonate.

In some embodiments, the base is a carbonate. In some embodiments, the base is lithium carbonate, sodium carbonate, potassium carbonate, cesium carbonate, or a combination thereof. In some embodiments, the base is lithium carbonate, sodium carbonate, potassium carbonate, or a combination thereof. In some embodiments, the base is sodium carbonate, potassium carbonate, cesium carbonate, or a combination thereof. In some embodiments, the base is sodium carbonate, potassium carbonate, or a combination thereof. In some embodiments, the base is lithium carbonate. In some embodiments, the base is sodium carbonate. In some embodiments, the base is potassium carbonate. In some embodiments, the base is cesium carbonate.

In some embodiments, the base is a metal dibasic phosphate. In some embodiments, the base is sodium phosphate dibasic, potassium phosphate dibasic, or a combination thereof. In some embodiments, the base is sodium phosphate dibasic. In some embodiments, the base is potassium phosphate dibasic.

In some embodiments, the base is a metal tribasic phosphate. In some embodiments, the base is sodium phosphate tribasic, potassium phosphate tribasic, or a combination thereof. In some embodiments, the base is sodium phosphate tribasic. In some embodiments, the base is potassium phosphate tribasic.

In some embodiments, the base is a nitrogen containing base. In some examples the base is an azaarene, amine, or amidine. In some embodiments, the base is pyridine, 2,6-lutidine, triethylamine, N,N-diisopropylethylamine, 1,4-diazabicyclo[2.2.2]octane, 1,8-diazabicyclo[5.4.0]undec-7-ene, or a combination thereof. In some embodiments, the base is an azaarene. In some embodiments, the base is pyridine or 2,6-lutidine. In some embodiments, the base is an amine. In some embodiments, the base is triethylamine, N,N-diisopropylethylamine, or 1,4-diazabicyclo[2.2.2]octane. In some embodiments, the base is an amidine. In some embodiments, the base is 1,8-diazabicyclo[5.4.0]undec-7-ene.

Any suitable amount of base can be used. In some embodiments, the amount of base used is about 0.0 to 10.0 eq. (mol/mol) with respect to the compound of Formula A. In some embodiments, the amount of base used is about 0.0, 0.1, 0.5, 1.0, 2.0, 3.0, 4.0, 5.0, 6.0, 7.0, 8.0, 9.0, or 10.0 eq. (mol/mol) with respect to the compound of Formula A. In some embodiments, the amount of base used is about 0.0-1.0 eq. (mol/mol) with respect to the compound of Formula A. In some embodiments, the amount of base used is about 0.0-2.0 eq. (mol/mol) with respect to the compound of Formula A. In some embodiments, the amount of base used is about 0.0-3.0 eq. (mol/mol) with respect to the compound of Formula A. In some embodiments, the amount of base used is about 0.0-0.5 eq. (mol/mol) with respect to the compound of Formula A. In some embodiments, no base is used.

Coupling of the compound of Formula A with the coupling partner of Formula B may be done in presence of a solvent. Any suitable solvent may be used. In some embodiments, the solvent is an organic ether solvent, a halogenated solvent, a polar aprotic solvent, an organic ketone solvent, an organic ester solvent, a hydrocarbon solvent, or a nitrile solvent. In some embodiments, the solvent further comprises water.

In some embodiments, the solvent is an organic ether. In some examples, the solvent is diethyl ether, tert-butyl methyl ether, tetrahydrofuran (THF), methyltetrahydrofuran (MeTHF), or a combination thereof. In some embodiments, the solvent is diethyl ether. In some embodiments, the solvent is tert-butyl methyl ether. In some embodiments, the solvent is THF. In some embodiments, the solvent is MeTHF. In some embodiments, the solvent is a combination of an organic ether and water. In some embodiments, the solvent comprises diethyl ether, tert-butyl methyl ether, tetrahydrofuran (THF), methyltetrahydrofuran (MeTHF), or a combination thereof and water. In some embodiments, the solvent comprises water and diethyl ether. In some embodiments, the solvent comprises water and tert-butyl methyl ether. In some embodiments, the solvent comprises water and THF. In some embodiments, the solvent comprises water and MeTHF.

In some embodiments, the solvent is a halogenated solvent. In some embodiments, the solvent is dichloromethane (DCM), 1,2-dichloroethane, or chlorobenzene. In some embodiments, the solvent is DCM. In some embodiments, the solvent is 1,2-dichloroethane. In some embodiments, the solvent is chlorobenzene. In some embodiments, the solvent further comprises water. In some embodiments, the solvent comprises water and chlorobenzene. In some embodiments, the solvent comprises water and dichloromethane (DCM). In some embodiments, the solvent comprises water and 1,2-dichloroethane.

In some embodiments, the solvent is a polar aprotic solvent. In some embodiments, the solvent is N,N-dimethylformamide, N,N-dimethylacetamide, or N-methyl-2-pyrrolidone. In some embodiments, the solvent is N,N-dimethylformamide. In some embodiments, the solvent is N,N-dimethylacetamide. In some embodiments, the solvent is N-methyl-2-pyrrolidone. In some embodiments, the solvent further comprises water. In some embodiments, the solvent comprises water and N,N-dimethylformamide. In some embodiments, the solvent comprises water and N,N-dimethylacetamide. In some embodiments, the solvent comprises water and N-methyl-2-pyrrolidone.

In some embodiments, the solvent is an organic ketone solvent. In some embodiments, the solvent is acetone, 2-butanone, or 4-methyl-2-pentanone. In some embodiments, the solvent is acetone. In some embodiments, the solvent is 2-butanone. In some embodiments, the solvent is 4-methyl-2-pentanone. In some embodiments, the solvent further comprises water. In some embodiments, the solvent comprises water and acetone. In some embodiments, the solvent comprises water and 2-butanone. In some embodiments, the solvent comprises water and 4-methyl-2-pentanone.

In some embodiments, the solvent is an organic ester. In some embodiments, the solvent is ethyl acetate or isopropyl acetate. In some embodiments, the solvent is ethyl acetate. In some embodiments, the solvent is isopropyl acetate. In some embodiments, the solvent further comprises water. In some embodiments, the solvent comprises water and ethyl acetate. In some embodiments, the solvent comprises water and isopropyl acetate.

In some embodiments, the solvent is a hydrocarbon. In some embodiments, the solvent is hexane, n-heptane, pentane or toluene. In some embodiments, the solvent is toluene or n-heptane. In some embodiments, the solvent is toluene. In some embodiments, the solvent is n-heptane. In some embodiments, the solvent further comprises water. In some embodiments, the solvent comprises water and toluene. In some embodiments, the solvent comprises water and n-heptane.

In some embodiments, the solvent is a nitrile solvent. In some embodiments, the solvent is acetonitrile. In some embodiments, the solvent further comprises water. In some embodiments, the solvent comprises water and acetonitrile.

The coupling reaction can be carried out at any suitable temperature. In some embodiments, the coupling reaction is performed at about −35° C. to 60° C. In some examples, the coupling reaction is performed at a temperature of about −25° C. to 50° C. In some examples, the coupling reaction is performed at a temperature of about −15° C. to 40° C. In some examples, the coupling reaction is performed at a temperature of about −5° C. to 30° C. In some examples, the coupling reaction is performed at a temperature of about 5° C. to 20° C. In some examples, the coupling reaction is performed at a temperature of about 5° C. to 15° C. In some examples, the coupling reaction is performed at a temperature of about 0° C. to 10° C. In some examples, the coupling reaction is performed at a temperature of about 5° C.

Deprotection of the Compound of Formula C

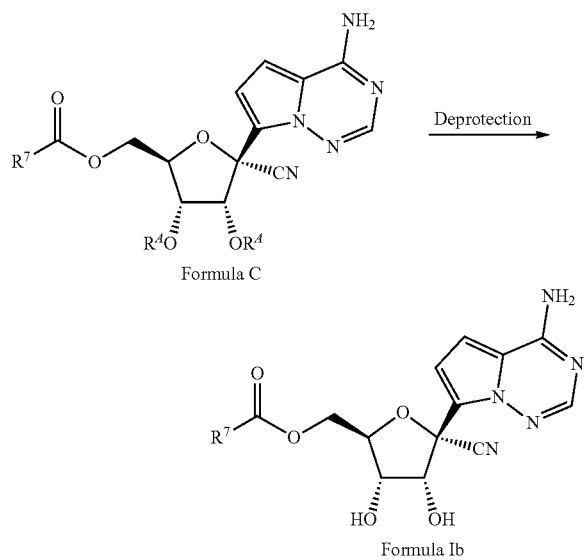

In some embodiments, the coupling of Formula A with the coupling partner of Formula B results in compound of Formula C and the method of making the compound of Formula Ib, further comprises deprotection of the compound of Formula C. Any suitable deprotecting agent can be used for the deprotection. In some embodiments, the deprotecting agent is an acid. In some embodiments, the deprotecting agent is an inorganic acid, a carboxylic acid, or a sulfonic acid.

In some embodiments, the deprotecting agent is an inorganic acid. In some embodiments, the deprotecting agent is hydrochloric acid, hydrobromic acid, sulfuric acid, or a combination thereof. In some embodiments, the deprotecting agent is hydrochloric acid. In some embodiments, the deprotecting agent is hydrobromic acid. In some embodiments, the deprotecting agent is sulfuric acid. In some embodiments, the deprotecting agent is phosphoric acid.

In some embodiments, the deprotecting agent is solid supported acidic resin. In some embodiments, the deprotecting agent is a strong cation exchange resin, containing sulfonic acid groups or the corresponding salts. In some embodiments, the deprotecting agent is Amberlite®/Amberlyst®/Amberjet® (sulfonic acid) IR-120 Plus(H), IR-120 Plus, IRP-69, 15, or 1200(H). In some embodiments, the deprotecting agent is Dowex® (sulfonic acid), 50WX2-100, 50WX2-200, 50WX2-400, 50WX4-50, 50WX4-100, 50WX4-200, 50WX4-200R, 50WX4-400, 50WX8-100, 50WX8-200, 50WX8-400, HCR-S, HCR-W2, 88, 650C, Marathon C, or MSC-1. In some embodiments, the deprotecting agent is Duolite® (Sulfonic Acid) C-26. In some embodiments, the deprotecting agent is a weak cation exchange resins, containing carboxylic acid groups or the corresponding salts. In some embodiments, the deprotecting agent is Amberlite® (carboxylic acid) CG-50 Type I, IRC-50, IRC-50s, or IRP-64.

In some embodiments, the deprotecting agent is a carboxylic acid. In some embodiments, the deprotecting agent is formic acid; maleic acid, oxalic acid, butyric acid, isobutyric acid, acetic acid, trifluoroacetic acid, trichloroacetic acid, propionic acid, or a combination thereof. In some embodiments, the deprotecting agent is acetic acid. In some embodiments, the deprotecting agent is trifluoroacetic acid. In some embodiments, the deprotecting agent is trichloroacetic acid. In some embodiments, the deprotecting agent is propionic acid. In some embodiments, the deprotecting agent is formic acid. In some embodiments, the deprotecting agent is maleic acid. In some embodiments, the deprotecting agent is oxalic acid. In some embodiments, the deprotecting agent is butyric acid. In some embodiments, the deprotecting agent is isobutyric acid. In some embodiments, the deprotecting agent is a amino acid. In some embodiments, the deprotecting agent is L-aspartic acid.

In some embodiments, the deprotecting agent is a sulfonic acid. In some embodiments, the deprotecting agent is methanesulfonic acid, ethanesulfonic acid, benzenesulfonic acid, p-toluenesulfonic acid, pyridinium p-toluenesulfonate, or a combination thereof. In some embodiments, the deprotecting agent is benzenesulfonic acid. In some embodiments, the deprotecting agent is p-toluenesulfonic acid. In some embodiments, the deprotecting agent is pyridinium p-toluenesulfonate. In some embodiments, the deprotecting agent is methanesulfonic acid. In some embodiments, the deprotecting agent is ethanesulfonic acid.

In some embodiments, the deprotecting agent is a Lewis acid. In some embodiments, the deprotecting agent is trimethylsilyl triflate, boron trichloride, magnesium bromide, cerium chloride, or a combination thereof. In some embodiments, the deprotecting agent is boron trichloride. In some embodiments, the deprotecting agent is magnesium bromide. In some embodiments, the deprotecting agent is cerium chloride. In some embodiments, the deprotecting agent is trimethylsilyl triflate.

Any suitable amount of the deprotecting agent can be used. In some embodiments, the amount of deprotecting agent used is about 0.01-10.0 eq. (mol/mol) with respect to the compound of Formula A. In some embodiments, the amount of deprotecting agent used is about 0.1-5.0 eq. (mol/mol) with respect to the compound of Formula A. In some embodiments, the amount of deprotecting agent used is about 1.0-5.0 eq. (mol/mol) with respect to the compound of Formula A. In some embodiments, the amount of deprotecting agent used is about 2.0-4.0 eq. (mol/mol) with respect to the compound of Formula A. In some embodiments, the amount of deprotecting agent used is about 3.0 eq. (mol/mol) with respect to the compound of Formula A. In some embodiments, the amount of deprotecting agent used is about 1.0, 2.0, 3.0, 4.0, 5.0, 6.0, 7.0, 8.0, 9.0, or 10.0 eq. (mol/mol) with respect to the compound of Formula A.

In some embodiments, the deprotecting agent is an inorganic acid and the amount of deprotecting agent used is about 1.0-5.0 eq. (mol/mol) with respect to the compound of Formula A. In some embodiments, the deprotecting agent is hydrochloric acid and the amount of deprotecting agent used is about 1.0-5.0 eq. (mol/mol) with respect to the compound of Formula A. In some embodiments, the deprotecting agent is hydrochloric acid and the amount of deprotecting agent used is about 3.0 eq. (mol/mol) with respect to the compound of Formula A.

The deprotection step can be performed in any suitable solvent. In some embodiments, the solvent for the deprotection step comprises an ether solvent, a polar aprotic solvent, an alcohol, an ester solvent, a halogenated solvent, hydrocarbon, nitrile solvent, or a combination thereof.

In some embodiments, the solvent for the deprotection step is an ether solvent. In some embodiments, the solvent for the deprotection step is THF, MeTHF, tert-butyl methyl ether, or a combination thereof. In some embodiments, the solvent further comprises water. In some embodiments, the solvent comprises water and THF. In some embodiments, the solvent further comprises water. In some embodiments, the solvent comprises water and MeTHF. In some embodiments, the solvent further comprises water. In some embodiments, the solvent comprises water and tert-butyl methyl ether.

In some embodiments, the solvent for the deprotection step is a polar aprotic solvent. In some embodiments, the solvent for the deprotection step is N,N-dimethylformamide, N,N-dimethylacetamide, N-methyl-2-pyrrolidone, or a combination thereof. In some embodiments, the solvent for the deprotection step is N,N-dimethylformamide. In some embodiments, the solvent for the deprotection step is N,N-dimethylacetamide. In some embodiments, the solvent for the deprotection step is N-methyl-2-pyrrolidone. In some embodiments, the solvent further comprises water. In some embodiments, the solvent comprises water and N,N-dimethylformamide. In some embodiments, the solvent further comprises water. In some embodiments, the solvent comprises water and N,N-dimethylacetamide. In some embodiments, the solvent further comprises water. In some embodiments, the solvent comprises water and N-methyl-2-pyrrolidone.

In some embodiments, the solvent for the deprotection step is an alcohol. In some embodiments, the solvent is methanol, ethanol, 2-propanol, or a combination thereof. In some embodiments, the solvent is methanol. In some embodiments, the solvent is ethanol. In some embodiments, the solvent is 2-propanol. In some embodiments, the solvent further comprises water. In some embodiments, the solvent comprises water and methanol, ethanol, 2-propanol, or a combination thereof. In some embodiments, the solvent comprises water and methanol. In some embodiments, the solvent comprises water and ethanol. In some embodiments, the solvent comprises water and 2-propanol.

In some embodiments, the solvent for the deprotection step is an organic ester. In some embodiments, the solvent is ethyl acetate or isopropyl acetate. In some embodiments, the solvent is ethyl acetate. In some embodiments, the solvent is isopropyl acetate. In some embodiments, the solvent further comprises water. In some embodiments, the solvent comprises water and ethyl acetate. In some embodiments, the solvent comprises water and isopropyl acetate.

In some embodiments, the solvent for the deprotection step is a halogenated solvent. In some embodiments, the solvent is dichloromethane (DCM), 1,2-dichloroethane, or chlorobenzene. In some embodiments, the solvent is DCM. In some embodiments, the solvent is 1,2-dichloroethane. In some embodiments, the solvent is chlorobenzene. In some embodiments, the solvent further comprises water. In some embodiments, the solvent comprises water and chlorobenzene. In some embodiments, the solvent comprises water and dichloromethane (DCM). In some embodiments, the solvent comprises water and 1,2-dichloroethane.

In some embodiments, the solvent for the deprotection step is a hydrocarbon. In some embodiments, the solvent is hexane, heptane, pentane or toluene. In some embodiments, the solvent is toluene or n-heptane. In some embodiments, the solvent is toluene. In some embodiments, the solvent is n-heptane. In some embodiments, the solvent further comprises water. In some embodiments, the solvent comprises water and toluene. In some embodiments, the solvent comprises water and n-heptane.

In some embodiments, the solvent for the deprotection step is a nitrile solvent. In some embodiments, the solvent is acetonitrile, propionitrile, butyronitrile, benzonitrile, or a combination thereof. In some embodiments, the solvent is acetonitrile. In some embodiments, the solvent is propionitrile. In some embodiments, the solvent is butyronitrile. In some embodiments, the solvent is benzonitrile. In some embodiments, the solvent further comprises water. In some embodiments, the solvent comprises water and acetonitrile. In some embodiments, the solvent comprises water and propionitrile. In some embodiments, the solvent comprises water and butyronitrile. In some embodiments, the solvent comprises water and benzonitrile.

The deprotection reaction can be carried out at any suitable temperature. In some embodiments, the deprotection reaction is performed at about −20° C. to 50° C. In some embodiments, the deprotection reaction is performed at about −10° C. to 40° C. In some embodiments, the deprotection reaction is performed at about 0° C. to 30° C. In some embodiments, the deprotection reaction is performed at about 10° C. to 30° C. In some embodiments, the deprotection reaction is performed at about 15° C. to 25° C. In some embodiments, the deprotection reaction is performed at about 10° C. to 30° C. In some embodiments, the deprotection reaction is performed at about 20° C.

Free Base Formation

In some embodiments, the use of an acid of general structure HX (where X is the conjugate base) for deprotection of the compound of Formula C results in a salt of the compound of Formula Ib (Formula Ib•HX). When the deprotected compound is obtained as a salt, an additional fee free basing step may optionally be performed.

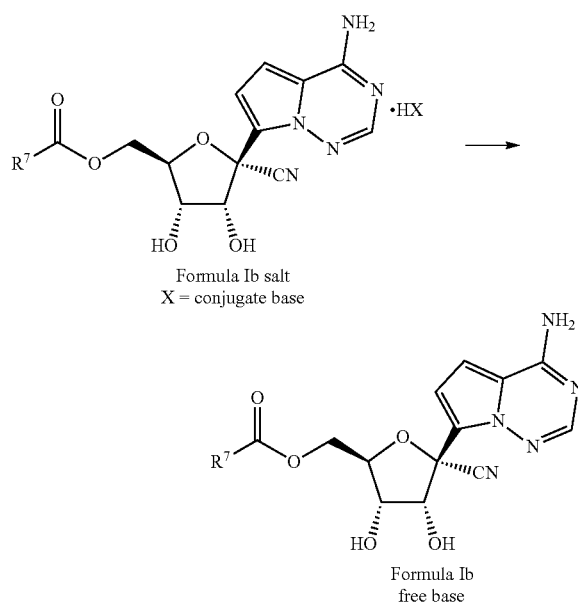

Formula Ib salt
X = conjugate base

Formula Ib
free base

In some embodiments, the free basing involves treatment with a base. Any suitable base can be used. In some embodiments, the base used is an inorganic base. For example, a bicarbonate. In some example the base is lithium bicarbonate, sodium bicarbonate, potassium bicarbonate or a combination thereof. In some example the base is sodium bicarbonate, potassium bicarbonate or a combination thereof. In some example the base is lithium bicarbonate. In some example the base is sodium bicarbonate. In some example the base is potassium bicarbonate.

In some embodiments, the base is a carbonate. In some embodiments, the base is lithium carbonate, sodium carbonate, potassium carbonate, cesium carbonate, or a combination thereof. In some embodiments, the base is lithium carbonate, sodium carbonate, potassium carbonate, or a combination thereof. In some embodiments, the base is sodium carbonate, potassium carbonate, cesium carbonate, or a combination thereof. In some embodiments, the base is sodium carbonate, potassium carbonate, or a combination thereof. In some embodiments, the base is lithium carbonate. In some embodiments, the base is sodium carbonate. In some embodiments, the base is potassium carbonate. In some embodiments, the base is cesium carbonate.

In some embodiments, the base is an alkoxide. In some embodiments, the base is sodium methoxide, sodium ethoxide, sodium tert-butoxide, sodium tert-pentoxide, lithium tert-butoxide, potassium tert-butoxide, or a combination thereof. In some embodiments, the base is sodium methoxide, sodium ethoxide, sodium tert-butoxide, sodium tert-pentoxide, lithium tert-butoxide, potassium tert-butoxide. In some embodiments, the base is sodium methoxide. In some embodiments, the base is sodium ethoxide. In some embodiments, the base is sodium tert-butoxide. In some embodiments, the base is sodium tert-pentoxide. In some embodiments, the base is lithium tert-butoxide. In some embodiments, the base is potassium tert-butoxide.

In some embodiments, the base is a metal hydroxide. In some embodiments, the base is lithium hydroxide, sodium hydroxide, potassium hydroxide, or a combination thereof. In some embodiments, the base is lithium hydroxide. In some embodiments, the base is sodium hydroxide. In some embodiments, the base is potassium hydroxide.

In some embodiments, the base is a metal dibasic phosphate. In some embodiments, the base is sodium phosphate dibasic, potassium phosphate dibasic, or a combination thereof. In some embodiments, the base is sodium phosphate dibasic. In some embodiments, the base is potassium phosphate dibasic.

In some embodiments, the base is a metal tribasic phosphate. In some embodiments, the base is sodium phosphate tribasic, potassium phosphate tribasic, or a combination thereof. In some embodiments, the base is sodium phosphate tribasic. In some embodiments, the base is potassium phosphate tribasic.

In some embodiments, the base is a nitrogen containing base. In some examples the base is an azaarene, amine, or amidine. In some embodiments, the base is pyridine, 2,6-lutidine, triethylamine, N,N-diisopropylethylamine, 1,4-diazabicyclo[2.2.2]octane, 1,8-diazabicyclo[5.4.0]undec-7-ene, or a combination thereof. In some embodiments, the base is an azaarene. In some embodiments, the base is pyridine or 2,6-lutidine. In some embodiments, the base is an amine. In some embodiments, the base is triethylamine, N,N-diisopropylethylamine, or 1,4-diazabicyclo[2.2.2]octane. In some embodiments, the base is an amidine. In some embodiments, the base is 1,8-diazabicyclo[5.4.0]undec-7-ene.

The free basing step can be performed in any suitable solvent. In some embodiments, the solvent for the free basing step comprises an ether solvent, a polar aprotic solvent, an alcohol, an ester solvent, a halogenated solvent, hydrocarbon, nitrile solvent, or a combination thereof.

In some embodiments, the solvent for the free basing step is an ether solvent. In some embodiments, the solvent for the free basing step is THF, MeTHF, tert-butyl methyl ether, or a combination thereof. In some embodiments, the solvent further comprises water. In some embodiments, the solvent comprises water and THF. In some embodiments, the solvent further comprises water. In some embodiments, the solvent comprises water and MeTHF. In some embodiments, the solvent further comprises water. In some embodiments, the solvent comprises water and tert-butyl methyl ether.

In some embodiments, the solvent for the free basing step is a polar aprotic solvent. In some embodiments, the solvent for the free basing step is N,N-dimethylformamide, N,N-dimethylacetamide, N-methyl-2-pyrrolidone, or a combination thereof. In some embodiments, the solvent for the free basing step is N,N-dimethylformamide. In some embodiments, the solvent for the free basing step is N,N-dimethylacetamide. In some embodiments, the solvent for the free basing step is N-methyl-2-pyrrolidone. In some embodiments, the solvent further comprises water. In some embodiments, the solvent comprises water and N,N-dimethylformamide. In some embodiments, the solvent further comprises water. In some embodiments, the solvent comprises water and N,N-dimethylacetamide. In some embodiments, the solvent further comprises water. In some embodiments, the solvent comprises water and N-methyl-2-pyrrolidone.

In some embodiments, the solvent for the free basing step is an alcohol. In some embodiments, the solvent is methanol, ethanol, 2-propanol, or a combination thereof. In some embodiments, the solvent is methanol. In some embodiments, the solvent is ethanol. In some embodiments, the solvent is 2-propanol. In some embodiments, the solvent further comprises water. In some embodiments, the solvent comprises water and methanol, ethanol, 2-propanol, or a combination thereof. In some embodiments, the solvent comprises water and methanol. In some embodiments, the solvent comprises water and ethanol. In some embodiments, the solvent comprises water and 2-propanol.

In some embodiments, the solvent for the free basing step is an organic ester. In some embodiments, the solvent is ethyl acetate or isopropyl acetate. In some embodiments, the solvent is ethyl acetate. In some embodiments, the solvent is isopropyl acetate. In some embodiments, the solvent further comprises water. In some embodiments, the solvent comprises water and ethyl acetate. In some embodiments, the solvent comprises water and isopropyl acetate.

In some embodiments, the solvent for the free basing step is a halogenated solvent. In some embodiments, the solvent is dichloromethane (DCM), 1,2-dichloroethane, or chlorobenzene. In some embodiments, the solvent is DCM. In some embodiments, the solvent is 1,2-dichloroethane. In some embodiments, the solvent is chlorobenzene. In some embodiments, the solvent further comprises water. In some embodiments, the solvent comprises water and chlorobenzene. In some embodiments, the solvent comprises water and dichloromethane (DCM). In some embodiments, the solvent comprises water and 1,2-dichloroethane.

In some embodiments, the solvent for the free basing step is a hydrocarbon. In some embodiments, the solvent is hexane, heptane, pentane or toluene. In some embodiments, the solvent is toluene or n-heptane. In some embodiments, the solvent is toluene. In some embodiments, the solvent is n-heptane. In some embodiments, the solvent further comprises water. In some embodiments, the solvent comprises water and toluene. In some embodiments, the solvent comprises water and n-heptane.

In some embodiments, the solvent for the free basing step is a nitrile solvent. In some embodiments, the solvent is acetonitrile propionitrile, butyronitrile, benzonitrile, or a combination thereof. In some embodiments, the solvent is acetonitrile. In some embodiments, the solvent is propionitrile. In some embodiments, the solvent is butyronitrile. In some embodiments, the solvent is benzonitrile. In some embodiments, the solvent further comprises water. In some embodiments, the solvent comprises water and acetonitrile. In some embodiments, the solvent comprises water and propionitrile. In some embodiments, the solvent comprises water and butyronitrile. In some embodiments, the solvent comprises water and benzonitrile.

The free basing can be carried out at any suitable temperature. In some embodiments, the coupling reaction is performed at about 10° C. to 30° C. In some embodiments, the coupling reaction is performed at about 20° C.

XI. Crystalline Forms of Compound 15

A polymorphic form or polymorph may have properties such as bioavailability and stability at certain conditions that may be suitable for medical or pharmaceutical uses. A crystalline form of Compound 15 may provide the advantage of bioavailability and stability, suitable for use as an active ingredient in a pharmaceutical composition. Variations in the crystal structure of a pharmaceutical drug substance or active ingredient may affect the dissolution rate (which may affect bioavailability, etc.), manufacturability (e.g., ease of handling, ability to consistently prepare doses of known strength) and stability (e.g., thermal stability, shelf life, etc.) of a pharmaceutical drug product or active ingredient. Such variations may affect the preparation or formulation of pharmaceutical compositions in different dosage or delivery forms, such as solid oral dosage form including tablets and capsules. Compared to other forms such as non-crystalline or amorphous forms, crystalline forms may provide desired or suitable hygroscopicity, particle size controls, dissolution rate, solubility, purity, physical and chemical stability, manufacturability, yield, and/or process control. Thus, crystalline forms of Compound 15 may provide advantages such as: improving the manufacturing process of an active agent or the stability or storability of a drug product form of the compound or an active ingredient, and/or having suitable bioavailability and/or stability as an active agent.

Compound 15, Form I

Figure 10:
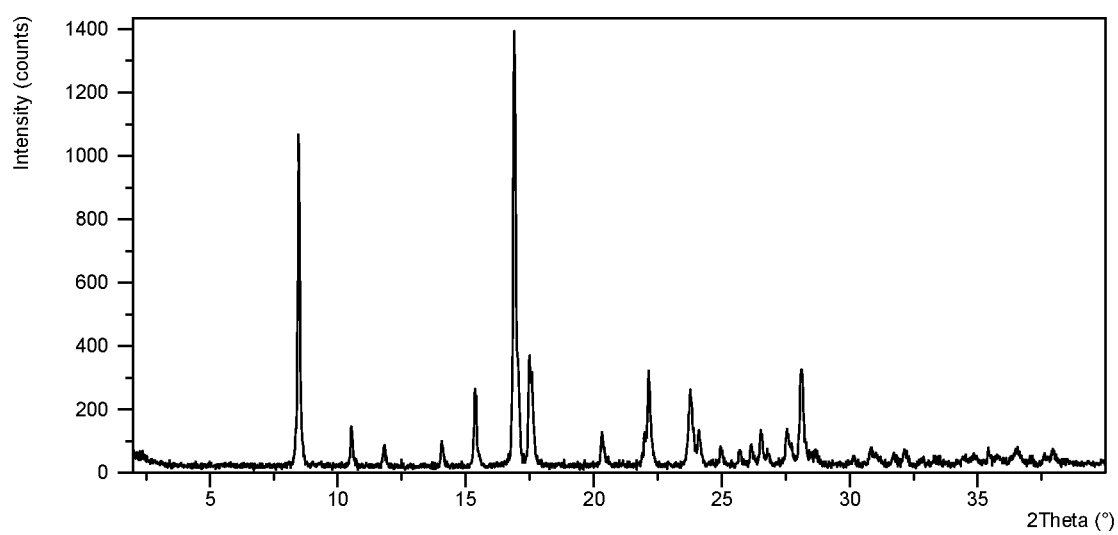
FIG. 10: Shows the XRPD pattern of Compound 15 freebase Form I.
Figure 11:
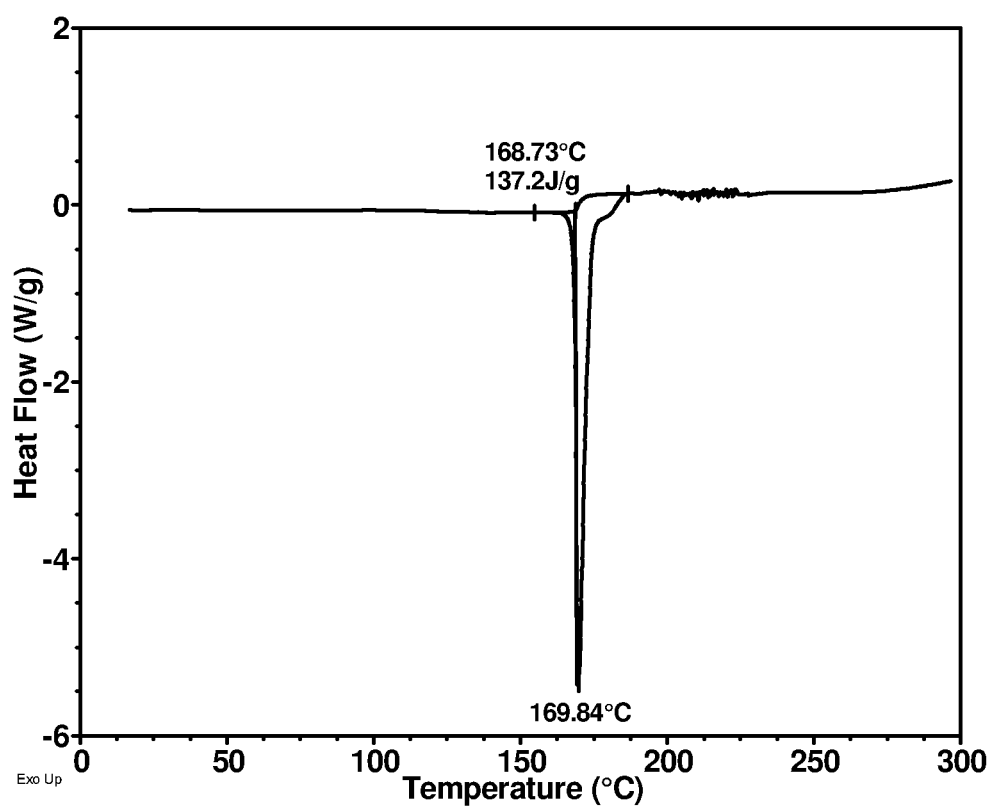
FIG. 11: Shows the DSC thermogram of Compound 15 freebase Form I.
Figure 12:
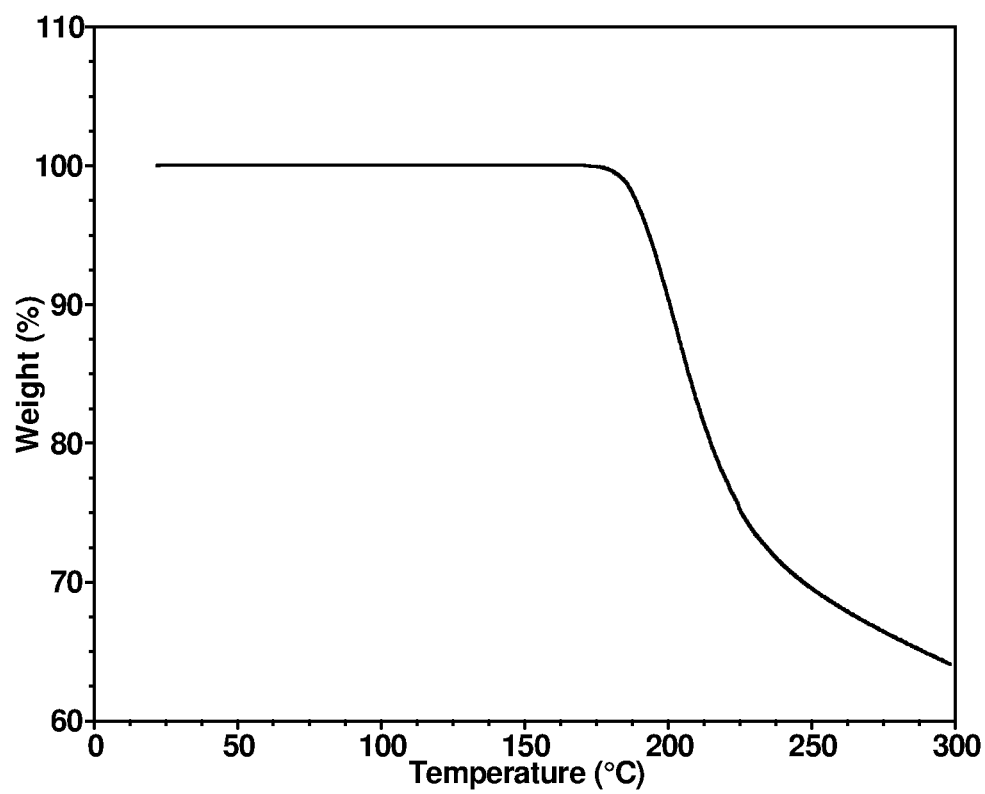
FIG. 12: Shows the TGA thermogram of Compound 15 freebase Form I.

In some embodiments, provided is crystalline Form I of Compound 15 (crystalline Compound 15 Form I), wherein the crystal structure exhibits an X-ray powder diffraction (XRPD) pattern substantially as shown in FIG. 10. Crystalline Compound 15 Form I may exhibit a differential scanning calorimetry (DSC) thermogram substantially as shown in FIG. 11. Crystalline Compound 15 Form I may exhibit a thermogravimetric analysis (TGA) graph substantially as shown in FIG. 12.

In some embodiments of crystalline Compound 15 Form I, at least one, at least two, or all of the following (a)-(c) apply: (a) crystalline Compound 15 Form I has an XRPD pattern substantially as shown in FIG. 10; (b) crystalline Compound 15 Form I has a DSC thermogram substantially as shown in FIG. 11; (c) crystalline Compound 15 Form I has a TGA graph substantially as shown in FIG. 12.

In some embodiments, crystalline Compound 15 Form I has the following properties:
  (a) an XRPD pattern substantially as shown in FIG. 10;
  (b) a DSC thermogram substantially as shown in FIG. 11; and
  (c) a TGA graph substantially as shown in FIG. 12.

In some embodiments, crystalline Compound 15 Form I has an XRPD pattern displaying at least two, at least three, at least four, at least five, or at least six of the degree 2θ-reflections with the greatest intensity as the XRPD pattern substantially as shown in FIG. 10.

In some embodiments, crystalline Compound 15 Form I has an XRPD pattern comprising degree 2θ-reflections (+/−0.2 degrees 2θ) at 8.5°, 22.1°, and 23.8°. In some embodiments, crystalline Compound 15 Form I has an XRPD pattern comprising degree 2θ-reflections (+/−0.2 degrees 2θ) at 8.5°, 22.1°, and 23.8°, and one, two or three of the degree 2θ-reflections (+/−0.2 degrees 2θ) at 15.4°, 16.9°, and 28.1°. In some embodiments, crystalline Compound 15 Form I has an XRPD pattern comprising degree 2θ-reflections (+/−0.2 degrees 2θ) at 8.5°, 22.1°, and 23.8°, and one or two of the degree 2θ-reflections (+/−0.2 degrees 2θ) at 15.4°, 16.9°, and 28.1°. In some embodiments, crystalline Compound 15 Form I has an XRPD pattern comprising degree 2θ-reflections (+/−0.2 degrees 2θ) at 8.5°, 22.1°, and 23.8°, and one of the degree 2θ-reflections (+/−0.2 degrees 2θ) at 15.4°, 16.9°, and 28.1°. In some embodiments, crystalline Compound 15 Form I has an XRPD pattern comprising degree 2θ-reflections (+/−0.2 degrees 2θ) at 8.5°, 22.1°, and 23.8°, and two of the degree 2θ-reflections (+/−0.2 degrees 2θ) at 15.4°, 16.9°, and 28.1°. In some embodiments, crystalline Compound 15 Form I has an XRPD pattern comprising degree 2θ-reflections (+/−0.2 degrees 2θ) at 8.5°, 15.4°, 16.9°, 22.1°, 23.8° and 28.1°. In some embodiments, crystalline Compound 15 Form I has an XRPD pattern comprising any three degree 2θ-reflections (+/−0.2 degrees 2θ) selected from the group consisting of 8.5°, 15.4°, 16.9°, 22.1°, 23.8° and 28.1°.

In some embodiments, crystalline Compound 15 Form I has an XRPD pattern comprising degree 2θ-reflections (+/−0.2 degrees 2θ) at 8.5°, 15.4°, 16.9°, 22.1°, 23.8° and 28.1°, and one, two, or three of the degree 2θ-reflections (+/−0.2 degrees 2θ) at 10.5°, 17.5°, and 27.5°. In some embodiments, crystalline Compound 15 Form I has an XRPD pattern comprising degree 2θ-reflections (+/−0.2 degrees 2θ) at 8.5°, 15.4°, 16.9°, 22.1°, 23.8° and 28.1°, and one or two of the degree 2θ-reflections (+/−0.2 degrees 2θ) at 10.5°, 17.5°, and 27.5°. In some embodiments, crystalline Compound 15 Form I has an XRPD pattern comprising degree 2θ-reflections (+/−0.2 degrees 2θ) at 8.5°, 15.4°, 16.9°, 22.1°, 23.8° and 28.1°, and one of the degree 2θ-reflections (+/−0.2 degrees 2θ) at 10.5°, 17.5°, and 27.5°. In some embodiments, crystalline Compound 15 Form I has an XRPD pattern comprising degree 2θ-reflections (+/−0.2 degrees 2θ) at 8.5°, 15.4°, 16.9°, 22.1°, 23.8° and 28.1°, and two of the degree 2θ-reflections (+/−0.2 degrees 2θ) at 10.5°, 17.5°, and 27.5°. In some embodiments, crystalline Compound 15 Form I has an XRPD pattern comprising degree 2θ-reflections (+/−0.2 degrees 2θ) at 8.5°, 10.5°, 15.4°, 16.9°, 17.5°, 22.1°, 23.8°, 27.5°, and 28.1°. In some embodiments, crystalline Compound 15 Form I has an XRPD pattern comprising three of the degree 2θ-reflections (+/−0.2 degrees 2θ) at 8.5°, 10.5°, 15.4°, 16.9°, 17.5°, 22.1°, 23.8°, 27.5°, and 28.1°.

Compound 15, Form II

Figure 13:
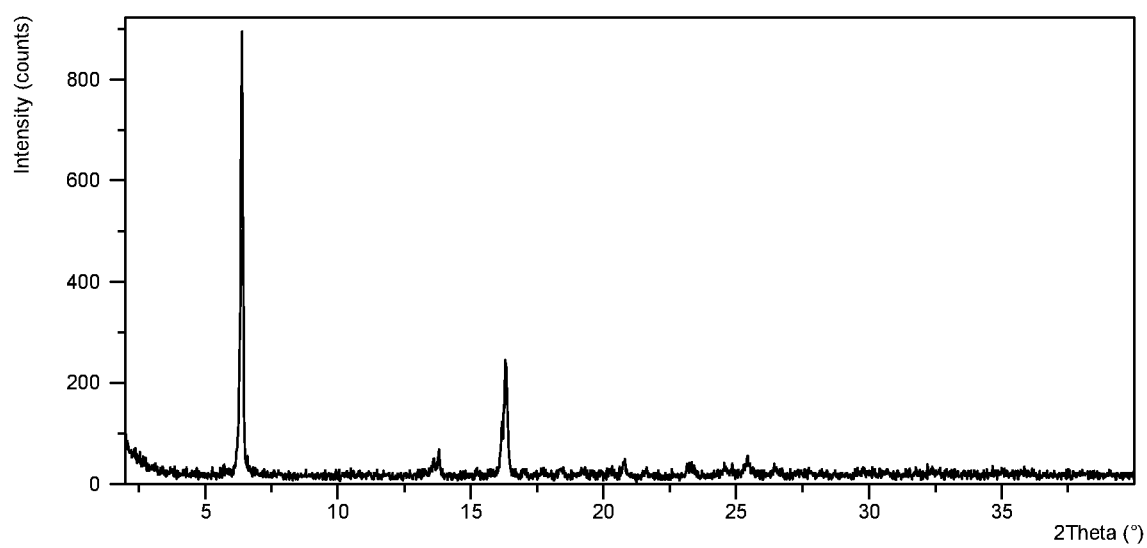
FIG. 13: Shows the XRPD pattern of Compound 15 freebase Form II.
Figure 14:
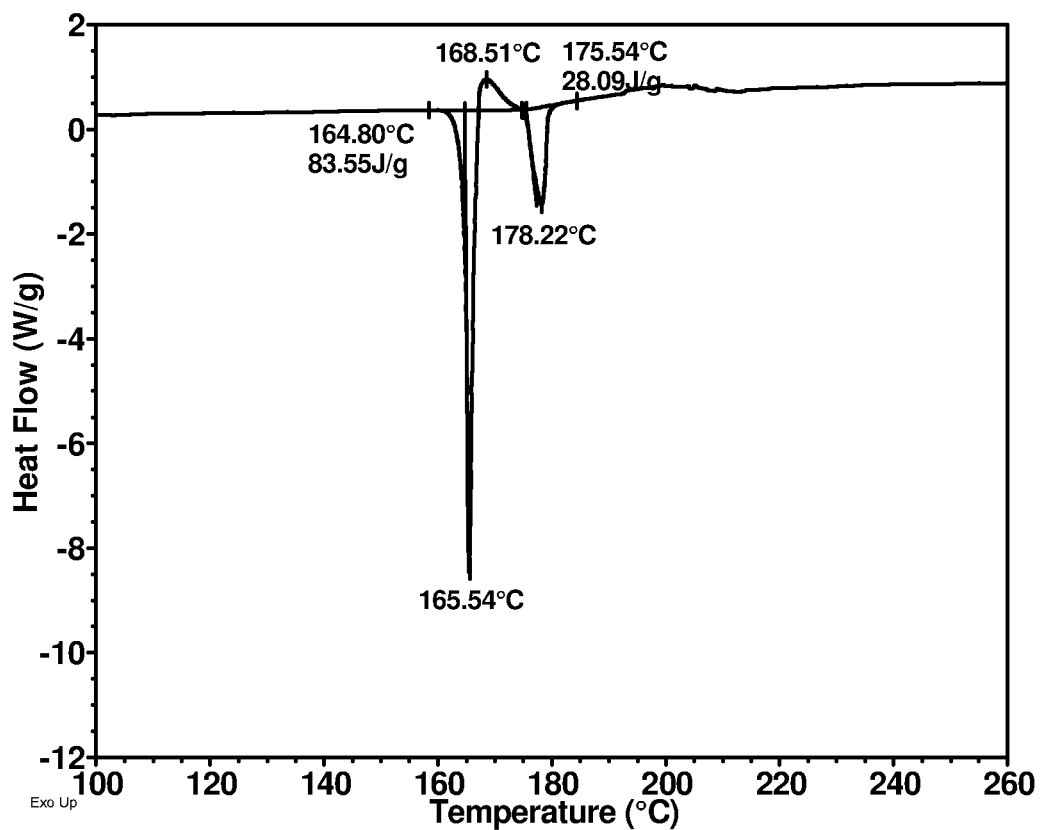
FIG. 14: Shows the DSC thermogram of Compound 15 freebase Form II.
Figure 15:
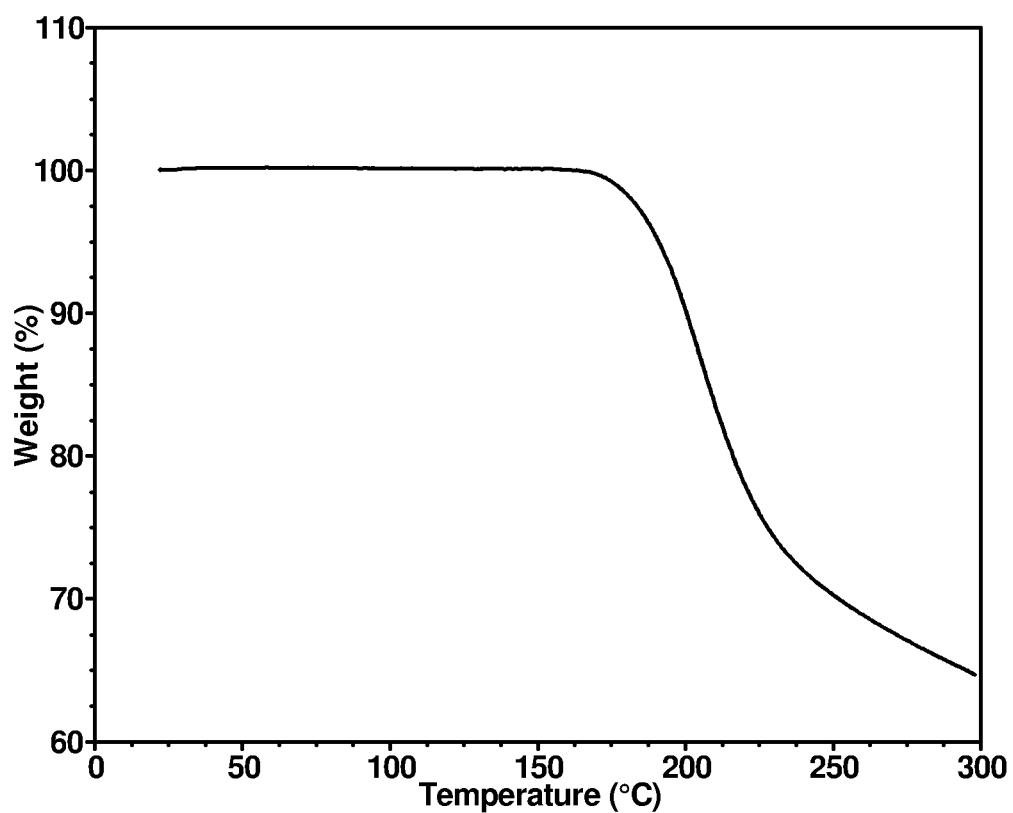
FIG. 15: Shows the TGA thermogram of Compound 15 freebase Form II.

In some embodiments, provided is crystalline Form II of Compound 15 (crystalline Compound 15 Form II), wherein the crystal structure exhibits an X-ray powder diffraction (XRPD) pattern substantially as shown in FIG. 13. Crystalline Compound 15 Form II may exhibit a DSC thermogram substantially as shown in FIG. 14. Crystalline Compound 15 Form II may exhibit a TGA graph substantially as shown in FIG. 15.

In some embodiments of crystalline Compound 15 Form II, at least one, at least two, or all of the following (a)-(c) apply: (a) crystalline Compound 15 Form II has an XRPD pattern substantially as shown in FIG. 13; (b) crystalline Compound 15 Form II has a DSC thermogram substantially as shown in FIG. 14; (c) crystalline Compound 15 Form II has a TGA graph substantially as shown in FIG. 15.

In some embodiments, crystalline Compound 15 Form II has the following properties:
  (a) an XRPD pattern substantially as shown in FIG. 13;
  (b) a DSC thermogram substantially as shown in FIG. 14; and
  (c) a TGA graph substantially as shown in FIG. 15.

In some embodiments, crystalline Compound 15 Form II has an XRPD pattern displaying at least two, at least three, at least four, at least five, or at least six of the degree 2θ-reflections with the greatest intensity as the XRPD pattern substantially as shown in FIG. 13.

In some embodiments, crystalline Compound 15 Form II has an XRPD pattern comprising degree 2θ-reflections (+/−0.2 degrees 2θ) at 6.4°, 13.7°, and 16.3°. In some embodiments, crystalline Compound 15 Form II has an XRPD pattern comprising degree 2θ-reflections (+/−0.2 degrees 2θ) at 6.4°, 13.7°, and 16.3°, and one, two or three of the degree 2θ-reflections (+/−0.2 degrees 2θ) at 18.4°, 20.8°, and 23.3°. In some embodiments, crystalline Compound 15 Form II has an XRPD pattern comprising degree 2θ-reflections (+/−0.2 degrees 2θ) at 6.4°, 13.7°, and 16.3°, and one or two of the degree 2θ-reflections (+/−0.2 degrees 2θ) at 18.4°, 20.8°, and 23.3°. In some embodiments, crystalline Compound 15 Form II has an XRPD pattern comprising degree 2θ-reflections (+/−0.2 degrees 2θ) at 6.4°, 13.7°, and 16.3°, and one of the degree 2θ-reflections (+/−0.2 degrees 2θ) at 18.4°, 20.8°, and 23.3°. In some embodiments, crystalline Compound 15 Form II has an XRPD pattern comprising degree 2θ-reflections (+/−0.2 degrees 2θ) at 6.4°, 13.7°, and 16.3°, and two of the degree 2θ-reflections (+/−0.2 degrees 2θ) at 18.4°, 20.8°, and 23.3°. In some embodiments, crystalline Compound 15 Form II has an XRPD pattern comprising degree 2θ-reflections (+/−0.2 degrees 2θ) at 6.4°, 13.7°, 16.3°, 18.4°, 20.8°, and 23.3°. In some embodiments, crystalline Compound 15 Form II has an XRPD pattern comprising any three degree 2θ-reflections (+/−0.2 degrees 2θ) selected from the group consisting of 6.4°, 13.7°, 16.3°, 18.4°, 20.8°, and 23.3°.

In some embodiments, crystalline Compound 15 Form II has an XRPD pattern comprising any three degree 2θ-reflections (+/−0.2 degrees 2θ) selected from the group consisting of 6.4°, 13.7°, 16.3°, 18.4°, 20.8°, 23.3°, and 25.4°. In some embodiments, crystalline Compound 15 Form II has an XRPD pattern comprising degree 2θ-reflections (+/−0.2 degrees 2θ) at 6.4°, 13.7°, 16.3°, 18.4°, 20.8°, 23.3°, and 25.4°.

Compound 15, Form III

Figure 16:
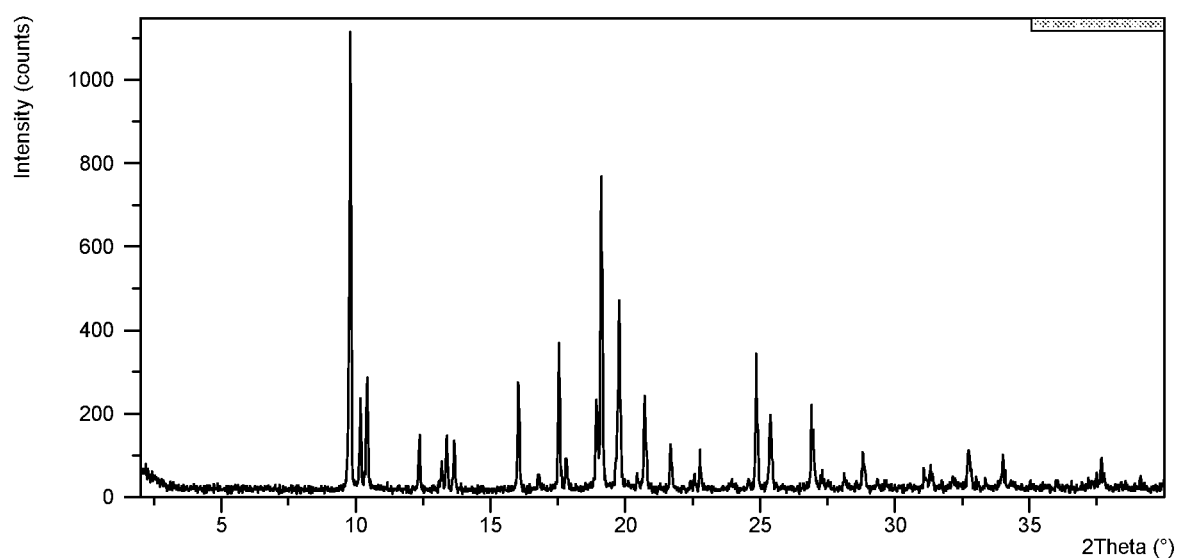
FIG. 16: Shows the XRPD pattern of Compound 15 freebase Form III.
Figure 17:
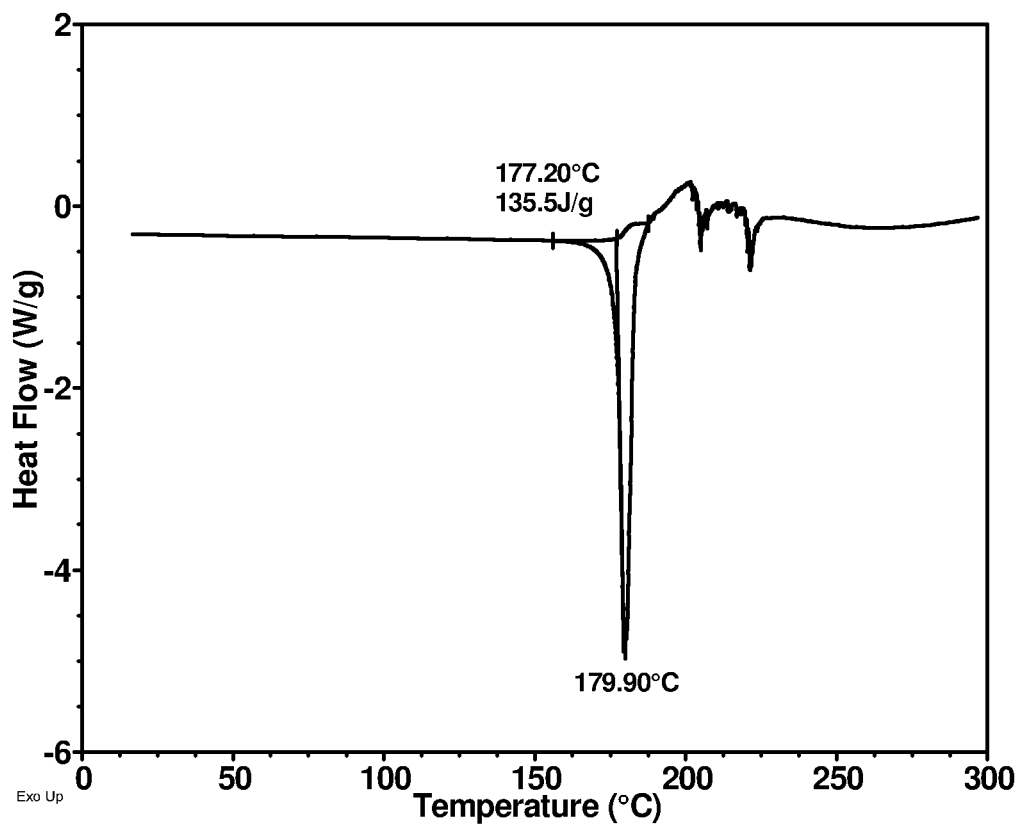
FIG. 17: Shows the DSC thermogram of Compound 15 freebase Form III.
Figure 18:
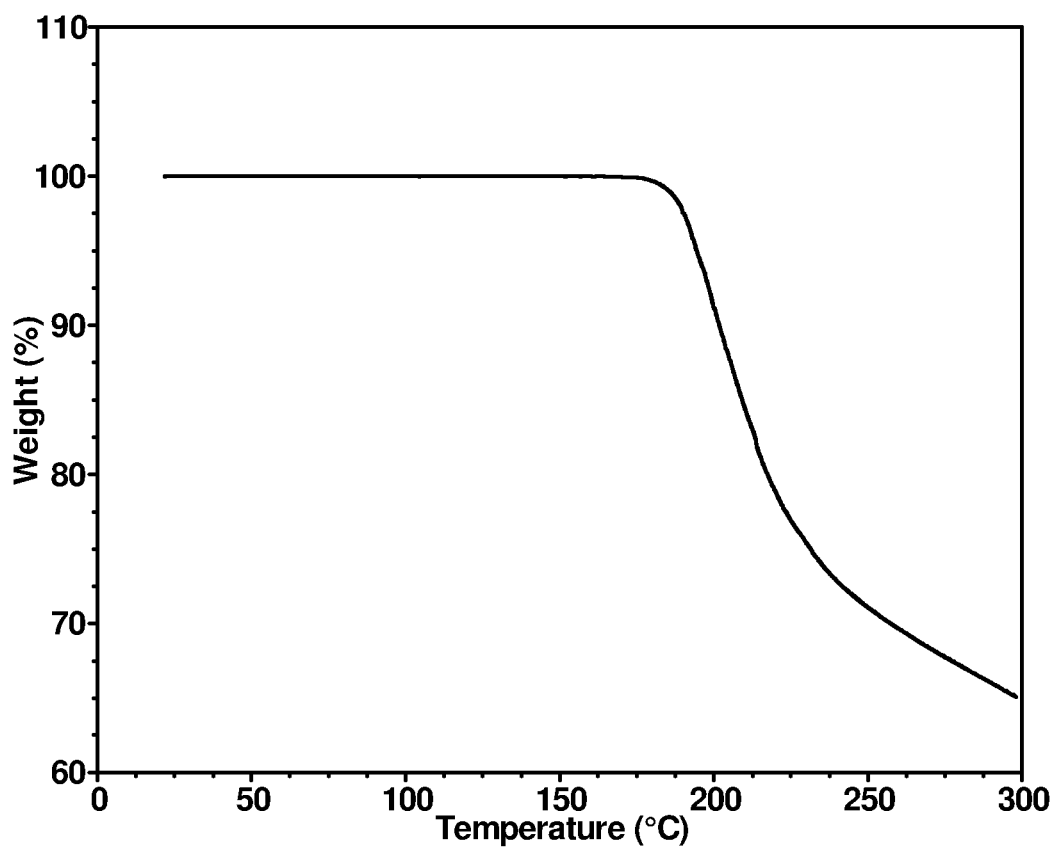
FIG. 18: Shows the TGA thermogram of Compound 15 freebase Form III.

In some embodiments, provided is crystalline Form III of Compound 15 (crystalline Compound 15 Form III), wherein the crystal structure exhibits an XRPD pattern substantially as shown in FIG. 16. Crystalline Compound 15 Form III may exhibit a DSC thermogram substantially as shown in FIG. 17. Crystalline Compound 15 Form III may exhibit a TGA graph substantially as shown in FIG. 18.

In some embodiments of crystalline Compound 15 Form III, at least one, at least two, or all of the following (a)-(c) apply: (a) crystalline Compound 15 Form III has an XRPD pattern substantially as shown in FIG. 16; (b) crystalline Compound 15 Form III has a DSC thermogram substantially as shown in FIG. 17; (c) crystalline Compound 15 Form III has a TGA graph substantially as shown in FIG. 18.

In some embodiments, crystalline Compound 15 Form III has the following properties:
  (a) an XRPD pattern substantially as shown in FIG. 16;
  (b) a DSC thermogram substantially as shown in FIG. 17; and
  (c) a TGA graph substantially as shown in FIG. 18.

In some embodiments, crystalline Compound 15 Form III has an XRPD pattern displaying at least two, at least three, at least four, at least five, or at least six of the degree 2θ-reflections with the greatest intensity as the XRPD pattern substantially as shown in FIG. 16.

In some embodiments, crystalline Compound 15 Form III has an XRPD pattern comprising degree 2θ-reflections (+/−0.2 degrees 2θ) at 9.8°, 16.0°, and 25.4°. In some embodiments, crystalline Compound 15 Form III has an XRPD pattern comprising degree 2θ-reflections (+/−0.2 degrees 2θ) at 9.8°, 16.0°, and 25.4°, and one, two or three of the degree 2θ-reflections (+/−0.2 degrees 2θ) at 10.2°, 19.1°, and 26.9°. In some embodiments, crystalline Compound 15 Form III has an XRPD pattern comprising degree 2θ-reflections (+/−0.2 degrees 2θ) at 9.8°, 16.0°, and 25.4°, and one or two of the degree 2θ-reflections (+/−0.2 degrees 2θ) at 10.2°, 19.1°, and 26.9°. In some embodiments, crystalline Compound 15 Form III has an XRPD pattern comprising degree 2θ-reflections (+/−0.2 degrees 2θ) at 9.8°, 16.0°, and 25.4°, and one of the degree 2θ-reflections (+/−0.2 degrees 2θ) at 10.2°, 19.1°, and 26.9°. In some embodiments, crystalline Compound 15 Form III has an XRPD pattern comprising degree 2θ-reflections (+/−0.2 degrees 2θ) at 9.8°, 16.0°, and 25.4°, and two of the degree 2θ-reflections (+/−0.2 degrees 2θ) at 10.2°, 19.1°, and 26.9°. In some embodiments, crystalline Compound 15 Form III has an XRPD pattern comprising degree 2θ-reflections (+/−0.2 degrees 2θ) at 9.8°, 10.2°, 16.0°, 19.1°, 25.4°, and 26.9°. In some embodiments, crystalline Compound 15 Form III has an XRPD pattern comprising any three of the degree 2θ-reflections (+/−0.2 degrees 2θ) at 9.8°, 10.2°, 16.0°, 19.1°, 25.4°, and 26.9°.

In some embodiments, crystalline Compound 15 Form III has an XRPD pattern comprising degree 2θ-reflections (+/−0.2 degrees 2θ) at 9.8°, 10.2°, 16.0°, 19.1°, 25.4°, and 26.9°, and one, two or three of the degree 2θ-reflections (+/−0.2 degrees 2θ) at 10.4°, 19.8°, and 20.7°. In some embodiments, crystalline Compound 15 Form III has an XRPD pattern comprising degree 2θ-reflections (+/−0.2 degrees 2θ) at 9.8°, 10.2°, 16.0°, 19.1°, 25.4°, and 26.9°, and one or two of the degree 2θ-reflections (+/−0.2 degrees 2θ) at 10.4°, 19.8°, and 20.7°. In some embodiments, crystalline Compound 15 Form III has an XRPD pattern comprising degree 2θ-reflections (+/−0.2 degrees 2θ) at 9.8°, 10.2°, 16.0°, 19.1°, 25.4°, and 26.9°, and one of the degree 2θ-reflections (+/−0.2 degrees 2θ) at 10.4°, 19.8°, and 20.7°. In some embodiments, crystalline Compound 15 Form III has an XRPD pattern comprising degree 2θ-reflections (+/−0.2 degrees 2θ) at 9.8°, 10.2°, 16.0°, 19.1°, 25.4°, and 26.9°, and two of the degree 2θ-reflections (+/−0.2 degrees 2θ) at 10.4°, 19.8°, and 20.7°. In some embodiments, crystalline Compound 15 Form III has an XRPD pattern comprising degree 2θ-reflections (+/−0.2 degrees 2θ) at 9.8°, 10.2°, 10.4°, 16.0°, 19.1°, 19.8°, 20.7°, 25.4°, and 26.9°. In some embodiments, crystalline Compound 15 Form III has an XRPD pattern comprising any three of the degree 2θ-reflections (+/−0.2 degrees 2θ) at 9.8°, 10.2°, 10.4°, 16.0°, 19.1°, 19.8°, 20.7°, 25.4°, and 26.9°.

XII. Salts of Compound 15

Compound 15 Xinafoate

In some embodiments, the disclosure provides xinafoate salt of the compound 15 (Compound 15 xinafoate). In some embodiments, the Compound 15 xinafoate is unsolvated.

Figure 19:
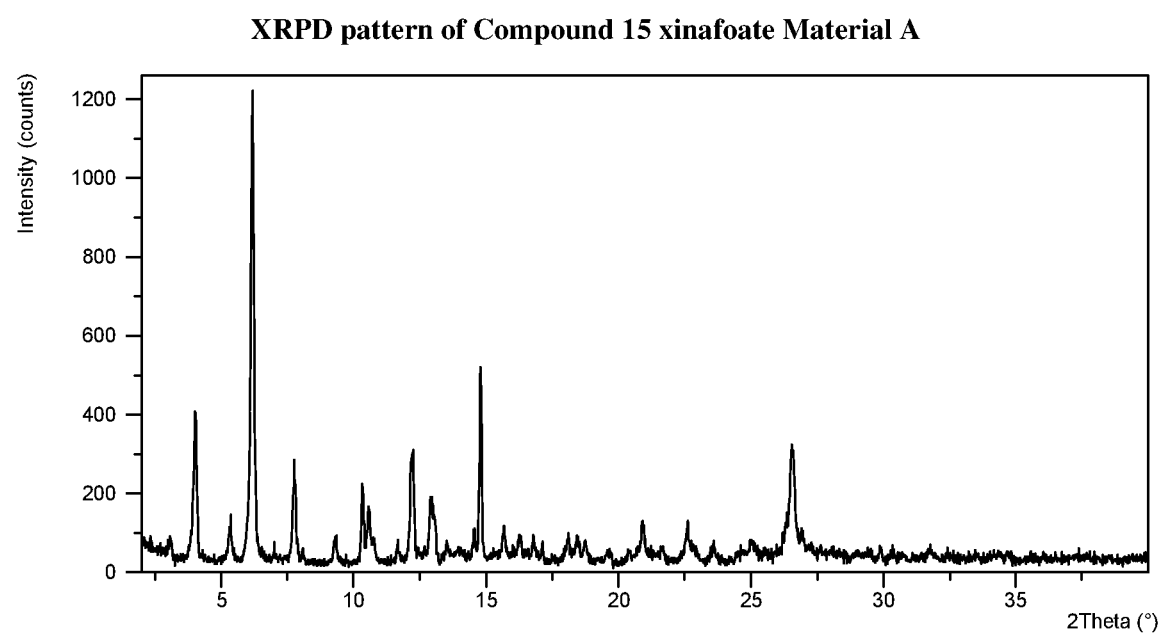
FIG. 19: Shows the XRPD pattern of Compound 15 xinafoate Material A.
Figure 20:
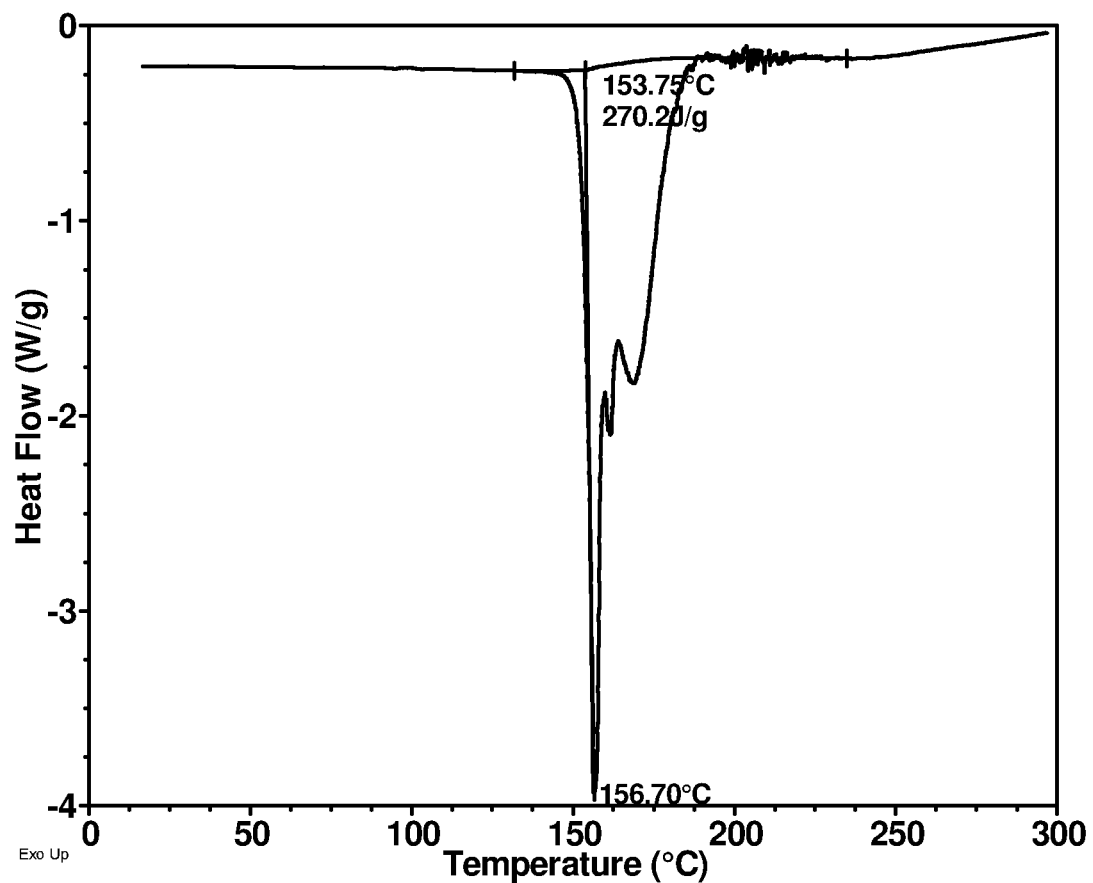
FIG. 20: Shows the DSC thermogram of Compound 15 xinafoate Material A.
Figure 21:
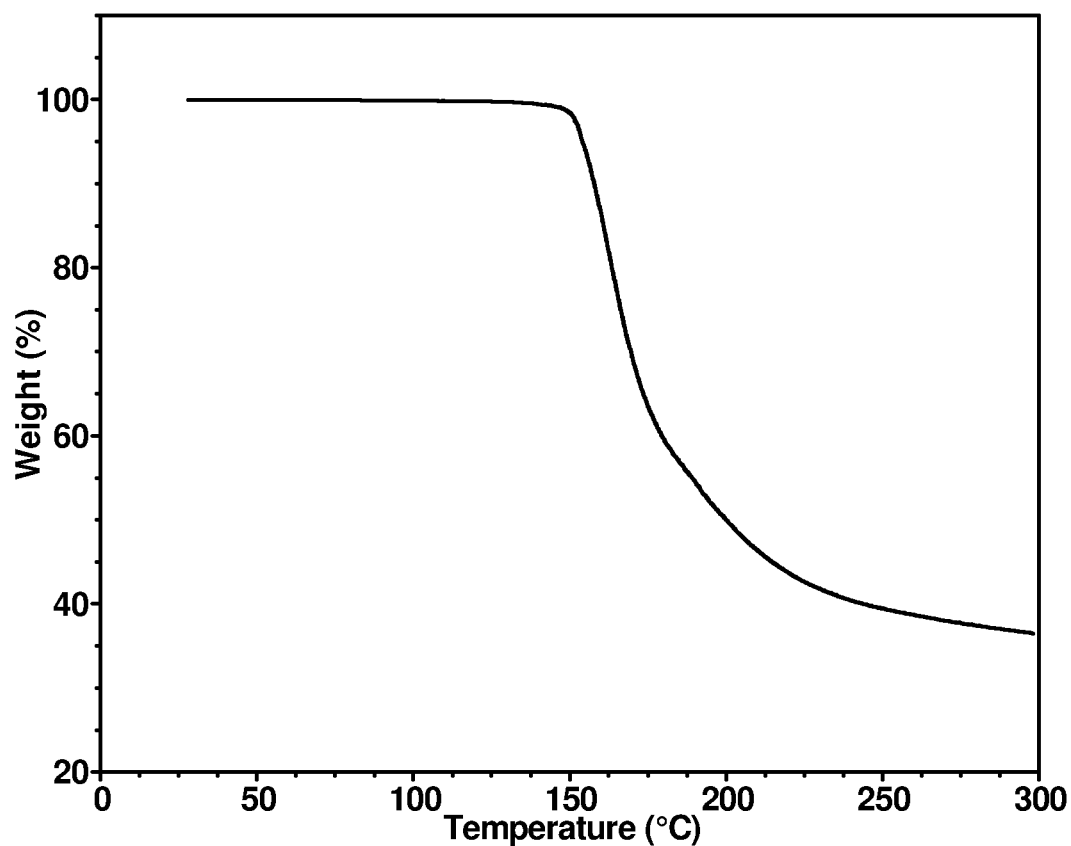
FIG. 21: Shows the TGA thermogram of Compound 15 xinafoate Material A.

In some embodiments, the disclosure provides a crystalline form of the Compound 15 xinafoate. In some embodiments, the crystalline form of the Compound 15 xinafoate exhibits an XRPD pattern substantially as shown in FIG. 19. In some embodiments, the crystalline form of the Compound 15 xinafoate may exhibit a DSC thermogram substantially as shown in FIG. 20. In some embodiments, the crystalline form of the Compound 15 xinafoate may exhibit a TGA graph substantially as shown in FIG. 21.

In some embodiments of the crystalline form of the Compound 15 xinafoate, at least one, at least two, at least three, or all of the following (a)-(c) apply: (a) crystalline form of the Compound 15 xinafoate has an XRPD pattern substantially as shown in FIG. 19; (b) crystalline form of the Compound 15 xinafoate has a DSC thermogram substantially as shown in FIG. 20; (c) crystalline form of the Compound 15 xinafoate has a TGA graph substantially as shown in FIG. 21.

In some embodiments, crystalline form of the Compound 15 xinafoate has the following properties:
  (a) an XRPD pattern substantially as shown in FIG. 19;
  (b) a DSC thermogram substantially as shown in FIG. 20; and
  (c) a TGA graph substantially as shown in FIG. 21.

In some embodiments, crystalline form of the Compound 15 xinafoate has an XRPD pattern displaying at least two, at least three, at least four, at least five, or at least six of the degree 2θ-reflections with the greatest intensity as the XRPD pattern substantially as shown in FIG. 19.

In some embodiments, crystalline form of the Compound 15 xinafoate has an XRPD pattern comprising degree 2θ-reflections (+/−0.2 degrees 2θ) at 4.0°, 12.2°, and 14.8°. In some embodiments, crystalline form of the Compound 15 xinafoate has an XRPD pattern comprising degree 2θ-reflections (+/−0.2 degrees 2θ) at 4.0°, 12.2°, and 14.8° and one, two or three of the degree 2θ-reflections (+/−0.2 degrees 2θ) at 6.2°, 12.9° and 26.6°. In some embodiments, crystalline form of the Compound 15 xinafoate has an XRPD pattern comprising degree 2θ-reflections (+/−0.2 degrees 2θ) at 4.0°, 12.2°, and 14.8° and one or two of the degree 2θ-reflections (+/−0.2 degrees 2θ) at 6.2°, 12.9° and 26.6°. In some embodiments, crystalline form of the Compound 15 xinafoate has an XRPD pattern comprising degree 2θ-reflections (+/−0.2 degrees 2θ) at 4.0°, 12.2°, and 14.8° and one of the degree 2θ-reflections (+/−0.2 degrees 2θ) at 6.2°, 12.9° and 26.6°. In some embodiments, crystalline form of the Compound 15 xinafoate has an XRPD pattern comprising degree 2θ-reflections (+/−0.2 degrees 2θ) at 4.0°, 12.2°, and 14.8° and two of the degree 2θ-reflections (+/−0.2 degrees 2θ) at 6.2°, 12.9° and 26.6°. In some embodiments, crystalline form of the Compound 15 xinafoate has an XRPD pattern comprising degree 2θ-reflections (+/−0.2 degrees 2θ) at 4.0°, 6.2°, 12.2°, 12.9°, 14.8° and 26.6°. In some embodiments, crystalline form of the Compound 15 xinafoate has an XRPD pattern comprising any three of the degree 2θ-reflections (+/−0.2 degrees 2θ) at 4.0°, 6.2°, 12.2°, 12.9°, 14.8° and 26.6°.

In some embodiments, crystalline form of the Compound 15 xinafoate has an XRPD pattern comprising degree 2θ-reflections (+/−0.2 degrees 2θ) at 4.0°, 6.2°, 12.2°, 12.9°, 14.8° and 26.6°, and one, two, or three of the degree 2θ-reflections (+/−0.2 degrees 2θ) at 7.8°, 10.3°, and 15.7°. In some embodiments, crystalline form of the Compound 15 xinafoate has an XRPD pattern comprising degree 2θ-reflections (+/−0.2 degrees 2θ) at 4.0°, 6.2°, 12.2°, 12.9°, 14.8° and 26.6°, and one or two of the degree 2θ-reflections (+/−0.2 degrees 2θ) at 7.8°, 10.3°, and 15.7°. In some embodiments, crystalline form of the Compound 15 xinafoate has an XRPD pattern comprising degree 2θ-reflections (+/−0.2 degrees 2θ) at 4.0°, 6.2°, 12.2°, 12.9°, 14.8° and 26.6°, and one of the degree 2θ-reflections (+/−0.2 degrees 2θ) at 7.8°, 10.3°, and 15.7°. In some embodiments, crystalline form of the Compound 15 xinafoate has an XRPD pattern comprising degree 2θ-reflections (+/−0.2 degrees 2θ) at 4.0°, 6.2°, 12.2°, 12.9°, 14.8° and 26.6°, and two of the degree 2θ-reflections (+/−0.2 degrees 2θ) at 7.8°, 10.3°, and 15.7°. In some embodiments, crystalline form of the Compound 15 xinafoate has an XRPD pattern comprising degree 2θ-reflections (+/−0.2 degrees 2θ) at 4.0°, 6.2°, 7.8°, 10.3°, 12.2°, 12.9°, 14.8°, 15.7°, and 26.6°. In some embodiments, crystalline form of the Compound 15 xinafoate has an XRPD pattern comprising any three of the degree 2θ-reflections (+/−0.2 degrees 2θ) at 4.0°, 6.20, 7.8°, 10.30, 12.2°, 12.9°, 14.8°, 15.7°, and 26.6°.

Compound 15 HCl Salt

In some embodiments, the disclosure provides HCl salt of the compound 15 (Compound 15 HCl salt).

In some embodiments, the disclosure provides a crystalline form of the Compound 15 HCl salt.

Compound 15 HCl Salt Form I

Figure 22:
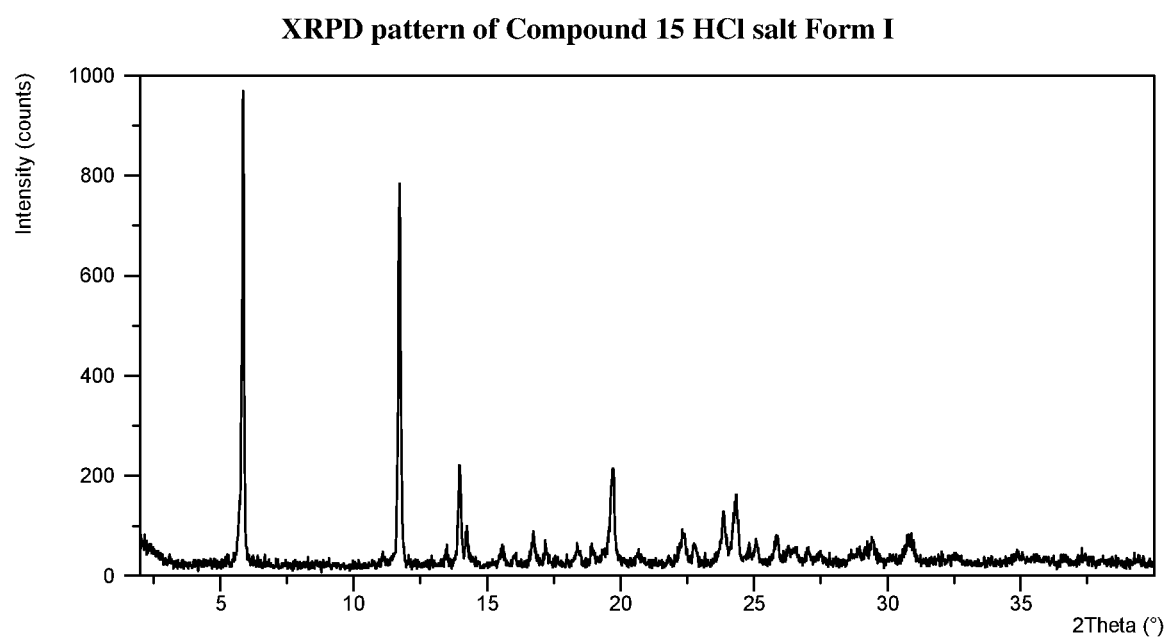
FIG. 22: Shows the XRPD pattern of Compound 15 HCl salt Form I.
Figure 23:
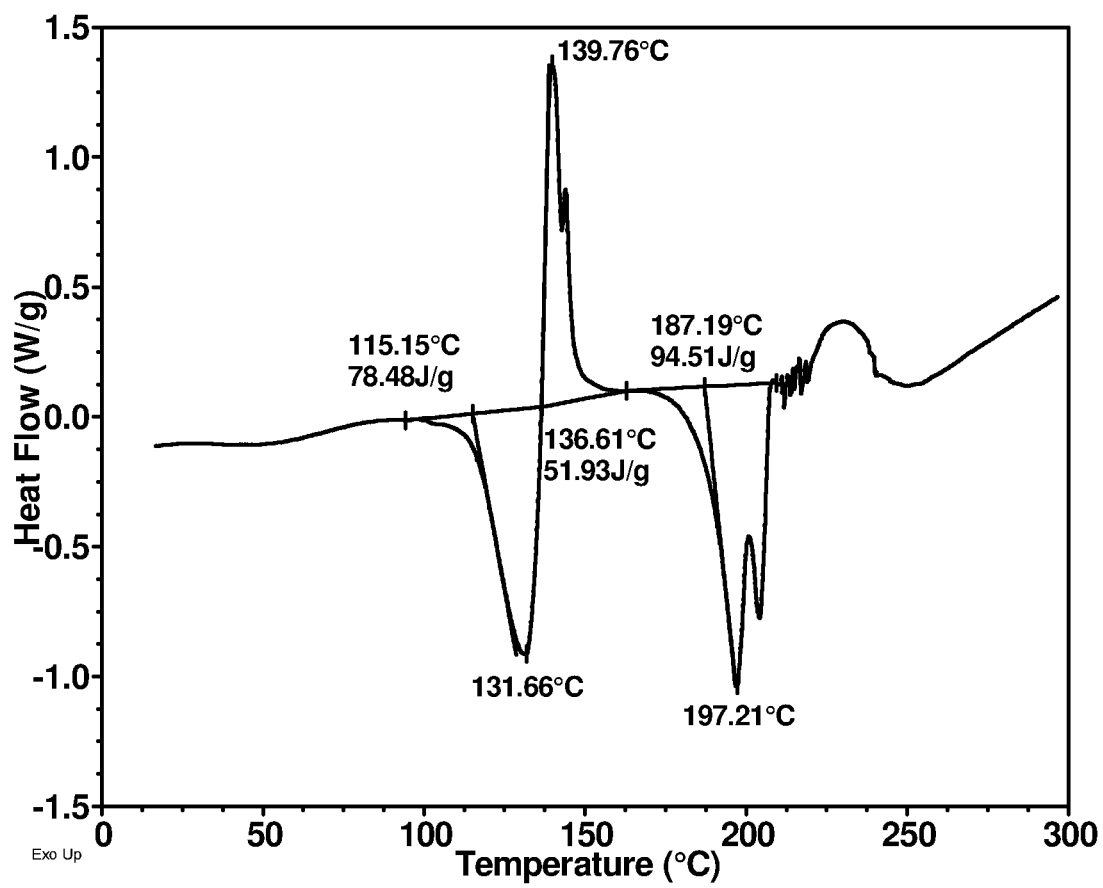
FIG. 23: Shows the DSC thermogram of Compound 15 HCl salt Form I.
Figure 24:
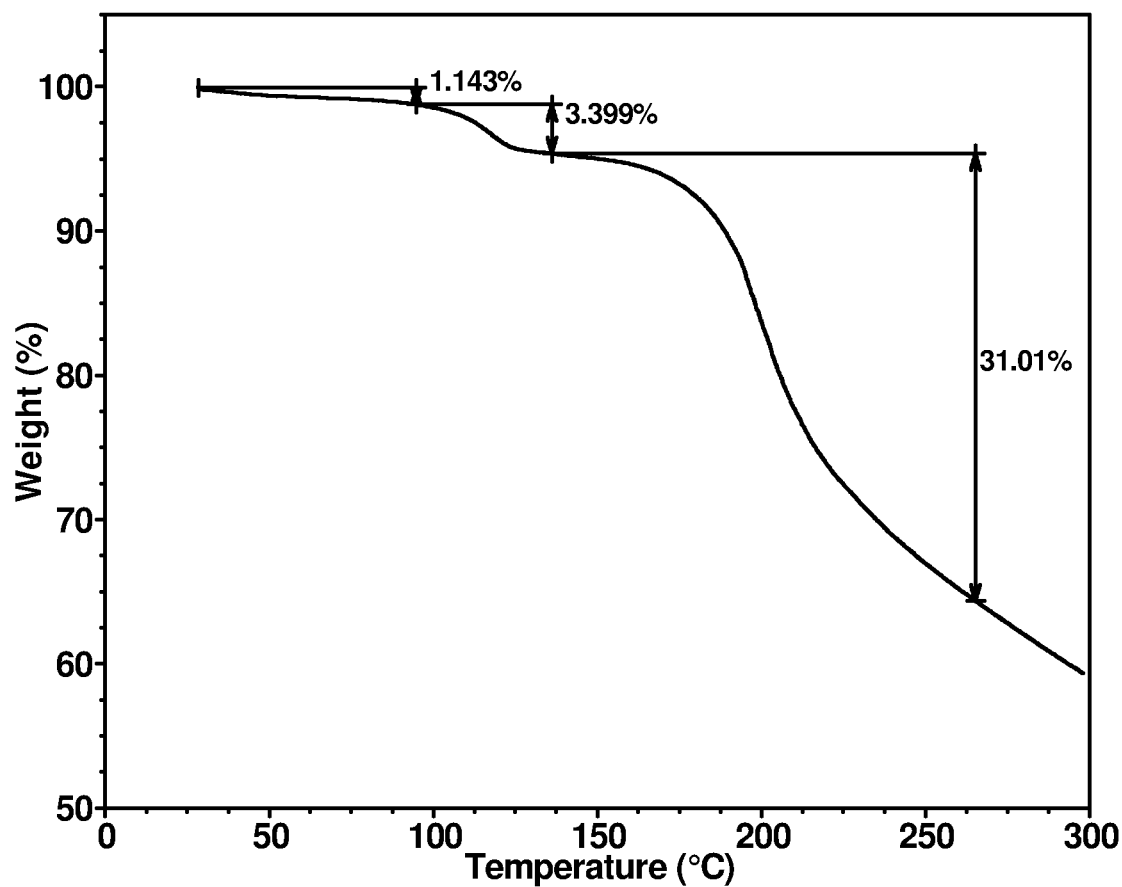
FIG. 24: Shows the TGA thermogram of Compound 15 HCl salt Form I.

In some embodiments, the disclosure provides a crystalline Form I of the Compound 15 HCl salt ("Compound 15 HCl salt Form I"). In some embodiments, the Compound 15 HCl salt Form I exhibits an XRPD pattern substantially as shown in FIG. 22. In some embodiments, the Compound 15 HCl salt Form I may exhibit a DSC thermogram substantially as shown in FIG. 23. In some embodiments, the Compound 15 HCl salt Form I may exhibit a TGA graph substantially as shown in FIG. 24.

In some embodiments of the Compound 15 HCl salt Form I, at least one, at least two, or all of the following (a)-(c) apply: (a) Compound 15 HCl salt Form I has an XRPD pattern substantially as shown in FIG. 22; (b) Compound 15 HCl salt Form I has a DSC thermogram substantially as shown in FIG. 23; (c) Compound 15 HCl salt Form I has a TGA graph substantially as shown in FIG. 24.

In some embodiments, Compound 15 HCl salt Form I has the following properties:
 (a) an XRPD pattern substantially as shown in FIG. 22;
 (b) a DSC thermogram substantially as shown in FIG. 23; and
 (c) a TGA graph substantially as shown in FIG. 24.

In some embodiments, Compound 15 HCl salt Form I has an XRPD pattern displaying at least two, at least three, at least four, at least five, or at least six of the degree 2θ-reflections with the greatest intensity as the XRPD pattern substantially as shown in FIG. 22.

In some embodiments, Compound 15 HCl salt Form I has an XRPD pattern comprising degree 2θ-reflections (+/−0.2 degrees 2θ) at 5.9°, 14.0°, and 24.3°. In some embodiments, Compound 15 HCl salt Form I has an XRPD pattern comprising degree 2θ-reflections (+/−0.2 degrees 2θ) at 5.9°, 14.0°, and 24.3°, and one, two or three of the degree 2θ-reflections (+/−0.2 degrees 2θ) at 11.7°, 16.7°, and 23.9°. In some embodiments, Compound 15 HCl salt Form I has an XRPD pattern comprising degree 2θ-reflections (+/−0.2 degrees 2θ) at 5.9°, 14.0°, and 24.3°, and one or two of the degree 2θ-reflections (+/−0.2 degrees 2θ) at 11.7°, 16.7°, and 23.9°. In some embodiments, Compound 15 HCl salt Form I has an XRPD pattern comprising degree 2θ-reflections (+/−0.2 degrees 2θ) at 5.9°, 14.0°, and 24.3°, and one of the degree 2θ-reflections (+/−0.2 degrees 2θ) at 11.7°, 16.7°, and 23.9°. In some embodiments, Compound 15 HCl salt Form I has an XRPD pattern comprising degree 2θ-reflections (+/−0.2 degrees 2θ) at 5.9°, 14.0°, and 24.3°, and two of the degree 2θ-reflections (+/−0.2 degrees 2θ) at 11.7°, 16.7°, and 23.9°. In some embodiments, Compound 15 HCl salt Form I has an XRPD pattern comprising degree 2θ-reflections (+/−0.2 degrees 2θ) at 5.9°, 11.7°, 14.0°, 16.7°, 23.9°, and 24.3°. In some embodiments, Compound 15 HCl salt Form I has an XRPD pattern comprising any three of the degree 2θ-reflections (+/−0.2 degrees 2θ) at 5.9°, 11.7°, 14.0°, 16.7°, 23.9°, and 24.3°.

In some embodiments, Compound 15 HCl salt Form I has an XRPD pattern comprising degree 2θ-reflections (+/−0.2 degrees 2θ) at 5.9°, 11.7°, 14.0°, 16.7°, 23.9°, and 24.3°, and one, two, or three of the degree 2θ-reflections (+/−0.2 degrees 2θ) at 14.2°, 19.7°, and 22.4°. In some embodiments, Compound 15 HCl salt Form I has an XRPD pattern comprising degree 20-reflections (+/−0.2 degrees 2θ) at 5.9°, 11.7°, 14.0°, 16.7°, 23.9°, and 24.3°, and one or two of the degree 2θ-reflections (+/−0.2 degrees 2θ) at 14.2°, 19.7°, and 22.4°. In some embodiments, Compound 15 HCl salt Form I has an XRPD pattern comprising degree 2θ-reflections (+/−0.2 degrees 2θ) at 5.9°, 11.7°, 14.0°, 16.7°, 23.9°, and 24.3°, and one of the degree 2θ-reflections (+/−0.2 degrees 2θ) at 14.2°, 19.7°, and 22.4°. In some embodiments, Compound 15 HCl salt Form I has an XRPD pattern comprising degree 2θ-reflections (+/−0.2 degrees 2θ) at 5.9°, 11.7°, 14.0°, 16.7°, 23.9°, and 24.3°, and two of the degree 2θ-reflections (+/−0.2 degrees 2θ) at 14.2°, 19.7°, and 22.4°. In some embodiments, Compound 15 HCl salt Form I has an XRPD pattern comprising degree 2θ-reflections (+/−0.2 degrees 2θ) at 5.9°, 11.7°, 14.0°, 14.2°, 16.7°, 19.7°, 22.4°, 23.9°, and 24.3°. In some embodiments, Compound 15 HCl salt Form I has an XRPD pattern comprising any three of the degree 2θ-reflections (+/−0.2 degrees 2θ) at 5.9°, 11.7°, 14.0°, 14.2°, 16.7°, 19.7°, 22.4°, 23.9°, and 24.3°.

Compound 15 HCl Salt Material A

Figure 25:
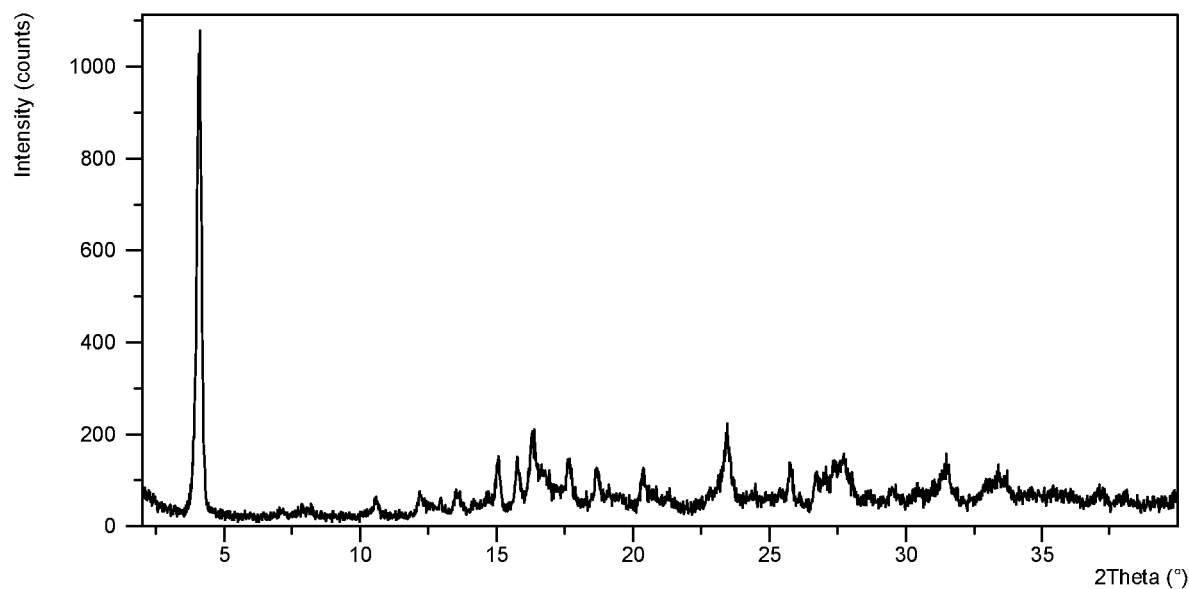
FIG. 25: Shows the XRPD pattern of Compound 15 HCl salt Material A.
Figure 26:
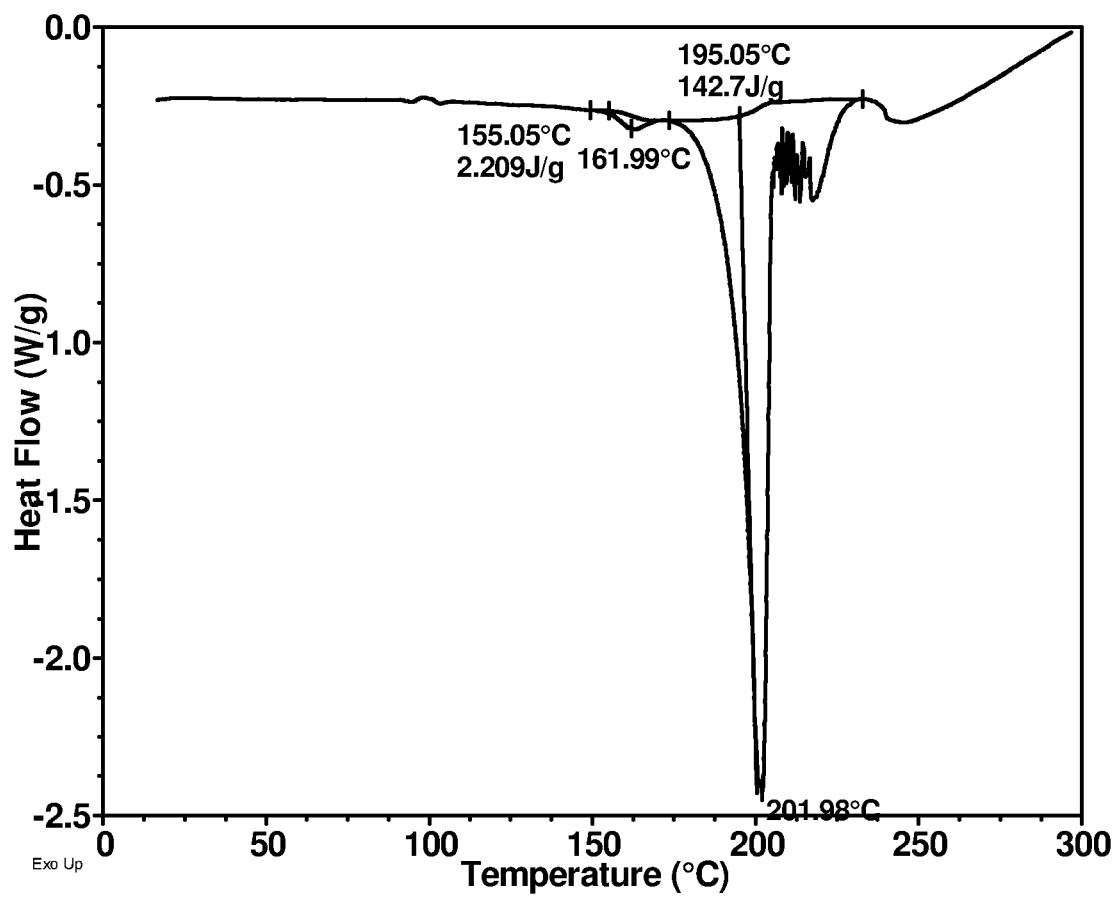
FIG. 26: Shows the DSC thermogram of Compound 15 HCl salt Material A.
Figure 27:
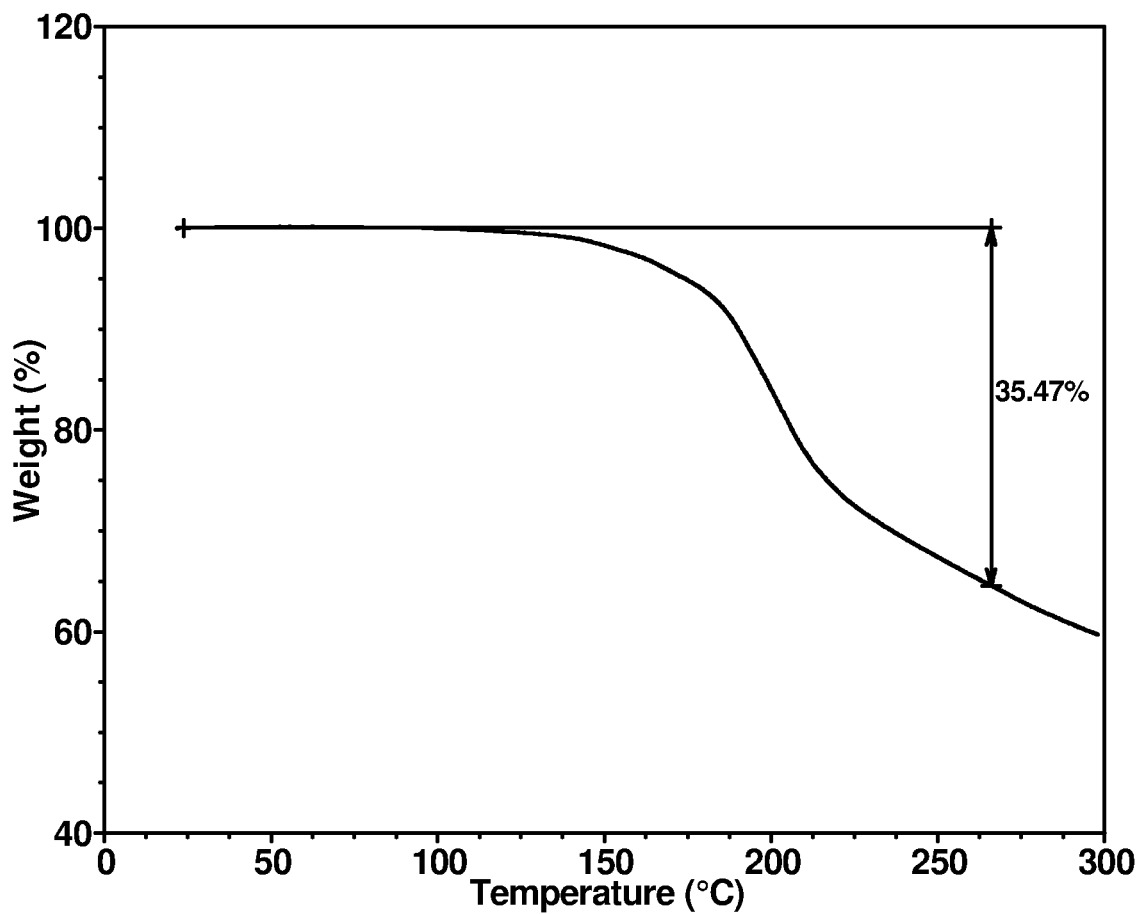
FIG. 27: Shows the TGA thermogram of Compound 15 HCl salt Material A.

In some embodiments, the disclosure provides a crystalline Material A of the Compound 15 HCl salt ("Compound 15 HCl salt Material A"). In some embodiments, the Compound 15 HCl salt Material A exhibits an XRPD pattern substantially as shown in FIG. 25. In some embodiments, the Compound 15 HCl salt Material A may exhibit a DSC thermogram substantially as shown in FIG. 26. In some embodiments, the Compound 15 HCl salt Material A may exhibit a TGA graph substantially as shown in FIG. 27.

In some embodiments of the Compound 15 HCl salt Material A, at least one, at least two, or all of the following (a)-(c) apply: (a) Compound 15 HCl salt Material A has an XRPD pattern substantially as shown in FIG. 25; (b) Compound 15 HCl salt Material A has a DSC thermogram substantially as shown in FIG. 26; (c) Compound 15 HCl salt Material A has a TGA graph substantially as shown in FIG. 27.

In some embodiments, Compound 15 HCl salt Material A has the following properties:
 (a) an XRPD pattern substantially as shown in FIG. 25;
 (b) a DSC thermogram substantially as shown in FIG. 26; and
 (c) a TGA graph substantially as shown in FIG. 27.

In some embodiments, Compound 15 HCl salt Material A has an XRPD pattern displaying at least two, at least three, at least four, at least five, or at least six of the degree 2θ-reflections with the greatest intensity as the XRPD pattern substantially as shown in FIG. 25.

In some embodiments, Compound 15 HCl salt Material A has an XRPD pattern comprising degree 2θ-reflections (+/−0.2 degrees 2θ) at 4.0°, 15.0°, and 25.8°. In some embodiments, Compound 15 HCl salt Material A has an XRPD pattern comprising degree 2θ-reflections (+/−0.2 degrees 2θ) at 4.0°, 15.0°, and 25.8°, and one, two or three of the degree 2θ-reflections (+/−0.2 degrees 2θ) at 10.6°, 16.3°, and 26.7°. In some embodiments, Compound 15 HCl salt Material A has an XRPD pattern comprising degree 2θ-reflections (+/−0.2 degrees 2θ) at 4.0°, 15.0°, and 25.8°, and one or two of the degree 2θ-reflections (+/−0.2 degrees 2θ) at 10.6°, 16.3°, and 26.7°. In some embodiments, Compound 15 HCl salt Material A has an XRPD pattern comprising degree 2θ-reflections (+/−0.2 degrees 2θ) at 4.0°, 15.0°, and 25.8°, and one of the degree 2θ-reflections (+/−0.2 degrees 2θ) at 10.6°, 16.3°, and 26.7°. In some embodiments, Compound 15 HCl salt Material A has an XRPD pattern comprising degree 2θ-reflections (+/−0.2 degrees 2θ) at 4.0°, 15.0°, and 25.8°, and two of the degree 2θ-reflections (+/−0.2 degrees 2θ) at 10.6°, 16.3°, and 26.7°. In some embodiments, Compound 15 HCl salt Material A has an XRPD pattern comprising degree 2θ-reflections (+/−0.2 degrees 2θ) at 4.0°, 10.6°, 15.0°, 16.3°, 25.8°, and 26.7°. In some embodiments, Compound 15 HCl salt Material A has an XRPD pattern comprising any three of the degree 2θ-reflections (+/−0.2 degrees 2θ) at 4.0°, 10.6°, 15.0°, 16.3°, 25.8°, and 26.7°.

In some embodiments, Compound 15 HCl salt Material A has an XRPD pattern comprising degree 2θ-reflections (+/−0.2 degrees 2θ) at 4.0°, 10.6°, 15.0°, 16.3°, 25.8°, and 26.7°, and one, two, or three of the degree 2θ-reflections (+/−0.2 degrees 2θ) at 12.2°, 15.7°, and 31.5°. In some embodiments, Compound 15 HCl salt Material A has an XRPD pattern comprising degree 2θ-reflections (+/−0.2 degrees 2θ) at 4.0°, 10.6°, 15.0°, 16.3°, 25.8°, and 26.7°, and one or two of the degree 2θ-reflections (+/−0.2 degrees 2θ) at 12.2°, 15.7°, and 31.5°. In some embodiments, Compound 15 HCl salt Material A has an XRPD pattern comprising degree 2θ-reflections (+/−0.2 degrees 2θ) at 4.0°, 10.6°, 15.0°, 16.3°, 25.8°, and 26.7°, and one of the degree 2θ-reflections (+/−0.2 degrees 2θ) at 12.2°, 15.7°, and 31.5°. In some embodiments, Compound 15 HCl salt Material A has an XRPD pattern comprising degree 2θ-reflections (+/−0.2 degrees 2θ) at 4.0°, 10.6°, 15.0°, 16.3°, 25.8°, and 26.7°, and two of the degree 2θ-reflections (+/−0.2 degrees 2θ) at 12.2°, 15.7°, and 31.5°. In some embodiments, Compound 15 HCl salt Material A has an XRPD pattern comprising degree 2θ-reflections (+/−0.2 degrees 2θ) at 4.0°, 10.6°, 12.2°, 15.0°, 15.7°, 16.3°, 25.8°, 26.7°, and 31.5°. In some embodiments, Compound 15 HCl salt Material A has an XRPD pattern comprising any three of the degree 2θ-reflections (+/−0.2 degrees 2θ) at 4.0°, 10.6°, 12.2°, 15.0°, 15.7°, 16.3°, 25.8°, 26.7°, and 31.5°.

Compound 15 HCl Salt Material B

Figure 28:
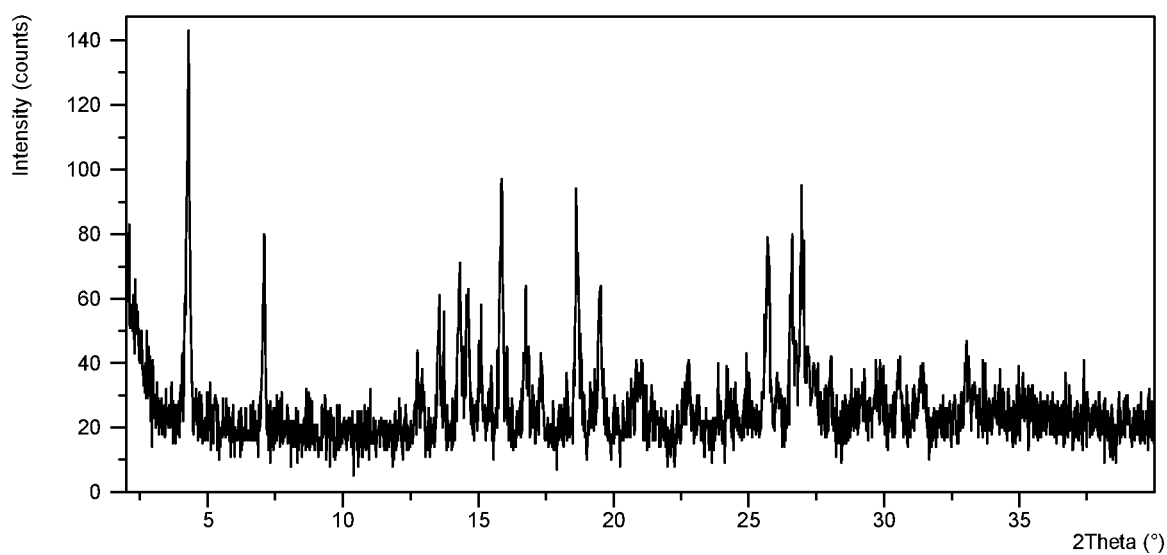
FIG. 28: Shows the XRPD pattern of Compound 15 HCl salt Material B.
Figure 29:
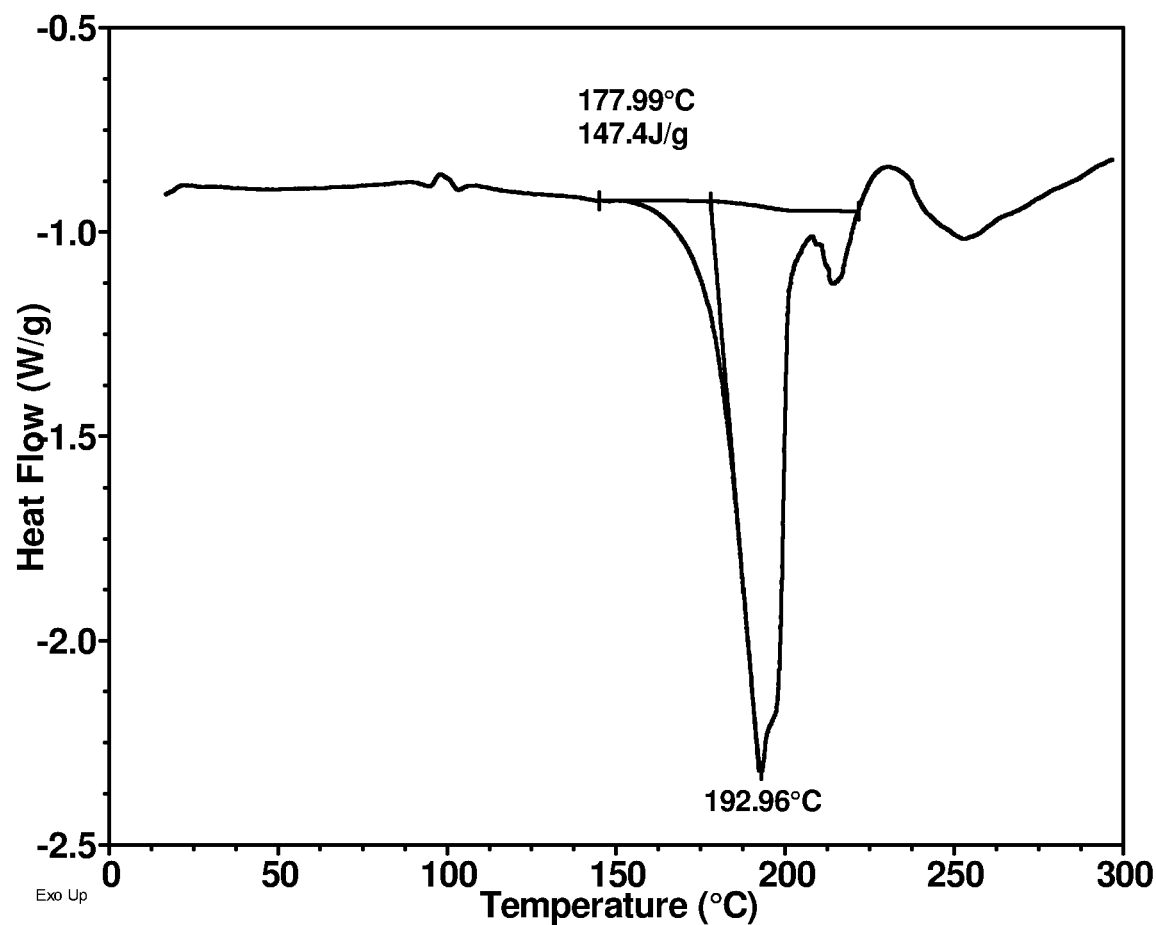
FIG. 29: Shows the DSC thermogram of Compound 15 HCl salt Material B.
Figure 30:
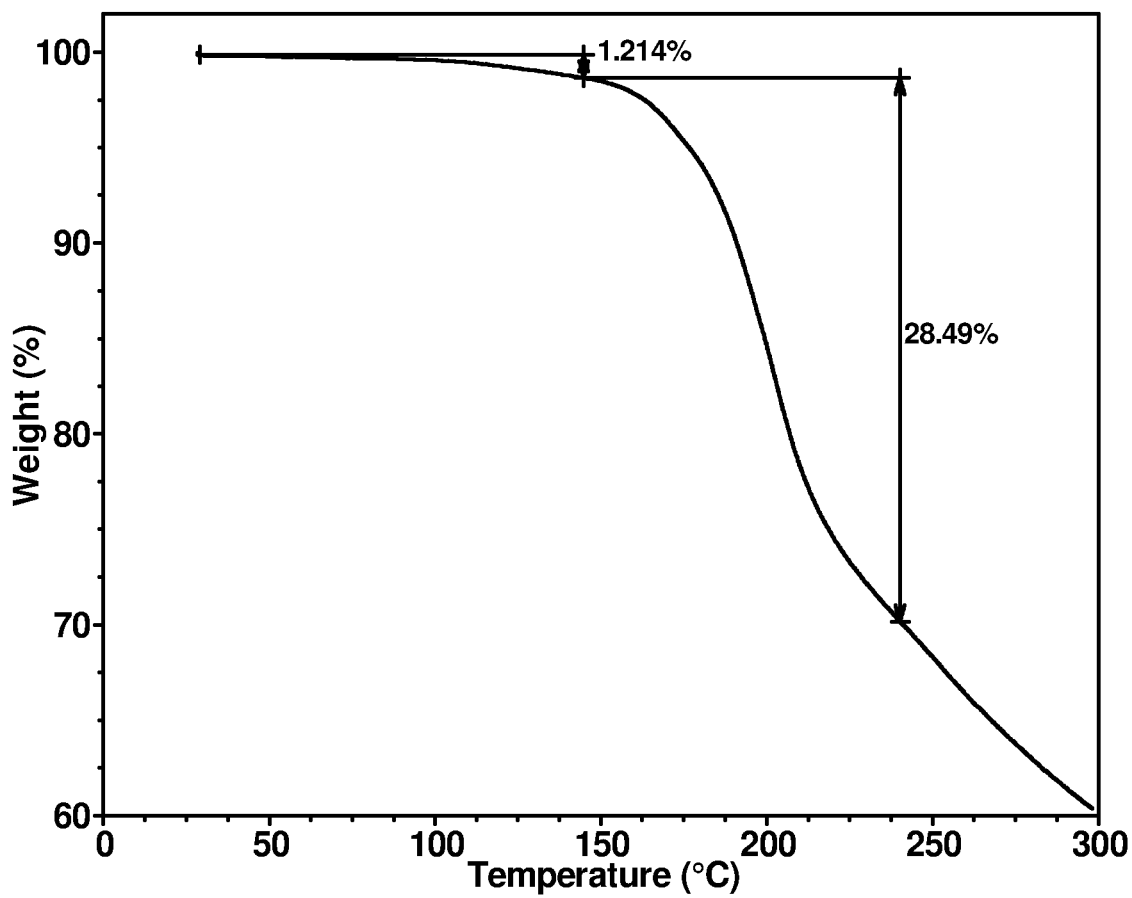
FIG. 30: Shows the TGA thermogram of Compound 15 HCl salt Material B.

In some embodiments, the disclosure provides a crystalline Material B of the Compound 15 HCL salt ("Compound 15 HCl salt Material B"). In some embodiments, the Compound 15 HCl salt Material B exhibits an XRPD pattern substantially as shown in FIG. 28. In some embodiments, the Compound 15 HCl salt Material B may exhibit a DSC thermogram substantially as shown in FIG. 29. In some embodiments, the Compound 15 HCl salt Material B may exhibit a TGA graph substantially as shown in FIG. 30.

In some embodiments of the Compound 15 HCl salt Material B, at least one, at least two, or all of the following (a)-(c) apply: (a) Compound 15 HCl salt Material B has an XRPD pattern substantially as shown in FIG. 28; (b) Compound 15 HCl salt Material B has a DSC thermogram substantially as shown in FIG. 29; (c) Compound 15 HCl salt Material B has a TGA graph substantially as shown in FIG. 30.

In some embodiments, Compound 15 HCl salt Material B has the following properties:
(a) an XRPD pattern substantially as shown in FIG. 28;
(b) a DSC thermogram substantially as shown in FIG. 29; and
(c) a TGA graph substantially as shown in FIG. 30.

In some embodiments, Compound 15 HCl salt Material B has an XRPD pattern displaying at least two, at least three, at least four, at least five, or at least six of the degree 2θ-reflections with the greatest intensity as the XRPD pattern substantially as shown in FIG. 28.

In some embodiments, Compound 15 HCl salt Material B has an XRPD pattern comprising degree 2θ-reflections (+/−0.2 degrees 2θ) at 4.3°, 15.9°, and 26.6°. In some embodiments, Compound 15 HCl salt Material B has an XRPD pattern comprising degree 2θ-reflections (+/−0.2 degrees 2θ) at 4.3°, 15.9°, and 26.6°, and one, two or three of the degree 2θ-reflections (+/−0.2 degrees 2θ) at 7.1°, 16.8°, and 25.7°. In some embodiments, Compound 15 HCl salt Material B has an XRPD pattern comprising degree 2θ-reflections (+/−0.2 degrees 2θ) at 4.3°, 15.9°, and 26.6°, and one or two of the degree 2θ-reflections (+/−0.2 degrees 2θ) at 7.10, 16.8°, and 25.7°. In some embodiments, Compound 15 HCl salt Material B has an XRPD pattern comprising degree 2θ-reflections (+/−0.2 degrees 2θ) at 4.3°, 15.9°, and 26.6°, and one of the degree 2θ-reflections (+/−0.2 degrees 2θ) at 7.10, 16.8°, and 25.7°. In some embodiments, Compound 15 HCl salt Material B has an XRPD pattern comprising degree 2θ-reflections (+/−0.2 degrees 2θ) at 4.3°, 15.9°, and 26.6°, and two of the degree 2θ-reflections (+/−0.2 degrees 2θ) at 7.1°, 16.8°, and 25.7°. In some embodiments, Compound 15 HCl salt Material B has an XRPD pattern comprising degree 2θ-reflections (+/−0.2 degrees 2θ) at 4.3°, 7.1°, 15.9°, 16.8°, 25.7°, and 26.6°. In some embodiments, Compound 15 HCl salt Material B has an XRPD pattern comprising any three of the degree 2θ-reflections (+/−0.2 degrees 2θ) at 4.3°, 7.1°, 15.9°, 16.8°, 25.7°, and 26.6°.

In some embodiments, Compound 15 HCl salt Material B has an XRPD pattern comprising degree 2θ-reflections (+/−0.2 degrees 2θ) at 4.3°, 7.1°, 15.9°, 16.8°, 25.7°, and 26.6°, and one, two, or three of the degree 2θ-reflections (+/−0.2 degrees 2θ) at 14.3°, 18.7°, and 27.0°. In some embodiments, Compound 15 HCl salt Material B has an XRPD pattern comprising degree 2θ-reflections (+/−0.2 degrees 2θ) at 4.3°, 7.1°, 15.9°, 16.8°, 25.7°, and 26.6°, and one or two of the degree 2θ-reflections (+/−0.2 degrees 2θ) at 14.3°, 18.7°, and 27.0°. In some embodiments, Compound 15 HCl salt Material B has an XRPD pattern comprising degree 2θ-reflections (+/−0.2 degrees 2θ) at 4.3°, 7.1°, 15.9°, 16.8°, 25.7°, and 26.6°, and one of the degree 2θ-reflections (+/−0.2 degrees 2θ) at 14.3°, 18.7°, and 27.0°. In some embodiments, Compound 15 HCl salt Material B has an XRPD pattern comprising degree 2θ-reflections (+/−0.2 degrees 2θ) at 4.3°, 7.1°, 15.9°, 16.8°, 25.7°, and 26.6°, and two of the degree 2θ-reflections (+/−0.2 degrees 2θ) at 14.3°, 18.7°, and 27.0°. In some embodiments, Compound 15 HCl salt Material B has an XRPD pattern comprising degree 2θ-reflections (+/−0.2 degrees 2θ) at 4.3°, 7.1°, 14.3°, 15.9°, 16.8°, 18.7°, 25.7°, 26.6°, and 27.0°. In some embodiments, Compound 15 HCl salt Material B has an XRPD pattern comprising any three of the degree 2θ-reflections (+/−0.2 degrees 2θ) at 4.3°, 7.10, 14.3°, 15.9°, 16.8°, 18.7°, 25.7°, 26.6°, and 27.0°.

Compound 15 HCl Salt Material C

Figure 31:
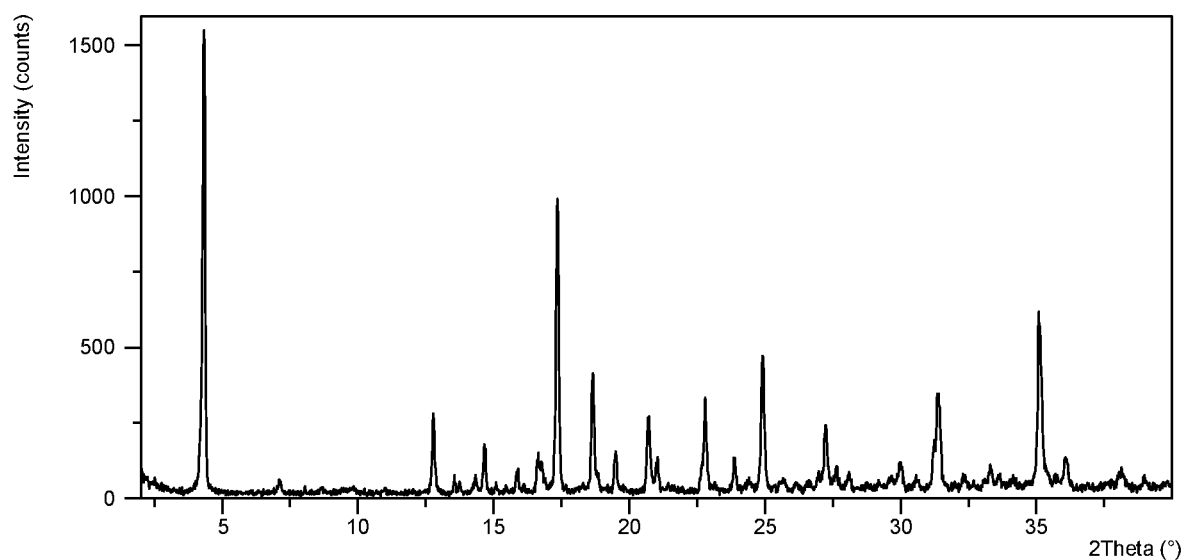
FIG. 31: Shows the XRPD pattern of Compound 15 HCl salt Material C.
Figure 32:
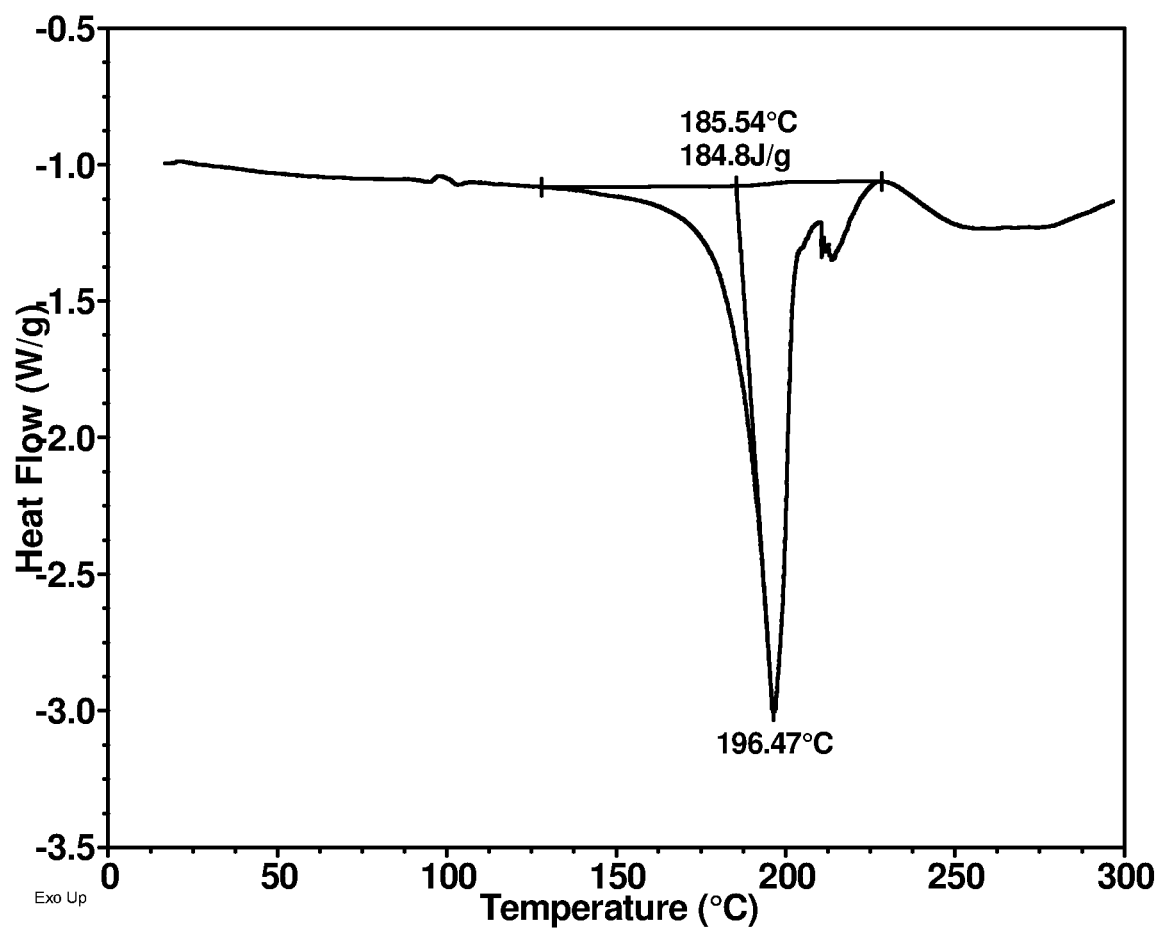
FIG. 32: Shows the DSC thermogram of Compound 15 HCl salt Material C.
Figure 33:
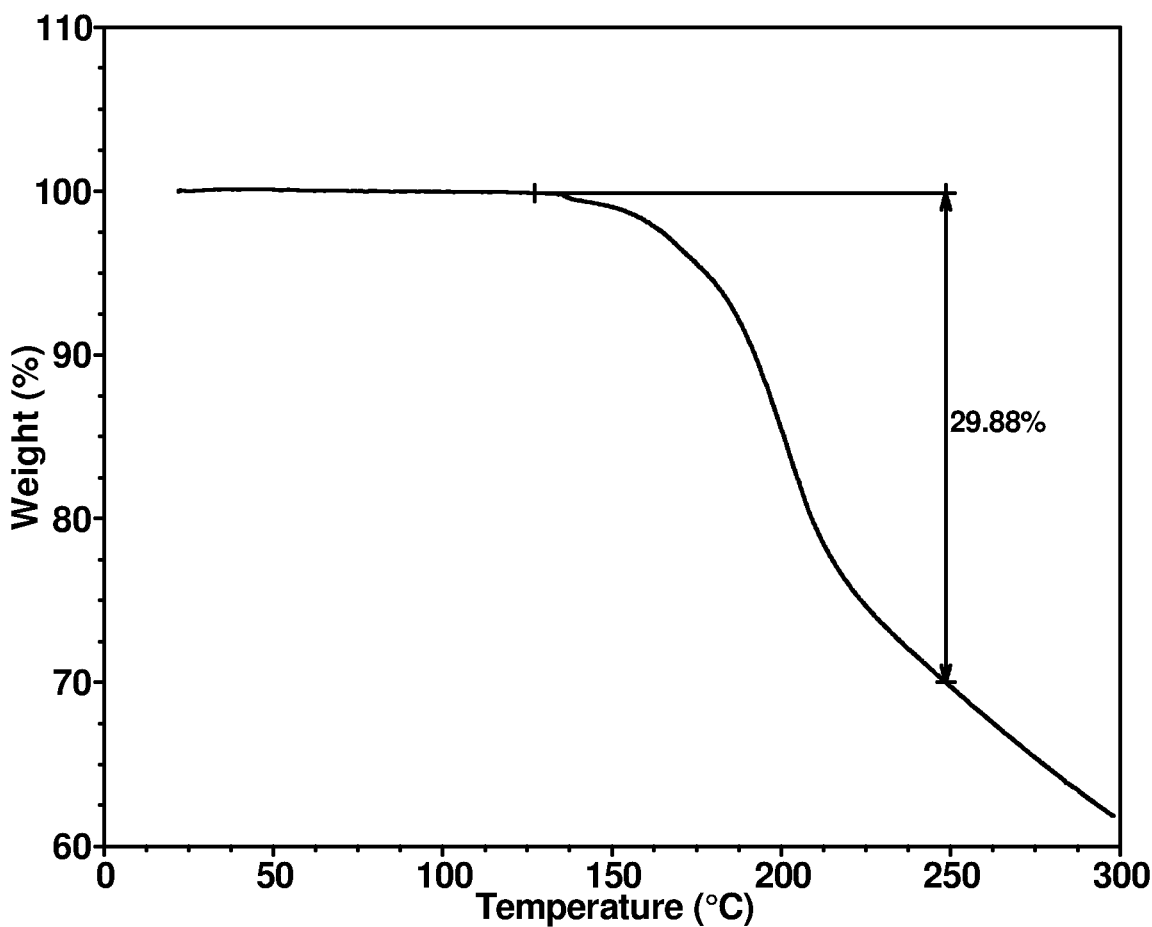
FIG. 33: Shows the TGA thermogram of Compound 15 HCl salt Material C.

In some embodiments, the disclosure provides a crystalline Material C of the Compound 15 HCl salt ("Compound 15 HCl salt Material C"). In some embodiments, the Compound 15 HCl salt Material C exhibits an XRPD pattern substantially as shown in FIG. 31. In some embodiments, the Compound 15 HCl salt Material C may exhibit a DSC thermogram substantially as shown in FIG. 32. In some embodiments, the Compound 15 HCl salt Material C may exhibit a TGA graph substantially as shown in FIG. 33.

In some embodiments of the Compound 15 HCl salt Material C, at least one, at least two, or all of the following (a)-(c) apply: (a) Compound 15 HCl salt Material C has an XRPD pattern substantially as shown in FIG. 31; (b) Compound 15 HCl salt Material C has a DSC thermogram substantially as shown in FIG. 32; (c) Compound 15 HCl salt Material C has a TGA graph substantially as shown in FIG. 33.

In some embodiments, Compound 15 HCl salt Material C has the following properties:
(a) an XRPD pattern substantially as shown in FIG. 31;
(b) a DSC thermogram substantially as shown in FIG. 32; and
(c) a TGA graph substantially as shown in FIG. 33.

In some embodiments, Compound 15 HCl salt Material C has an XRPD pattern displaying at least two, at least three, at least four, at least five, or at least six of the degree 2θ-reflections with the greatest intensity as the XRPD pattern substantially as shown in FIG. 31.

In some embodiments, Compound 15 HCl salt Material C has an XRPD pattern comprising degree 2θ-reflections (+/−0.2 degrees 2θ) at 4.3°, 14.7°, and 31.4°. In some embodiments, Compound 15 HCl salt Material C has an XRPD pattern comprising degree 2θ-reflections (+/−0.2 degrees 2θ) at 4.3°, 14.7°, and 31.4°, and one, two or three of the degree 2θ-reflections (+/−0.2 degrees 2θ) at 12.8°, 17.3°, and 35.1°. In some embodiments, Compound 15 HCl salt Material C has an XRPD pattern comprising degree 2θ-reflections (+/−0.2 degrees 2θ) at 4.3°, 14.7°, and 31.4°, and one or two of the degree 2θ-reflections (+/−0.2 degrees 2θ) at 12.8°, 17.3°, and 35.1°. In some embodiments, Compound 15 HCl salt Material C has an XRPD pattern comprising degree 2θ-reflections (+/−0.2 degrees 2θ) at 4.3°, 14.7°, and 31.4°, and one of the degree 2θ-reflections (+/−0.2 degrees 2θ) at 12.8°, 17.3°, and 35.1°. In some embodiments, Compound 15 HCl salt Material C has an XRPD pattern comprising degree 2θ-reflections (+/−0.2 degrees 2θ) at 4.3°, 14.7°, and 31.4°, and two of the degree 2θ-reflections (+/−0.2 degrees 2θ) at 12.8°, 17.3°, and 35.1°. In some embodiments, Compound 15 HCl salt Material C has an XRPD pattern comprising degree 2θ-reflections (+/−0.2 degrees 2θ) at 4.3°, 12.8°, 14.7°, 17.3°, 31.4°, and 35.1°. In some embodiments, Compound 15 HCl salt Material C has an XRPD pattern comprising any three of the degree 2θ-reflections (+/−0.2 degrees 2θ) at 4.3°, 12.8°, 14.7°, 17.3°, 31.4°, and 35.1°.

In some embodiments, Compound 15 HCl salt Material C has an XRPD pattern comprising degree 2θ-reflections (+/−0.2 degrees 2θ) at 4.3°, 12.8°, 14.7°, 17.3°, 31.4°, and 35.1°, and one, two, or three of the degree 2θ-reflections (+/−0.2 degrees 2θ) at 16.6°, 24.9°, and 27.2°. In some embodiments, Compound 15 HCl salt Material C has an XRPD pattern comprising degree 2θ-reflections (+/−0.2 degrees 2θ) at 4.3°, 12.8°, 14.7°, 17.3°, 31.4°, and 35.1°, and one or two of the degree 2θ-reflections (+/−0.2 degrees 2θ) at 16.6°, 24.9°, and 27.2°. In some embodiments, Compound 15 HCl salt Material C has an XRPD pattern comprising degree 2θ-reflections (+/−0.2 degrees 2θ) at 4.3°, 12.8°, 14.7°, 17.3°, 31.4°, and 35.1°, and one of the degree 2θ-reflections (+/−0.2 degrees 2θ) at 16.6°, 24.9°, and 27.2°. In some embodiments, Compound 15 HCl salt Material C has an XRPD pattern comprising degree 2θ-reflections (+/−0.2 degrees 2θ) at 4.3°, 12.8°, 14.7°, 17.3°, 31.4°, and 35.1°, and two of the degree 2θ-reflections (+/−0.2 degrees 2θ) at 16.6°, 24.9°, and 27.2°. In some embodiments, Compound 15 HCl salt Material C has an XRPD pattern comprising degree 2θ-reflections (+/−0.2 degrees 2θ) at 4.3°, 12.8°, 14.7°, 16.6°, 17.3°, 24.9°, 27.2°, 31.4°, and 35.1°. In some embodiments, Compound 15 HCl salt Material C has an XRPD pattern comprising any three of the degree 2θ-reflections (+/−0.2 degrees 2θ) at 4.3°, 12.8°, 14.7°, 16.6°, 17.3°, 24.9°, 27.2°, 31.4°, and 35.1°.

XIII. Examples

Intermediate A: ((2R,3S,4R,5R)-5-(4-aminopyrrolo[2,1-f][1,2,4]triazin-7-yl)-5-cyano-3,4-dihydroxytetrahydrofuran-2-yl)methyl 2-((tert-butoxycarbonyl)amino)-2-methylpropanoate

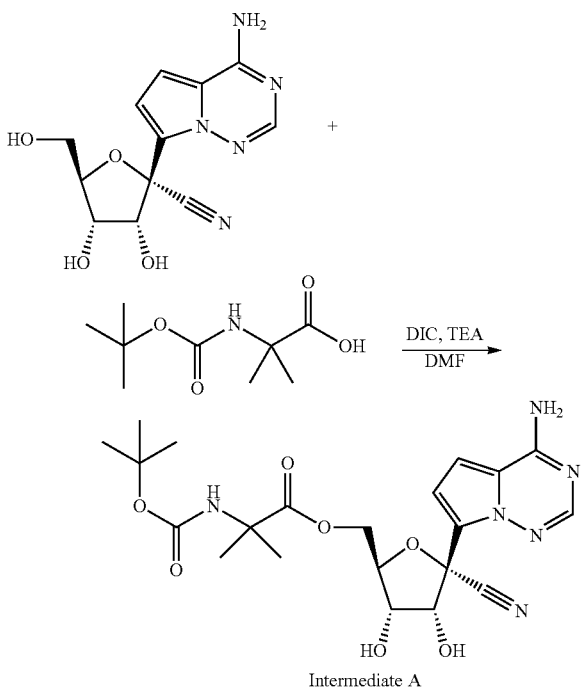

Intermediate A (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (Compound 13 in WO2009132135; compound 4 in J. Med. Chem. 2017, 60, 1648-1661) and 2-((Tert-butoxycarbonyl)amino)-2-methylpropanoic acid (209 mg, 1.03 mmol) were dissolved in anhydrous DMF (3 mL). To this mixture was added N, N'-Diisopropylcarbodiimide (177 uL, 1.13 mmol) and stirred for 20 min followed by addition of the nucleoside (150 mg, 0.52 mmol) and triethylamine (180 uL, 1.29 mmol). The resulting mixture was stirred for 16 hr. More 2-((tert-butoxycarbonyl)amino)-2-methylpropanoic acid (1 equiv) and N, N-diisopropylcarbodiimide (1 equiv) were added at this time and heated at 60° C. for 4 hrs followed by an additional 16 hrs of stirring at room temperature. Diluted with ethyl acetate, washed with saturated NaHCO₃ and saturated brine. The organic layer was dried over Na₂SO₄, concentrated in vacuo and purified by column chromatography eluting with ethyl acetate in hexane (0%-100%) to afford intermediate A.

MS m/z=475.1 [M−1].

Intermediate B: ((2R,3S,4R,5R)-5-(4-aminopyrrolo[2,1-f][1,2,4]triazin-7-yl)-5-cyano-3,4-dihydroxytetrahydrofuran-2-yl)methyl (tert-butoxycarbonyl)-L-valinate

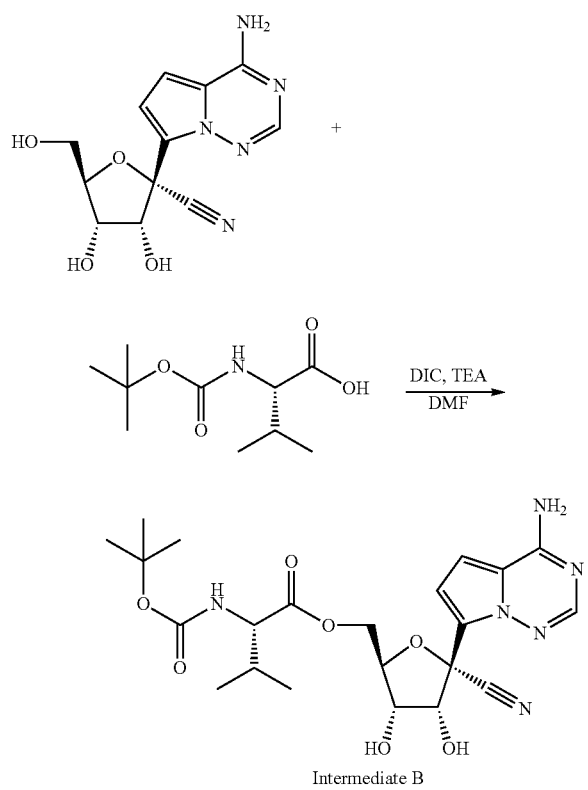

Intermediate B

Intermediate B was made in a similar manner as Intermediate A except that (tert-butoxy carbonyl)-L-valine (55 mg, 0.26 mmol) was used instead of 2-((tert-butoxycarbonyl)amino)-2-methylpropanoic acid.

Example 1: (2R,3R,4R,5R)-2-(4-aminopyrrolo[2,1-f][1,2,4]triazin-7-yl)-2-cyano-5-((isobutyryloxy)methyl)tetrahydrofuran-3,4-diyl bis(2-methylpropanoate)

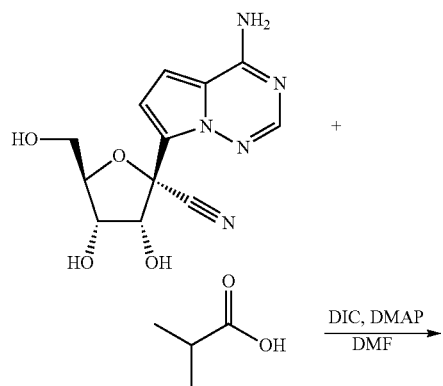

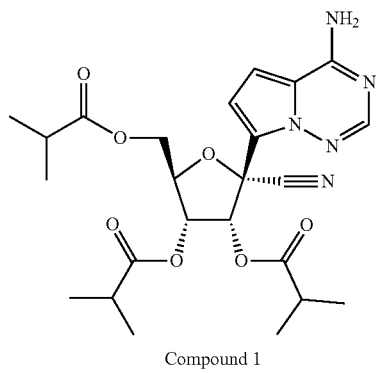

Compound 1

(2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (29 mg, 0.1 mmol) was dissolved in anhydrous DMF (1 mL). Isobutyric acid (46 uL, 0.5 mmol) was added in one portion. N, N'-Diisopropylcarbodiimide (78 uL, 0.5 mmol) was added dropwise. Reaction was stirred for 15 mins. 4-(Dimethylamino)pyridine (12.2 mg, 0.1 mmol) was added. Reaction was then stirred for 16 hrs. Diluted with acetonitrile (1 mL) and filtered off solid. Purified filtrate with Prep HPLC (0-95% acetonitrile in water). Fractions were combined and freeze-dried to give title compound.

$^1$H NMR (300 MHz, CDCl$_3$) δ 11.15 (bs, 1H), 8.27 (bs, 1H), 7.95 (s, 1H), 7.32 (m, 1H), 7.07 (m, 1H), 6.05 (d, J=6.0 Hz, 1H), 5.44 (t, J=5.1 Hz, 1H), 4.66 (t, J=3.6 Hz, 1H), 4.32 (m, 2H), 2.73-2.52 (m, 3H), 1.27-1.14 (m, 18H).

LC/MS: t$_R$=2.60 min, MS m/z=502.2 [M+1], 500.1 [M−1]; LC/MS system: Thermo LCQ Advantage; Phenomenex Gemini, C$_{18}$, 5 u, 110 A, 30×4.6 mm; Buffer A: 0.1% Acetic acid in Water; Buffer B: 0.1% Acetic acid in Acetonitrile; 5-100% Buffer B in 2.5 mins then 100% for 0.9 min @ 2 m/min.

HPLC: t$_R$=3.33 min; HPLC system: Agilent 1100; Phenomenex Gemini, C$_{18}$, 5 u, 110 A, 50×4.6 mm; Buffer A: 0.05% TFA in Water; Buffer B: 0.05% TFA in Acetonitrile; 2-98% Buffer B in 5 minutes @ 2 mL/min.

Example 2: (2R,3R,4R,5R)-5-(acetoxymethyl)-2-(4-aminopyrrolo[2,1-f][1,2,4]triazin-7-yl)-2-cyanotetrahydrofuran-3,4-diyl diacetate

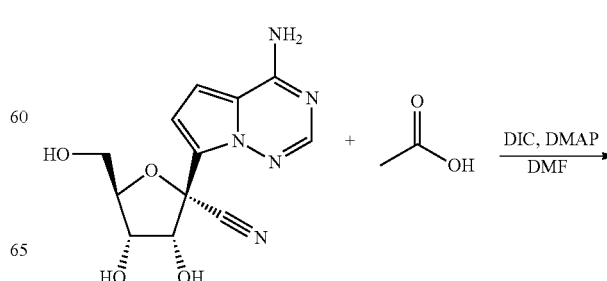

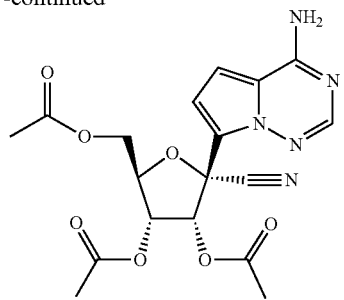

Compound 2

The title compound was made in a similar manner as compound 1 except that acetic acid (29 uL, 0.50 mmol) was used instead of isobutyric acid.

¹H NMR (300 MHz, CDCl₃) δ 11.15 (bs, 1H), 8.08 (bs, 1H), 7.97 (s, 1H), 7.35 (m, 1H), 7.12 (d, J=4.8 Hz, 1H), 6.06 (d, J=5.7 Hz, 1H), 5.40 (t, J=6.0 Hz, 1H), 4.67 (m, 1H), 4.48-4.32 (m, 2H), 2.20 (s, 3H), 2.17 (s, 3H), 2.09 (s, 3H).

LC/MS: $t_R$=2.00 min, MS m/z=418.0 [M+1], 416.0 [M−1].

Example 3: (2R,3R,4R,5R)-2-(4-aminopyrrolo[2,1-f][1,2,4]triazin-7-yl)-2-cyano-5-((propionyloxy)methyl)tetrahydrofuran-3,4-diyl dipropionate

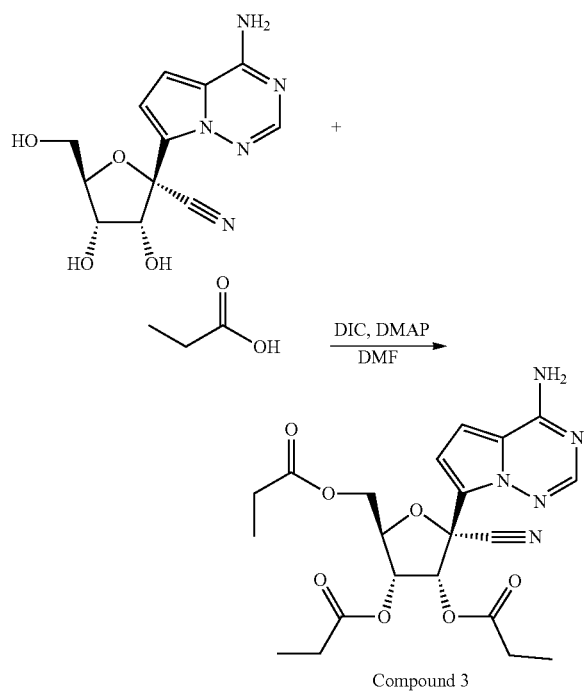

Compound 3

The title compound was prepared in a similar manner as compound 1 except that propionic acid (37 uL, 0.50 mmol) was used instead of isobutyric acid.

¹H NMR: (400 MHz, Methanol-d4) δ 8.04 (s, 1H), 7.23 (d, J=4.7 Hz, 1H), 7.03 (d, J=4.7 Hz, 1H), 6.20 (d, J=5.7 Hz, 1H), 5.51 (dd, J=5.7, 4.6 Hz, 1H), 4.67 (td, J=4.5, 3.5 Hz, 1H), 4.49 (dd, J=12.3, 3.6 Hz, 1H), 4.38 (dd, J=12.3, 4.6 Hz, 1H), 2.56-2.40 (m, 4H), 2.36 (qd, J=7.6, 5.1 Hz, 2H), 1.30-1.06 (m, 9H).

LC/MS: $t_R$=0.89 min, MS m/z=460.2 [M+1].

Example 4: (3aR,4R,6R,6aR)-4-(4-aminopyrrolo[2,1-f][1,2,4]triazin-7-yl)-6-(hydroxymethyl)-2-phenyltetrahydrofuro[3,4-d][1,3]dioxole-4-carbonitrile

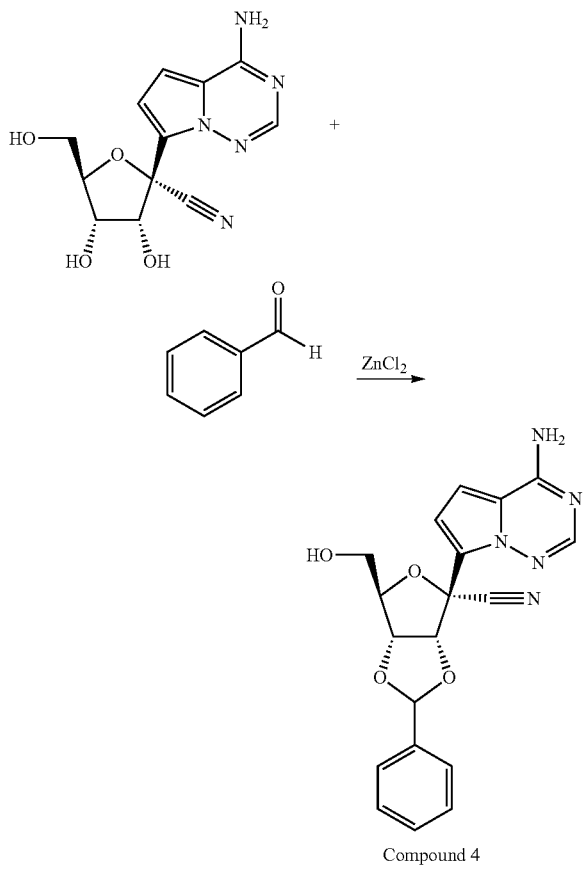

Compound 4

(2R,3R,4S,5R)-2-(4-aninopyrrolo[2,1-f][1,2,4]triazin-7-yl)-3,4-dihydroxy-5-(hydroxymethyl)tetrahydrofuran-2-carbonitrile (58 mg, 0.20 mmol) was combined with benzaldehyde (3 mL) followed by addition of zinc (II) chloride (41 mg, 0.3 mmol). The resulting reaction mixture was stirred at ambient temperature for 16 hrs. The reaction mixture was then diluted with ethyl acetate, washed with saturated NaHCO₃ and saturated brine. The organic layer was dried over Na₂SO₄, concentrated in vacuo and purified by column chromatography eluting with ethyl acetate in hexane (0%-30%-50%) to give desired product.

¹H NMR (400 MHz, Methanol-d4) δ 7.90 (s, 1H), 7.80-7.70 (m, 2H), 7.51-7.39 (m, 3H), 7.03-6.91 (m, 2H), 6.14 (s, 1H), 5.55 (d, J=7.2 Hz, 1H), 5.09 (dd, J=7.2, 3.8 Hz, 1H), 4.60 (q, J=4.4 Hz, 1H), 3.89-3.77 (m, 2H).

LC/MS: $t_R$=−0.77 min, MS m/z=380.1 [M+1].

Example 5: ((3aR,4R,6R,6aR)-6-(4-aminopyrrolo[2,1-f][1,2,4]triazin-7-yl)-6-cyano-2-phenyltetrahydrofuro[3,4-d][1,3]dioxol-4-yl)methyl isobutyrate

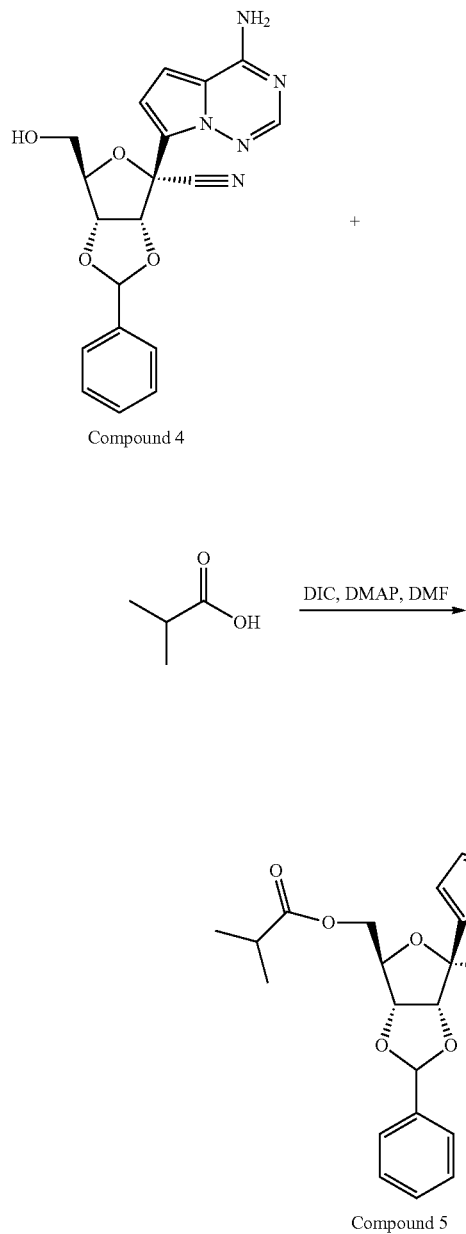

Compound 4

Compound 5

The title compound was made in a similar manner as compound 1 except that compound 4 (32 mg, 0.084 mmol) was used instead of (2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile.

$^1$H NMR (400 MHz, Methanol-d4) δ 8.05 (s, 1H), 7.77-7.70 (m, 2H), 7.52-7.40 (m, 3H), 7.24 (d, J=4.7 Hz, 1H), 7.04 (d, J=4.7 Hz, 1H), 6.13 (s, 1H), 5.50 (d, J=7.0 Hz, 1H), 5.07 (dd, J=6.9, 3.6 Hz, 1H), 4.78 (dt, J=5.4, 4.0 Hz, 1H), 4.42 (dd, J 12.0, 4.2 Hz, 1H), 4.30 (dd, J=12.1, 5.5 Hz, 1H), 2.49 (hept, J=7.0 Hz, 1H), 1.18-1.05 (m, 6H).

LC/MS: $t_R$=0.94 min, MS m/z=450.2 [M+1].

Example 6: ((3aR,4R,6R,6aR)-6-(4-aminopyrrolo[2,1-f][1,2,4]triazin-7-yl)-6-cyano-2-phenyltetrahydrofuro[3,4-d][1,3]dioxol-4-yl)methyl L-valinate

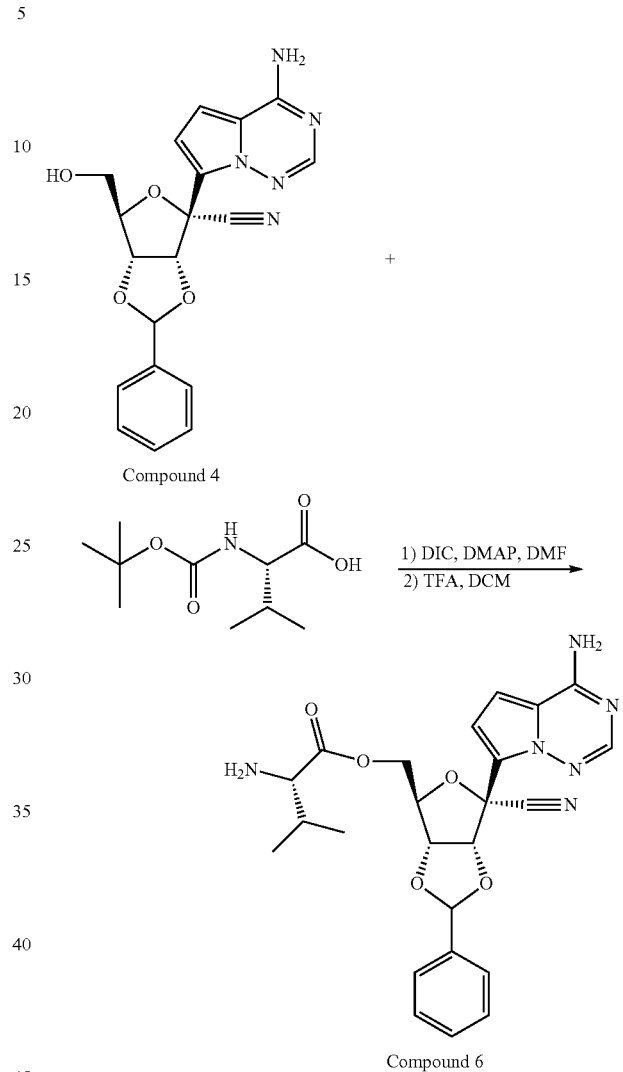

Compound 4

Compound 6

(3aR,4R,6R,6aR)-4-(4-aminopyrrolo[2,1-f][1,2,4]triazin-7-yl)-6-(hydroxymethyl)-2-phenyltetrahydrofuro[3,4-d][1,3]dioxole-4-carbonitrile (32 mg, 0.084 mmol) was dissolved in anhydrous DMF (1 mL). (Tert-butoxycarbonyl)-L-valine (37 mg, 0.168 mmol) and N, N'-diisopropylcarbodiimide (26 uL, 0.168 mmol) were added. The resulting mixture was stirred for 20 min. 4-(Dimethylamino)pyridine (10 mg, 0.084 mmol) was then added and reaction mixture was stirred for 16 hrs at room temperature. Diluted with acetonitrile and filtered off solid. Purified filtrate with Prep HPLC. The fractions were combined and concentrated in vacuo. The residue was dissolved in 20% trifluoracetic acid in dichloromethane (3 mL) and stirred for 45 min. The mixture was then concentrated and purified on preparative HPLC to give title compound.

$^1$H NMR (400 MHz, Methanol-d4) δ 8.00 (s, 1H), 7.60-7.49 (m, 2H), 7.50-7.39 (m, 3H), 7.12 (d, J=4.7 Hz, 1H), 7.05 (d, J=4.7 Hz, 1H), 6.44 (s, 1H), 5.56 (d, J=6.7 Hz, 1H), 5.23 (dd, J=6.7, 5.6 Hz, 1H), 4.74 (q, J=5.6 Hz, 1H), 4.70-4.55 (m, 2H), 4.01-3.92 (m, 1H), 2.31 (pd, J=7.0, 4.5 Hz, 1H), 1.09-0.94 (m, 6H).

LC/MS: $t_R$=0.85 min, MS m/z=479.2 [M+1].

Example 7: ((2R,3S,4R,5R)-5-(4-aminopyrrolo[2,1-f][1,2,4]triazin-7-yl)-5-cyano-3,4-dihydroxytetrahydrofuran-2-yl)methyl 2-amino-2-methylpropanoate

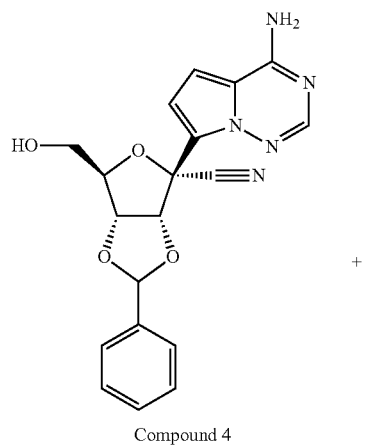

Compound 4

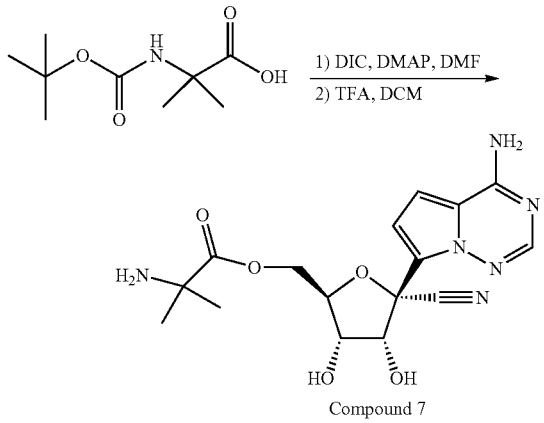

Compound 7

The title compound was made in a similar manner as compound 6 except that 2-((tert-butoxycarbonyl)amino)-2-methylpropanoic acid (80 mg, 0.40 mmol) was used instead of (tert-butoxycarbonyl)-L-valine, and the deprotection step was stirred at room temperature for 3 hrs instead of 45 min.

$^1$H NMR (400 MHz, Methanol-d4) δ 7.98 (s, 1H), 7.13 (d, J=4.7 Hz, 1H), 7.01 (d, J=4.7 Hz, 1H), 4.89 (s, 1H), 4.57 (d, J=5.1 Hz, 2H), 4.44 (dt, J=7.2, 5.1 Hz, 1H), 4.14 (dd, J=7.0, 5.4 Hz, 1H), 1.58 (d, J=6.7 Hz, 6H).

LC/MS: $t_R$=0.20 min, MS m/z=377.2 [M+1].

Example 8: ((2R,3S,4R,5R)-5-(4-aminopyrrolo[2,1-f][1,2,4]triazin-7-yl)-5-cyano-3,4-dihydroxytetrahydrofuran-2-yl)methyl L-valinate

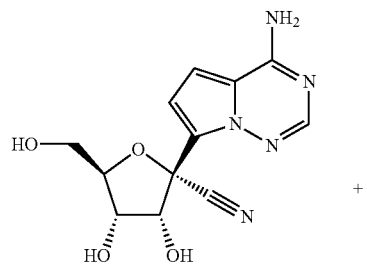

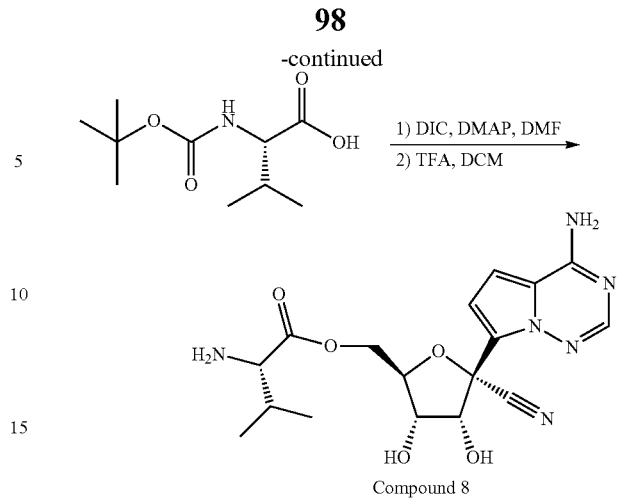

Compound 8

(2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile and (tert-butoxycarbonyl)-L-valine (55 mg, 0.56 mmol) were dissolved in anhydrous DMF (2 mL). To this mixture was added N, N'-diisopropylcarbodiimide (40 uL, 0.26 mmol) and stirred for 15 min followed by addition of the nucleoside (50 mg, 0.17 mmol) and triethylamine (47 uL, 0.34 mmol). The resulting mixture was stirred for 16 hr. At this time, more (tert-butoxycarbonyl)-L-valine (55 mg, 0.56 mmol) and N, N'-diisopropylcarbodiimide (40 uL, 0.25 mmol) were added, and the mixture was stirred for another 5 hrs at room temperature. The reaction was then heated at 50° C. for 3 hrs followed by an additional 72 hrs stirring at room temperature. Diluted with ethyl acetate, washed with saturated NaHCO$_3$ and saturated brine. The organic layer was dried over Na$_2$SO$_4$, concentrated in vacuo and purified by column chromatography eluting with ethyl acetate in hexane (0%-70%) and then further purified by reversed phase HPLC. The fractions were combined and concentrated in vacuo. The residue was dissolved in 20% trifluoroacetic acid in dichloromethane and stirred for 30 min. The mixture was then concentrated and purified on preparative HPLC to give the tittle compound.

$^1$H NMR (400 MHz, Methanol-d4) δ 7.92 (s, 1H), 7.05 (s, 2H), 5.57 (dd, J=5.8, 2.3 Hz, 1H), 5.31 (d, J=5.8 Hz, 1H), 4.49 (q, J=3.0 Hz, 1H), 4.18-4.04 (m, 1H), 3.93-3.77 (m, 2H), 2.53 (qd, J=7.0, 4.5 Hz, 1H), 1.16 (dd, J=7.0, 4.9 Hz, 6H).

LC/MS: $t_R$=0.48 min, MS m/z=391.2 [M+1].

Example 9: ((2R,3S,4R,5R)-5-(4-aminopyrrolo[2,1-f][1,2,4]triazin-7-yl)-5-cyano-3,4-dihydroxytetrahydrofuran-2-yl)methyl D-valinate

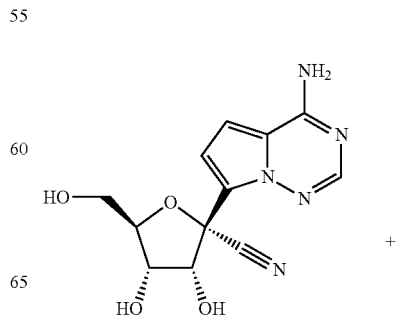

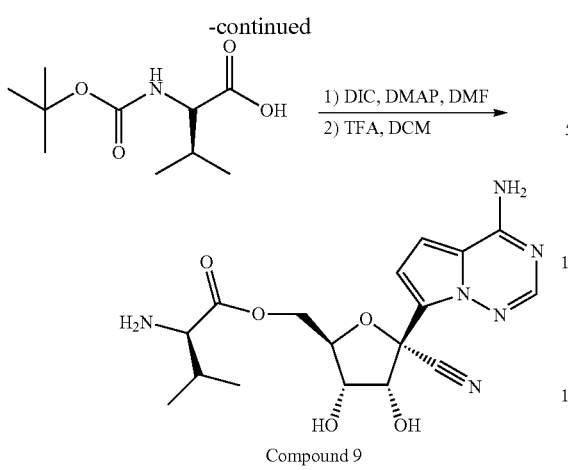

Compound 9

The title compound was made in a similar manner as compound 8 except that (tert-butoxycarbonyl)-D-valine (75 mg, 0.34 mmol) was used instead of (tert-butoxycarbonyl)-L-valine.

$^1$H NMR (400 MHz, Methanol-d4) δ 7.90 (s, 1H), 7.02 (q, J=4.7 Hz, 2H), 5.60 (ddd, J=19.1, 5.9, 2.3 Hz, 1H), 5.31 (dd, J=18.0, 5.9 Hz, 1H), 4.56-4.47 (m, 1H), 4.11 (dd, J=4.2, 2.4 Hz, 1H), 3.97-3.75 (m, 2H), 2.68 (pd, J=7.1, 3.8 Hz, 1H), 1.17 (dt, J=7.0, 4.8 Hz, 6H).

LC/MS: $t_R$=0.44 min, MS m/z=391.2 [M+1].

Example 10: ((2R,3S,4R,5R)-5-(4-aminopyrrolo[2,1-f][1,2,4]triazin-7-yl)-5-cyano-3,4-dihydroxytetrahydrofuran-2-yl)methyl L-phenylalaninate

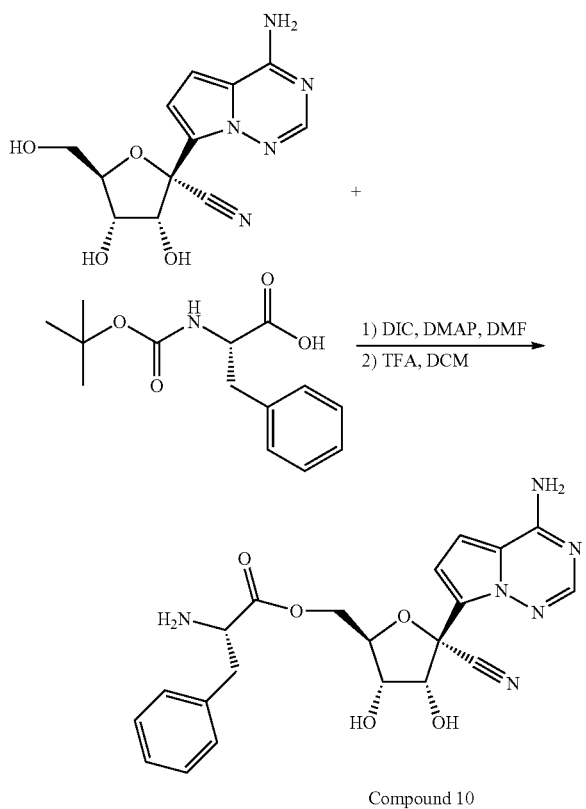

Compound 10

The title compound was made in a similar manner as compound 8 except that (tert-butoxycarbonyl)-L-phenylalanine (55 mg, 0.26 mmol) was used instead of (tert-butoxycarbonyl)-L-valine.

$^1$H NMR (400 MHz, Methanol-d4) δ 7.94 (s, 1H), 7.48-7.28 (m, 5H), 7.12-7.03 (m, 2H), 5.53 (dd, J=5.8, 2.1 Hz, 1H), 5.29 (d, J=5.7 Hz, 1H), 4.48 (dd, J=8.1, 6.1 Hz, 1H), 4.24 (q, J=3.0 Hz, 1H), 3.77 (qd, J=12.4, 3.2 Hz, 2H), 3.46 (dd, J=14.3, 6.2 Hz, 1H), 3.29-3.24 (m, 1H).

LC/MS: $t_R$=0.58 min, MS m/z=439.2 [M+1].

Example 11: (2R,3R,4R,5R)-5-(((2-amino-2-methylpropanoyl)oxy) methyl)-2-(4-aminopyrrolo[2,1-f][1,2,4]triazin-7-yl)-2-cyanotetrahydrofuran-3,4-diyl bis(2-methylpropanoate)

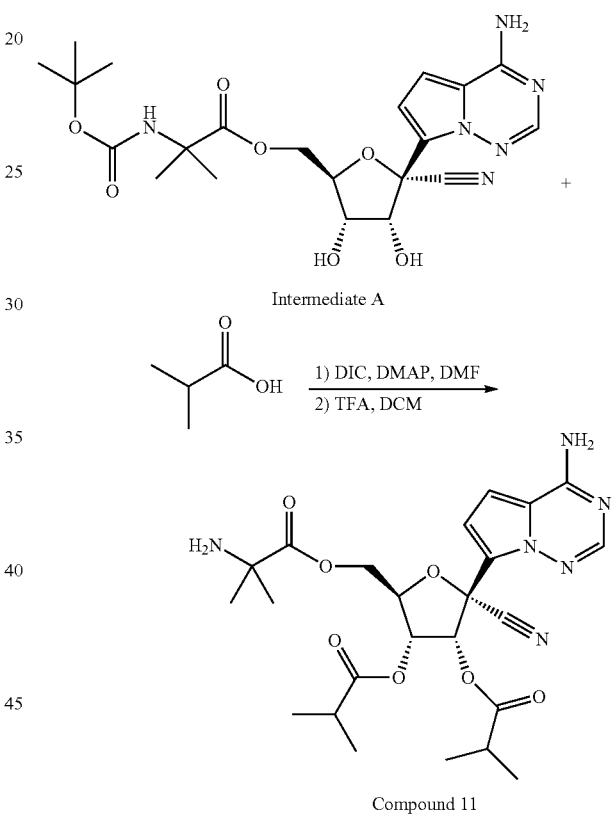

Compound 11

Intermediate A (45 mg, 0.094 mmol) was dissolved in anhydrous DMF (3 mL). Isobutyric acid (26 uL, 0.28 mmol) and N, N'-diisopropylcarbodiimide (44 uL, 0.28 mmol) were added. Reaction was stirred for 15-20 mins followed by addition of 4-(dimethylamino)pyridine (11.6 mg, 0.09 mmol). Reaction was then stirred for 4 hrs. At this time, more isobutyric acid (3 equiv.) and N, N'-diisopropylcarbodiimide (3 equiv.) and 4-(dimethylamino)pyridine (1 equiv.) were added. The resulting mixture was stirred at ambient temperature for an additional 16 hrs.

Diluted with ethyl acetate, washed with saturated NaHCO$_3$ and saturated brine. The organic layer was dried over Na$_2$SO$_4$, concentrated in vacuo, and purified by reversed phase HPLC. The fractions were combined and concentrated in vacuo. The residue was dissolved in 20% trifluoracetic acid in dichloromethane (3 mL) and stirred for 45 min. The mixture was then concentrated and purified on preparative HPLC to give tittle compound (32 mg, 66%).

¹H NMR (400 MHz, Methanol-d4) δ 7.96 (s, 1H), 7.08 (d, J=4.7 Hz, 1H), 6.97 (d, J=4.7 Hz, 1H), 6.39 (d, J=5.6 Hz, 1H), 5.68 (dd, J=5.6, 2.9 Hz, 1H), 4.74 (q, J=3.9 Hz, 1H), 4.58-4.39 (m, 2H), 2.62 (ddq, J=37.5, 14.0, 7.0 Hz, 2H), 1.73 (d, J=2.9 Hz, 6H), 1.28-1.05 (m, 12H).

LC/MS: $t_R$=0.77 min, MS m/z=517.3 [M+1].

Example 12: (2R,3R,4R,5R)-5-(((L-valyl)oxy)methyl)-2-(4-aminopyrrolo[2,1-f][1,2,4]triazin-7-yl)-2-cyanotetrahydrofuran-3,4-diyl bis(2-methylpropanoate)

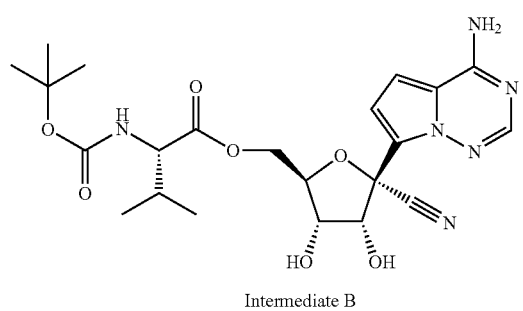

Intermediate B

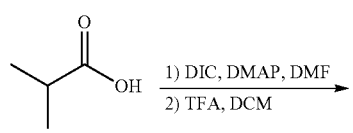

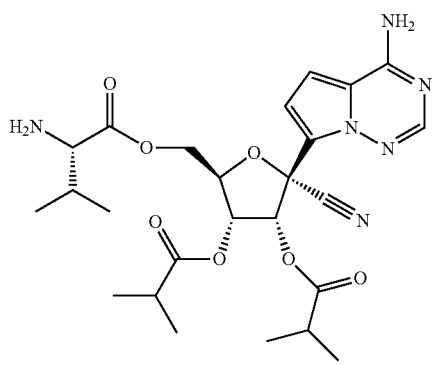

Compound 12

The title compound was made in a similar manner as compound 11 except that intermediate B (61 mg, 0.12 mmol) was used instead of intermediate A.

¹H NMR (400 MHz, Methanol-d4) δ 7.96 (s, 1H), 7.09 (d, J=4.7 Hz, 1H), 6.99 (d, J=4.7 Hz, 1H), 6.32 (d, J=5.8 Hz, 1H), 5.69 (dd, J=5.8, 4.1 Hz, 1H), 4.71 (q, J=4.0 Hz, 1H), 4.48 (qd, J=12.4, 3.9 Hz, 2H), 4.08 (d, J=4.1 Hz, 1H), 2.81-2.67 (m, 1H), 2.68-2.45 (m, 2H), 1.23 (d, J=7.0 Hz, 6H), 1.16 (d, J=7.3 Hz, 6H), 1.12 (d, J=6.6 Hz, 6H).

LC/MS: $t_R$=0.79 min, MS m/z=531.2 [M+1].

Example 13: (3aR,4R,6R,6aR)-4-(4-aminopyrrolo[2,1-f][1,2,4]triazin-7-yl)-6-(hydroxymethyl)-2-oxotetrahydrofuro[3,4-d][1,3]dioxole-4-carbonitrile

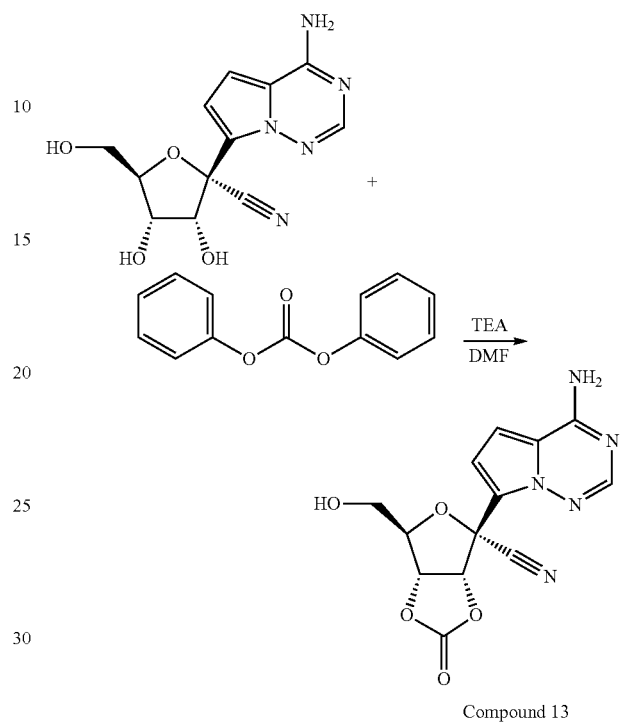

Compound 13

(2R,3R,4S,5R)-2-(4-aminopyrrolo[2,1-f][1,2,4]triazin-7-yl)-3,4-dihydroxy-5-(hydroxymethyl)tetrahydrofuran-2-carbonitrile (50 mg, 0.17 mmol) was dissolved in anhydrous DMF (3 mL). To this solution was added diphenyl carbonate (37 mg, 0.17 mmol) and the resulting reaction mixture was stirred at 130° C. for 1 hr. Triethylamine (60 uL, 0.43 mmol) was then added and continued with heating at 130° C. for another 2 hrs. The reaction mixture was cooled, then diluted with ethyl acetate, washed with saturated NaHCO₃ and saturated brine. The organic layer was dried over Na₂SO₄ and concentrated in vacuo and purified by column chromatography eluting with methanol in dichloromethane (0%-5%) to give desired product.

LC/MS: $t_R$=0.56 min, MS m/z=318.0 [M+1].

Example 14: ((2R,3S,4R,5R)-5-(4-aminopyrrolo[2,1-f][1,2,4]triazin-7-yl)-5-cyano-3,4-dihydroxytetrahydrofuran-2-yl)methyl (S)-3-amino-4-phenylbutanoate

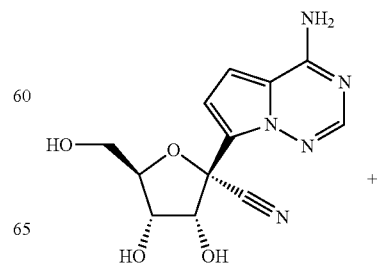

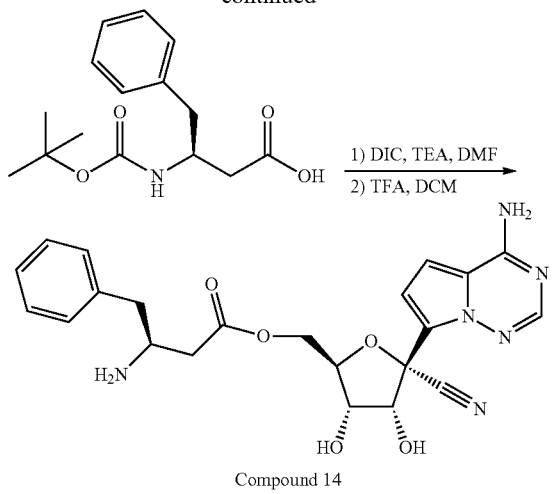

Compound 14

The title compound was made in a similar manner as compound 8 except that L-beta-homophenylalanine (96 mg, 0.34 mmol) was used instead of (tert-butoxycarbonyl)-L-valine.

$^1$H NMR 1H NMR (400 MHz, Methanol-d4) δ 7.96 (s, 1H), 7.49-7.28 (m, 5H), 7.17-7.02 (m, 2H), 5.59 (dd, J=6.0, 2.4 Hz, 1H), 5.27 (d, J=6.0 Hz, 1H), 4.46 (q, J=3.0 Hz, 1H), 4.08 (dt, J=12.8, 7.6 Hz, 1H), 3.92-3.74 (m, 2H), 3.15-2.91 (m, 4H), 2.76 (dd, J=16.8, 8.1 Hz, 1H).

LC/MS: $t_R$=0.63 min.

Example 15: ((2R,3S,4R,5R)-5-(4-aminopyrrolo[2,1-f][1,2,4]triazin-7-yl)-5-cyano-3,4-dihydroxytetrahydrofuran-2-yl)methyl isobutyrate

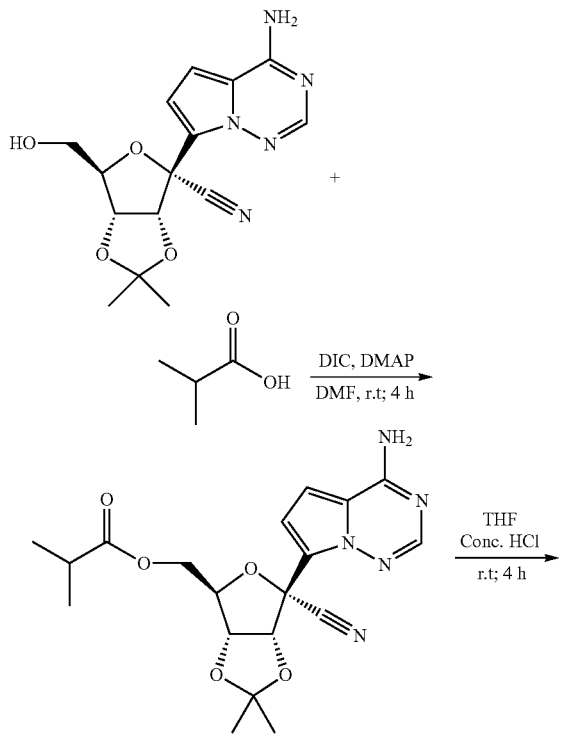

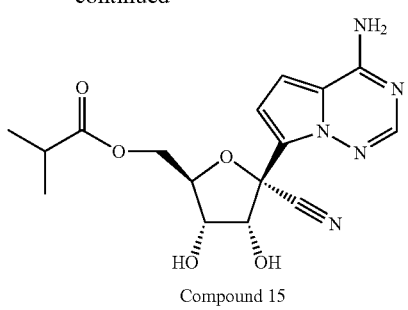

Compound 15

To a solution of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (2000 mg, 6.0 mmol) (Siegel et. al. J. Med. Chem. 2017, 60, 1648-1661) and isobutyric acid (638 ng, 7.2 mmol) in DMF (5 mL), N,N'-diisopropylcarbodiimide (914 mg, 7.2 mmol) was added slowly followed by 4-dimethylaminopyridine (737 mg, 6.0 mmol) at r.t and stirred for 4 h. The reaction mixture was diluted with ethyl acetate, washed with water, brine, dried and concentrated. The resulting product was purified by flash chromatography using DCM/Methanol (20% methanol/DCM) as eluent to get the intermediate ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl) methyl isobutyrate.

MS m/z=402.2 (M+1).

To a solution of intermediate acetonide (1500 mg) in THF (10 mL), conc. HCl (2 mL) was added and stirred at r.t for 4 h. LC-MS shows the product formation along with SM. Reaction stopped after 4 h, diluted the reaction mixture with dichloromethane, washed with water, saturated bicarbonate, and brine, dried over sodium sulphate, concentrated and purified by flash chromatography using DCM/Methanol (30% methanol/DCM) as eluent to get the title compound.

$^1$H NMR (400 MHz, Methanol-d4) δ 7.88 (s, 1H), 6.96-6.85 (m, 2H), 4.50-4.27 (m, 4H), 4.16 (dd, J=6.2, 5.3 Hz, 1H), 2.56 (p, J=7.0 Hz, 1H), 1.14 (dd, J=7.0, 3.8 Hz, 6H).

MS m/z: 362.1 (M+1).

Alternate Synthesis of Compound 15:

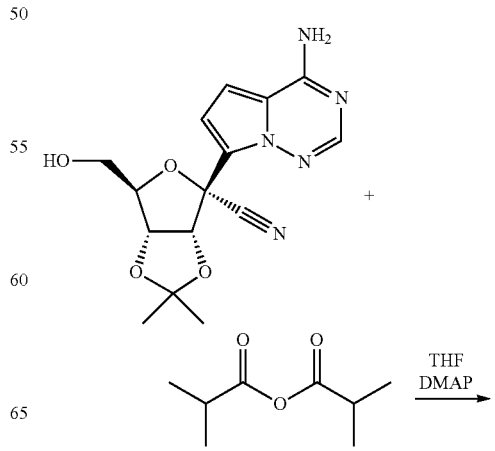

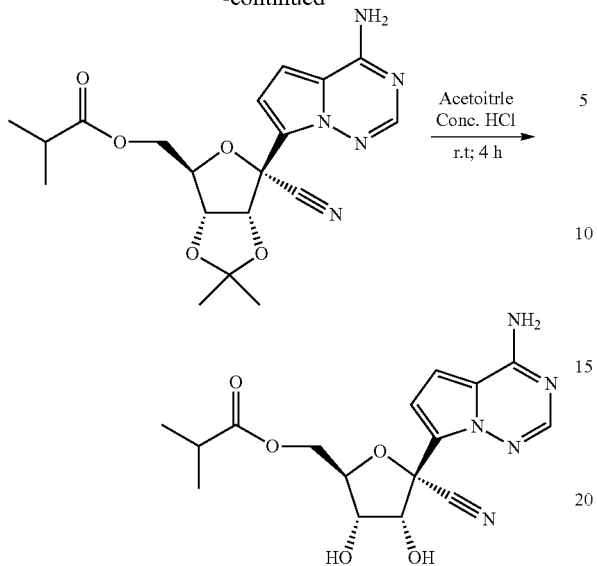

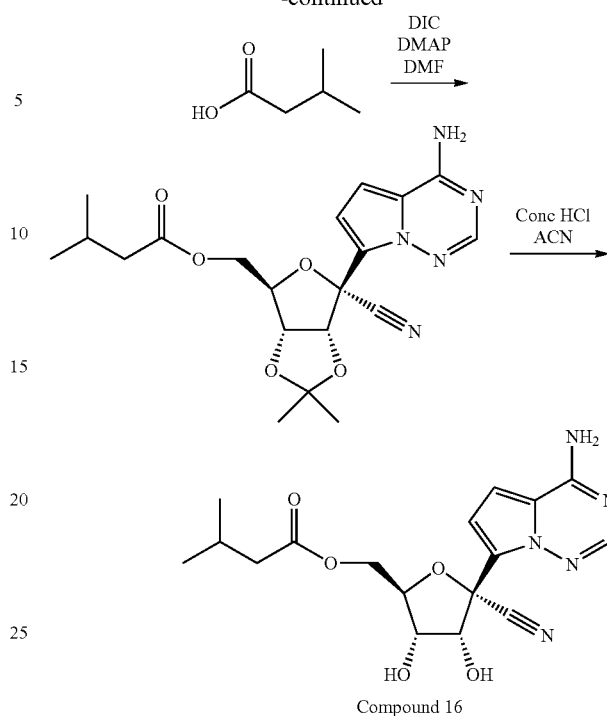

Compound 16

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 3-methylbutanoate To a solution of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (2000 mg, 6.0 mmol) in THF, N,N-dimethyl aminopyridine (0.03 eq) was added. To the reaction mixture isobutyric anhydride (1.1 eq) was added slowly. After the completion of the staring material, the reaction mixture was concentrated and purified by flash chromatography using DCM/Methanol (20% methanol/DCM) as eluent to get the intermediate ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyrate. MS m/z=402.2 (M+1).

To a solution of intermediate acetonide (1000 mg) in acetonitrile (10 mL), conc. HCl (5 eq, 1 mL) was added and stirred at r.t for 2 h. LC-MS shows the product formation. Reaction was stopped after 4 h, the reaction mixture was diluted with ethyl acetate, quenched with saturated bicarbonate. The organic layer was separated, washed with brine, dried over sodium sulphate, and concentrated. The residue was purified by flash chromatography using DCM/Methanol (30% methanol/DCM) as eluent, concentrated the factions to get the title compound. $^1$H NMR (400 MHz, Methanol-d4) δ 7.88 (s, 1H), 6.96-6.85 (m, 2H), 4.50-4.27 (m, 4H), 4.16 (dd, J=6.2, 5.3 Hz, 1H), 2.56 (p, J=7.0 Hz, 1H), 1.14 (dd, J=7.0, 3.8 Hz, 6H); MS m/z: 362.1 (M+1). The obtained compound was identified as Compound 15, Form II.

Example 16: ((2R,3S,4R,5R)-5-(4-aminopyrrolo[2,1-f][1,2,4]triazin-7-yl)-5-cyano-3,4-dihydroxytetrahydrofuran-2-yl)methyl 3-methylbutanoate

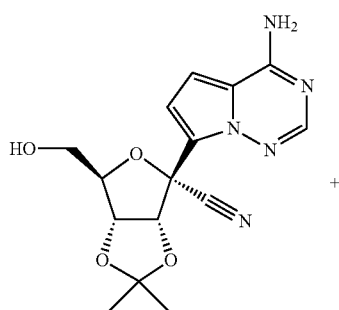

+

To a mixture of (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (200 mg, 0.6 mmol) and 3-methylbutanoic acid (92 mg, 0.91 mmol) in DMF (2 mL) was added N,N'-diisopropylcarbodiimide (0.14 mL, 0.91 mmol). The mixture was stirred at rt for 20 min and DMAP (74 mg, 0.6 mmol) added. The resulting mixture was stirred at rt for 2 h and purified by reverse phase HPLC (10 to 100% ACN in water for 15 min, then 100% ACN for 3 min) to provide the intermediate (188 mg, 75%). LCMS: MS m/z=416.16 [M+1]; $t_R$=1.56 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 l/min.

To a solution of above Intermediate (188 mg, 0.226 mmol) in ACN (2 mL) was added conc. HCl (0.2 mL) at rt. The mixture was stirred for 3 h, neutralized with TEA, and purified by reverse phase HPLC (10 to 100% ACN in water for 15 min, then 100% ACN for 3 min) to give the title compound 16 (146 mg, 86%).

Compound 16:
$^1$H NMR (400 MHz, Acetonitrile-d3) δ 7.97 (s, 1H), 6.87 (d, J=4.6 Hz, 1H), 6.81 (d, J=4.6 Hz, 1H), 6.38 (s, 2H), 4.93-4.72 (m, 2H), 4.43-4.30 (m, 2H), 4.28-4.16 (m, 2H), 3.71 (d, J=5.0 Hz, 1H), 2.14 (dd, J=7.2, 2.5 Hz, 2H), 1.99 (m, 1H), 0.90 (d, J=6.7 Hz, 6H).
LCMS: MS m/z=376.14 [M+1]; $t_R$=1.21 min; LC system: Thermo Accela 1250 UHPLC; MS system: Thermo LCQ Fleet; Column: Phenomenex Kinetex 2.6μ XB-C18 100A, 50×3.0 mm; Solvents: acetonitrile with 0.1% formic acid, water with 0.1% formic acid; Gradient: 0 min-1.8 min 2-100% acetonitrile, 1.8 min-1.85 min 100%-2% acetonitrile, 1.85 min-2.00 min 2% ACN at 1800 μl/min.

HPLC: $t_R$=3.69 min; HPLC system: 1290 Infinity II.; Column: Phenomenex 2.6p C18 100A, 100×4.6 mm; Solvents: Acetonitrile with 0.1% TFA, Water with 0.1% TFA; Gradient: 0 min-8.5 min 2-98% ACN at 1.5 mL/min.

Example 17: ((2R,3S,4R,5R)-5-(4-aminopyrrolo[2,1-f][1,2,4]triazin-7-yl)-5-cyano-3,4-dihydroxytetrahydrofuran-2-yl)methyl cyclohexanecarboxylate

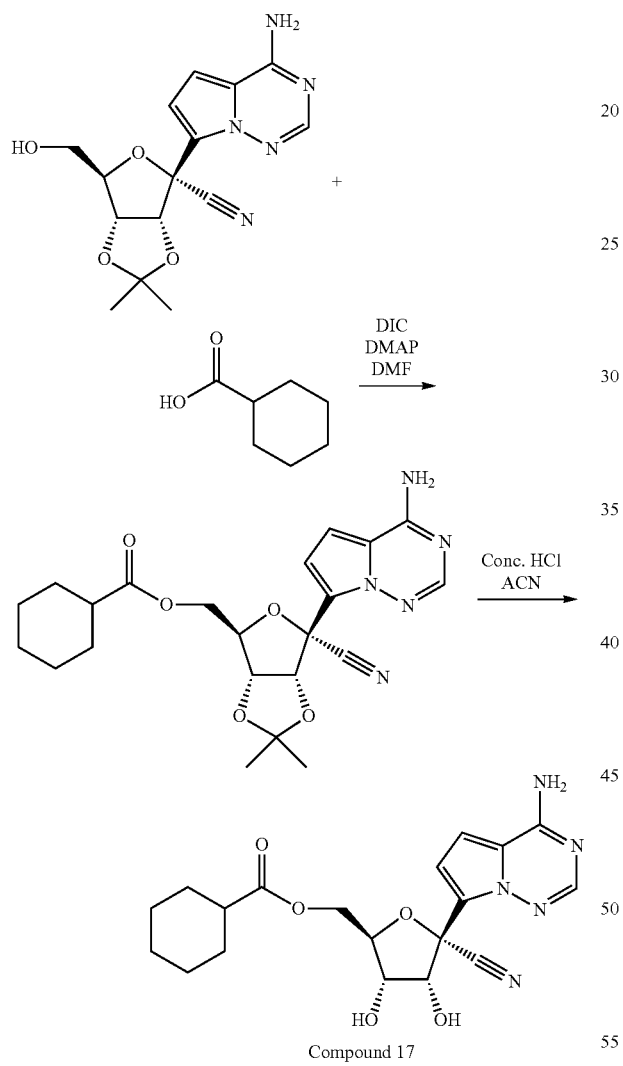

Compound 17

The title compound was synthesized as explained in Example 16 starting from cyclohexanoic acid instead of 3-methylbutanoic acid.

Intermediate 17a: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl cyclohexanecarboxylate: LCMS: MS m/z=442.16 [M+1]; $t_R$=1.64 min.

Compound 17:
$^1$H NMR (400 MHz, DMSO-d6) δ 8.03-7.75 (m, 3H), 6.92 (d, J=4.5 Hz, 1H), 6.81 (d, J=4.5 Hz, 1H), 6.33 (d, J=5.9 Hz, 1H), 5.37 (d, J=5.9 Hz, 1H), 4.70 (t, J=5.4 Hz, 1H), 4.31 (dd, J=12.1, 2.8 Hz, 1H), 4.23 (ddd, J=7.2, 4.8, 2.7 Hz, 1H), 4.15 (dd, J=12.0, 4.9 Hz, 1H), 4.03-3.92 (m, 1H), 2.25 (m, 1H), 1.82-1.51 (m, 4H), 1.37-1.03 (m, 6H).

LCMS: MS m/z=402.17 [M+1]; $t_R$=1.29 min.
HPLC: $t_R$=4.05 min.

Example 18: ((2R,3S,4R,5R)-5-(4-aminopyrrolo[2,1-f][1,2,4]triazin-7-yl)-5-cyano-3,4-dihydroxytetrahydrofuran-2-yl)methyl 2-propylpentanoate

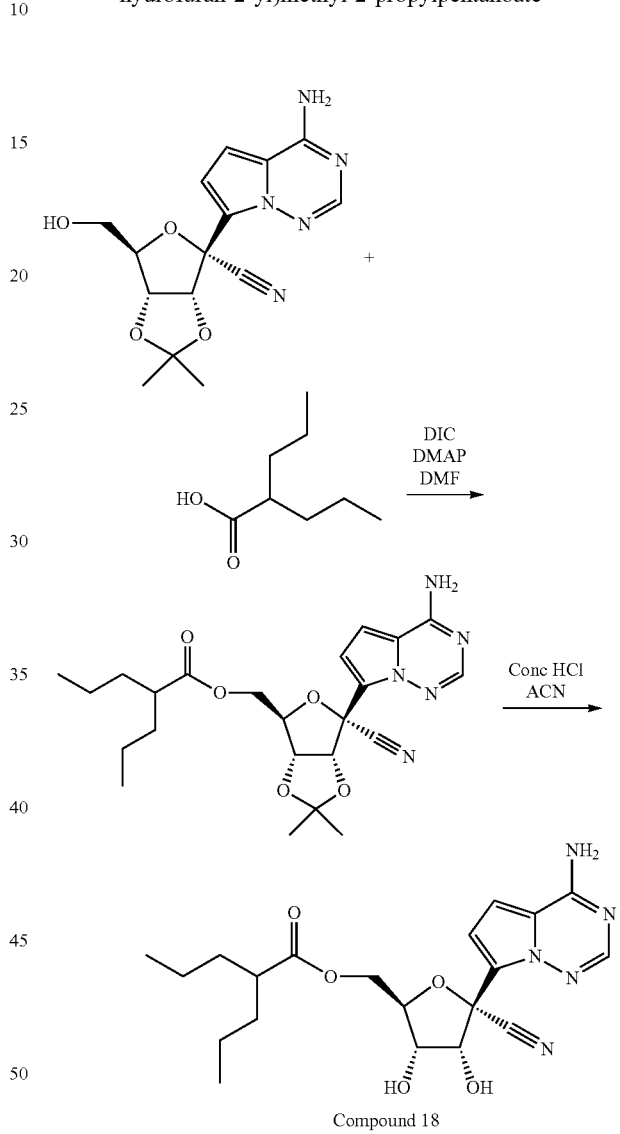

Compound 18

The title compound was synthesized as explained in Example 16 starting from 2-propylpentanoic acid instead of 3-methylbutanoic acid.

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-propylpentanoate: LCMS: MS m/z=458.19 [M+1]; $t_R$=1.81 min.

Compound 18:
$^1$H NMR (400 MHz, Methanol-d4) δ 7.88 (s, 1H), 6.92 (s, 2H), 4.90 (d, J=5.3 Hz, 1H), 4.45-4.33 (m, 3H), 4.16 (t, J=5.5 Hz, 1H), 2.38 (m, 1H), 1.54 (m, 2H), 1.40 (m, 2H), 1.31-1.19 (m, 4H), 0.86 (td, J=7.3, 5.4 Hz, 6H).

LCMS: MS m/z=418.20 [M+1]; $t_R$=1.43 min.
HPLC: $t_R$=4.60 min.

Example 19: ((2R,3S,4R,5R)-5-(4-aminopyrrolo[2,1-f][1,2,4]triazin-7-yl)-5-cyano-3,4-dihydroxytetrahydrofuran-2-yl)methyl 2-ethylbutanoate The title compound was synthesized as explained in Example 16 starting from 2-ethylbutanoic acid instead of 3-methylbutanoic acid.

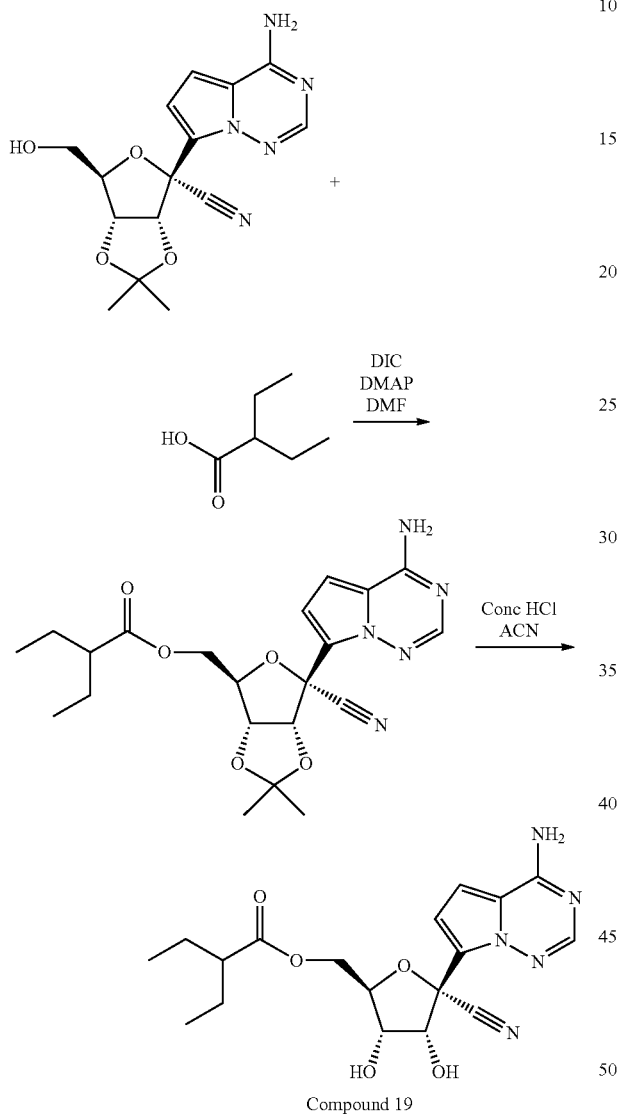

Compound 19

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-ethylbutanoate: LCMS: MS m/z=430.18 [M+1]; $t_R$=1.64 min.

Compound 19:

$^1$H NMR (400 MHz, DMSO-d6) δ 8.05-7.72 (m, 3H), 6.92 (d, J=4.5 Hz, 1H), 6.82 (d, J=4.5 Hz, 1H), 6.33 (d, J=6.0 Hz, 1H), 5.38 (d, J=5.9 Hz, 1H), 4.70 (dd, J=6.0, 4.9 Hz, 1H), 4.35-4.18 (m, 3H), 3.96 (m, 1H), 2.17 (m, 1H), 1.57-1.34 (m, 4H), 0.79 (m, 6H).

LCMS: MS m/z=390.15 [M+1]; $t_R$=1.27 min.

HPLC: $t_R$=3.95 min.

Example 20: ((2R,3S,4R,5R)-5-(4-aminopyrrolo[2,1-f][1,2,4]triazin-7-yl)-5-cyano-3,4-dihydroxytetrahydrofuran-2-yl)methyl octanoate The title compound was synthesized as explained in Example 16 starting from octanoic acid instead of 3-methylbutanoic acid.

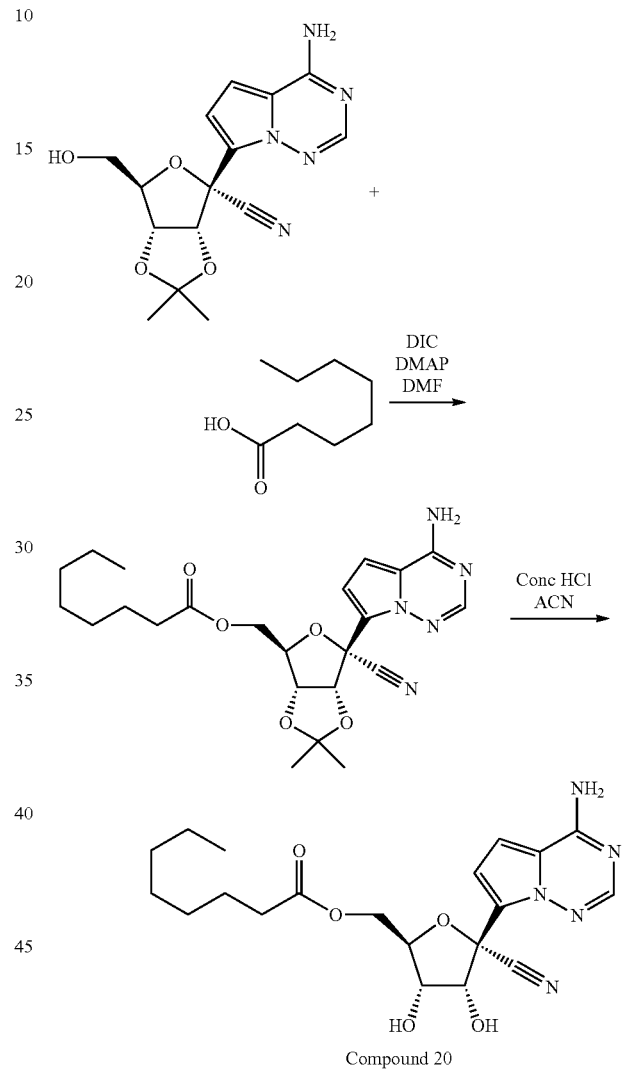

Compound 20

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl octanoate: LCMS: MS m/z=458.17 [M+1]; $t_R$=1.83 min.

Compound 20:

$^1$H NMR (400 MHz, DMSO-d6): δ 8.08-7.78 (m, 3H), 6.92 (d, J=4.5 Hz, 1H), 6.81 (d, J=4.5 Hz, 1H), 6.32 (d, J=6.0 Hz, 1H), 5.38 (d, J=5.9 Hz, 1H), 4.69 (dd, J=6.0, 4.9 Hz, 1H), 4.32 (dd, J=11.9, 2.6 Hz, 1H), 4.27-4.20 (m, 1H), 4.17 (dd, J=11.8, 5.5 Hz, 1H), 3.94 (td, J=6.2, 4.9 Hz, 1H), 2.28 (td, J=7.4, 2.0 Hz, 2H), 1.48 (m, 2H), 1.29-1.15 (m, 8H), 0.88-0.78 (m, 3H).

LCMS: MS m/z=418.21 [M+1]; $t_R$=1.48 min.

HPLC: $t_R$=3.97 min.

Example 21: ((2R,3S,4R,5R)-5-(4-aminopyrrolo[2,1-f][1,2,4]triazin-7-yl)-5-cyano-3,4-dihydroxytetrahydrofuran-2-yl)methyl 3,3-dimethylbutanoate The title compound was synthesized as explained in Example 16 starting from 3,3-dimethylbutanoic acid instead of 3-methylbutanoic acid.

Example 22: ((2R,3S,4R,5R)-5-(4-aminopyrrolo[2,1-f][1,2,4]triazin-7-yl)-5-cyano-3,4-dihydroxytetrahydrofuran-2-yl)methyl 2-phenylacetate The title compound was synthesized as explained in Example 16 starting from 2-phenylacetic acid instead of 3-methylbutanoic acid.

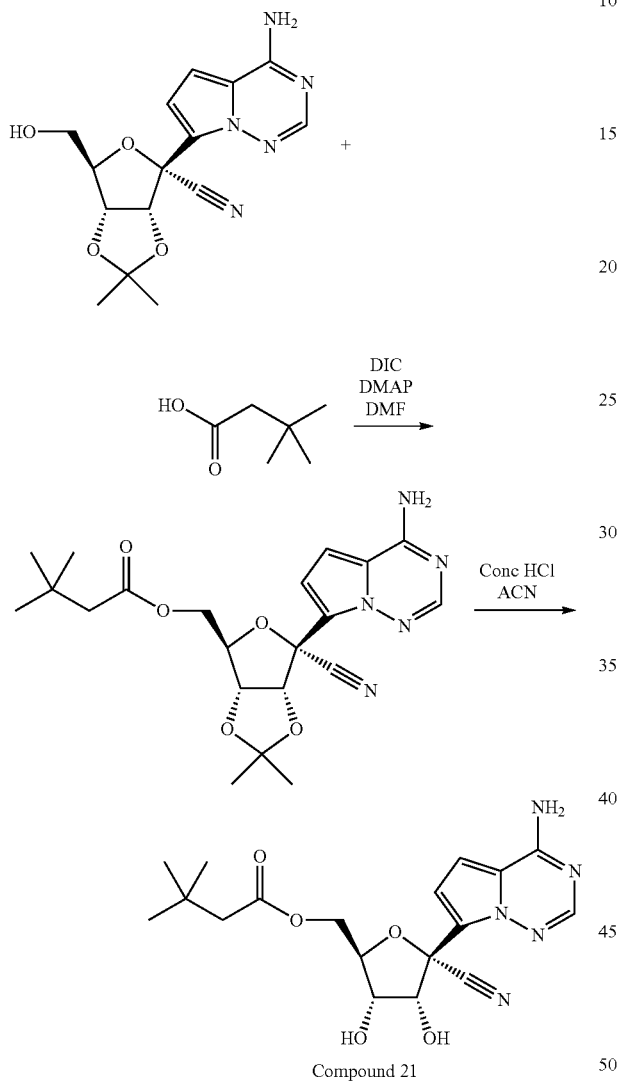

Compound 21

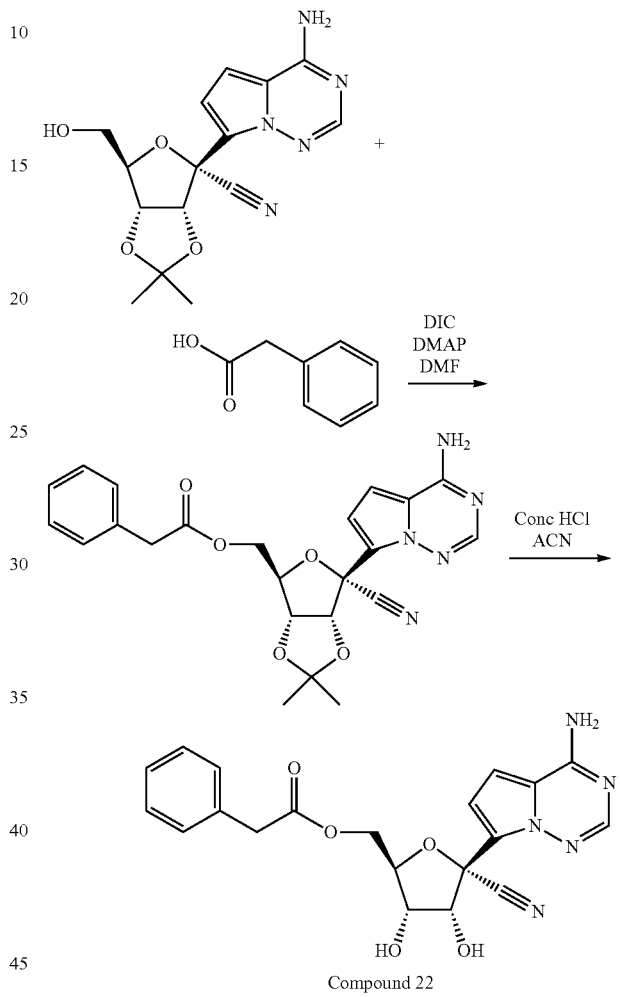

Compound 22

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 3,3-dimethylbutanoate: LCMS: MS m/z=430.16 [M+1]; $t_R$=1.63 min.

Compound 21:

$^1$H NMR (400 MHz, DMSO-d6) δ 8.04-7.71 (m, 3H), 6.92 (d, J=4.5 Hz, 1H), 6.82 (d, J=4.5 Hz, 1H), 6.33 (d, J=6.0 Hz, 1H), 5.38 (d, J=5.9 Hz, 1H), 4.71 (dd, J=6.0, 4.9 Hz, 1H), 4.30 (dd, J=11.9, 2.7 Hz, 1H), 4.26-4.21 (m, 1H), 4.16 (dd, J=11.8, 5.7 Hz, 1H), 3.94 (td, J=6.3, 4.9 Hz, 1H), 2.16 (s, 2H), 0.94 (s, 9H).

LCMS: MS m/z=390.19 [M+1]; $t_R$=1.28 min.

HPLC: $t_R$=4.84 min.

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 2-phenylacetate: LCMS: MS m/z=450.24 [M+1]; $t_R$=1.52 min.

Compound 22:

$^1$H NMR (400 MHz, DMSO-d6) δ 8.00-7.77 (m, 3H), 7.37-7.18 (m, 5H), 6.98-6.88 (m, 1H), 6.79 (d, J=4.5 Hz, 1H), 6.31 (d, J=6.0 Hz, 1H), 5.39 (d, J=5.8 Hz, 1H), 4.67 (t, J=5.5 Hz, 1H), 4.36 (dd, J=11.6, 2.3 Hz, 1H), 4.28-4.17 (m, 2H), 3.95 (m, 1H), 3.68 (s, 2H).

LCMS: MS m/z=410.18 [M+1]; $t_R$=1.23 min.

HPLC: $t_R$=3.80 min.

Example 23: ((2R,3S,4R,5R)-5-(4-aminopyrrolo[2,1-f][1,2,4]triazin-7-yl)-5-cyano-3,4-dihydroxytetrahydrofuran-2-yl)methyl 4-methylbenzoate The title compound was synthesized as explained in Example 16 starting from 4-methylbenzoic acid instead of 3-methylbutanoic acid.

113

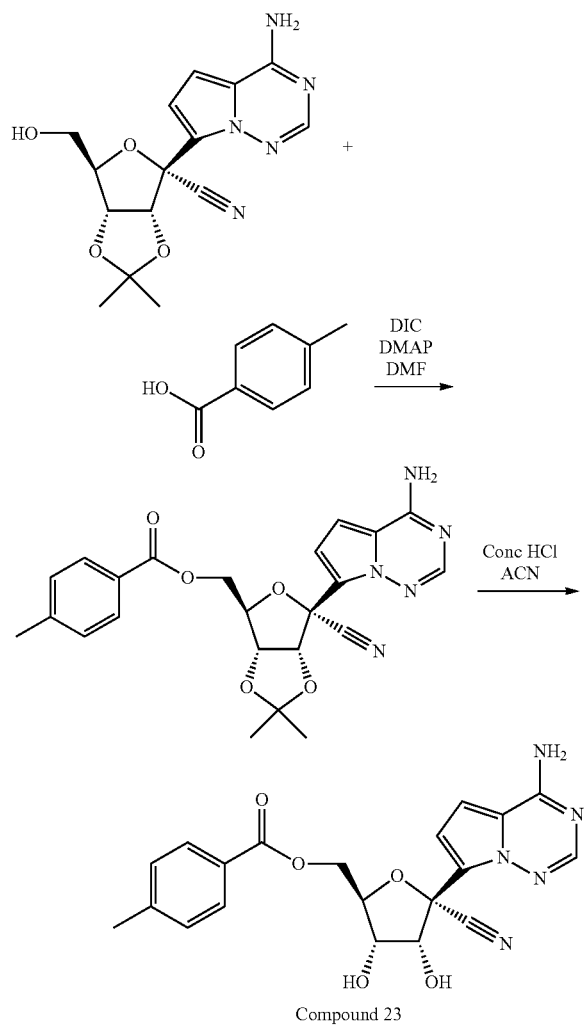

Compound 23

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl 4-methylbenzoate: LCMS: MS m/z=450.12 [M+1]; $t_R$=1.55 min.

Compound 23:

$^1$H NMR (400 MHz, DMSO-d6) δ 8.03-7.82 (m, 3H), 7.79 (dt, J=8.1, 1.8 Hz, 2H), 7.32 (d, J=7.8 Hz, 2H), 6.92-6.87 (m, 1H), 6.80 (dd, J=4.5, 1.5 Hz, 1H), 6.36 (dd, J=6.0, 1.5 Hz, 1H), 5.44 (dd, J=5.9, 1.5 Hz, 1H), 4.87-4.73 (m, 1H), 4.57 (dd, J=11.8, 2.6 Hz, 1H), 4.46-4.33 (m, 2H), 4.12 (q, J=6.4, 5.8 Hz, 1H), 2.40 (s, 3H).

LCMS: MS m/z=410.09 [M+1]; $t_R$=1.25 min.

HPLC: $t_R$=3.86 min.

Example 24: ((2R,3S,4R,5R)-5-(4-aminopyrrolo[2,1-f][1,2,4]triazin-7-yl)-5-cyano-3,4-dihydroxytetrahydrofuran-2-yl)methyl octahydropentalene-2-carboxylate The title compound was synthesized as explained in Example 16 starting from octahydropentalene-2-carboxylic acid instead of 3-methylbutanoic acid provided mixture of cis and trans isomers.

114

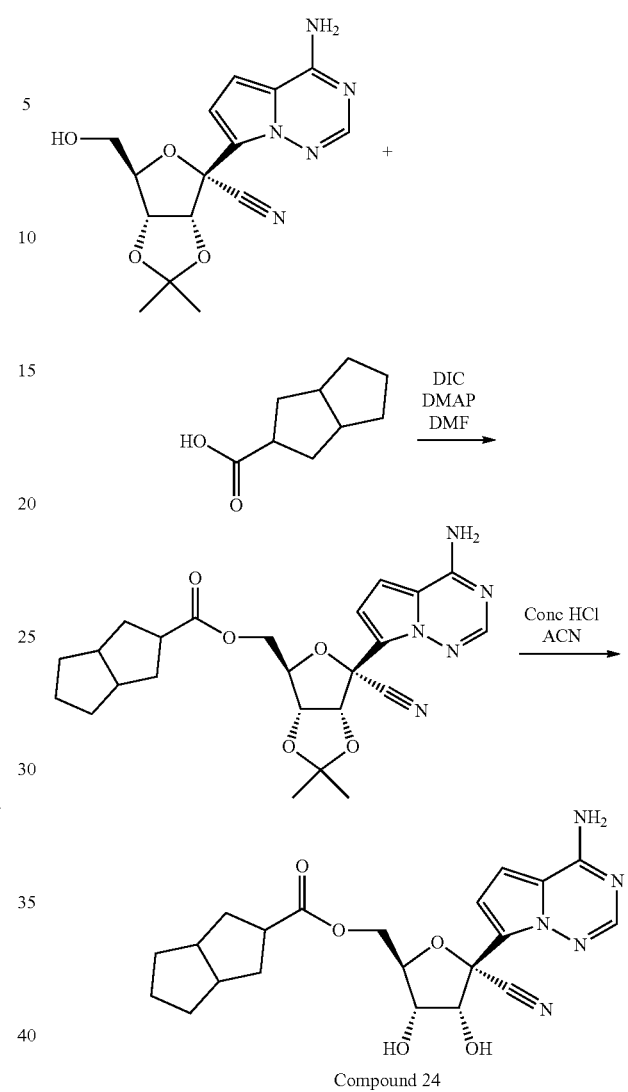

Compound 24

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl octahydropentalene-2-carboxylate: LCMS: MS m/z=468.20 [M+1]; $t_R$=1.73 min.

Compound 24:

$^1$H NMR (400 MHz, DMSO-d6) δ 8.04-7.71 (m, 3H), 6.92 (m, 1H), 6.81 (m, 1H), 6.33 (m, 1H), 5.37 (d, J=5.9 Hz, 1H), 4.74-4.62 (m, 1H), 4.39-4.27 (m, 1H), 4.28-4.10 (m, 2H), 4.01-3.90 (m, 1H), 2.72-2.52 (m, 1H), 2.42 (m, 2H), 2.13-1.85 (m, 2H), 1.84-1.67 (m, 2H), 1.65-1.42 (m, 4H), 1.33 (m, 1H), 1.26-0.95 (m, 1H); LCMS: MS m/z=428.19 [M+1]; $t_R$=1.40 min; HPLC: $t_R$=4.47 min (85%), 4.56 min (15%).

Example 25: ((2R,3S,4R,5R)-5-(4-aminopyrrolo[2,1-f][1,2,4]triazin-7-yl)-5-cyano-3,4-dihydroxytetrahydrofuran-2-yl)methyl butyrate The title compound was synthesized as explained in Example 16 starting from butanoic acid instead of 3-methylbutanoic acid.

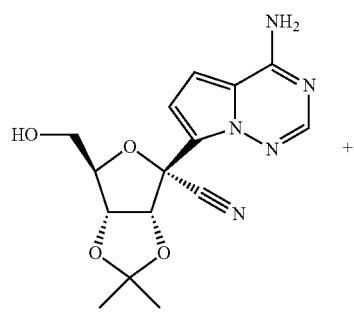
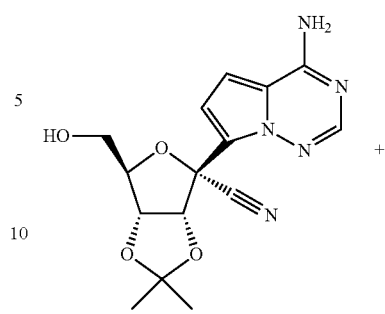
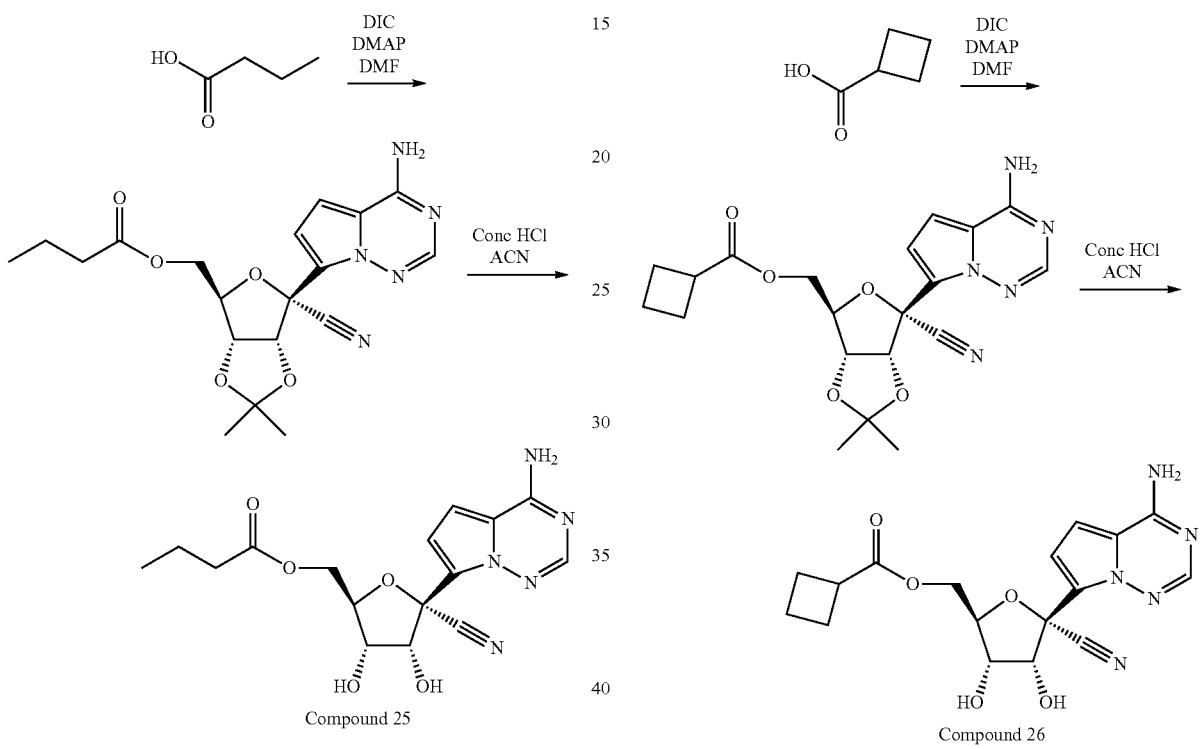

Compound 25

Compound 26

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl butyrate: LCMS: MS m/z=402.12 [M+1];]; $t_R$=0.76 min.

Compound 25:

$^1$H NMR (400 MHz, DMSO-d6) δ 8.05-7.78 (m, 3H), 6.92 (d, J=4.5 Hz, 1H), 6.81 (d, J=4.5 Hz, 1H), 6.32 (d, J=6.0 Hz, 1H), 5.38 (d, J=5.9 Hz, 1H), 4.70 (t, J=5.5 Hz, 1H), 4.34 (dd, J=11.9, 2.7 Hz, 1H), 4.23 (td, J=6.1, 2.6 Hz, 1H), 4.16 (dd, J=11.9, 5.5 Hz, 1H), 3.98-3.91 (m, 1H), 2.27 (td, J=7.3, 1.9 Hz, 2H), 1.51 (m, 2H), 0.86 (t, J=7.4 Hz, 3H).

LCMS: MS m/z=362.11 [M+1]; $t_R$=1.14 min.

HPLC: $t_R$=3.36 min.

Example 26: ((2R,3S,4R,5R)-5-(4-aminopyrrolo[2,1-f][1,2,4]triazin-7-yl)-5-cyano-3,4-dihydroxytetrahydrofuran-2-yl)methyl cyclobutanecarboxylate The title compound was synthesized as explained in Example 16 starting from cyclobutanoic acid instead of 3-methylbutanoic acid.

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl cyclobutanecarboxylate LCMS: MS m/z=414.13 [M+1]; $t_R$=1.50 min.

Compound 26:

$^1$H NMR (400 MHz, DMSO-d6) δ 8.09-7.76 (m, 3H), 6.92 (d, J=4.5 Hz, 1H), 6.80 (d, J=4.5 Hz, 1H), 6.33 (d, J=6.0 Hz, 1H), 5.38 (d, J=5.9 Hz, 1H), 4.67 (dd, J=6.0, 4.9 Hz, 1H), 4.33 (dd, J=11.9, 2.7 Hz, 1H), 4.27-4.14 (m, 2H), 3.94 (td, J=6.3, 4.9 Hz, 1H), 3.15 (m, 1H), 2.20-2.05 (m, 4H), 2.01-1.85 (m, 1H), 1.84-1.70 (m, 1H); LCMS: MS m/z=374.11 [M+1]; $t_R$=1.16 min; HPLC: $t_R$=3.47 min.

Example 27: ((2R,3S,4R,5R)-5-(4-aminopyrrolo[2,1-f][1,2,4]triazin-7-yl)-5-cyano-3,4-dihydroxytetrahydrofuran-2-yl)methyl spiro[3.3]heptane-2-carboxylate The title compound was synthesized as explained in Example 16 starting from spiro[3.3]heptane-2-carboxylic acid instead of 3-methylbutanoic acid.

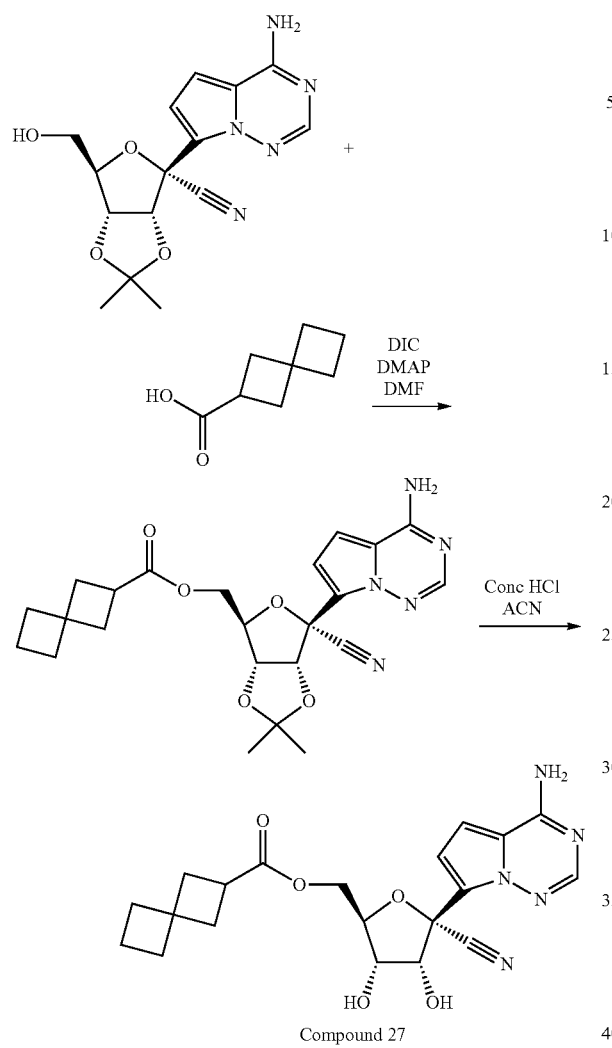

Compound 27

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl spiro[3.3]heptane-2-carboxylate: LCMS: MS m/z=454.14 [M+1]; $t_R$=1.25 min.

Compound 27:

$^1$H NMR (400 MHz, DMSO-d6) δ 8.05-7.74 (m, 3H), 6.92 (d, J=4.5 Hz, 1H), 6.79 (d, J=4.5 Hz, 1H), 6.33 (d, J=6.0 Hz, 1H), 5.37 (d, J=5.8 Hz, 1H), 4.67 (t, J=5.4 Hz, 1H), 4.32 (dd, J=12.0, 2.7 Hz, 1H), 4.25-4.19 (m, 1H), 4.15 (dd, J=12.0, 5.2 Hz, 1H), 3.93 (q, J=5.9 Hz, 1H), 2.95 (m, 1H), 2.19-2.11 (m, 2H), 2.11-2.03 (m, 2H), 2.02-1.95 (m, 2H), 1.89-1.80 (m, 2H), 1.78-1.69 (m, 2H).

LCMS: MS m/z=414.11 [M+1]; $t_R$=1.35 min.

HPLC: $t_R$=4.32 min.

Example 28: ((2R,3S,4R,5R)-5-(4-aminopyrrolo[2,1-f][1,2,4]triazin-7-yl)-5-cyano-3,4-dihydroxytetrahydrofuran-2-yl)methyl cyclopentanecarboxylate The title compound was synthesized as explained in Example 16 starting from cyclopentanecarboxylic acid instead of 3-methylbutanoic acid.

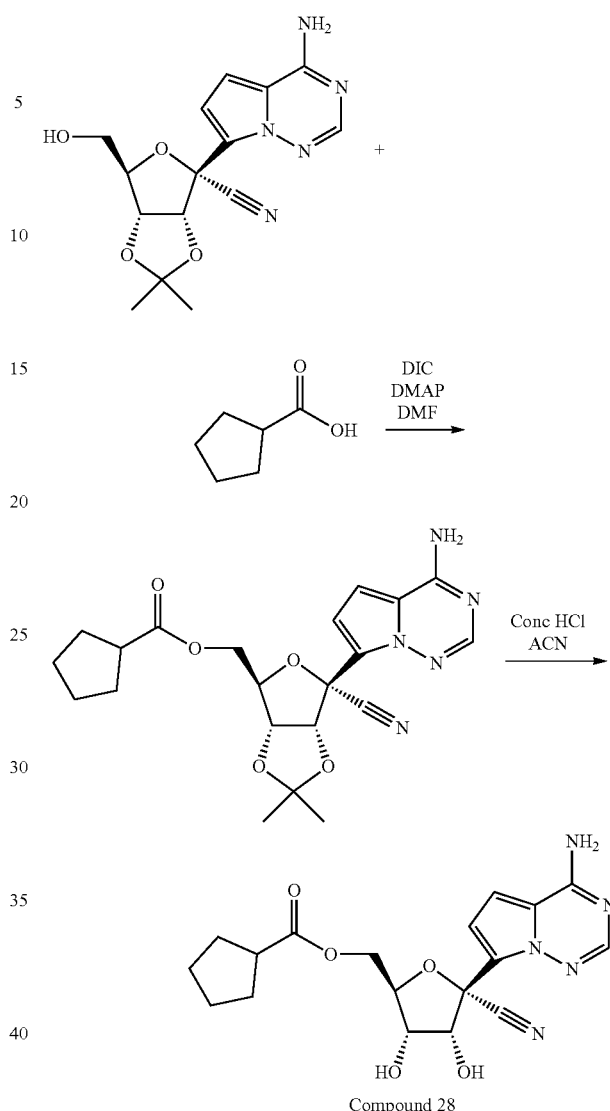

Compound 28

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl cyclopentanecarboxylate: LCMS: MS m/z=428.13 [M+1]; $t_R$=1.57 min.

Compound 28:

$^1$H NMR (400 MHz, DMSO-d6) δ 7.80-7.73 (m, 3H), 6.92 (d, J=4.5 Hz, 1H), 6.81 (d, J=4.5 Hz, 1H), 6.32 (d, J=6.0 Hz, 1H), 5.37 (d, J=5.8 Hz, 1H), 4.74-4.64 (m, 1H), 4.32 (dd, J=11.9, 2.8 Hz, 1H), 4.23 (m, 1H), 4.17 (dd, J=12.0, 5.1 Hz, 1H), 3.95 (q, J=5.9 Hz, 1H), 2.71 (m, 1H), 1.92-1.38 (m, 8H); LCMS: MS m/z=388.14 [M+1]; $t_R$=1.23 min; HPLC: $t_R$=3.78 min.

Example 29: ((2R,3S,4R,5R)-5-(4-aminopyrrolo[2,1-f][1,2,4]triazin-7-yl)-5-cyano-3,4-dihydroxytetrahydrofuran-2-yl)methyl cycloheptanecarboxylate The title compound was synthesized as explained in Example 16 starting from cycloheptanecarboxylic acid instead of 3-methylbutanoic acid.

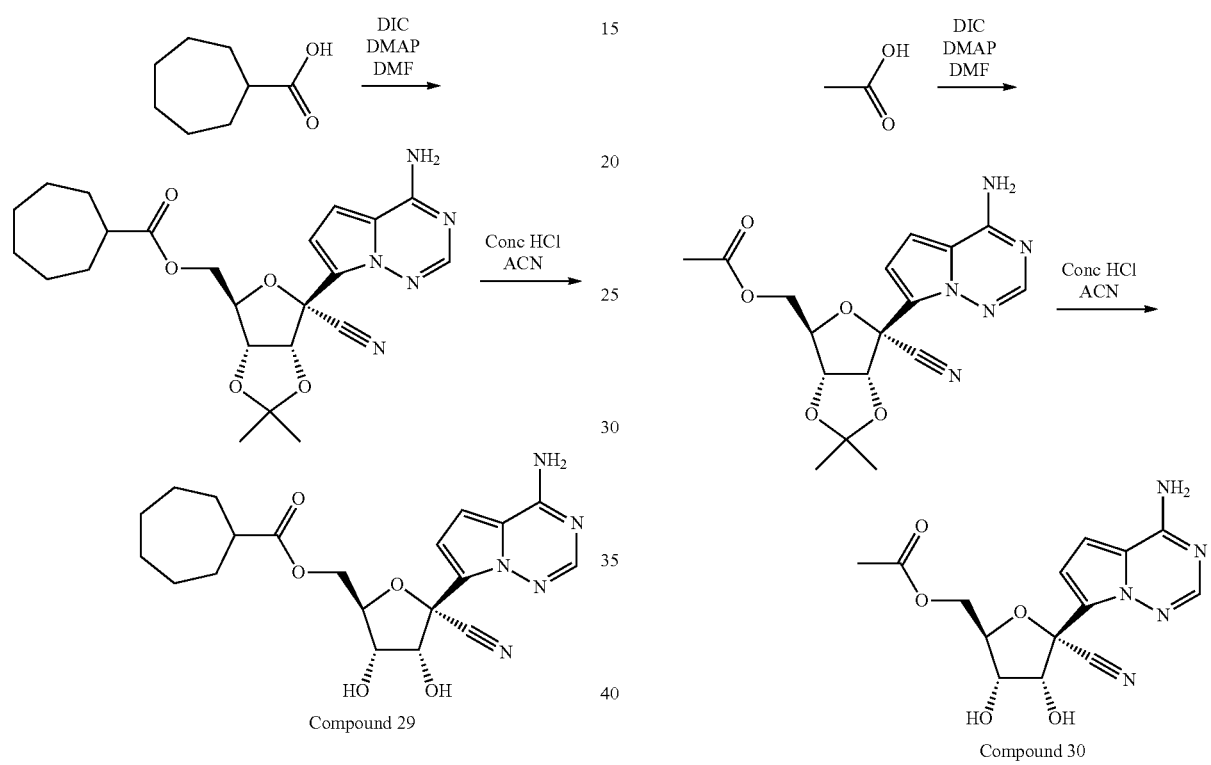

Compound 29

Compound 30

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl cycloheptanecarboxylate: LCMS: MS m/z=456.19 [M+1]; $t_R$=1.71 min.

Compound 29:

$^1$H NMR (400 MHz, DMSO-d6) δ 8.08-7.75 (m, 3H), 6.92 (d, J=4.5 Hz, 1H), 6.81 (d, J=4.5 Hz, 1H), 6.33 (d, J=6.0 Hz, 1H), 5.37 (d, J=5.9 Hz, 1H), 4.69 (t, J=5.4 Hz, 1H), 4.30 (dd, J=12.0, 2.8 Hz, 1H), 4.23 (m, 1H), 4.15 (dd, J=12.0, 4.9 Hz, 1H), 3.96 (q, J=5.9 Hz, 1H), 2.44 (m, 1H), 1.79 (m, 2H), 1.68-1.32 (m, 10H).

LCMS: MS m/z=416.20 [M+1]; $t_R$=1.37 min.

HPLC: $t_R$=4.34 min.

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl acetate: LCMS: MS m/z=374.10 [M+1]; $t_R$=1.30 min.

Compound 30:

$^1$H NMR (400 MHz, DMSO-d6) δ 8.03-7.96 (m, 3H), 6.92 (d, J=4.5 Hz, 1H), 6.81 (d, J=4.5 Hz, 1H), 6.31 (d, J=6.0 Hz, 1H), 5.39 (d, J=5.9 Hz, 1H), 4.70 (t, J=5.5 Hz, 1H), 4.33 (dd, J=11.9, 2.8 Hz, 1H), 4.23 (m, 1H), 4.14 (dd, J=12.0, 5.9 Hz, 1H), 3.94 (q, J=5.9 Hz, 1H), 2.02 (s, 3H).

LCMS: MS m/z=334.11 [M+1]; $t_R$=0.99 min.

HPLC: $t_R$=2.67 min.

Example 30: ((2R,3S,4R,5R)-5-(4-aminopyrrolo[2,1-f][1,2,4]triazin-7-yl)-5-cyano-3,4-dihydroxytetrahydrofuran-2-yl)methyl acetate The title compound was synthesized as explained in Example 16 starting from acetic acid instead of 3-methylbutanoic acid.

Example 31: ((2R,3S,4R,5R)-5-(4-aminopyrrolo[2,1-f][1,2,4]triazin-7-yl)-5-cyano-3,4-dihydroxytetrahydrofuran-2-yl)methyl hexanoate The title compound was synthesized as explained in Example 16 starting from hexanoic acid instead of 3-methylbutanoic acid.

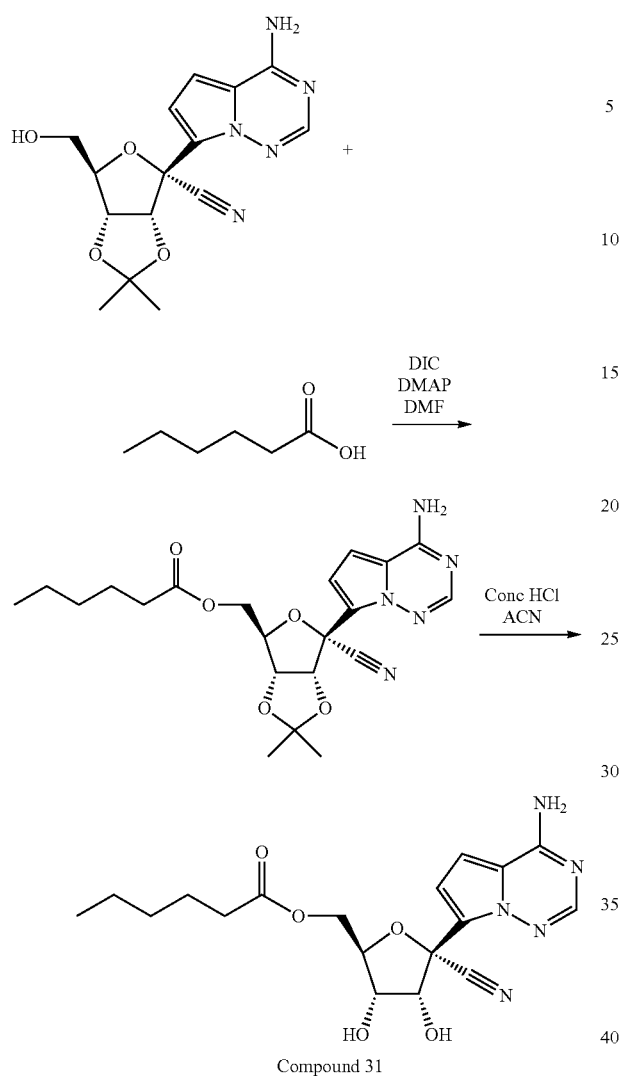

Compound 31

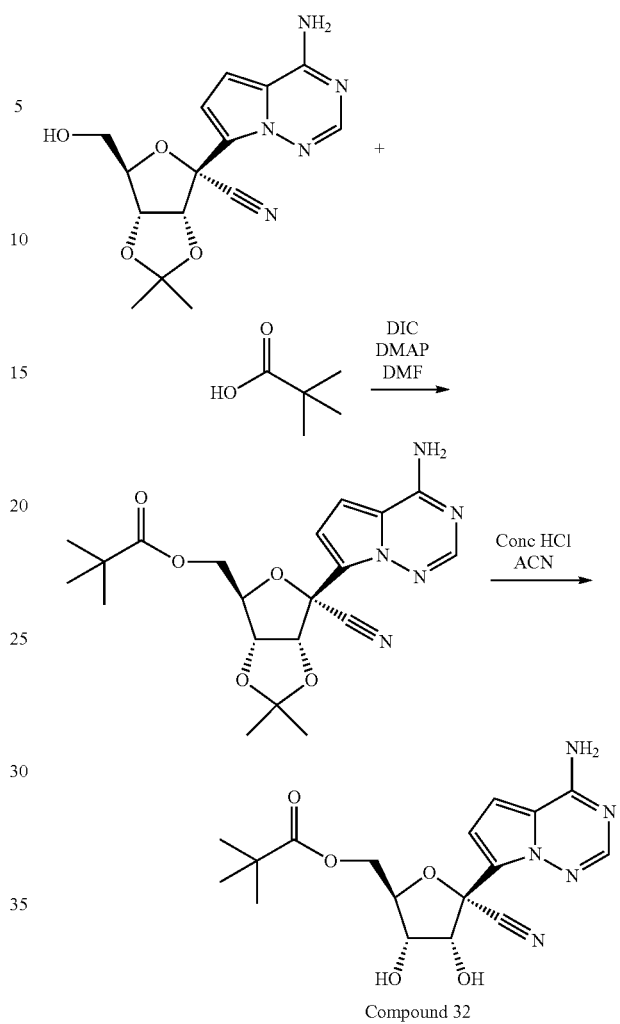

Compound 32

Intermediate: ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl hexanoate: LCMS: MS m/z=430.14 [M+1]; $t_R$=1.65 min.

Compound 31:

$^1$H NMR (400 MHz, DMSO-d6) δ 8.03-7.74 (m, 3H), 6.92 (d, J=4.5 Hz, 1H), 6.80 (d, J=4.5 Hz, 1H), 6.32 (d, J=6.0 Hz, 1H), 5.38 (d, J=5.9 Hz, 1H), 4.69 (t, J=5.5 Hz, 1H), 4.33 (dd, J=11.9, 2.7 Hz, 1H), 4.23 (m, 1H), 4.16 (dd, J=11.9, 5.5 Hz, 1H), 3.94 (m, 1H), 2.27 (m, 2H), 1.49 (m, 2H), 1.23 (m, 4H), 0.84 (t, J=6.8 Hz, 3H).

LCMS: MS m/z=390.15 [M+1]; $t_R$=0.99 min.

HPLC: $t_R$=4.14 min.

Example 32: ((2R,3S,4R,5R)-5-(4-aminopyrrolo[2,1-f][1,2,4]triazin-7-yl)-5-cyano-3,4-dihydroxytetrahydrofuran-2-yl)methyl pivalate The title compound was synthesized as explained in Example 16 starting from pivaloyl acid instead of 3-methylbutanoic acid.

Intermediate ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl pivalate: LCMS: MS m/z=416.20 [M+1]; $t_R$=1.54 min.

Compound 32:

$^1$H NMR (400 MHz, DMSO-d6) δ 8.06-7.78 (m, 3H), 6.92 (d, J=4.5 Hz, 1H), 6.81 (d, J=4.5 Hz, 1H), 6.33 (d, J=6.0 Hz, 1H), 5.37 (s, 1H), 4.70 (m, 1H), 4.32-4.14 (m, 3H), 3.98 (m, 1H), 1.10 (s, 9H).

LCMS: MS m/z=376.21 [M+1]; $t_R$=1.18 min.

HPLC: $t_R$=3.65 min.

Example 33: Compound 15 Form I

Compound 15 Form I was prepared via a slurry of Compound Form II (example 34) in water. To about 1 g of Compound 15 Form II was added about 40 mL of water. The resulting slurry was stirred at ambient temperatures for about 2 days. The solids were then evaluated by vacuum filtration and dried in the vacuum oven at about 40° C.

Alternatively, Compound 15 Form I was also prepared by stirring 40 mg of Compound 15 Form III (example 35) in about 0.4 mL of solvents such as acetone, and methyl ethyl ketone at ambient temperature for about one day. The solids were isolated by centrifugation and dried in the vacuum oven at about 40° C.

Compound 15 Form I was also prepared by stirring about 40 mg of Compound 15 Form II (example 34) in about 0.4 mL of solvents such as water, methanol/water about 80/20 (v/v), acetone, and acetonitrile for about one day. The solids were isolated by centrifugation and dried in the vacuum oven at about 40° C.

Form I was recovered when Form I was slurried in solvents such as water, isopropanol, acetonitrile, ethyl acetate, isopropyl acetate, dichloromethane, methyl ethyl ketone, acetone, and toluene. In those experiments the slurries were stirred at ambient and the solids were isolated by centrifugation and dried in the oven at about 40° C. or at ambient temperature.

Characterization

Compound 15 Form I is an unsolvated phase. Its XRPD pattern is shown in FIG. 10 and a complete list of peaks is presented in the Table below. The DSC thermogram is shown in FIG. 11 and displays one endothermic transition at about 169° C. The TGA thermogram is shown in FIG. 12 and indicates that the phase is unsolvated.

| Complete XRPD peak list for Compound 15 free base Form I | |
|---|---|
| Pos. [°2Th.] | Rel. Int. [%] |
| 8.5 | 74 |
| 10.5 | 9 |
| 11.8 | 4 |
| 14.1 | 6 |
| 15.4 | 17 |
| 16.9 | 100 |
| 17.5 | 23 |
| 17.6 | 13 |
| 20.3 | 7 |
| 22.1 | 20 |
| 23.8 | 17 |
| 24.1 | 8 |
| 25.0 | 4 |
| 25.7 | 3 |
| 26.2 | 4 |
| 26.5 | 7 |
| 27.5 | 7 |
| 28.1 | 20 |
| 30.1 | 2 |
| 30.8 | 3 |
| 32.1 | 3 |
| 34.7 | 1 |
| 35.4 | 3 |
| 36.5 | 3 |
| 38.0 | 3 |

Example 34: Compound 15 Form II

Compound 15 was obtained in Form II following the procedure described in Example 15.

Characterization

The XRPD pattern of Compound 15 freebase Form II is presented in FIG. 13 and a complete XPRD peak list is presented in the Table below.

The DSC thermogram of Form II is shown in FIG. 14. It shows two endothermic events around 165° C. and 176° C. and an exothermic event around 169° C. The TGA thermogram is presented in FIG. 15. It shows that the material is unsolvated.

| Complete XRPD peak list for Compound 15 free base Form II | |
|---|---|
| Pos. [°2Th.] | Rel. Int. [%] |
| 6.4 | 100 |
| 13.7 | 4 |
| 16.3 | 25 |
| 18.4 | 2 |
| 20.8 | 3 |
| 23.3 | 2 |
| 25.4 | 3 |

Example 35: Compound 15, Form III

Compound 15 freebase Form III was first prepared from the residue of the workup used at the end of the preparation of Compound 15 freebase Form II (Example 34) in the following way: the residue from the workup was suspended in acetonitrile (3 vol) and stirred at room temperature for about 30 hrs. The residue dissolved in acetonitrile and solids were observed to precipitate out of solution immediately. The precipitate was filtered, washed with acetonitrile and dried and the Compound 15 was obtained as Form III.

Characterization

The XRPD pattern of Form III is shown in FIG. 16 and a complete list of XRPD peaks is presented in the Table below. The DSC thermogram of freebase Form III is shown in FIG. 17. It displays an endothermic event at approximately 177° C. The TGA thermogram is shown in FIG. 18. It shows that the material is unsolvated.

| Complete XRPD peak list for Compound 15 free base Form III | |
|---|---|
| Pos. [°2Th.] | Rel. Int. [%] |
| 9.8 | 100 |
| 10.2 | 19 |
| 10.4 | 25 |
| 12.4 | 11 |
| 13.2 | 6 |
| 13.4 | 12 |
| 13.7 | 9 |
| 16.0 | 24 |
| 16.8 | 3 |
| 17.5 | 29 |
| 17.8 | 7 |
| 18.9 | 19 |
| 19.1 | 64 |
| 19.8 | 39 |
| 20.7 | 21 |
| 21.7 | 9 |
| 22.8 | 8 |
| 24.8 | 26 |
| 25.4 | 16 |
| 26.9 | 15 |
| 27.3 | 3 |
| 28.8 | 8 |
| 31.4 | 3 |
| 32.7 | 7 |
| 34.0 | 7 |
| 37.7 | 6 |

Example 36: Compound 15 Xinafoate Material A

Compound 15 xinafoate material A was prepared by suspending about 40 mg of Compound 15 freebase Form II (example 34) in 0.4 mL of acetonitrile. Approximately one molar equivalent of 1-hydroxy-2-naphthoic acid was added to the suspension and the resulting slurry was stirred at ambient temperature for about one day. An immobile slurry was then present in the vial. After another day, 0.35 mL of acetonitrile was added, resulting in a mobile slurry. The solids were isolated by centrifugation and dried in the vacuum oven at about 40° C.

Characterization

Compound 15 xinafoate Material A is an unsolvated form. Its XRPD pattern is shown in FIG. 19 and a complete list of XRPD peaks is presented in the Table below.

| Pos. [°2Th.] | Rel. Int. [%] |
|---|---|
| 3.1 | 5 |
| 4.0 | 31 |
| 5.3 | 8 |
| 6.2 | 100 |
| 7.8 | 18 |
| 9.3 | 5 |
| 10.3 | 16 |
| 10.6 | 11 |
| 11.7 | 4 |
| 12.2 | 20 |
| 12.9 | 13 |
| 13.5 | 3 |
| 14.5 | 6 |
| 14.8 | 41 |
| 15.7 | 7 |
| 16.3 | 5 |
| 16.8 | 5 |
| 17.1 | 3 |
| 18.1 | 5 |
| 18.5 | 5 |
| 18.7 | 4 |
| 20.9 | 8 |
| 22.6 | 7 |
| 23.6 | 3 |
| 25.1 | 3 |
| 26.6 | 22 |

The DSC curve is shown in 20. It shows one endothermic event at about 154° C. The TGA thermogram is shown in 21. It shows that the material is unsolvated.

Example 37: Compound 15 HCl Salt Form I

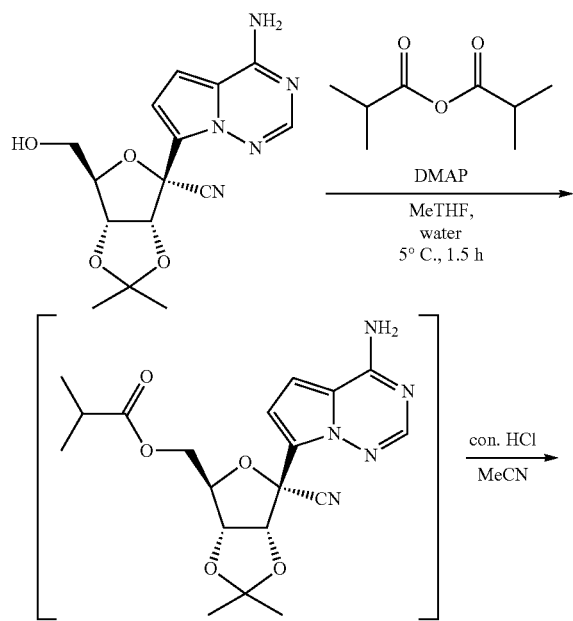

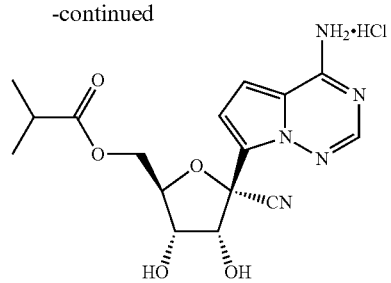

To a reactor was charged 3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile, 4-dimethylaminopyridine (0.03 equiv.), 2-methyltetrahydrofuran (10.0 volumes), and water (0.1 volumes). The internal temperature was adjusted to about 0° C. Isobutyric anhydride (1.2 equiv.) was charged slowly, keeping the internal temperature below about 5° C. The mixture was agitated at about 2° C. until the reaction was deemed complete. Methanol (3 equiv.) was then charged, and the internal temperature was adjusted to about 20° C. The mixture was agitated at about 20° C. for about 1 hour. 15% aqueous potassium bicarbonate (5.0 volumes) was charged, and the mixture was agitated for about 45 minutes. The aqueous layer was removed, and 15% aqueous potassium bicarbonate (5.0 volumes) was charged. The mixture was agitated for about 30 minutes, and the aqueous layer was removed. Water (5.0 volumes) was charged, and the mixture was agitated for about 15 minutes. The aqueous layer was then removed. The organic layer was heated to about 50° C., concentrated to a minimum volume, and co-distilled with acetonitrile to achieve removal of 2-methyltetrahydrofuran. Sufficient acetonitrile was charged to the reaction vessel to dilute the total volume to about 7 volumes, affording ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyrate as a solution in acetonitrile. $^1$H NMR (400 MHz, Chloroform-d) δ 7.93 (s, 1H), 6.93 (d, J=4.7 Hz, 1H), 6.57 (d, J=4.7 Hz, 1H), 5.60 (br s, 2H), 5.41 (d, J=6.8 Hz, 1H), 4.85 (dd, J=6.8, 4.3 Hz, 1H), 4.56-4.48 (m, 1H), 4.35 (dd, J=12.0, 4.4 Hz, 1H), 4.21 (dd, J=12.0, 5.6 Hz, 1H), 2.56-2.41 (m, 1H), 1.70 (s, 3H), 1.34 (s, 3H), 1.12-1.04 (m, 6H); $^{13}$C NMR (101 MHz, Chloroform-d) δ 176.70, 155.33, 147.36, 123.39, 117.22, 116.75, 115.65, 112.53, 99.98, 83.86, 82.98, 82.06, 81.40, 63.09, 33.82, 26.44, 25.56, 18.90.

Concentrated hydrochloric acid (3.0 equiv) was charged to the solution containing ((3aR,4R,6R,6aR)-6-(4-aminopyrrolo[2,1-f][1,2,4]triazin-7-yl)-6-cyano-2,2-dimethyltetrahydrofuro[3,4-d][1,3]dioxol-4-yl)methyl isobutyrate. The mixture was agitated at about 20° C. until the reaction was deemed complete, then filtered. The cake was washed with acetonitrile (1.5 volumes) and then dried to afford Compound 15 HCl salt Form I. $^1$H NMR (400 MHz, DMSO-$d_6$) δ 10.10 (br s, 1H), 9.31 (br s, 1H), 8.24 (s, 1H), 7.49 (d, J=4.6 Hz, 1H), 6.98 (d, J=4.7 Hz, 1H), 4.60 (d, J=4.8 Hz, 1H), 4.31-4.22 (m, 2H), 4.15 (dd, J=13.0, 5.8 Hz, 1H), 3.92 (dd, J=6.3, 4.8 Hz, 1H), 2.50-2.45 (m, 1H), 1.03 (dd, J=7.0, 2.1 Hz, 6H) ppm; $^{13}$C NMR (101 MHz, DMSO) δ 175.9, 149.3, 137.4, 128.9, 116.4, 114.3, 112.2, 109.2, 81.8, 78.2, 75.0, 70.2, 62.9, 33.2, 18.8, 18.7 ppm.

Compound 15 HCl salt Form I was recovered after suspending about 40 mg of HCl salt Form I in about 0.4 mL of solvents such as dichloromethane, heptane, and acetonitrile. The solids were isolated by centrifugation and dried in the vacuum oven at 40° C.

Characterization

The XRPD pattern of Compound 15 HCl salt Form I is shown in FIG. 22 and a complete XRPD peak list is presented in the Table below. The DSC thermogram is shown in FIG. 23. It displays two endothermic transitions at about 115° C. and 187° C. It also displays an exothermic event at about 140° C. The TGA thermogram is shown in FIG. 24. It shows three weight loss events of about 1.1%, 3.4% and 31% by weight starting between about 20° C. and 100° C., between about 100° C. and 135° C. and between about 135° C. and 265° C., respectively.

| Complete XRPD peak list for Compound 15 HCl salt Form I | |
| --- | --- |
| Pos. [°2Th.] | Rel. Int. [%] |
| 5.9 | 100 |
| 11.7 | 81 |
| 13.5 | 3 |
| 14.0 | 21 |
| 14.2 | 8 |
| 15.6 | 3 |
| 16.7 | 6 |
| 17.2 | 4 |
| 18.4 | 4 |
| 18.9 | 3 |
| 19.7 | 20 |
| 20.7 | 2 |
| 22.4 | 6 |
| 22.8 | 4 |
| 23.9 | 10 |
| 24.3 | 14 |
| 25.1 | 4 |
| 25.9 | 5 |
| 26.5 | 3 |
| 29.4 | 4 |
| 30.9 | 5 |

Example 38: Compound 15 HCl Salt Material A

Compound 15 HCl salt Material A was first prepared by suspending approximately 40 mg of Compound freebase Form II (example 34) in 0.4 mL of isopropanol. About one molar equivalent of hydrochloric acid in isopropanol was then added. The mixture was stirred at ambient temperature for about a day. A thick slurry was obtained. The solids were isolated by centrifugation and dried in the vacuum oven at about 40° C.

In another experiment, about 40 mg of Compound HCl salt Form I (example 37) was suspended in about 0.4 mL of solvents such as isopropanol, methyl ethyl ketone, and tetrahydrofuran, and stirred at ambient temperature for about a day. The solids were then isolated by centrifugation and dried in the vacuum oven at about 40° C., resulting in Compound 15 HCl salt Material A.

Characterization

The XRPD pattern of Compound 15 HCl salt Material A is shown in FIG. 25 and a complete XRPD peak list is presented in the Table below. The DSC thermogram is shown in FIG. 26 and displays two endothermic transitions at about 155° C. and 195° C. The TGA thermogram is shown in FIG. 27 and shows an approximately 35% weight loss between about 100° C. and 260° C.

| Complete XRPD peak list for Compound 15 HCl salt Material A | |
| --- | --- |
| Pos. [°2Th.] | Rel. Int. [%] |
| 4.0 | 100 |
| 8.0 | 1 |
| 10.6 | 4 |
| 12.2 | 5 |
| 13.5 | 5 |
| 15.0 | 12 |
| 15.7 | 12 |
| 16.3 | 18 |
| 17.6 | 12 |
| 18.7 | 9 |
| 20.4 | 8 |
| 23.4 | 17 |
| 25.8 | 9 |
| 26.7 | 7 |
| 27.7 | 11 |
| 29.5 | 3 |
| 31.5 | 8 |
| 33.5 | 4 |
| 37.1 | 2 |
| 38.0 | 2 |

Example 39: Compound 15 HCl Salt Material B

Compound 15 HCl salt Material B was first prepared by placing about 2 mg of Compound 15 HCl salt Form I (example 37) on a moisture balance and exposing it to humidity values ranging from 10% to 90% RH at 10% RH increments, at ambient temperature.

In another experiment, Compound 15 HCl salt Material B was prepared by suspending about 40 mg of Compound 15 HCl salt Form I (example 37) in about 0.4 mL of acetone and stirred at ambient conditions for about a day. The solids were isolated by centrifugation and dried in the vacuum oven at 40° C.

Characterization

The XRPD pattern of Compound HCl salt Material B is shown in 28 and a complete XRPD list is presented in the Table below. The DSC thermogram of Compound HCl salt Material B is shown in FIG. 29 and displays one endothermic transition at about 178° C. The TGA thermogram of Compound HCl salt Material B is shown in FIG. 30 and shows an approximately 1.2% and 28% weight loss between about 20° C. and 100° C. and between about 100° C. and 240° C., respectively.

| Complete XRPD peak list for Compound 15 HCl salt Material B | |
| --- | --- |
| Pos. [°2Th.] | Rel. Int. [%] |
| 4.3 | 100 |
| 7.1 | 52 |
| 12.8 | 8 |
| 13.5 | 34 |
| 14.3 | 45 |
| 14.6 | 36 |
| 15.9 | 72 |
| 16.8 | 26 |
| 18.7 | 58 |
| 19.5 | 38 |
| 21.0 | 16 |
| 22.8 | 13 |
| 25.7 | 48 |
| 26.6 | 44 |
| 27.0 | 48 |
| 30.6 | 14 |
| 33.2 | 8 |

Example 40: Compound 15 HCl Salt Material C

Compound 15 HCl salt Material C was prepared by suspending approximately 40 mg of HCl salt Form I (example 37) in about 0.4 mL of ethanol. The resulting slurry was stirred at ambient temperature for about a day. The solids were then isolated by centrifugation and dried in the vacuum oven at about 40° C.

Characterization

The XRPD pattern of Compound 15 HCl salt Material C is shown in FIG. 31 and a complete XRPD list is presented in the Table below. The DSC thermogram is shown in FIG. 32 and displays one endothermic transition at about 186° C. The TGA thermogram is shown in FIG. 33 and shows an approximately 30% weight loss between about 100° C. and 250° C.

| Complete XRPD peak list for Compound 15 HCl salt Material C | |
|---|---|
| Pos. [°2Th.] | Rel. Int. [%] |
| 4.3 | 100 |
| 7.1 | 3 |
| 12.8 | 19 |
| 14.4 | 3 |
| 14.7 | 11 |
| 15.9 | 6 |
| 16.6 | 8 |
| 17.3 | 77 |
| 18.6 | 32 |
| 19.5 | 9 |
| 20.7 | 21 |
| 21.0 | 8 |
| 22.8 | 19 |
| 23.9 | 8 |
| 24.9 | 34 |
| 27.0 | 4 |
| 27.2 | 16 |
| 27.6 | 6 |
| 28.1 | 4 |
| 30.0 | 7 |
| 30.6 | 4 |
| 31.4 | 25 |
| 32.4 | 4 |
| 33.3 | 5 |
| 33.6 | 4 |
| 35.1 | 48 |
| 36.1 | 9 |
| 38.1 | 5 |
| 39.0 | 3 |

Example 41: Alternate Synthesis Compound 15

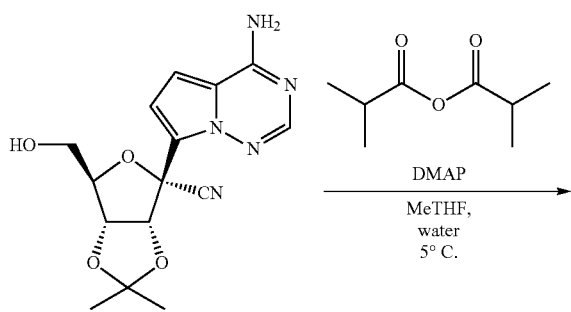

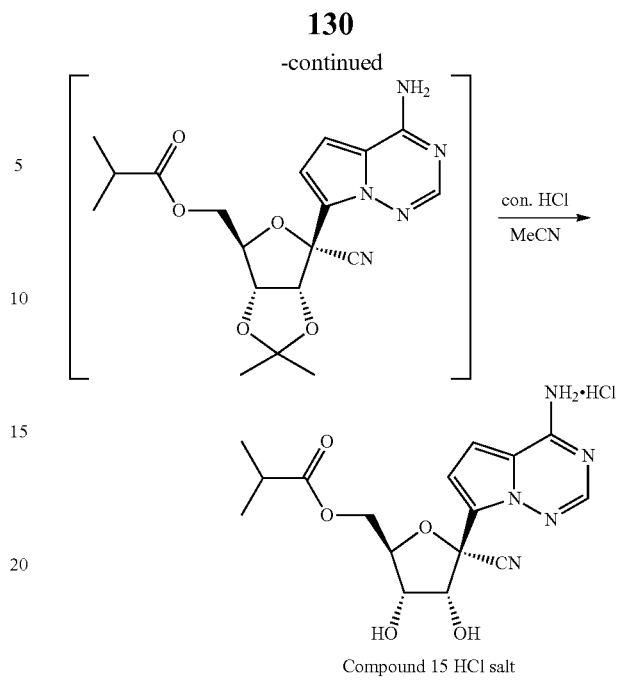

Compound 15 HCl salt

To a reactor was charged (3aR,4R,6R,6aR)-4-(4-aminopyrrolo[2,1-f][1,2,4]triazin-7-yl)-6-(hydroxymethyl)-2,2-dimethyltetrahydrofuro[3,4-d][1,3]dioxole-4-carbonitrile (1.00 equiv, scaling factor), 4-dimethylaminopyridine (0.03 equiv.), 2-methyltetrahydrofuran (10.0 volumes), and water (0.1 volumes). The internal temperature was adjusted to about 0° C. Isobutyric anhydride (1.2 equiv.) was charged slowly, keeping the internal temperature below about 5° C. The mixture was agitated at about 2° C. until the reaction was deemed complete. Methanol (3 equiv.) was then charged, and the internal temperature was adjusted to about 20° C. The mixture was agitated at about 20° C. for about 1 hour. 15% aqueous potassium bicarbonate (5.0 volumes) was charged, and the mixture was agitated for about 45 minutes. The aqueous layer was removed, and 15% aqueous potassium bicarbonate (5.0 volumes) was charged. The mixture was agitated for about 30 minutes, and the aqueous layer was removed. Water (5.0 volumes) was charged, and the mixture was agitated for about 15 minutes. The aqueous layer was then removed. The organic layer was heated to about 50° C., concentrated to a minimum volume, and co-distilled with acetonitrile to achieve removal of 2-methyltetrahydrofuran. Sufficient acetonitrile was charged to the reaction vessel to dilute the total volume to about 7 volumes, affording the intermediate acetonide as a solution in acetonitrile.

$^1$H NMR (400 MHz, Chloroform-d) δ 7.93 (s, 1H), 6.93 (d, J=4.7 Hz, 1H), 6.57 (d, J=4.7 Hz, 1H), 5.60 (br s, 2H), 5.41 (d, J=6.8 Hz, 1H), 4.85 (dd, J=6.8, 4.3 Hz, 1H), 4.56-4.48 (m, 1H), 4.35 (dd, J=12.0, 4.4 Hz, 1H), 4.21 (dd, J=12.0, 5.6 Hz, 1H), 2.56-2.41 (m, 1H), 1.70 (s, 3H), 1.34 (s, 3H), 1.12-1.04 (m, 6H).

$^{13}$C NMR (101 MHz, Chloroform-d) δ 176.70, 155.33, 147.36, 123.39, 117.22, 116.75, 115.65, 112.53, 99.98, 83.86, 82.98, 82.06, 81.40, 63.09, 33.82, 26.44, 25.56, 18.90.

Concentrated hydrochloric acid (3.0 equiv) was charged to the solution containing intermediate acetonide. The mixture was agitated at about 20° C. until the reaction was deemed complete, then cooled to about −5° C. and the resulting slurry filtered. The cake was washed with acetonitrile (1.5 volumes) and then dried to afford Compound 15 as an HCl salt.

$^1$H NMR (400 MHz, DMSO-$d_6$) δ 10.10 (br s, 1H), 9.31 (br s, 1H), 8.24 (s, 1H), 7.49 (d, J=4.6 Hz, 1H), 6.98 (d, J=4.7 Hz, 1H), 4.60 (d, J=4.8 Hz, 1H), 4.31-4.22 (m, 2H), 4.15 (dd, J=13.0, 5.8 Hz, 1H), 3.92 (dd, J=6.3, 4.8 Hz, 1H), 2.50-2.45 (m, 1H), 1.04 (d, J=7.0 Hz, 3H), 1.03 (d, J=7.0 Hz, 3H) ppm.

$^{13}$C NMR (101 MHz, DMSO) δ 175.9, 149.3, 137.4, 128.9, 116.4, 114.3, 112.2, 109.2, 81.8, 78.2, 75.0, 70.2, 62.9, 33.2, 18.8, 18.7 ppm.

Free-Basing of the HCl Salt of Compound 15

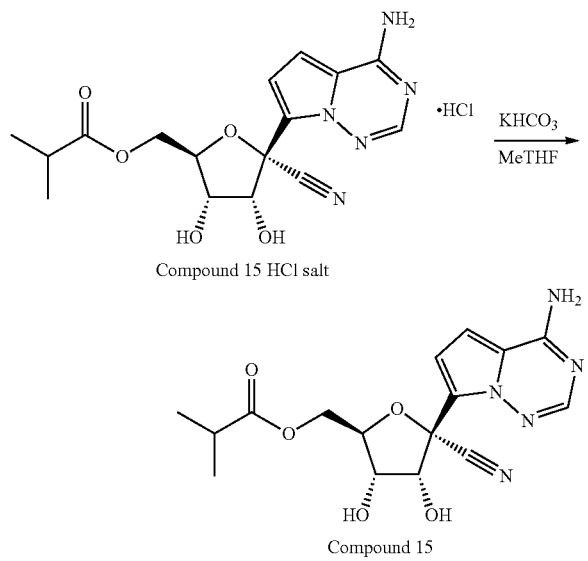

Compound 15 HCl salt

Compound 15

15 wt % aqueous potassium bicarbonate (7.0 volumes) was charged portion-wise to a reactor containing Compound 15 HCl salt (1.00 equiv, scaling factor) in 2-methyltetrahydrofuran (7.0 volumes). The mixture was agitated at about 20° C. until the reaction was deemed complete. The aqueous layer was removed, the organic layer washed with water (5.0 volumes), then heated to about 50° C. and concentrated to a minimum volume. Acetonitrile (7.0 volumes) was charged. The reactor was rinsed with acetonitrile (1.0 volumes). The combined filtrates were concentrated to about 3 volumes, then diluted with dichloromethane (4.0 volumes). The contents were adjusted to about 20° C., seeded with Compound 15, Form III (0.25 wt %), then adjusted to about −5° C. The slurry was filtered, the filter cake was washed with a cold solution of acetonitrile (1.0 volumes) and dichloromethane (1.0 volumes), then dried to afford Compound 15, Form III.

$^1$H NMR (400 MHz, DMSO-$d_6$) δ 7.94 (s, 1H), 7.92 (br s, 2H), 6.93 (d, J=4.6 Hz, 1H), 6.82 (d, J=4.5 Hz, 1H), 6.34 (d, J=6.0 Hz, 1H), 5.39 (d, J=5.8 Hz, 1H), 4.79-4.66 (m, 1H), 4.39-4.13 (m, 3H), 4.05-3.92 (m, 1H), 2.55-2.42 (m, 1H), 1.04 (d, J=7.0 Hz, 3H), 1.03 (d, J=7.0 Hz, 3H) ppm.

$^{13}$C NMR (101 MHz, DMSO) δ 175.9, 155.6, 147.9, 123.5, 116.9, 116.6, 110.2, 100.8, 81.3, 79.0, 74.0, 70.2, 62.9, 33.2, 18.7, 18.6.

Example 42: RSV Antiviral Assay (Hep2)

Compound Source and Destination (Assay) Plate Preparation

Compounds were prepared in 384 well compound dilution plates (Greiner LDV) according to HTBS standardized layouts with 8 compounds per plate in grouped replicates of 4 at 10 serially diluted concentrations (1:3). Alternatively, a 40 compound format could be used that contain single replicate dilutions with 8 dilution points. The top concentration was usually 10 or 20 mM in DMSO, which worked out to 50 or 100 uM respectively in this assay format. Some controls required lower starting concentrations (i.e., Pleconaril, BTA-798 and Rupintrivir at 10, 10 and 1 uM final assay concentrations respectively). Column 2 was the designated negative control and column 23 the positive control standards for each assay plate. For $EC_{50}$ assessments, a positive control was placed in column 23 and DMSO only in 1, 2 & 24. Column 2 generally served as the negative control for both assays. These prepared plates were sealed and stored at −20 until use.

$EC_{50}$-Hep2/B1-384

Hep2 cells ($5.0 \times 10^4$ cells/ml in MEM supplemented with Glutamine, 10% FBS and Pen/Strep) were prepared as above from harvested stock in batch to at least 40 mLs excess of the number of sample plates (8 mLs cell mix per plate) and infected with vendor supplied (ABI) RSV strain A2 to arrive at an MOI of 1:1000 (virus:cell #) or 1:1500 (vol virus: cell vol). Immediately after addition of virus, the RSV infected Hep2 cell suspension was added to each 384-well compound plate at 20 uL per well using a uFlow dispenser, or 1000 infected cells/well. It was useful to prime at least 5 mLs mix before dispensing to plates. Also, infectious mix was intermittently swirled to maintain consistent cell density. The plates were then incubated for 4 days at 37° C. and 5% $CO_2$.

Following incubation, 16 μL of Cell-Titer Glo viability reagent (Promega) was added to each well via uFlow. After a 15-20 minute 37° C. incubation, the plates were read using an EnVision (Perkin-Elmer) with a luminescence program for 384-well plates with 0.1 sec integration time. The data was then uploaded and analysed on the Bioinformatics portal under the RSV Cell Infectivity and 8-sample $EC_{50}$-Hep2-384 or 40-sample $EC_{50}$-Hep2-Envision protocols. Curves are fitted and $EC_{50}$ values were recorded. The results for exemplary compounds are summarized in Table 1.

$CC_{50}$-Hep2/B1-384

1. Hep2 cells ($5 \times 10^4$ cells/ml) are added to each prespotted test plate at 20 ul per well to give a total of 1000 cells/well. The plates are then incubated for 4 days at 37° C. and 5% $C_{02}$. Following incubation, the Cell-Titer Glo viability reagent (Promega) is prewarmed to 37 deg and 16 ul added to each well via uFlow. Following a 10-20 minute incubation at 37 deg, the plates are read using an EnVision using the luminescence readout procedure above. The data are then uploaded and analyzed on the Bioinformatics portal under the Cytotoxicity assays using the 8-plate CC50-Hep2 or 8-plate CC50-Hep2 Envision protocols.

Example 43: SARS-CoV-2 Antiviral Assay $1.2 \times 10^4$ A549-hACE2 cells in 50 μL phenol red-free DMEM medium supplemented with 2% FBS were seeded in each well of a white opaque 96-well plate (Corning, Cat #3916). On the next day, 2-fold serial dilutions of compounds were prepared in DMSO. The compounds were further diluted as 100 folds in the 2% FBS culture medium. Cell culture fluids were removed and incubated with 50 μL diluted compound solutions and 50 μL of SARS-CoV2-Nano viruses (MOI 0.025). At 48 h post-infection, 50 μL Nano luciferase substrates (Promega, Cat #N1150) were added to each well. Luciferase signals were measured using a Synergy™ Neo2 Multi-Mode microplate reader (BioTek). The relative luciferase signals were calculated by normalizing the luciferase signals of the compound-treated groups to that of the DMSO-treated groups (expressed in percentages). The relative luciferase signals (Y axis) to the log 10 values of compound concentration (X axis) were plotted in the software GraphPad Prism 8. The $EC_{50}$ (compound concentration for reducing 50% of luciferase signals) were calculated using a nonlinear regression model (four parameters). The values (µM) of exemplary compounds are shown in Table 1 below.

Alternatively, A549-hACE2 cells (12,000 cells per well in medium containing 2% FBS) were plated into a white clear-bottomed 96-well plate (Corning) at a volume of 50 µL. On the next day, compounds were added directly to cultures as 3-fold serial dilutions with a Tecan D300e digital liquid dispenser, with DMSO volumes normalized to that of the highest compound concentration (final DMSO concentration <0.1%). To the diluted compound solutions, 50 µL of SARS-CoV-2-Nluc viruses (MOI 0.025 pfu/cell), expressing a nano luciferase reporter protein, were added. At 48 h post-infection, 75 µL Nano luciferase substrate solution (Promega) was added to each well. Luciferase signals were measured using an Envision microplate reader (Perkin Elmer). The relative luciferase signals were calculated by normalizing the luciferase signals of the compound-treated groups to that of the DMSO-treated groups (set as 100%). $EC_{50}$ values (Table 1) were calculated using a nonlinear four parameter variable slope regression model.

Example 44: A549-hACE2 $CC_{50}$ Assay

The cytotoxicity of compounds was determined in A549-hACE2 cells in the following manner. Compounds (200 nL) were spotted onto 384-well Grenier plates prior to seeding 5000 A549-hACE2 cells/well in a volume of 40 µL culture medium. The plates were incubated at 37° C. for 48 hours with 5% $CO_2$. On day 2, 40 µL of CellTiter-Glo (Promega) was added and mixed 5 times. Plates were read for luminescence on an Envision (PerkinElmer) and the $CC_{50}$ (compound concentration for reducing 50% of luminescence signal as a measure of cell viability) were calculated using a nonlinear regression model (four parameters) and are shown in Table 1 below.

Example 45: RSV Antiviral Assay (NHBE)

Normal human brochial epithelial (NHBE) cells were purchased from Lonza (Walkersville, MD Cat #CC-2540) and maintained in Bronchial Epithelial Cell Growth Medium (BEGM) (Lonza, Walkersville, MD, Cat #CC-3170) with all provided supplements in the BulletKit. Cells were passaged 2-3 times per week to maintain sub-confluent densities and were used for experiments at passages 2-4.

Recombinant Respiratory Syncytial virus strain A2 containing the firefly luciferase reporter between the P and M genes (RSV-Fluc, $6.3 \times 10^6$ TCID50/mL) was purchased from Viratree (Durham, NC, Cat #R145).

NHBE cells ($5 \times 10^3$/well) were seeded in 100 µL white wall/clear bottom 96-well plates (Corning) with culture medium and incubated for 24 hours at 37° C. with 5% $CO_2$. On the following day, three-fold serial dilutions (starting at 5 µM and ending at 0.002 µM) of compounds prepared in DMSO were added to the wells using the HP D300e digital dispenser with normalization to the highest concentration of DMSO in all wells (>0.1% final volume). The cells were then infected with RSV-Fluc diluted with BEGM media at an MOI of 0.1 for a final volume of 200 µl media/well. Uninfected and untreated wells were included as controls to determine compound efficacy against RSV-Fluc. Following incubation with compound and virus for three days at 37° C. with 5% $CO_2$, 100 µL of culture supernatant was removed from each well and replaced with 100 µL of ONE-Glo luciferase reagent (Promega, Madison, WI, Cat #E6110). The plates were gently mixed by rocking for 10 minutes at 25° C. and luminescence signal was measured using an Envision plate reader (PerkinElmer). Values were normalized to the uninfected and infected DMSO controls (0% and 100% infection, respectively). Non-linear regression analysis was applied to determine the compound concentration at which 50% luminescence signal was reduced ($EC_{50}$) using the XLfit4 add-in for Microsoft®; Excel®. All experiments were performed in duplicate with two technical repeats each. Data from these experiments is presented in Table 2 below.

TABLE 1

Antiviral activity of exemplary compounds

| Compound | RSV $EC_{50}$ Hep2-384 (nM) | SARS-CoV2 $EC_{50}$ (µM) | A549-hACE2 $CC_{50}$ (µM) |
| --- | --- | --- | --- |
| 1 | 261.0 | 2.7 | >50 |
| 2 | 536.9 | 1.9 | >50 |
| 3 | 425.3 | 3.1 | >100 |
| 4 | 26302.5 | >10 | >100 |
| 5 | 13123.6 | >10 | >100 |
| 6 | 23648.5 | >10 | >71.2 |
| 7 | 859.4 | 3.1 | >50 |
| 8 | 904.1 | 2.7 | >100 |
| 9 | 797.8 | 2.4 | >50 |
| 10 | 1201.0 | 2.2 | >100 |
| 11 | 386.7 | 2.6 | >100 |
| 12 | 420.2 | 3.3 | >50 |
| 13 | 506.0 | 1.3 | >50 |
| 14 | 825.4 | 2.7 | >50 |
| 15 | 407.0 | 1.03 | >50 |
| 16 | 216.4 | 1.22 | >10 |
| 17 | 213.0 | 0.79 | >10 |
| 18 | 172.4 | 0.94 | >10 |
| 19 | 238.1 | 1.45 | >10 |
| 20 | 271.8 | 0.61 | >10 |
| 21 | 2280.4 | 11.4 | >10 |
| 22 | 217.8 | 0.85 | >10 |
| 23 | 197.1 | 1.09 | >10 |
| 24 | 184.6 | 0.80 | >10 |
| 25 | 224.5 | 1.22 | >10 |
| 26 | 337.1 | 1.19 | >10 |
| 27 | 243.3 | 0.56 | >10 |
| 28 | 268.2 | 0.43 | 40 |
| 29 | 193.7 | 0.30 | 38 |
| 30 | 642.6 | 2.32 | >50 |
| 31 | 198.0 | 0.32 | 24 |
| 32 | 589.5 | 2.32 | >50 |

TABLE 2

RSV NHBE antiviral activity of exemplary compounds

| Compound | RSV NHBE $EC_{50}$ (nM) |
|---|---|
| Reference Compound A | 1970 |

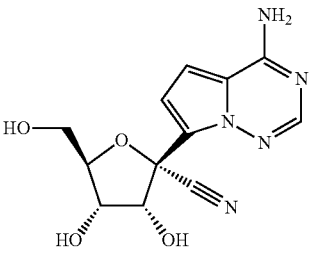

| | |
|---|---|
| 1 | 389 |
| 2 | 287 |
| 3 | 831 |
| 8 | >5000 |
| 11 | 301 |
| 12 | 169 |
| 15 | 588 |
| 16 | 575 |
| 17 | 1181 |
| 18 | 224 |
| 19 | 261 |
| 20 | 841 |
| 21 | 1852 |
| 22 | 790 |
| 23 | 249 |
| 24 | 801 |
| 25 | 601 |
| 26 | 1085 |
| 27 | 1486 |
| 28 | 1798 |
| 29 | 2644 |
| 30 | 2373 |
| 31 | 2742 |
| 32 | 581 | concentration with blood added) and processed to plasma at 6 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference compound A and either Compound 1 or Compound 15 in plasma. Data for Reference Compound A following oral administration of Compound A, Compound 1 or Compound 15 is tabulated below.

Reference Compound A

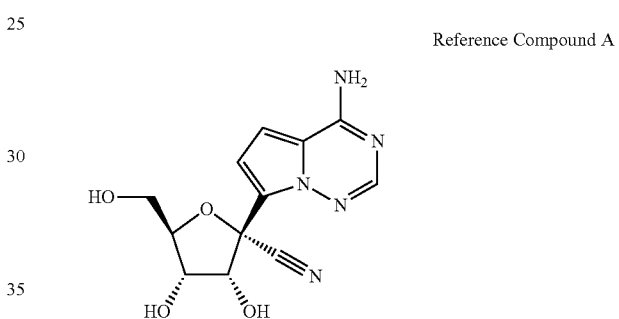

| Compound | Oral Dose mg/kg | Oral Dose (mg-eq Compound A)/ kg | Reference Compound A $C_{max}$ (nM) | Reference Compound A $AUC_{inf.}$ (nM · h) | Reference Compound A F %[a] | Reference Compound A F %[b] |
|---|---|---|---|---|---|---|
| Reference Compound A | 5 | — | 536 | 1861 | — | 3.4 |
| Compound 1 | 20 | 11.6 | 5110 | 19780 | 16 | 28 |
| Compound 1 | repeat | repeat | 7830 | 34300 | 28 | 48 |
| Compound 15 | 11.7 | 9.4 | 7570 | 21800 | 30 | 38 |

[a]Based on prodrug dose including salt,
[b]based on compound A mg-eq dose.

Example 46: Monkey Pharmacokinetics Assay

Reference Compound A, Compound 1 and Compound 15 were dosed orally by gavage to male cynomolgus monkeys (n=3/group); Compound A at 5 mg/kg in 5% Ethanol; 30% Propylene glycol, 45% Polyethylene glycol 400, and 20% water+1 equiv. HCl; Compound 1 at 20 mg/kg in 10% Ethanol; 40% Kolliphor HS-15; 40% Labrasol; 10% Propylene glycol; Compound 1 at 20 mg/kg (repeat study) in 2.5% DMSO; 10% Kolliphor HS-15; 10% Labrasol; 2.5% Propylene glycol and 75% water, pH 2.1; Compound 15 at 11.7 mg/kg in 2.5% DMSO; 10% Kolliphor HS-15; 10% Labrasol; 2.5% Propylene glycol and 75% water, pH 2.9. Blood samples were collected into pre-chilled collection tubes containing $K_2EDTA$ with dichlorvos (2 mM final

Example 47: Dog Pharmacokinetics Assay

Reference Compound A, Compound 1 and Compound 15 were dosed orally by gavage to male beagle dogs (n=3/group); Compound A at 5 mg/kg in 5% Ethanol; 30% Propylene glycol, 45% Polyethylene glycol 400, and 20% water+1 equiv. HCl; Compound 1 at 20 mg/kg in 2.5% DMSO; 10% Kolliphor HS-15; 10% Labrasol; 2.5% Propylene glycol and 75% water, pH 2; Compound 15 at 14.4 mg/kg in 0.5% DMSO; 2% Kolliphor HS-15; 2% Labrasol; 0.5% Propylene glycol and 95% water, pH 2.5. Blood samples were collected into pre-chilled collection tubes containing $K_2EDTA$ with dichlorvos (2 mM final concentration with blood added) and processed to plasma at 6 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference compound A and either Compound 1 or Compound 15 in plasma. Data for Reference Compound A following oral administration of Compound A, Compound 1 or Compound 15 is tabulated below.

| Compound | Oral Dose mg/kg | Oral Dose (mg-eq Compound A)/kg | Reference Compound A $C_{max}$ (nM) | Reference Compound A $AUC_{inf.}$ (nM · h) | Reference Compound A F %[a] | Reference Compound A F %[b] |
| --- | --- | --- | --- | --- | --- | --- |
| Reference Compound A | 5 | — | 27300 | 83900 | — | 89 |
| Compound 1 | 20 | 11.6 | 35200 | 147000 | 40 | 68 |
| Compound 15 | 14.4 | 11.6 | 57800 | 204000 | 76 | 94 |

[a]Based on prodrug dose including salt,
[b]based on compound A mg-eq dose.

Example 48: Rat Pharmacokinetics Assay

Reference Compound A, Compound 1 and Compound 15 were dosed orally by gavage to male Sprague-Dawley rats (n=3/group); Compound A (Study 1) at 10 mg/kg in 5% Ethanol; 55% Polyethylene glycol 400 and 40% water+1 equiv HCl, pH 3.4; (Study 2) at 5 mg/kg in 5% Ethanol; 30% Propylene glycol; 45% Polyethylene glycol 400 and 20% water+1 equiv HCl; (Study 3) at 5 mg/kg in 2.5% Dimethyl sulfoxide; 10% Kolliphor HS-15; 10% Labrasol; 2.5% Propylene glycol and 75% water, pH 2.0; Compound 1 at 8 mg/kg in 2.5% Dimethyl sulfoxide; 10% Kolliphor HS-15; 10% Labrasol; 2.5% Propylene glycol and 75% water, pH 7; Compound 15 at 6 mg/kg in 2.5% Dimethyl sulfoxide; 10% Kolliphor HS-15; 10% Labrasol; 2.5% Propylene glycol and 75% water, pH 2.5. Blood samples were collected into pre-chilled collection tubes containing K₂EDTA and processed to plasma at 6 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference compound A and either Compound 1 or Compound 15 in plasma. Data for Reference Compound A following oral administration of Compound A, Compound 1 or Compound 15 is tabulated below.

| Compound | Oral Dose mg/kg | Oral Dose (mg-eq Compound A)/kg | Reference Compound A $C_{max}$ (nM) | Reference Compound A $AUC_{inf.}$ (nM · h) | Reference Compound A F %[a] | Reference Compound A F %[b] |
| --- | --- | --- | --- | --- | --- | --- |
| Reference Compound A | 10 | — | 578 | 2361 | — | 21.6[d] |
| Reference Compound A | 5 | — | 875 | 3072 | — | 11.9[e] |
| Reference Compound A | 5 | — | 1340 | 4980 | — | 39.6[f] |
| Compound 1[c] | 8 | 4.7 | 5830 | 13400 | 67.0[f] | 117[f] |
| Compound 15 | 6 | 4.8 | 2100 | 7670 | 51.1[f] | 63.9[f] |

[a]Based on prodrug dose including salt;
[b]based on compound A mg-eq dose;
[c]as mono-TFA salt;
[d]using IV data from 2 mg/kg dose;
[e]using IV data from independent 1 mg/kg dose;
[f]using IV data from independent 1 mg/kg dose.

β-d-N⁴-hydroxy cytidine (NHC) was dosed orally by gavage to male Sprague-Dawley rats (n=3) at 10 mg/kg in 3.9% citric acid and 96.1% water, pH 2.8; Molnupiravir at 12.7 mg/kg in 2.5% kolliphor RH 40, 10% polyethylene glycol 300 and 87.5% water, pH 5.3. Blood samples were collected into pre-chilled collection tubes containing K₂EDTA and processed to plasma at 6 timepoints over a span of pre-dose to 24 h post-administration. Plasma samples were subject to protein precipitation with a 5-fold volume of 4:1 acetonitrile:water mixture, vortexed and centrifuged. Supernatants were transferred, filtered and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the NHC and Molnupiravir in plasma. Data for NHC following oral administration of NHC or Molnupiravir is tabulated below.

| Compound | Oral Dose mg/kg | Oral Dose (mg-eq NHC)/kg | NHC $C_{max}$ (nM) | NHC $AUC_{inf}$ (nM · h) | NHC F %[a] | NHC F %[b] |
|---|---|---|---|---|---|---|
| NHC | 10 | — | 3130 | 8480 | — | 37.0 |
| Molnupiravir | 12.7 | 10 | 4090 | 8960 | 30.8 | 39.1 |

[a]Based on molnupiravir dose,
[b]based on NHC mg-eq dose.

Example 49: Ferret Pharmacokinetics Assay

Reference Compound A, Compound 1 and Compound 15 were dosed orally by gavage to female ferrets (n=2 for Compound A; n=3/group for Compound 1 and Compound 15); Compound A at 20 mg/kg in 5% Ethanol; 30% Propylene glycol, 45% Polyethylene glycol 400, and 20% water pH 2; Compound 1 at 30 mg/kg in 2.5% DMSO; 10% Kolliphor HS-15; 10% Labrasol; 2.5% Propylene glycol and 75% water, pH 2; Compound 15 at 30 mg/kg in 2.5% DMSO; 10% Kolliphor HS-15; 10% Labrasol; 2.5% Propylene glycol and 75% water, pH 2.9. Blood samples were collected into pre-chilled collection tubes containing $K_2EDTA$ with dichlorvos (2 mM final concentration with blood added) and processed to plasma at 6 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference compound A and either Compound 1 or Compound 15 in plasma Data for Reference Compound A following oral administration of Compound A, Compound 1 or Compound 15 is tabulated below.

| Compound | Oral Dose mg/kg | Oral Dose (mg-eq Compound A)/kg | Reference Compound A $C_{max}$ (nM) | Reference Compound A $AUC_{inf}$ (nM · h) | Reference Compound A F %[a] | Reference Compound A F %[b] |
|---|---|---|---|---|---|---|
| Reference Compound A | 20 | — | 11700 | 70900 | — | 87 |
| Compound 1 | 30 | 17.4 | 15800 | 81100 | 66 | 114 |
| Compound 15 | 30 | 24.2 | 27000 | 152000 | 124 | 154 |

[a]Based on prodrug dose including salt,
[b]based on Reference Compound A mg-eq dose.

Example 50: Mouse Pharmacokinetics Assay

Reference Compound A, Compound 1 and Compound 15 were dosed orally by gavage to male Balb/c mice (n=4 per timepoint); Compound A at 24 mg/kg in 2.5% Dimethyl sulfoxide; 10% Kolliphor HS-15; 10% Labrasol; 2.5% Propylene glycol; 75% Water; pH 2.17; Compound 1 at 20 mg/kg in 2.5% Dimethyl sulfoxide; 10% Kolliphor HS-15; 10% Labrasol; 2.5% Propylene glycol; 75% Water; pH 7.5; Compound 15 at 30 mg/kg in 2.5% Dimethyl sulfoxide; 10% Kolliphor HS-15; 10% Labrasol; 2.5% Propylene glycol; 75% Water; pH 2.8. Blood samples were collected into pre-chilled collection tubes containing $K_2EDTA$ and processed to plasma at 5 timepoints over a span of pre-dose to 24 h post-administration. Plasma samples were subject to protein precipitation with a 12.5-fold volume of methanol, vortexed and centrifuged. Supernatants were transferred and evaporated to dryness under nitrogen and reconstituted with 5% acetonitrile in water. Separation was achieved on a Phenomenex Synergi Polar-RP column, a mobile phase A of 10 mM ammonium formate with 0.1% formic acid in water and a mobile phase B of 0.1% formic acid in acetonitrile with a step-wise linear gradient from 5 to 95% mobile phase B. An LC-MS/MS method was used to measure the concentrations of the Reference compound A and either Compound 1 or Compound 15 in plasma. Data for Reference Compound A following oral administration of Compound A, Compound 1 or Compound 15 is tabulated below.

| Compound | Oral Dose mg/kg | Oral Dose (mg-eq Compound A)/kg | Reference Compound A $C_{max}$ (nM) | Reference Compound A $AUC_{inf}$ (nM · h) | Reference Compound A F %[a] | Reference Compound A F %[b] |
|---|---|---|---|---|---|---|
| Reference Compound A | 24 | — | 13700 | 45100 | — | 33 |

-continued

| Compound | Oral Dose mg/kg | Oral Dose (mg-eq Compound A)/ kg | Reference Compound A $C_{max}$ (nM) | Reference Compound A $AUC_{inf.}$ (nM · h) | Reference Compound A F %[a] | Reference Compound A F %[b] |
|---|---|---|---|---|---|---|
| Compound 1 | 20 | 11.6 | 8850 | 31700 | 28 | 49 |
| Compound 15 | 30 | 24.2 | 22700 | 55200 | 33 | 41 |

[a]Based on prodrug dose including salt,
[b]based on compound A mg-eq dose.

Example 51: Ferret Efficacy Studies on Compound 1

Materials and Methods
Cells and Viruses

African green monkey kidney cells VeroE6 (ATCC®, cat #CRL-1586™), human lung adenocarcinoma epithelial cells Calu-3 (ATCC® HTB-55™), human epithelial/HeLa contaminant HEp-2 cells (ATCC®, cat #CCL-23™), baby hamster kidney cells BHK-21 (ATCC®, cat #CCL-10™) were cultivated in a humidified chamber at 37° C. and 5% $CO_2$ in Dulbecco's Modified Eagle's medium (DMEM) (Corning, cat #10-013-CV, lot #05721000) supplemented with 7.5% (10% for Calu-3) heat-inactivated fetal bovine serum (FBS) (Corning, cat #35-010-CV, lot #14020001). Human epithelial colon adenocarcinoma HCT-8 cells (ATCC® cat #CCL-244™ lot #70036111) were cultivated at 37° C. and 5% $CO_2$ in Roswell Park Memorial Institute (RPMI) medium (Quality biological, cat #112-024-101, lot #723411) supplemented with 2 mM L-glutamine (Gibco, cat #23030-081) and 10% heat-inactivated FBS.

A549-hACE2 cells that stably express human angiotensin-converting enzyme 2 (hACE2) were grown in the culture medium supplemented with 10 µg/mL Blasticidin S. Primary human airway epithelial (HAE) cells from multiple donors were cultivated at 37° C. and 5% $CO_2$ in Bronchial Epithelial Cell Growth Medium (BEGM) BulletKit following the provider's instructions (Lonza, cat #CC-3171 lot #0000889952 with supplement cat #CC-4175 lot #0000848033). Human Bronchial Tracheal Epithelial cells (HBTEC) were derived from the following donors: "F2" from a 29-year old Caucasian female (Lifeline, cat #FC-0035, lot #5101); "F3" from a 42-year old Caucasian female (Lonza, cat #CC-2540S, lot #0000519670); "M2" from a 40-year old Caucasian male (Lonza, cat #CC-25405, lot #0000667744); and "M6" from a 48-year old Caucasian male (Lonza, cat #CC-25405, lot #0000544414). Diseased (Asthma) Human Bronchial Epithelial (DHBE) cells "DF2" were from a 55-year old Caucasian female (Lonza, cat #001949115, lot #0000534647). Primary HAE were used for cytotoxicity assays at passage 53. Cell lines were routinely checked for *mycoplasma* and bacterial contamination. SARS-CoV-2 strains were propagated using Calu-3 cells supplemented with 2% FBS in accordance with approved biosafety level 3 protocols. Virus stocks were stored at −80° C. Stock virus titers were determined by plaque assay.

Plaque Assays

Vero E6 cells were seeded in 12-well plates at 3×10⁵ cells per well. The following day, samples were serially diluted in DMEM containing Antibiotic-Antimycotic (Gibco) supplemented with 2% FBS. Dilutions were then added to cells and incubated for 1 hour at 37° C. Cells were subsequently overlayed with 1.2% Avicel 581-NF (FMC BioPolymer) in DMEM containing Antibiotic-Antimycotic (Gibco) and allowed to incubate for 3 days at 37° C. with 5% $CO_2$. After 3 days, the overlay was removed, cells were washed once with phosphate buffered saline (PBS) and fixed with neutral buffered formalin (10%) for 15 minutes. Plaques were then visualized using 1% crystal violet.

Cytotoxicity Assays 7,500 cells were seeded in each well of 96-well plates (Corning, cat #3598). Cells were incubated with 3-fold serial dilutions of compound from a 100 µM maximum concentration. Each plate included 4 wells of positive (100 µM cycloheximide (Millipore Sigma, cat #C7698-5G)) and negative (vehicle (0.2% dimethyl sulfoxide (DMSO))) controls for normalization. Plates were incubated in a humidified chamber at 37° C. and 5% $CO_2$ for 72 hours. Presto-Blue™ Cell Viability Reagent (ThermoFisher Scientific, cat #A13262) was added in each well (10 µl/well) and fluorescence recorded on a Synergy H1 multimode microplate reader (BioTek) after 1-hour incubation (excitation 560 nm, emission 590 nm). Raw data was normalized with the formula: % cell viability=100×(signal sample−signal positive control)/(signal negative control−signal positive control). 50% cytotoxic concentrations ($CC_{50}$) and 95% confidence intervals after non-linear regression were determined using the inhibitor vs normalized response equation in Prism 9.1.0 for MacOS (GraphPad).

Virus Yield Reduction

2×10⁵ VeroE6 cells were seeded per well in 12-well plates 16 hours before infection. Confluent monolayers were then infected with the indicated virus at a multiplicity of infection (MOI) of 0.1 pfu/cell for 1 hour at 37° C. with frequent rocking. Inoculum was removed and replaced with 1 mL of DMEM with 2% FBS and the indicated concentration of compound. Cells were incubated at 37° C. and 5% $CO_2$ for 48 hours. Supernatant were harvested, aliquoted and stored at −80° C. before being analyzed by plaque assay.

Ferret Efficacy Studies

Female ferrets (6-10 months old, *Mustela putorius furo*) were purchased from Triple F Farms. Ferrets were rested for 7 days after arrival. Ferrets were then housed individually or in groups of 2 in ventilated negative-pressure cages in an ABSL-3 facility. Based on previous experiments[6], ferrets were randomly assigned to groups (n=4) and used as an in vivo model to examine the efficacy of orally administered compounds against SARS-CoV-2 infection. No blinding of investigators was performed. Ferrets were anesthetized using dexmedetomidine/ketamine and infected intranasally with 1×10⁵ pfu 2019-nCoV/USA-WA1/2020 in 1 mL (0.5 mL per nare). Body weight and temperature were measured once daily. Nasal lavages were performed twice daily using 1 mL sterile PBS (containing Antibiotic-Antimycotic (Gibco). Nasal lavage samples were stored at −80° C. until virus titration could be performed by plaque assay. Treatment (once daily (q.d.) or twice daily (b.i.d.)) was initiated at either 0 or 12 hours after infection and continued until 4 days post infection with either vehicle (2.5% dimethyl sulfoxide; 10% Kolliphor HS-15; 10% Labrasol; 2.5% propylene glycol; 75% water) or compound. Four days after infection, ferrets were euthanized, and tissues and organs were harvested and stored at −80° C. until processed.

Contact Transmission in Ferrets

Eight ferrets were anesthetized and inoculated intranasally with 1×10^5 pfu of hCoV-19/Japan/TY7-503/2021. Twelve hours after infection, ferrets were split into two groups (n=4; 2 ferrets per cage) and treated with vehicle or Compound 1 (10 mg kg-1) twice daily (b.i.d.) via oral gavage. At 54 hours after infection, uninfected and untreated contact ferrets (two contacts for Compound 1; three contacts for vehicle) were cohoused with source ferrets. Cohousing was continued until 96 hours after infection and source ferrets were euthanized. Contact ferrets were housed individually and monitored for an additional 4 days after separation from source ferrets and subsequently euthanized. Nasal lavages were performed on all source ferrets every 12 hours and all contact ferrets every 24 hours. For all ferrets, nasal turbinates and lung tissues were harvested to determine viral titers and the detection of viral RNA.

SARS-CoV-2 Titration in Tissue Extracts

Selected tissues were weighed and mechanically homogenized in sterile PBS. Homogenates were clarified by centrifugation (2,000×g) for 5 minutes at 4° C. Clarified homogenates were then serially diluted and used in plaque assays to determine virus titer.

Quantitation of SARS-CoV-2 RNA Copy Numbers

To probe viral RNA in selected tissues, samples were harvested and stored in RNAlater at −80° C. Total RNA from tissues was isolated using a RNeasy mini kit (Qiagen), in accordance with the manufacturer's protocol. For nasal lavage samples, total RNA was extracted using a ZR viral RNA kit (Zymo Research) in accordance with the manufacturer's protocol. SARS-CoV-2 RNA was detected as previously described[6] using the nCoV_IP2 primer-probe set (National Reference Center for Respiratory Viruses, Pasteur Institute). An Applied Biosystems 7500 using the StepOne-Plus real-time PCR system was used to perform RT-qPCR reactions. The nCoV_IP2 primer-probe set was using in combination with TaqMan fast virus 1-step master mix (Thermo Fisher Scientific) to detect viral RNA. SARS-CoV-2 RNA copy numbers were calculated using a standard curve created from serial dilutions of a PCR fragment (12669-14146 nt of the SARS-CoV-2 genome), as previously described (Nat Microbiol 6, 11-18, doi:10.1038/s41564-020-00835-2 (2021)). For RNA copies in tissue samples, RNA copies were normalized to the weights of the tissues used.

Next Generation Sequencing

To authenticate virus stocks, metagenomic sequencing was performed as described[37,38]. Viral RNA was treated with Turbo DNase I (Thermo Fisher). cDNA was generated from random hexamers using SuperScript III reverse transcriptase, second strand was generated using Sequenase 2.0, and cleaned using 0.8×Ampure XP beads purification on a SciClone IQ (Perkin Elmer). Sequencing libraries were generated using two-fifths volumes of Nextera XT on ds-cDNA with 18 cycles of PCR amplification. Libraries were cleaned using 0.8×Ampure XP beads and pooled equimolarly before sequencing on an Illumina NovaSeq (1×100 bp run). Raw fastq reads were trimmed using cutadapt (-q 20) (Martin). To interrogate potential resistance alleles, reference-based mapping to NC_045512.2 was carried out using our modified Longitudinal Analysis of Viral Alleles (LAVA—https://github.com/michellejlin/lava)[39] pipeline. LAVA constructs a candidate reference genome from early passage virus using bwa[40], removes PCR duplicates with Picard, calls variants with VarScan[41,42], and converts these changes into amino acid changes with Annovar (Nucleic Acids Res. 38, e164, doi:10.1093/nar/gkg603 (2010). Genome sequences repository IDs are as follows: input strain WA1/2020, aa; WA1/2020 recovered from ferrets, bb-cc; input strain BZ/2021, dd; BZ/2021 recovered from source ferrets, ee-ff; BZ/2021 recovered from contacts of vehicle-treated source ferrets, gg-hh.

Ethics Statement

All in vivo efficacy studies were conducted at Georgia State University in compliance with the Animal Welfare Act Code of Federal Regulations and the Guide for the Care and Use of Laboratory Animals of the National Institutes of Health. All studies involving SARS-CoV-2 infected ferrets were approved by the Georgia State Institutional Animal Care and Use Committee under protocol A20031. Experiments using infectious SARS-CoV-2 were performed in BSL-3/ABSL-3 facilities at Georgia State University and approved by the Georgia State Institutional Biosafety Committee under protocol B20016.

Statistics and Reproducibility

The Microsoft Excel (version 16.48), GraphPad Prism (version 9.1.0), and Numbers (version 10.1) software packages were used for data collection and analysis. One-way or two-way ANOVA with Dunnett's or Tukey's multiple comparisons post-hoc test were used to evaluate statistical significance when comparing more than two groups or two independent variables. When comparing two variables, a two-tailed unpaired t-test was performed to determine statistical significance. The specific statistical test used to individual studies is specified in the figure legends. RT-qPCR data were collected and analyzed using the StepOne-Plus (version 2.1; Applied Biosystems) software package. Final figures were assembled in Adobe Illustrator (version CS6). The Source Data file provides the summaries of individual statistical analyses used in each dataset. Effect sizes between groups in the ANOVAs were calculated as $\eta^2(SS_{effect})/(SS_{total})$ for one-way ANOVA and $\omega^2=(SS_{effect}-(df_{effect})(MS_{error}))/MS_{error}+SS_{total}$ for two-way ANOVA ($SS_{effect}$, sum of squares for the effect; $SS_{total}$, sum of squares for total; $df_{effect}$, degrees of freedom for the effect; $MS_{error}$, mean squared error). The statistical significance level a was set to <0.05 for all experiments. Exact P values are shown in the individual graphs.

Results

Oral PK Properties and Antiviral Potency of Compound 1

Assessment of Compound 1 PK parameters in the ferret efficacy model has revealed excellent oral bioavailability (FIG. 1a, Table 3), distribution to soft tissues including lung, and efficient anabolism to bioactive Reference Compound B (Table 4). After oral administration of Compound 1, essentially only the Reference Compound A metabolite appeared in the blood (Table 3), indicating near-quantitative conversion during intestinal absorption.

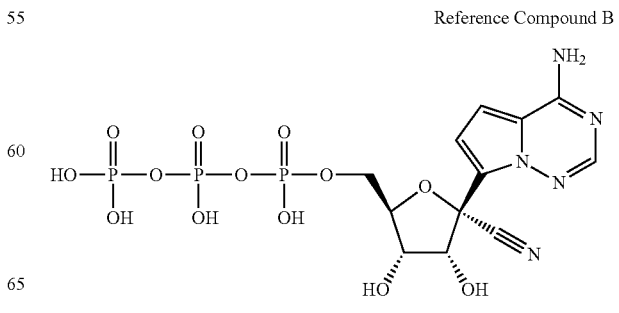

Reference Compound B

TABLE 3

Single dose pharmacokinetic parameters of Reference Compound A following administration of either intravenous Reference Compound A or remdesivir or oral Compound 1 in ferrets.

| Compound | Route | Dose [mg/kg] | $t_{1/2}$ [hours] PO-$T_{max}$ [hours] | IV-CL [L/hours/kg] | $C_{max}$ [μM] | $AUC_{last}$ [μM · h] | F [%] |
|---|---|---|---|---|---|---|---|
| Reference Compound A | i.v. | 20 | 3.4 | 0.86 | 54.2 | 81.1 | n/a |
| remdesivir | i.v. | 10 | 6.09 | n/a | 2.81 | 18.2 | n/a |
| Compound 1[a] | p.o. | 30 | 2.68 ± 0.15 | 4.0 ± 3.5 | 15.8 ± 4.7 | 80.8 ± 14.6 | 111 |

[a]approximately 10 nM Compound 1 transiently observed in first two hours.

TABLE 4

Reference Compound A and its metabolites concentrations in ferret lung tissue.

| Compound | Route | Dose | Lung Reference Compound B [nmol/g] | Lung total nuc [nmol/g] |
|---|---|---|---|---|
| Reference Compound A | i.v. | 20 mg kg$^{-1}$ | 0.53 ± 0.10 | 0.66 ± 0.21 |
| Remdesivir | i.v. | 10 mg kg$^{-1}$ | 1.28[a] | 2.96 |
| Compound 1 | p.o. | 30 mg kg$^{-1}$ | 0.30 ± 0.19 | 0.88 ± 0.13 |

[a]one lung from remdesivir i.v. dosing was BLQ for all metabolites.

Figure 1B:
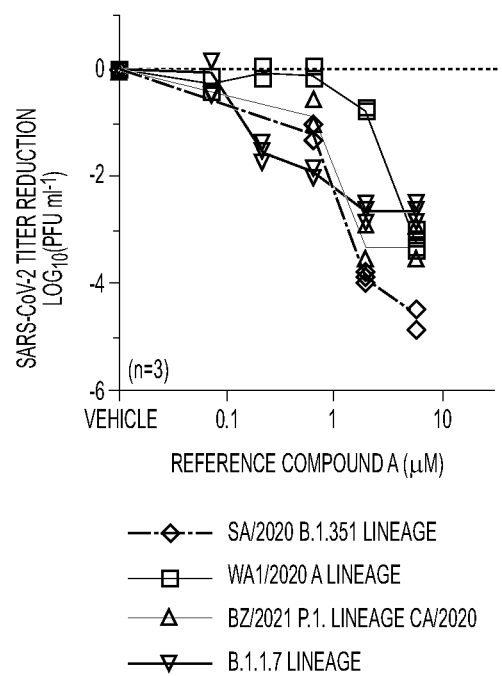
Figure 1E:
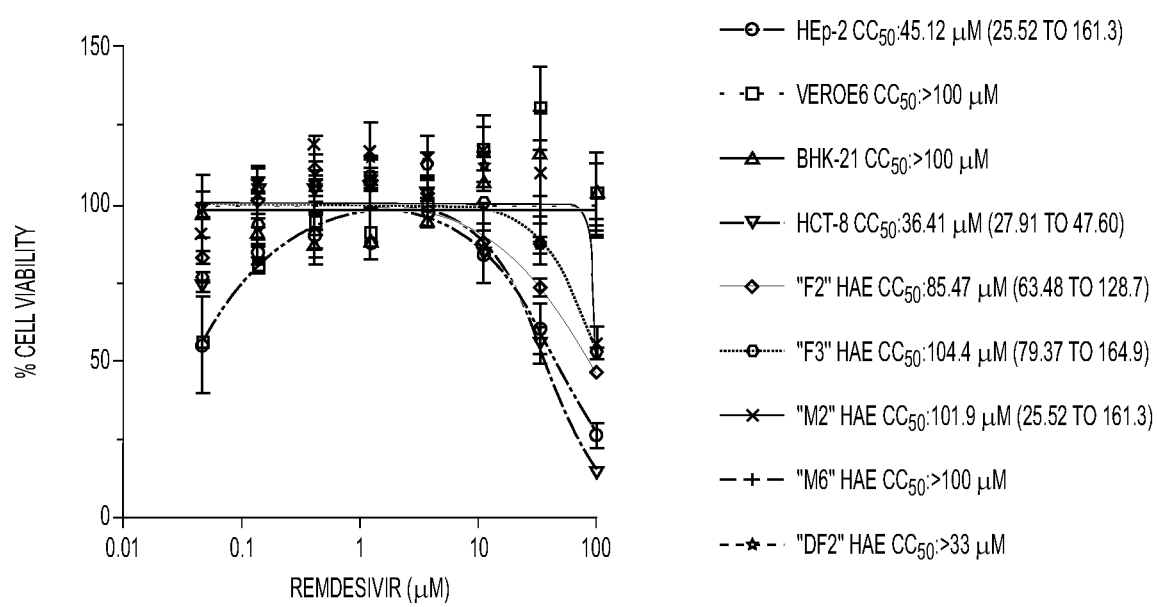

Antiviral potency of both Compound 1 and its metabolite Reference Compound A against the lineage A isolate SARS-CoV-2 USA-WA1/2020 (WA1/2020) and three recently emerged VoCs, hCoV-19/USA/CA_UCSD_5574/2020 (α lineage B.1.1.7; CA/2020), hCoV-19-South Africa/KRISP-K005325/2020 (β lineage B.1.351; SA/2020), and hCoV-9/Japan/TY7-503/2021 (γ lineage Brazil P.1; BZ/2021) were assessed in cultures cells. The results are shown in FIG. 1 and summarized in Table 5 below.

TABLE 5

Antiviral potency and cytotoxicity

| Virus | Host cells | Compound 1 $EC_{50}$ [μM] | Compound 1 $CC_{50}$ [μM] | Reference Compound A $EC_{50}$ [μM] | Reference Compound A $CC_{50}$ [μM] | Remdesivir $EC_{50}$ [μM] | Remdesivir $CC_{50}$ [μM] |
|---|---|---|---|---|---|---|---|
| WA1/2020-nano luciferase | A549-ACE2 | 0.98[a] | >50[a] | 1.6 + 0.85[b] | >50[a] | 0.067 ± 0.02[c] | >16.7[d] |
| SA/2020 B.1.351 | VeroE6 | 0.11 | >100 | 0.34 | >100 | n.d. | >100 |
| WA1/2020 A | VeroE6 | 0.73 | >100 | 0.68 | >100 | n.d. | >100 |
| BZ/2021 P.1 | VeroE6 | 0.22 | >100 | 0.55 | >100 | n.d. | >100 |
| CA/2020 | VeroE6 | 0.21 | >100 | 0.21 | >100 | n.d. | >100 |
| n.a. | HEp-2 | n.a. | 79.42 | n.a. | >100 | n.a. | 45.12 |
| n.a. | VeroE6 | n.a. | >100 | n.a. | >100 | n.a. | >100 |
| n.a. | BHK-21 | n.a. | >100 | n.a. | >100 | n.a. | >100 |
| n.a. | HCT-8 | n.a. | 74.61 | n.a. | >100 | n.a. | 36.41 |
| n.a. | "F2" HAE | n.a. | 43.76 | n.a. | >100 | n.a. | 85.47 |
| n.a. | "F3" HAE | n.a. | 43.77 | n.a. | >100 | n.a. | 104.4 |
| n.a. | "M2" HAE | n.a. | 39.73 | n.a. | >100 | n.a. | 101.9 |
| n.a. | "M6" HAE | n.a. | 92.34 | n.a. | >100 | n.a. | >100 |
| n.a. | "DF2" HAE | n.a. | 85.99 | n.a. | >100 | n.a. | >33 |

[a]mean (n = 2); data represent mean of two independent experiments, each with technical duplicates.
[b]mean ± SD (n = 15)
[c]mean ± SD (n = 18)
[d]mean (n = 15)

Prophylactic Efficacy in Ferrets

Figure 2A:
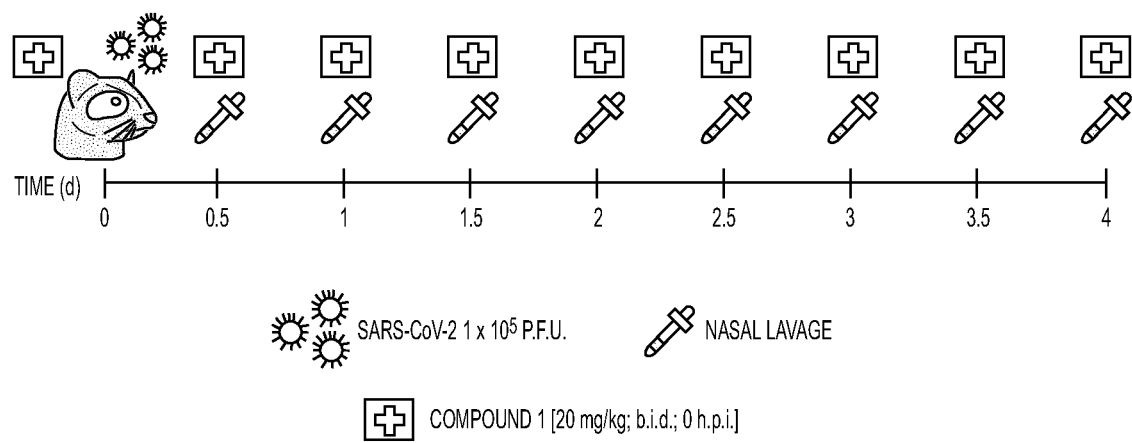
FIG. 2: Shows prophylactic efficacy of Compound 1 dosed orally. 2a: Schematic of the prophylactic efficacy study design. 2b: Virus titers from nasal lavages; LoD, limit of detection. 2c: Temperature measurements collected once daily. 2d: Body weight measured once daily. 2e: Infectious titers of SARS-CoV-2 in nasal turbinates harvested four days after infection. 2f: SARS-CoV-2 RNA copies present in nasal lavages. 2g: SARS-CoV-2 RNA copies detected in nasal turbinates. 2h-2i: SARS-CoV-2 infectious particles (h) and SARS-CoV-2 RNA copies (i) in lungs four days after infection. The number of independent biological repeats (individual animals) is shown in each subpanel, symbols represent independent biological repeats, lines (b, c, d, f) and bar graphs (e, g-i) connect or show samples mean, respectively, and P values are stated. 2-way ANOVA with Sidak's post-hoc multiple comparison tests (b, c, d, f) or two tailed t-test (e, g).
Figure 2B:
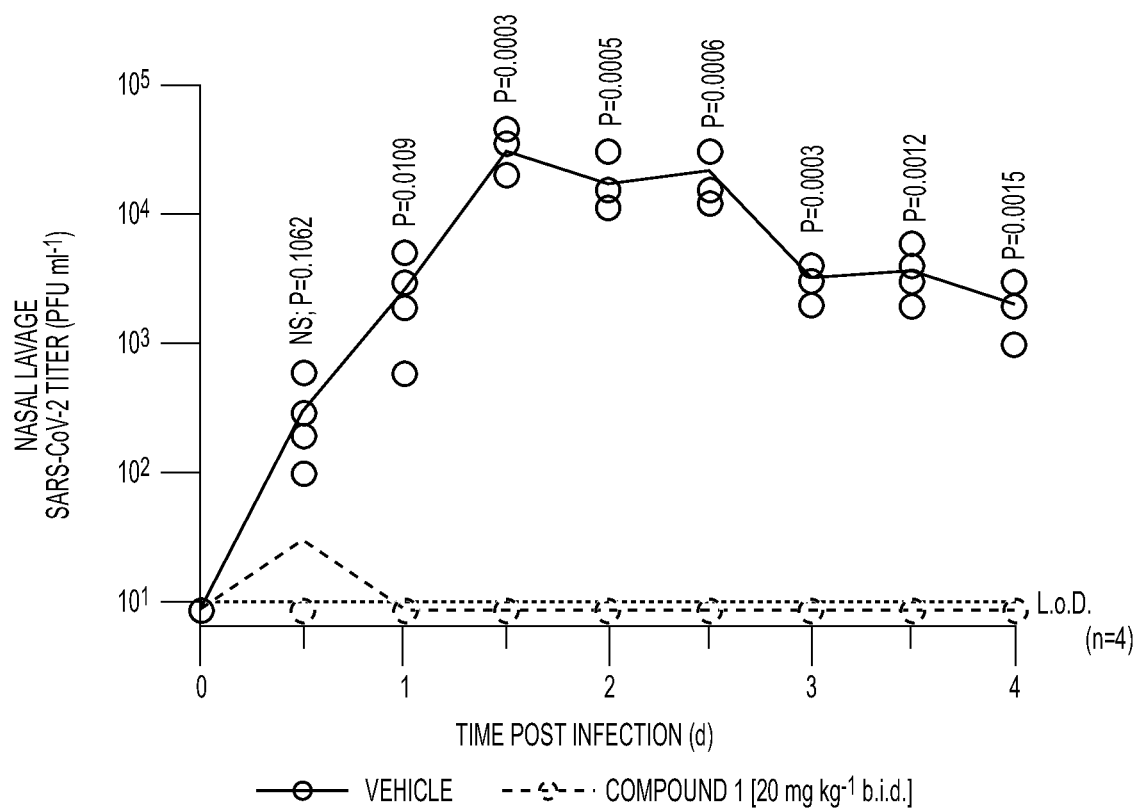
Figure 2C:
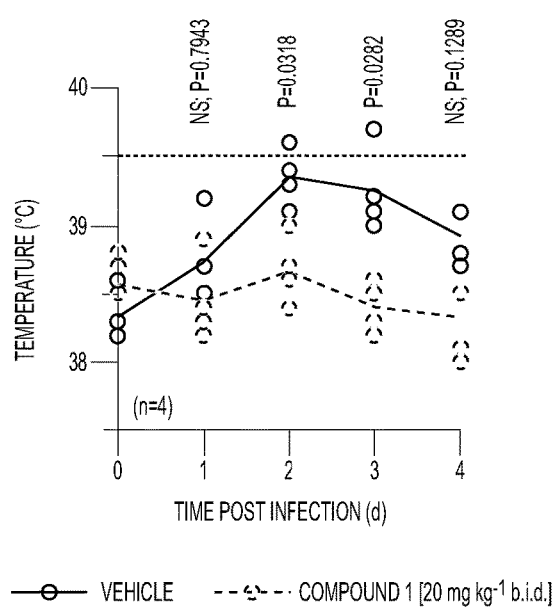
Figure 2D:
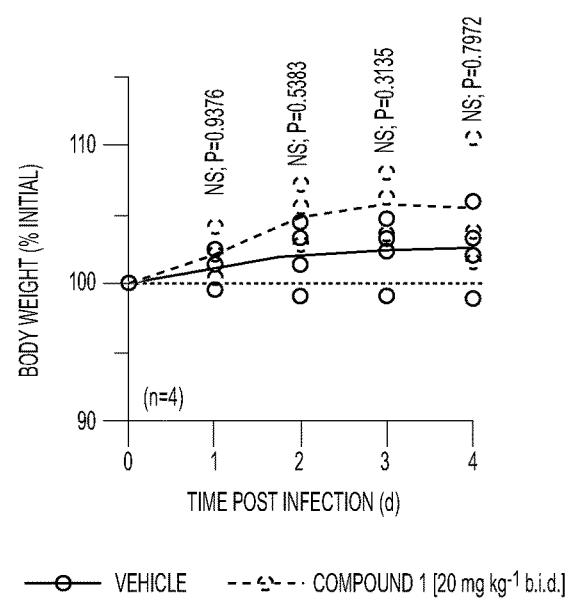

To test antiviral efficacy, ferrets were infected intranasally with 1×10$^5$ plaque forming units (pfu) of WA1/2020, followed by twice daily (b.i.d.) oral treatment with Compound 1 at 20 mg/kg body weight for four days (FIG. 2a). Treatment was initiated at the time of infection, nasal lavages collected in 12-hour intervals, and respiratory tissues harvested 4 days after infection. Shed SARS-CoV-2 load in nasal lavages of vehicle-treated animals reached plateau at day 1.5 after infection at approximately 1×10$^4$ pfu/mL, whereas virus was transiently detectable in lavages of only one ferret of the Compound 1 treatment group at 12 hours after infection (FIG. 2b). Clinical signs overall are minor in the ferret model. However, only animals of the vehicle group showed elevated body temperature (FIG. 2c) and reduced weight gain (FIG. 2d). Virus was undetectable in the nasal turbinates extracted from treated animals 4 days after infection, compared to a robust load of approximately 5×10$^4$ pfu/g nasal turbinate of animals of the vehicle group (FIG. 2e). Viral RNA copy numbers found in lavages (FIG. 2f) and turbinates (FIG. 2g) mirrored the infectious titer results, revealing a consistent, statistically significant difference between vehicle and treatment groups of two and three orders of magnitude, respectively. Consistent with prior studies (CITE COX), no infectious virions or viral RNA were detectable in the lower respiratory tract (FIG. 2h,i).

Therapeutic Efficacy and Lowest Efficacious Dose

Figure 3A:
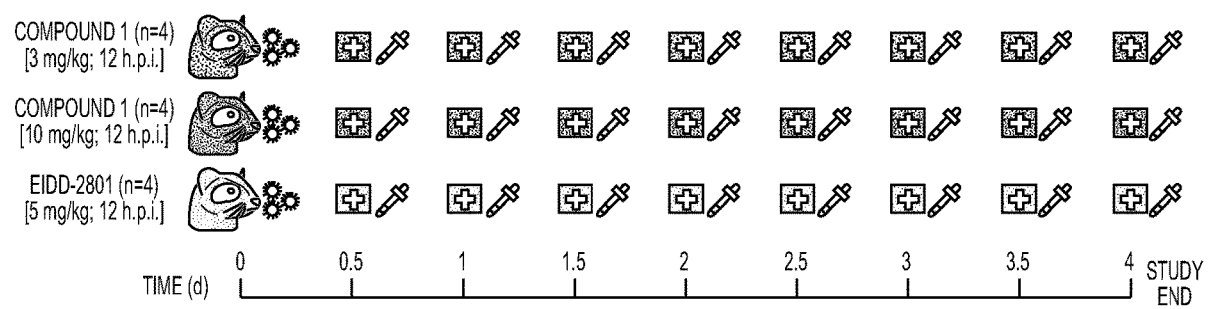
FIG. 3: Shows therapeutic efficacy of Compound 1 dosed orally against SARS-CoV2 in ferrets. 3a: Schematic of the therapeutic efficacy study design. 3b: Virus titers from nasal lavages. 3c: Infectious titers of SARS-CoV-2 in nasal turbinates harvested four days after infection. 3d: Temperature measurements collected once daily. 3e: Body weight measured once daily. 3f: SARS-CoV-2 RNA copies present in nasal lavages. 3g: SARS-CoV-2 RNA copies detected in nasal turbinates. The number of independent biological repeats (individual animals) is shown in each subpanel. Symbols represent independent biological repeats, lines (b, d, e, f) and bar graphs (c, g) connect or show samples mean, respectively, and P values are stated. 1-way (c, g) or 2-way (b, d, e, f) ANOVA with Dunnett's (b, d, e, f) post-hoc multiple comparison tests.
Figure 3A:
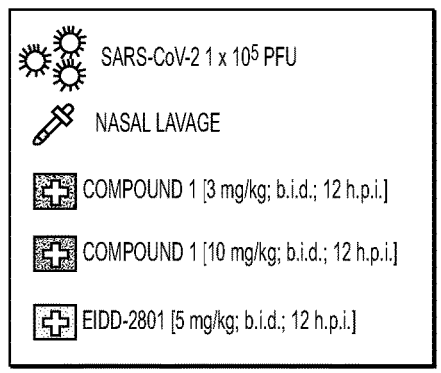
Figure 3B:
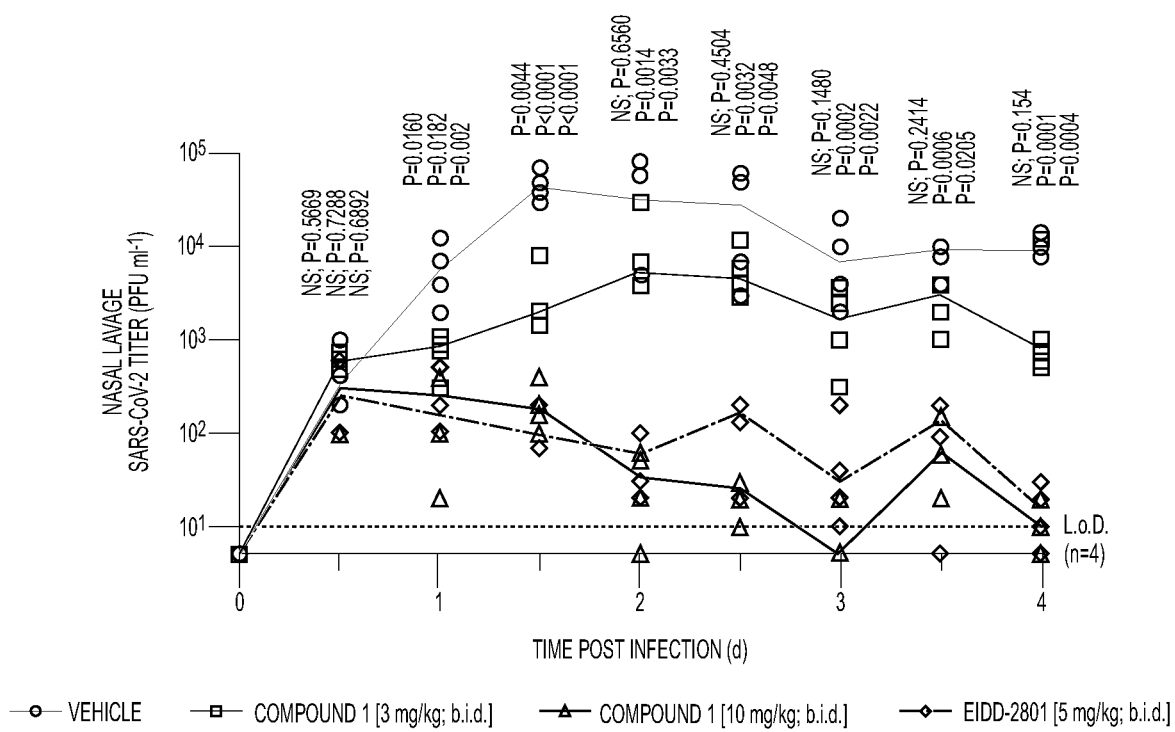
Figure 3C:
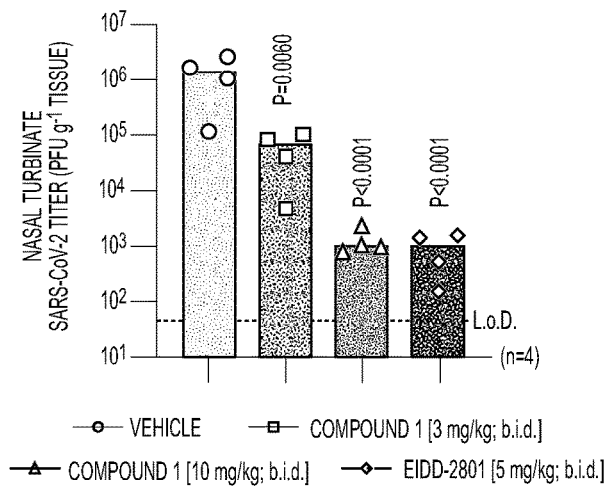
Figure 3D:
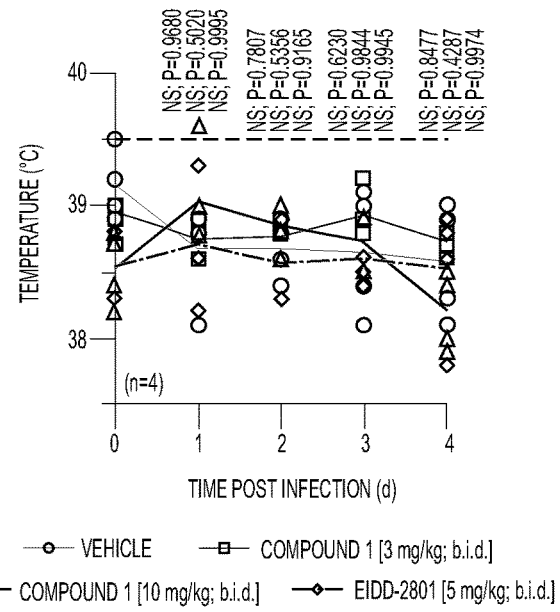
Figure 3E:
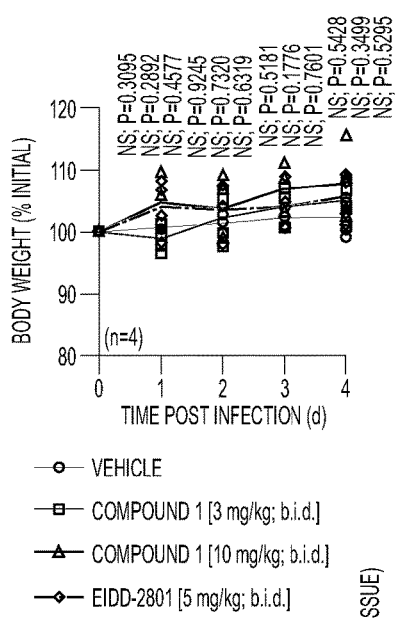

Oral treatment with Compound 1 was initiated 12 hours after infection at the 10 mg/kg and 3 mg/kg body weight levels, administered b.i.d. (FIG. 3a). EIDD-2801/molnupiravir at 5 mg/kg b.i.d. was given as reference following an identical therapeutic b.i.d. regimen. Shed virus load was lower in all treated animals than in the vehicle group within 12 hours of treatment onset (FIG. 3b). Consistent with this inhibitory effect, treated animals also exhibited reduced burden in the turbinates (FIG. 3c). No significant differences in clinical signs were noted between vehicle animals and any of the treatment groups (FIG. 3d,e).

Figure 3F:
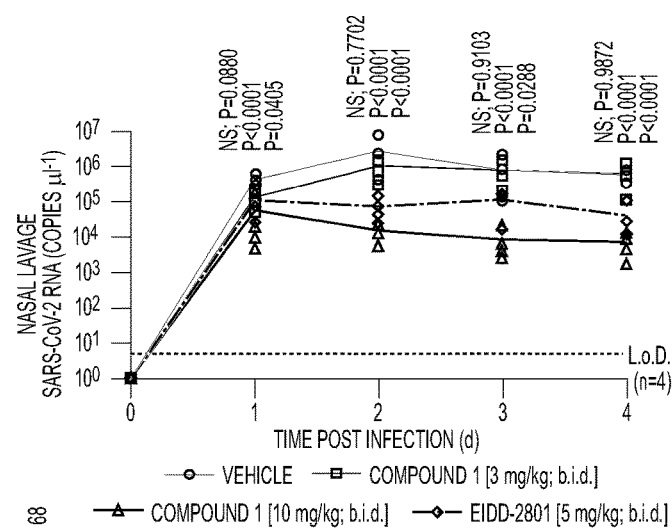
Figure 3G:
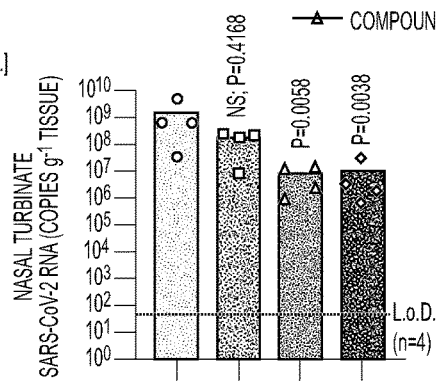

Viral RNA was detectable in nasal lavages and turbinates of all animals, underscoring efficient infection. However, RNA copies showed a statistically significant mean reduction in the 10 mg/kg Compound 1 and EIDD-2801/molnupiravir groups compared to vehicle (FIG. 3f,g). These results confirm oral efficacy of therapeutic Compound 1 against WA1/2020 in a relevant animal model of upper respiratory infection.

Inhibition of Replication and Transmission of a Major VoC

Figure 4A:
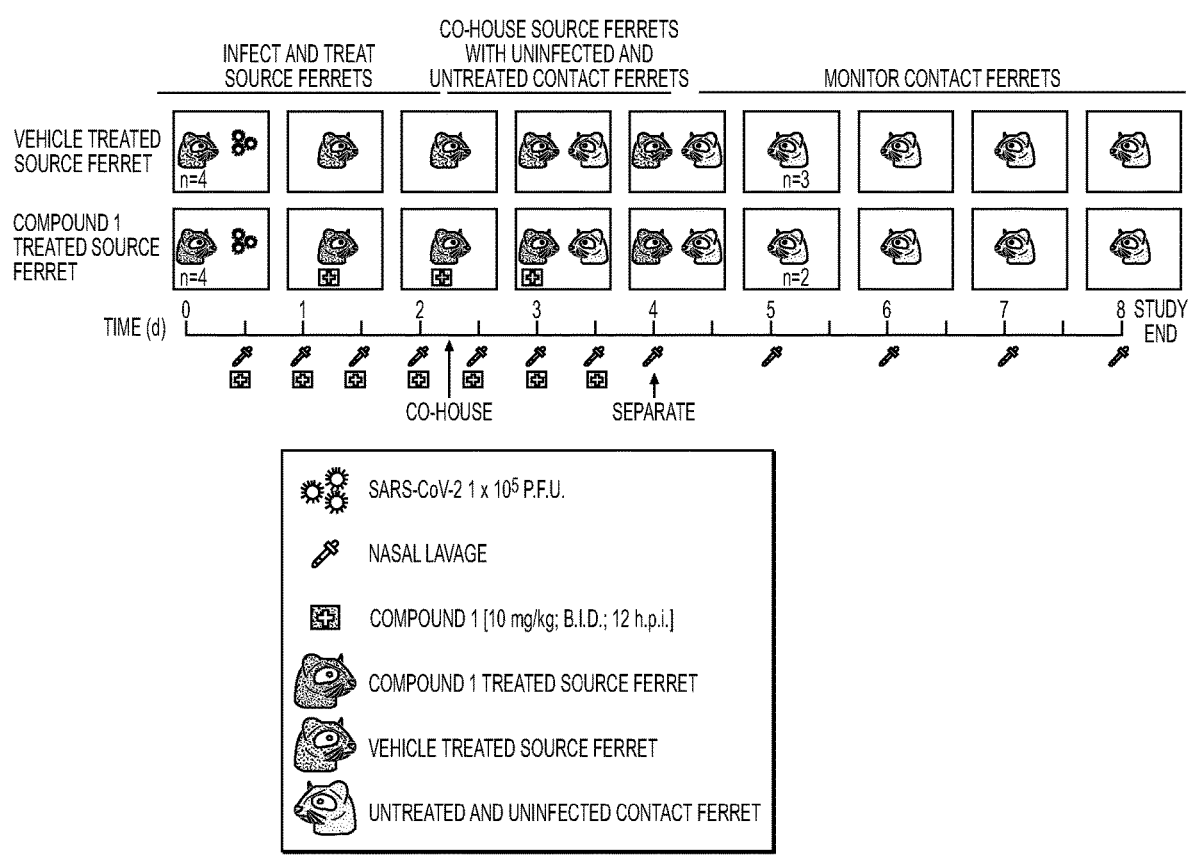
FIG. 4: Shows that Compound 1 dosed orally blocks replication and transmission of SARS-CoV-2 VoC BZ/2021. 4a: Schematic of the efficacy and contact transmission study design. 4b: Virus titers from nasal lavages. 4c: SARS-CoV-2 RNA copies present in nasal lavages. 4d: Infectious titers of SARS-CoV-2 in nasal turbinates harvested four days after infection. 4e: SARS-CoV-2 RNA copies detected in nasal turbinates. 4f: Infectious titers of SARS-CoV-2 in lung tissue. 4g: SARS-CoV-2 RNA copies present in lung tissue. In (b-g), the number of independent biological repeats (individual animals) is shown in each subpanel. Symbols represent independent biological repeats, lines (b, c) and bar graphs (d, e, f, g, h) connect or show samples mean, respectively, and P values are stated. 1-way (d, e) or 2-way (b, c) ANOVA with Tukey's (d, e) or Sidak's (b, c) post-hoc multiple comparison tests. 4h: Metagenome sequence analysis of inoculum WA1/2020 and BZ/2021 viruses, virus populations extracted from ferret nasal turbinates four days after infection, and BZ/2021 populations extracted from nasal lavages of contacts of vehicle-treated source animals. Relative allele frequencies of signature residues are shown. Symbols represent independent biological repeats (virus population of individual animals), columns, show group means.
Figure 4B:
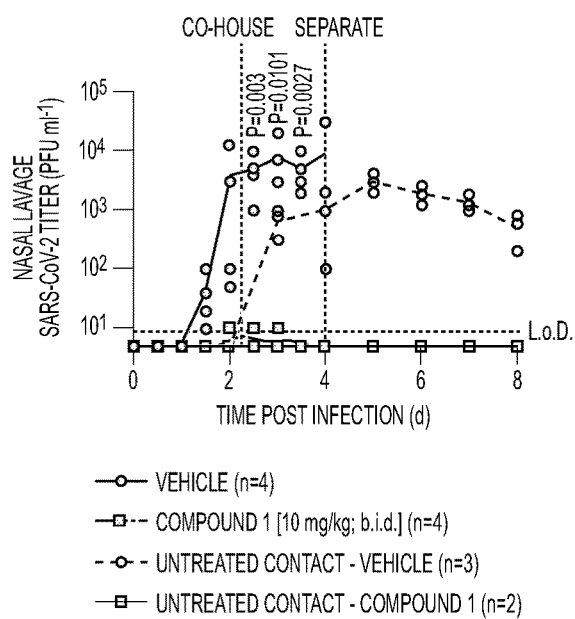
Figure 4C:
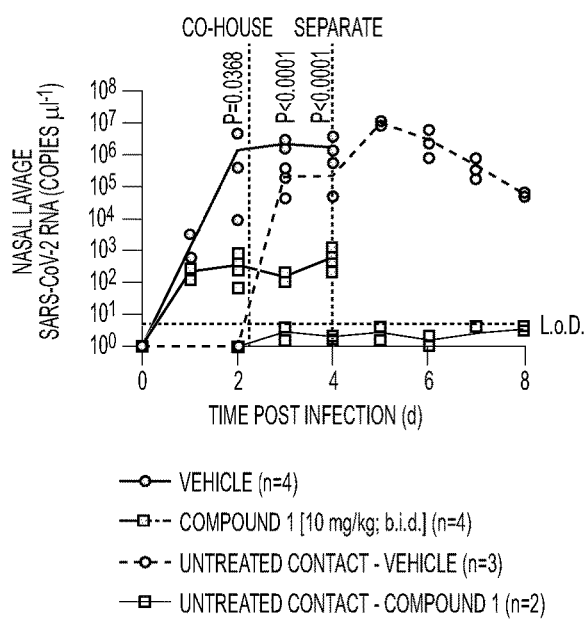
Figure 4F:
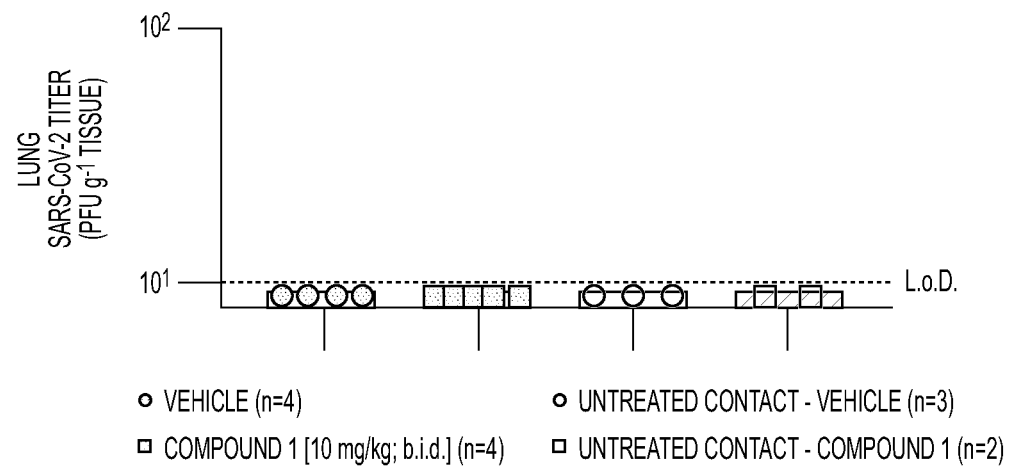
Figure 4G:
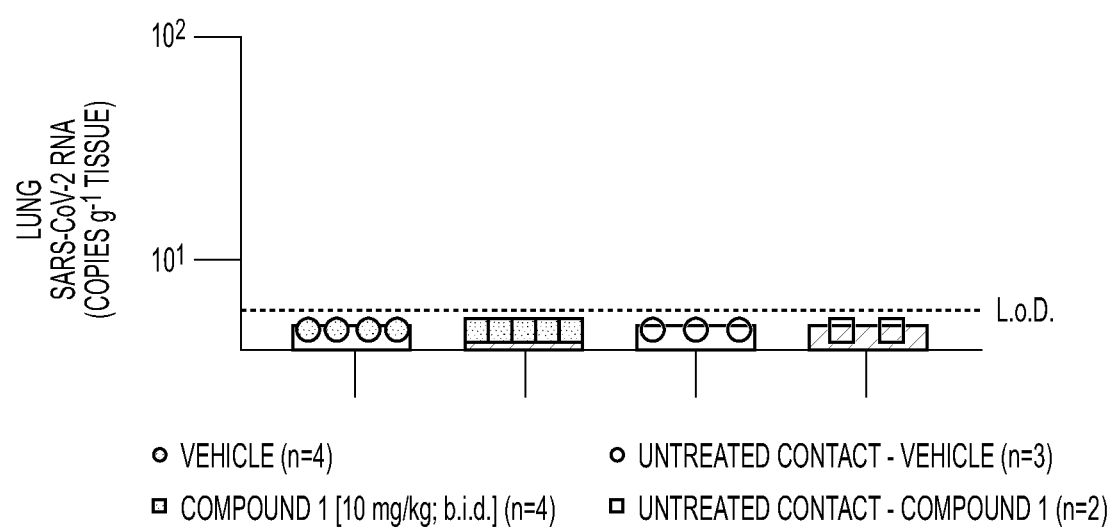
Figures 5A, 5B:
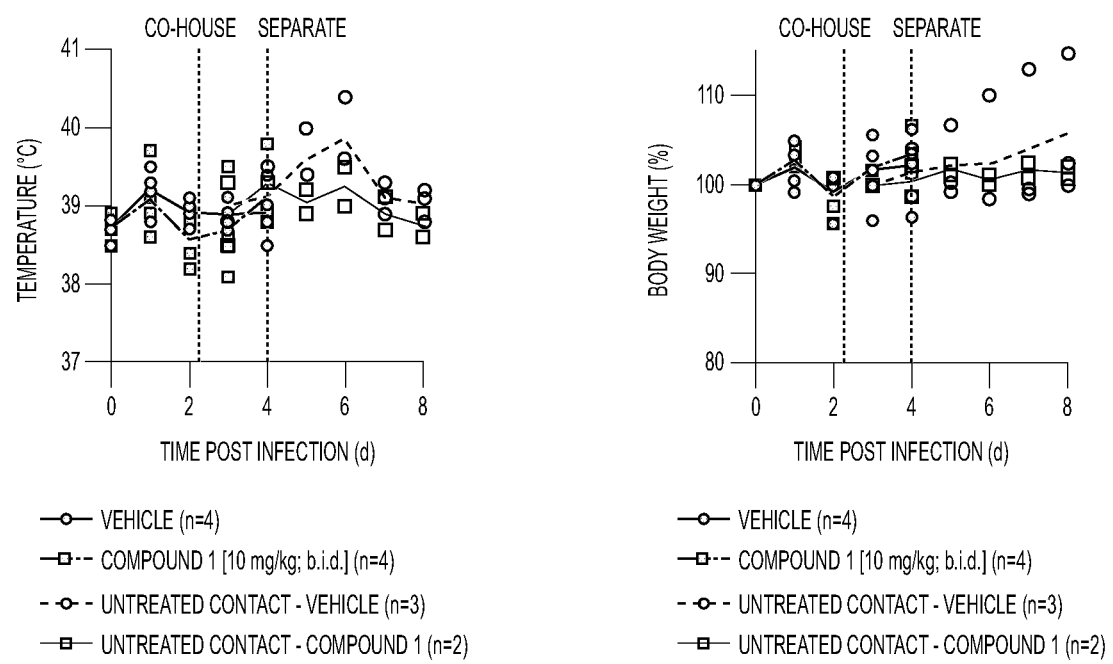
FIG. 5: Shows clinical signs in source and contact animals infected with BZ/2021. 5a: Temperature measurements collected once daily. 5b: Body weight measured once daily.

To probe the anti-SARS-CoV-2 indication spectrum of Compound 1, the efficacious regimen, 10 mg/kg Compound 1 delivered orally, b.i.d., started 12 hours after infection, was applied to recently emerged VoC BZ/2021[16] in a combined efficacy and transmission study (FIG. 4a). After an initial replication delay, shed virus became detectable in vehicle-treated animals 1.5 days after infection, then rapidly reached a robust plateau of nearly $10^4$ pfu/mL nasal lavage on day 2 after infection (FIG. 4b). Quantitation of viral RNA copies mimicked the profile of the infectious titers, although a low viral RNA load was present in lavages already on the first day after infection (FIG. 4c). Viral titers and RNA copies in nasal turbinates determined 4 days after infection were likewise high, ranging from $10^4$ to $10^5$ pfu/g tissue (FIG. 4d) and $10^1$ to $10^{10}$ RNA copies/g tissue (FIG. 4e), respectively. However, no infectious BZ/2021 virions or viral RNA were detected in the lungs of any of these animals (FIG. 4f,g), and no clinical signs such as changes in body weight or fever emerged (FIG. 5 a,b). Treatment of BZ/2021 infection with oral Compound 1 was highly efficacious, reducing both shed virus burden and tissue titers to undetectable (FIG. 4b,d) and lowering viral RNA copies in nasal lavages and turbinates by over three orders of magnitude (FIG. 4c,e).

Figure 4H:
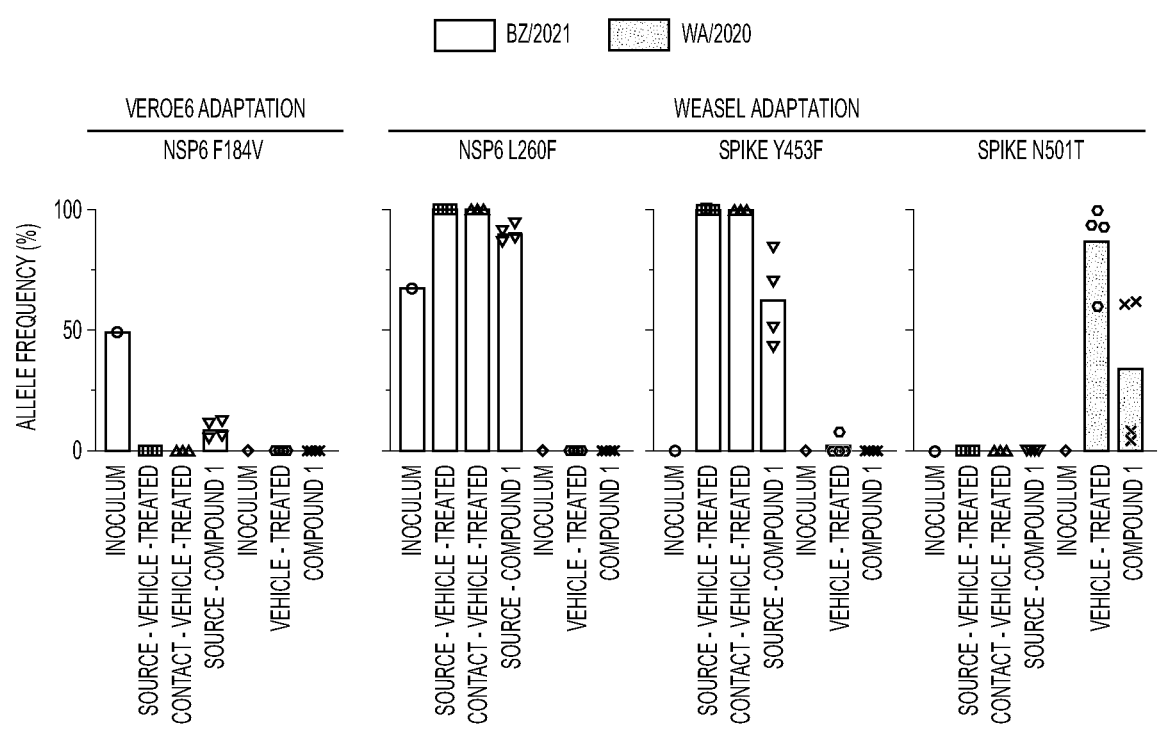
Figure 4H:
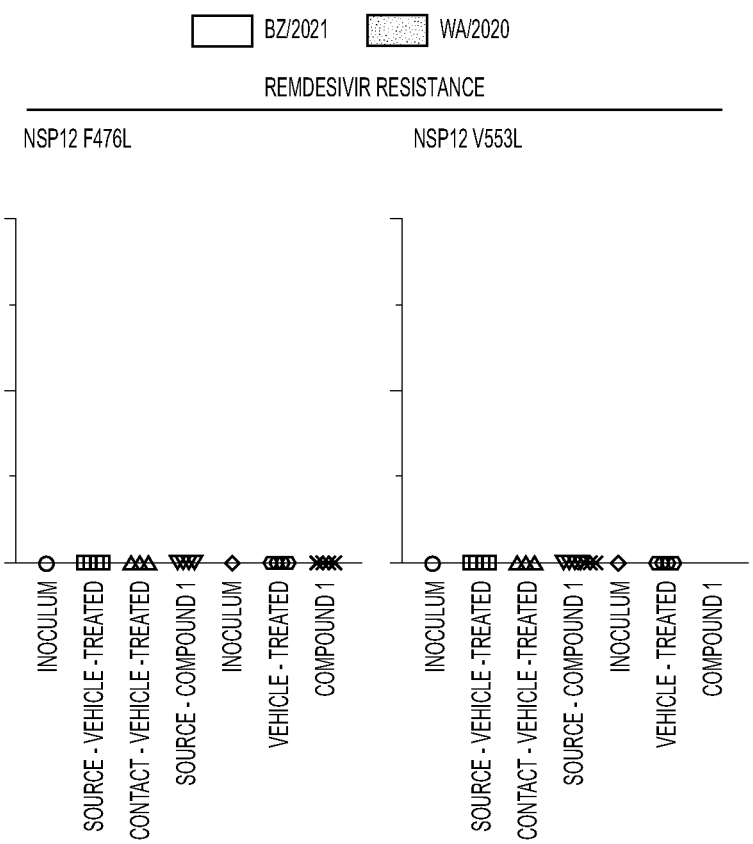

Whole genome sequencing of the virus inoculum and virus populations extracted from nasal turbinates revealed that an L260F substitution in nsp6 associated with SARS-CoV-2 adaptation to weasels had a 60%-allele frequency in the BZ/2021 inoculum (FIG. 4h). Four days after infection of ferrets, this mutation had become fully dominant and a second characteristic weasel mutation, Y453F in the spike protein that was first noted in several clusters of SARS-CoV-2 outbreaks in mink farms, had emerged in addition (FIG. 4h). Furthermore the presence of an F184V exchange in nsp6 of the BZ/2021 inoculum, which arose during amplification in VeroE6 cells and was rapidly counterselected against in the ferret host. In contrast, the WA1/2020 inoculum used for our ferret studies did not contain any unreported additional changes (FIG. 4h). WA1/2020 also acquired a weasel-characteristic mutation when passaged through ferrets, N501T in the receptor binding domain of the spike protein[10], but no Y453F substitution or changes in nsp6 were detected. Neither the Compound 1—experienced BZ/20201 nor WA1/2020 populations contained remdesivir resistance mutations previously selected in the related mouse hepatitis virus (i.e., F476 L and V553L in nsp12), when viruses were extracted from treated animals at the time of termination (FIG. 4h).

All vehicle-treated animals efficiently transmitted BZ/2021 to untreated direct contact ferrets (FIG. 4b-e). Co-housing was started 54 hours after infection and continued until termination of the source animals. Shed BZ/2021 replicated in the contacts without delay, becoming first detectable in nasal lavages within 12 hours after initiation of co-housing. This altered replication profile corroborated BZ/2021 adaptation to the ferret host in the source animals, and virus populations recovered from contacts of vehicle-treated source animals indeed contained both the L260F exchange in nsp6 and the Y453F mutation in spike (FIG. 4h). Consistent with efficient inhibition of BZ/2021 replication in the treated source animals by oral Compound 1, treatment completely blocked virus transmission to untreated direct-contact animals. None of the contacts of treated source ferrets shed infectious particles or viral RNA at any time (FIG. 4b,c), infectious viral particles were absent from nasal turbinates 5.5 days after initiation of co-housing (FIG. 4d), and only a low level of viral RNA (<$10^5$ copies/g nasal turbinate) was detected in nasal turbinates of the contact animals (FIG. 4e).

Example 52: In Vivo Efficacy of Compound 15 Against SARS-CoV-2 in Ferrets

Female ferrets (4 animals per dose group; 6-10 months old) were infected intranasally with $10^5$ PFU of SARS-CoV-2 and treated with either vehicle, 5 mg/kg EIDD-2801, or Compound 15 at 3, 10, or 20 mg/kg orally. Treatment was initiated 12 hours post infection. Ferrets were dosed either BID or QD as noted until day 3.5, then euthanized 12-hours afterwards on study day 4. SARS-CoV-2 infection of ferrets does not cause physiological effects on weight or lung function, and viral infection is limited to the nasopharynx, with no consistent detection of virus in the lungs. SARS-CoV-2 infectious titers were measured from daily nasal lavage fluid samples, as well as terminal nasal turbinates and lung tissue. As expected, no detectable virus gRNA by RT-qPCR were found in ferret lungs from any group (vehicle and treatment) at the terminal tissue harvest of this study (data not shown). Further, no detectable infectious titers (nor gRNA by RT-qPCR) were found in ferret lungs from any group during the evaluation of earlier compounds in prior studies. The results of these experiments are summarized in Table 6 below.

TABLE 6

Reductions in SARS-CoV-2 infectious titers and viral RNA levels in ferret nasal lavages and nasal turbinate compared to vehicle-dosed animals

| | | Change from vehicle ($\log_{10}$) | | | | | |
|---|---|---|---|---|---|---|---|
| Sample | Analysis | Compound 15 (5 mg/kg, BID) | Compound 15 (10 mg/kg, BID) | Compound 15 (20 mg/kg, BID) | Compound 15 (20 mg/kg, QD) | Compound 15 (40 mg/kg, QD) | EIDD-2801 (5 mg/kg, BID) |
| Nasal lavage | $AUC_{(0-96)}$ PFU/mL | −2.21 | −2.50 | −3.00 | −2.21 | −2.80 | −2.34 |

TABLE 6-continued

Reductions in SARS-CoV-2 infectious titers and viral RNA levels in ferret nasal lavages and nasal turbinate compared to vehicle-dosed animals

| | | Change from vehicle ($\log_{10}$) | | | | | |
|---|---|---|---|---|---|---|---|
| Sample | Analysis | Compound 15 (5 mg/kg, BID) | Compound 15 (10 mg/kg, BID) | Compound 15 (20 mg/kg, BID) | Compound 15 (20 mg/kg, QD) | Compound 15 (40 mg/kg, QD) | EIDD-2801 (5 mg/kg, BID) |
| | $AUC_{(0-96)}$ RNA copies/μL | −1.33 | −1.51 | −2.22 | −1.26 | −1.91 | −0.87 |
| Nasal turbinate | Terminal PFU/mL | −1.68 | −2.20 | −3.78 | −3.42 | −3.79 | −3.79 |
| | Terminal RNA copies/μL | −2.14 | −1.79 | −3.04 | −2.37 | −4.01 | −2.68 |

Example 53: In Vivo Efficacy of Orally Dosed Compound 1 Against SARS-CoV-2 in AGMs Compound 1 was evaluated by oral gavage dosing (PO) 8 hours after infection with SARS-CoV-2 (WA1). Compound 1 was dosed at 120 or 60 mg/kg QD for 6 days—the first dose was administered at 8 hr following infection and the five following doses were administered in 24 hr interval post infection. BALF and nasal and throat swabs were collected at days 1, 2, 4, and 6 days post-infection and assessed for viral load quantitation. Animals were euthanized on day 6 for terminal BALF and tissue collections. The complete procedures and study designs are detailed below.

The experimental groups for to evaluate Compound 1 by oral dosing are shown in the Table 7. A total of 18 AGM (9 M, 9 F) were used in this study. Animals were randomized into one of three treatment groups, with sex evenly distributed within each group. The study was conducted in 3 cohorts, each staggered by one day; each treatment group was evenly represented within each study cohort. On study day 0, animals were infected with approximately $3\times10^6$ $TCID_{50}$ SARS-CoV-2 by a combination of intranasal and intratracheal instillation. Starting at approximately 8 hours post-inoculation, animals in all groups were treated with either test article or vehicle by oral (PO) gavage. Dosing continued once daily thereafter for an additional 5 days (i.e., a total of 6 days of dosing). Animals were euthanized on study day 6 for terminal tissue collection and histopathology.

Following infection, animals were monitored daily for clinical disease. At 1, 2, 4, and 6 days post-infection, bronchoalveolar lavage fluid (BALF) and nasal and throat swabs were collected for quantification of both infectious viral titers and viral RNA. On study day 6, animals were euthanized for collection of respiratory tissues for quantification of tissue viral burden and for histopathology. On study day 0, oral dosing occurred approximately 8 hours post-infection in chair restrained animals. Collection of BALF and swabs on days 1, 2, 4 and 6 occurred as an anesthetized procedure in the morning, at approximate 24-hour intervals relative to infection, with oral dosing of test article immediately following, under the same anesthesia. On days without scheduled BALF or swab collections (i.e., study days 3 and 5), animals were chair restrained for dosing.

Oral Gavage

Animals in all groups received test compound (or vehicle) by oral gavage. As shown in Table 7, all animals were dosed at a volume of 2 mL/kg. Compound 1 was dosed at 120 mg/kg (Group 2) or 60 mg/kg (Group 3). Animals in Group 1 received vehicle control. Dosing was based on baseline body weights obtained prior to SARS-CoV-2 infections. Immediately following dosing, the test article was flushed with approximately 10 mL water. On study days 0, 3 and 5, dosing was performed in alert, chair-restrained animals. On study days 1, 2 and 4, dosing was performed in anesthetized animals, immediately following BALF and swab collections.

Virus Installations

AGMs were anesthetized with ketamine and isoflurane and placed in the prone position for SARS-CoV-2 infections by both intranasal and intratracheal instillation. The total inoculation will be delivered in 3 mL per animal (2 mL delivered intratracheal and 1 mL delivered intranasal). Virus was thawed, diluted with vehicle to $1\times10^6$ $TCID_{50}$/mL

TABLE 7

Experimental groups for the Compound 1 PO study

| Group | N | Challenge | Treatment | Concentration (mg/mL) | Dose Route | Dose (mg/kg) (mL/kg) |
|---|---|---|---|---|---|---|
| 1 | 6 | IN/IT SARS-CoV-2 | Vehicle | N/A | PO | N/A (2 mL/kg) |
| 2 | 6 | IN/IT SARS-CoV-2 | Compound 1 | 60 mg/mL | PO | 120 mg/kg (2 mL/kg) |
| 3 | 6 | IN/IT SARS-CoV-2 | Compound 1 | 30 mg/mL | PO | 60 mg/kg (2 mL/kg) | immediately prior to infections, and kept on ice until used for inoculation. For intratracheal instillation, a pediatric bronchoscope (Olympus XP-40) was advanced approximately midway into the trachea. Polyethylene (PE) tubing was advanced through the bronchoscope, and 2 mL virus was instilled through the tubing, followed by 0.5 mL sterile saline and approximately 1 mL air. For intranasal instillation, 0.5 mL of the viral inoculum was administered dropwise into each nostril (i.e., 0.5 mL per nostril, 1 mL total). Following infections, 2×0.5 mL aliquots were saved and stored at approximately −70° C. for back-titration by $TCID_{50}$ assay.

Nasal and Throat Swabs

Nasal and throat swabs were collected at baseline, and at 1, 2, 4, and 6 days post-infection from anesthetized animals, concurrent with BALF collections. On days 1, 2 and 4, collections were performed immediately prior to dose administration. Actual collection times were documented in the study files. Samples were collected with cotton tip applicators pre-soaked in sterile saline, advanced into the nasal cavity or the back of the throat, respectively. Two swabs were collected per site. Each swab was placed in a tube containing approximately 0.5 mL sterile saline and immediately frozen on dry ice prior to storage at approximately −70° C.

Bronchoscopy and Bronchoalveolar Lavage

Bronchoalveolar lavage fluid (BALF) was collected from anesthetized animals at baseline, and at 1, 2, 4, and 6 days post-infection. On days 1, 2 and 4, collections were performed immediately prior to dose administration, and on day 6, collections were performed immediately prior to euthanasia. Actual collection times were documented in the study files. Briefly, a pediatric bronchoscope (Olympus XP-40) was advanced into the left caudal lung lobe, 10 mL sterile saline was infused, and the maximum volume as aspirated. The process was repeated for the right caudal lung lobe. The collection time and the total recovered volume for both the left and right lung lavages were recorded, and the samples were stored on wet ice until processing.

Bronchoalveolar Lavage Fluid (BALF) Processing

Bronchoalveolar lavage fluid were stored on wet ice until processing. The BALF was centrifuged at approximately 1000×g for 10 minutes at 4° C., and the processing start time was recorded. The BALF supernatant was divided into ~1 mL aliquots in individually labeled tubes and were stored along with the cell pellet at approximately −70° C. until further analysis. A minimum of 4×~1 mL aliquots were saved from both the left and right lavage sample from each animal at each timepoint.

Nasal/Throat Swab Processing

Nasal and oropharyngeal (throat) swabs were placed in a tube containing approximately 0.5 mL sterile saline and immediately frozen on dry ice following collection. Samples were stored at approximately −70° C. until further analysis.

Euthanasia and Necropsy

Detailed gross necropsies were performed on all animals. Scheduled euthanasia occurred 6 days post-infection for gross necropsy and tissue collection. Animals were sedated with ketamine (10-20 mg/kg), and euthanasia was performed immediately following collection of BALF and swabs. The exact time of euthanasia was recorded. Terminal body weights and total lung weights were obtained, and a lung weight/body weight ratio was calculated for each animal. Gross necropsy was performed. The necropsy consisted of a complete external and internal examination including body orifices (ears, nostrils, mouth, anus, etc.) and cranial, thoracic, and abdominal organs and tissues. All gross findings (including those of lung and tracheobronchial lymph nodes) was recorded in descriptive terms. The thoracic trachea, left lungs, and tracheobronchial lymph nodes were fixed in 10% neutral buffered formalin (NBF) and then processed for microscopic examination. The right lung was reserved for sampling of respiratory tract tissues for quantification of infectious viral titers and viral RNA.

Tissue Collection and Preservation

The right lung was reserved for sampling of respiratory tract tissues for quantification of infectious viral titers, viral RNA, and for bioanalysis; the left lung was reserved for fixation and histopathology. Sampling of respiratory tract tissues was standardized in a necropsy guide and trim guide. Samples for bioanalysis (right middle lung and right middle bronchus) were collected from as soon as possible following euthanasia and after obtaining whole lung weights and gross photos of the dorsal and ventral surfaces; these samples were flash frozen liquid nitrogen immediately following collection, and the time of freezing was recorded. Additional sections of the right lung were collected and flash frozen in liquid nitrogen for viral quantification assays (RT-qPCR and $TCID_{50}$). All frozen samples were stored at approximately −70° C. until processing and analysis.

Quantitative PCR and Infectious Virus Titers

A total of 20 samples for each animal was evaluated for SARS-CoV-2 RNA and infectious virus titers by reverse transcription quantitative PCR (RT-qPCR) and median dose tissue culture infection ($TCID_{50}$) assay.

Tissue Processing and RNA Extraction

For BALF samples and nasal and throat swabs, viral RNA was extracted from liquid supernatants from samples processed and preserved. For tissue samples, approximately 75 mg was homogenized in Trizol using a TissueLyser. Samples were centrifuged at 4000×g for 5 minutes, and supernatants were saved RNA extraction. RNA was isolated from all samples using the QIAGEN RNeasy Kit or equivalent, according to the manufacturer's instructions. Extracted RNA was used for qRT-PCR analyses as described below.

Reverse Transcription Quantitative PCR

Each of the RNA samples was evaluated for SARS CoV-2 viral RNA and subgenomic RNA by RT-qPCR. Methods for each assay were optimized prior to sample analysis. Total SARS-CoV-2 viral RNA was quantified by a RT-qPCR assay targeting the SARS CoV-2 nucleocapsid phosphoprotein gene (N gene). Genome copies per mL or g equivalents were calculated from a standard curve generated from RNA standards of known copy concentration. All samples were run in triplicate.

The SARS CoV-2 N gene primers and probe sequences are as follows:

```
SARS CoV-2 Forward:
                                    (SEQ ID NO: 1)
5' TTACAAACATTGGCCGCAAA 3'

SARS CoV-2 Reverse:
                                    (SEQ ID NO: 2)
5' GCGCGACATTCCGAAGAA 3'

SARS CoV-2 Probe:
                                    (SEQ ID NO: 3)
6FAM-ACAATTTGCCCCCAGCGCTTCAG-BHQ-1
```

Amplification and detection were performed using a suitable real-time thermal cycler under the following cycling conditions: 50° C. for 5 minutes, 95° C. for 20 seconds and 40 cycles of 95° C. for 3 seconds, and 60° C. for 30 seconds.

SARS-CoV-2 subgenomic RNA was quantified by a RT-qPCR assay targeting the E gene. The assay was adapted from Wolfel et. al. (Virological assessment of hospitalized patients with COVID-2019. Nature. 581:465-470. doi.org/10.1038/s41586-020-2196-x), with the forward primer binding the E gene leader sequence and the reverse primer binding the E gene itself. All samples will be run in triplicate.

Infectious Virus Titers

Each sample was be evaluated for infectious SARS-CoV-2 virus by $TCID_{50}$ assay using Vero E6 cells in a 96-well format. Stock virus of known concentration and blank media served as positive and negative controls, respectively. At assay completion, cells were formalin fixed and stained, and $TCID_{50}$ titer was calculated according to the Reed-Muench method (A simple method of estimating fifty percent endpoints. Am. J. Hygiene. 27:493-497).

Figure 6A:
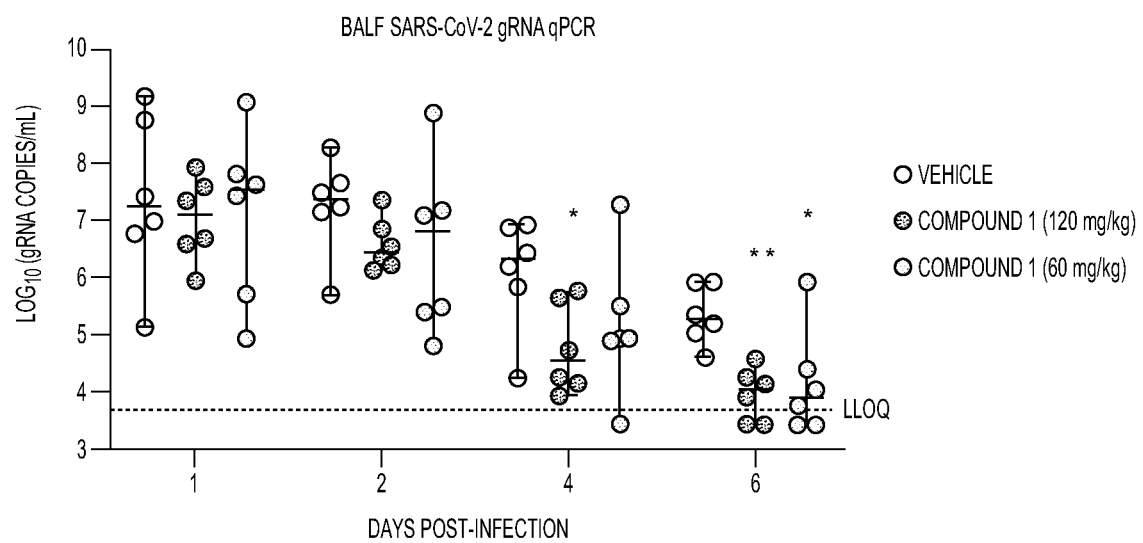
FIGS. 6a-6c: Shows the efficacy of orally dosed Compound 1 against SARS-CoV-2 AGMs.
Figure 6B:
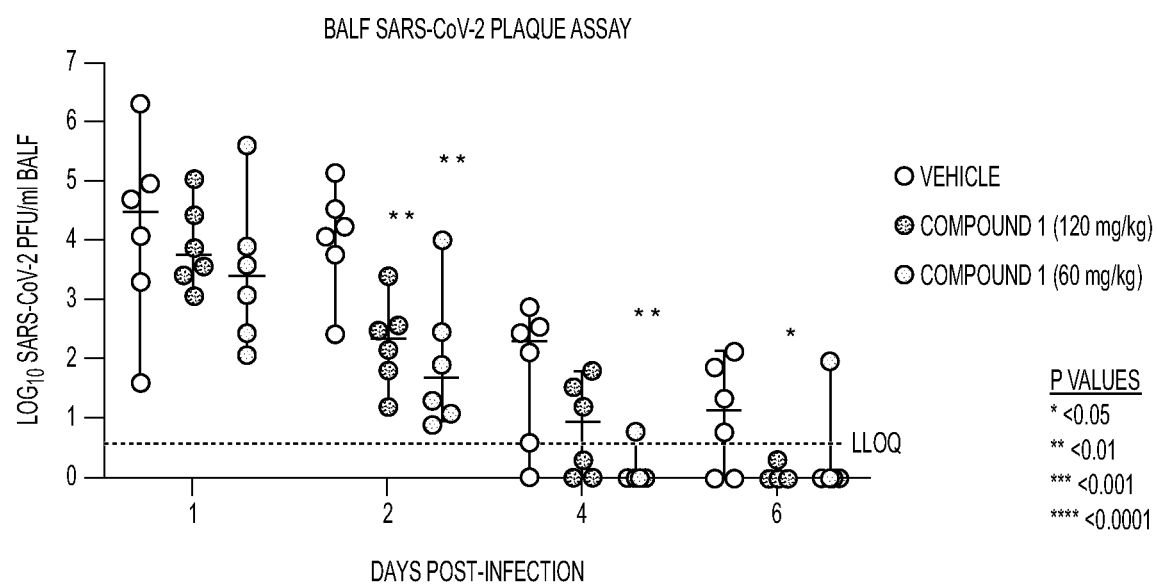
Figure 6C:
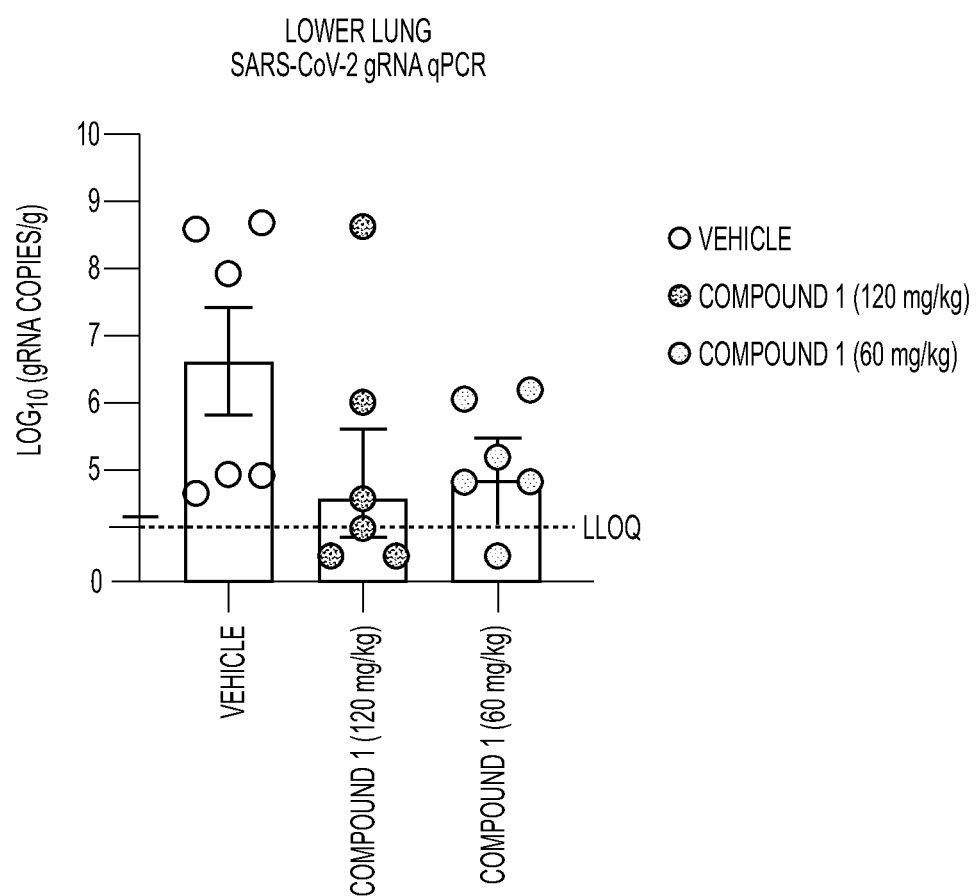
Figure 8:
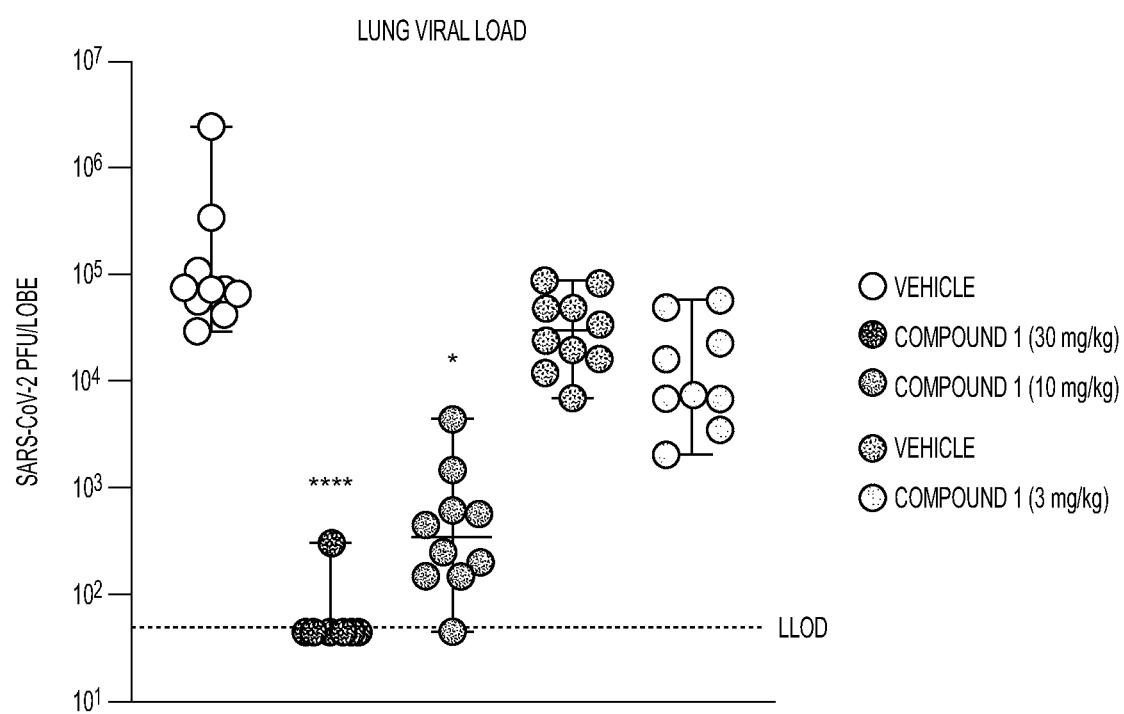
FIG. 8: Shows that dosed orally Compound 1 reduces terminal SARS-CoV-2 infectious titers in lungs of mice.

The results of these experiments are shown in FIG. 6. As seen, compared to AGMs dosed with vehicle, mean SARS-CoV-2 gRNA in BALF was significantly reduced in animals dosed with 120 mg/kg Compound 1 for 4 and 6 days (FIG. 8). On day 6, gRNA was significantly lower than vehicle animals in the lower 60 mg/kg group. Infectious SARS-CoV-2 titers among animals treated with either Compound 1 at 60 or 120 mg/kg trended lower than the vehicle group on days 2-6. Viral RNA loads in lower lung tissue trended lower with treatment of Compound 1 versus vehicle.

Example 54: In Vivo Efficacy of Compound 1 and Compound 15 Against Mouse-Adapted SARS-CoV-2 in Mice The virus stock utilized for SARS-CoV-2 in vivo studies was derived from the infectious clone of the mouse-adapted SARS-CoV-2 (MA10) strain generated as described in Dinnon, K H et al. (A mouse-adapted model of SARS-CoV-2 to test COVID-19 countermeasures. Nature. 586:560-566). Cohorts of 7-10-week-old female Balb/c mice (n=10/dose group), were administered vehicle or compound by oral gavage at the indicated times after intranasal infection with $1 \times 10^4$ PFU mouse-adapted SARS-CoV strain MA10 in 50 µL. Mice were anaesthetized with a mixture of ketamine/xylazine prior to intranasal infection. Vehicle or test article were administered BID or QD as described below. Mice were treated by PO dosing of 3, 10, or 30 mg/kg Compound 15 or EIDD-2801 (100 mg/kg) at twelve hours after intranasal infection with SARS-CoV-2 (MA10). A separate group of mice was treated with 30 mg/kg Compound 15 at 24 h.p.i. Thereafter, mice were treated BID with vehicle, Compound 15, or EIDD-2801 until day 4. In two separate studies, mice were treated by PO dosing of 3, 10, or 30 mg/kg Compound 1 eight hours after intranasal infection with SARS-CoV-2 (MA10). Mice were treated BID with vehicle or Compound 1 starting at +8 h.p.i., with the second dose occurring at 24 h.p.i., and subsequent doses at 12-hour intervals until day 4.

Body weight and pulmonary function by whole body plethysmography were measured daily. On 4 dpi, animals were sacrificed by isoflurane overdose, lungs were scored for lung hemorrhage (congestion score), and the inferior right lobe was frozen at −80° C. for viral titration via plaque assay. Briefly, 500,000 Vero E6 cells/well were seeded in 6-well plates. The following day, medium was removed and serial dilutions of clarified lung homogenate were added per plate ($10^{-1}$ to $10^{-6}$ dilutions) and incubated at 37° C. for 1-hr after which wells were overlaid with 1×DMEM, 5% Fetal Clone 2 serum, 1× antibiotic/antimycotic, 0.8% agarose. Two days after, plaques were enumerated to generate a plaque/ml value.

Lung hemorrhage (congestion scoring) is a gross pathological phenotype readily observed by the naked eye driven by the degree of virus replication where the coloration of the lung changes from pink to dark red. Pulmonary function (PenH) was monitored once daily via whole-body plethysmography (Buxco Respiratory Solutions, DSI Inc.). Mice intended for this analysis were randomly chosen prior to the initiation of the study. Briefly, after a 30-min acclimation time in the plethysmograph, data for 11 parameters was recorded every 2 s for 5 min.

All statistical data analyses were performed in Graphpad Prism 8. Statistical significance for each endpoint was determined with specific statistical tests. In general, for metrics with multiple treatment groups with longitudinal data (e.g., mouse weight loss or pulmonary function over time), two-way ANOVA was performed with the suggested multiple comparison test as advised by Prism. For comparative data with for a single timepoint (e.g., lung titer) Kruskal-Wallis or one-way ANOVA was performed with the suggested multiple comparison test. For each test, a p-value <0.05 was considered significant.

Figure 7A:
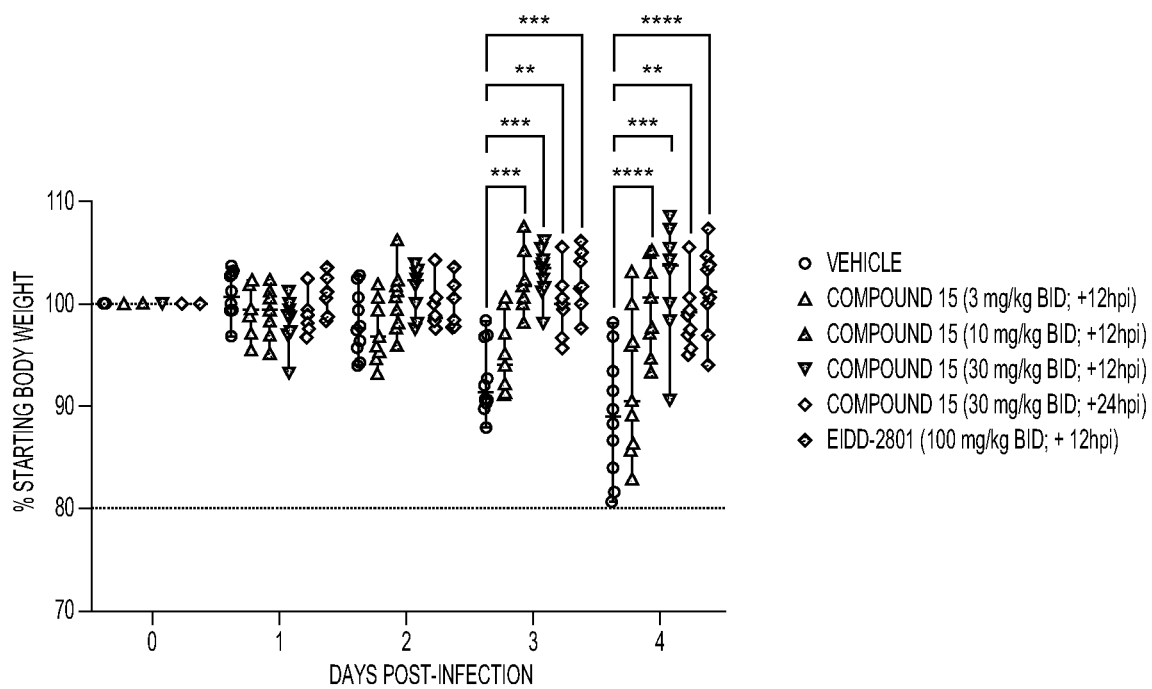
FIGS. 7a-7c: Shows the efficacy of orally dosed Compound 15 against SARS-CoV-2 in mice. As seen, Compound 15 treatment reduces physiological effects of SARS-CoV-2 in mice.
Figure 7B:
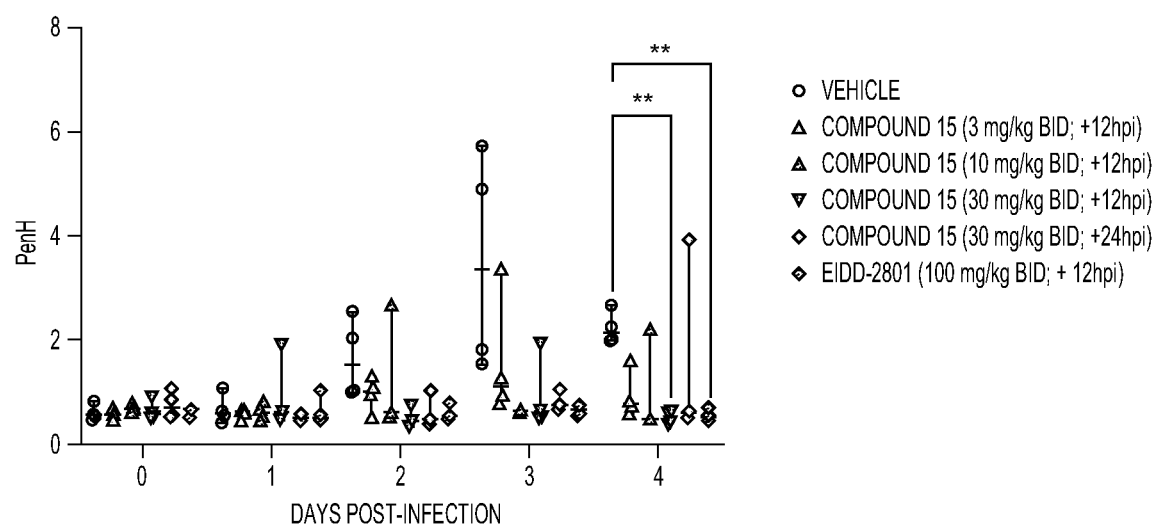
Figure 7C:
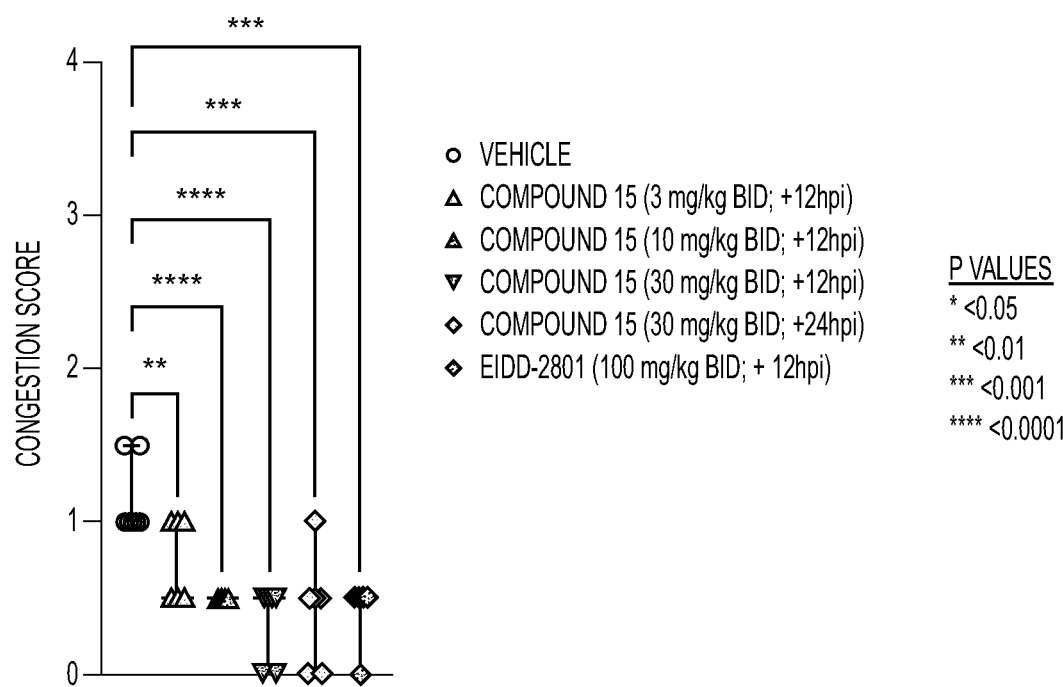

The results of these experiments for compound 15 are presented in FIG. 7. As seen, the mean body weights were maintained (or elevated due to the relatively young mouse age at study start) in the 10 and 30 mg/kg BID dose groups as well as the EIDD-2801-treated mice when treatment was initiated at 12 h.p.i. The effect of SARS-CoV-2 on pulmonary function was significantly reduced when mice were treated with 30 mg/kg Compound 1 or EIDD-2801 12 h.p.i. Congestion scores were significantly lower in all treatment groups, with less significant effects in mice treated with Compound 15 at 3 mg/kg BID at 12 h.p.i. or 30 mg/kg starting at 24 h.p.i. Delaying the 30 mg/kg Compound 15 treatment to 24 h.p.i. had minor effects on weight, lung function, and congestion scores.

Figure 9A:
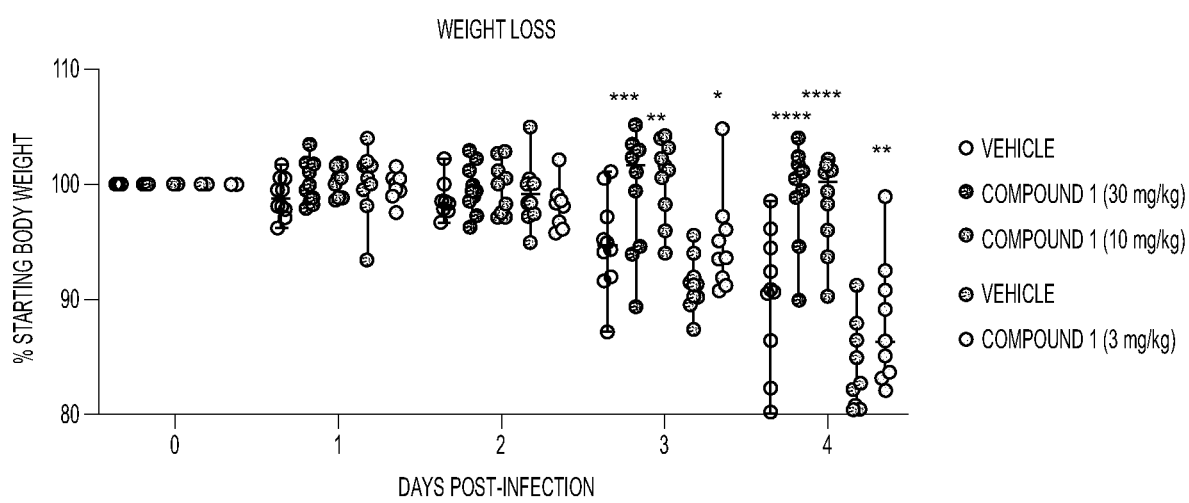
FIGS. 9a-9c: Shows that dosed orally Compound 1 reduces pathophysiological effects of SARS-CoV-2 in mice.
Figure 9B:
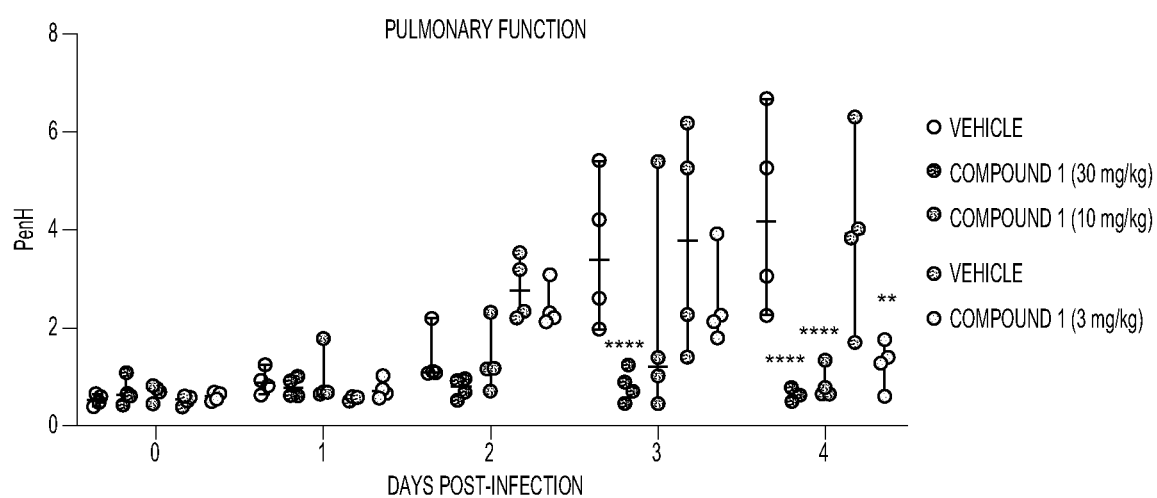
Figure 9C:
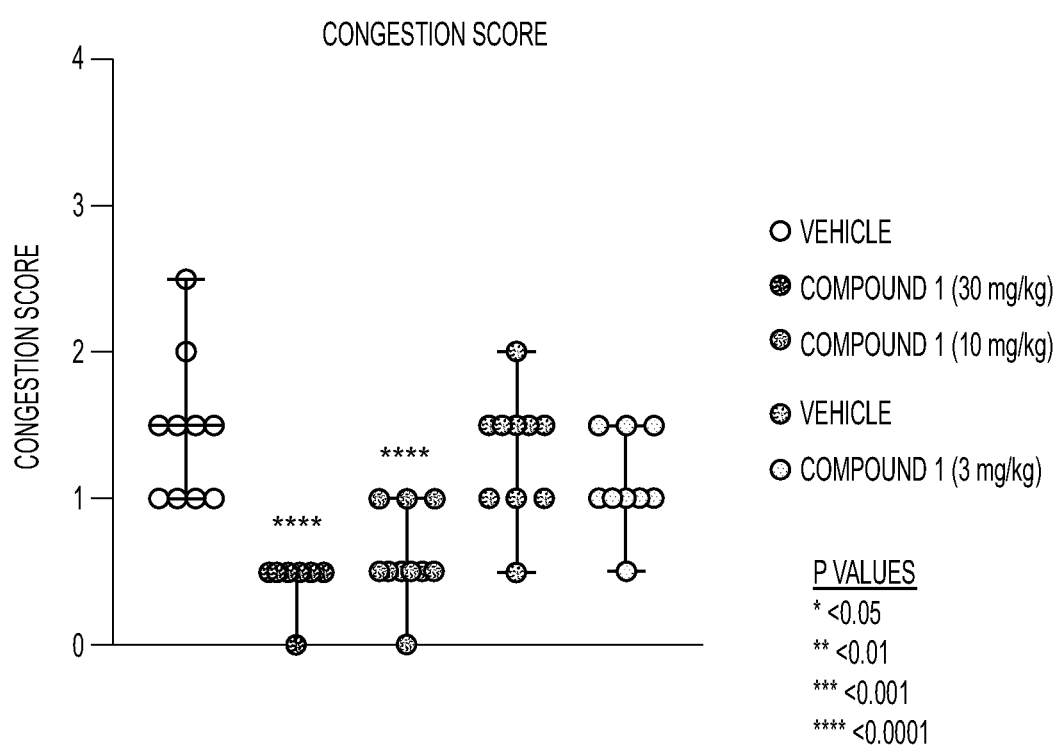

The results for Compound 1 are shown in FIGS. 8 and 9. As seen, oral dosing of Compound 1 reduced terminal lung titers of SARS-CoV-2 in a dose-dependent manner (FIG. 8). Consistent with these viral load reductions, mean body weights were maintained and congestion scores were lowest in the 10 and 30 mg/kg Compound 1 dose groups. The effect of SARS-CoV-2 on pulmonary function was significantly reduced in all Compound 1 treated mice regardless of dose (FIG. 9).

Example 55: GI S9 Stability

Duplicate aliquots of test compound or positive control substrate (GS-7340) were added to S9 stock diluted with 100 mM phosphate buffered saline, pH 7.4, to obtain a protein concentration of 1.0 mg/mL. The S9 metabolic reactions were initiated by the addition of the substrates to the S9 reaction mixture to a final concentration of 2 µM. At 0, 10, 20, 30, 60 and 120 min, 25 µL aliquots of the reaction mixture were transferred to plates containing 225 µl of IS/Q solution. After quenching, the plates were centrifuged at 3000×g for 30 minutes, and 150 µL aliquots of each supernatant were diluted with 150 µL water. Aliquots (10 µL) of the diluted supernatant were analyzed on a Thermo Q-Exactive mass spectrometer as described below.

Example 56: Plasma Stability

Duplicate aliquots of plasma were warmed to 37° C. and the metabolic reactions initiated by the addition of test compound (6 µL of 0.1 mM DMSO stock) or plasma stability standard (GS-7340) to obtain a final substrate concentration of 2 µM. At 0.05, 0.5, 1, 2, 3 and 4 hr, 25 µL aliquots of the reaction mixture were transferred to plates containing 225 µl of IS/Q quenching solution. After quenching, the plates were centrifuged at 3000×g for 30 minutes, and 150 µL supernatant was diluted with 150 µL water.

Aliquots (10 μL) of the diluted supernatant were analyzed on a Thermo Q-Exactive mass spectrometer as described below.

Example 57: CES1/2 Stability

Test compounds or positive control substrates (oseltamivir for CES1 enzymes or procaine for CES2) were incubated with individual Supersome preparations (final CES concentration 1.5 mg/ml) in 0.1 M potassium phosphate buffer (pH 7.4) at 37° C. Substrates were added to a final concentration of 2 μM to initiate the reaction. The final incubation volume was 250 μL. Aliquots were removed after incubation for 0, 10, 30, 60 and 120 min. The reactions were stopped by the addition of IS/Q. Following protein precipitation and centrifugation, 150 μL of supernatant was diluted with an equal volume of water prior to LC-MS analysis. For procaine 150 μL of supernatant was dried down and reconstituted with 250 μL water. All samples were analyzed by LC-MS and the PAR values were used for quantification.

Example 58: Hepatic S9 Stability

Duplicate aliquots of test compound or positive control substrate (GS-7340) were added to S9 stock diluted with 100 mM potassium phosphate buffer, pH 7.4, to obtain a protein concentration of 2.4 mg/mL. The S9 metabolic reactions were initiated by the addition of the substrates to the S9 reaction mixture to a final concentration of 2 μM. At 2, 12, 25, 45, 65 and 90 min, 25 μL aliquots of the reaction mixture were transferred to plates containing 225 μl of IS/Q solution. After quenching, the plates were centrifuged at 3000×g for 30 minutes, and 150 μL aliquots of each supernatant were diluted with 150 μL water. Aliquots (10 μL) of the diluted supernatant were analyzed on a Thermo Q-Exactive mass spectrometer as described below.

Example 59: Liquid Chromatography/Mass Spectroscopy Methods for S9 and Plasma Stability Quantification of test compounds and controls was performed by analyte/internal standard peak area ratio (PAR) values measured on a Thermo Q-Exactive mass spectrometer coupled to a Dionex UltiMate 3000 HPLC with a Leap Technologies HTC PAL autosampler. The column used was a Thermo Hypersil GOLD (1.9 μm particle size, 2.1×50 mm). Mobile phase A consisted of 0.1% (v/v) formic acid in water. Mobile phase B consisted of 0.1% (v/v) formic acid in acetonitrile. Elution of analytes was achieved by a series of linear gradients of acetonitrile in water containing 0.1% (v/v) formic acid. The mass spectrometer was calibrated on a weekly basis and mass tolerance of 5 ppm was used.

TABLE 8

Stability data

| Compound | Human GI S9 $T_{1/2}$ (min) | Human Plasma $T_{1/2}$ (min) | CES1 $T_{1/2}$ (min) | CES2 $T_{1/2}$ (min) | Hepatic S9 $T_{1/2}$ (min) |
|---|---|---|---|---|---|
| N-hydroxycytidine | >700 | >1500 | — | — | ND |
| Molnupiravir | >700 | 51 | 30-51 | 9.8 | ND |
| Reference Cpd A | >700 | >1500 | — | — | 592 |
| Compound 15 | 69 | 29 | 6 | <1 | 1.2 |
| Compound 1 | 0.37 | 5.5 | <1 | <1 | 2 |

All references, including publications, patents, and patent documents are incorporated by reference herein, as though individually incorporated by reference. The present disclosure provides reference to various embodiments and techniques. However, it should be understood that many variations and modifications may be made while remaining within the spirit and scope of the present disclosure. The description is made with the understanding that it is to be considered an exemplification of the claimed subject matter, and is not intended to limit the appended claims to the specific embodiments illustrated.

The invention claimed is:

1. A crystalline form of a compound of Formula:

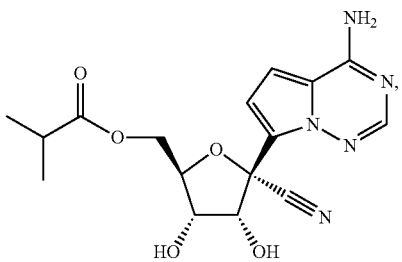 [SMILES: CC(C)C(=O)OC[C@H]1O[C@@](C#N)(c2ccc3c(N)ncnn23)[C@H](O)[C@@H]1O]

wherein the crystalline form is characterized by an XRPD pattern having degree 2θ-reflections (+/−0.2 degrees 2θ) at 9.8°, 16.0°, and 25.4°.

2. The crystalline form of claim 1, wherein the XRPD pattern further comprises one, two or three of the degree 2θ-reflections (+/−0.2 degrees 2θ) at 10.2°, 19.1°, and 26.9°.

3. The crystalline form of claim 1, wherein the XRPD pattern further comprises one or two of the degree 2θ-reflections (+/−0.2 degrees 2θ) at 10.2°, 19.1°, and 26.9°.

4. The crystalline form of claim 1, wherein the XRPD pattern further comprises one of the degree 2θ-reflections (+/−0.2 degrees 2θ) at 10.2°, 19.1°, and 26.9°.

5. The crystalline form of claim 1, wherein the XRPD pattern comprises degree 2θ-reflections (+/−0.2 degrees 2θ) at 9.8°, 10.2°, 16.0°, 19.1°, 25.4°, and 26.9°.

6. The crystalline form of claim 5, wherein the XRPD pattern further comprises one, two, or three of the degree 2θ-reflections (+/−0.2 degrees 2θ) at 10.4°, 19.8°, and 20.7°.

7. The crystalline form of claim 5, wherein the XRPD pattern further comprises one or two of the degree 2θ-reflections (+/−0.2 degrees 2θ) at 10.4°, 19.8°, and 20.7°.

8. The crystalline form of claim 5, wherein the XRPD pattern comprises degree 2θ-reflections (+/−0.2 degrees 2θ) at 9.8°, 10.2°, 10.4°, 16.0°, 19.1°, 19.8°, 20.7°, 25.4°, and 26.9°.

9. The crystalline for of claim 1, wherein the crystalline form is characterized by an XRPD pattern having degree 2θ-reflections (+/−0.2 degrees 2θ) at 9.8°, 10.2°, 10.4°, 12.4°, 13.2°, 13.4°, 13.7°, 16.0°, 16.8°, 17.5°, 17.8°, 18.9°, 19.1°, 19.8°, 20.7°, 21.7°, 22.8°, 24.8°, 25.4°, 26.9°, 27.3°, 28.8°, 31.4°, 32.7°, 34.0°, and 37.7°.

10. The crystalline form of claim 1, wherein the XRPD pattern comprises degree 2θ-reflections (+/−0.2 degrees 2θ) at:

| Pos. [°2 Th.] | Rel. Int. [%] |
|---|---|
| 9.8 | 100 |
| 10.2 | 19 |
| 10.4 | 25 |
| 12.4 | 11 |
| 13.2 | 6 |
| 13.4 | 12 |
| 13.7 | 9 |
| 16.0 | 24 |
| 16.8 | 3 |
| 17.5 | 29 |
| 17.8 | 7 |
| 18.9 | 19 |
| 19.1 | 64 |
| 19.8 | 39 |
| 20.7 | 21 |
| 21.7 | 9 |
| 22.8 | 8 |
| 24.8 | 26 |
| 25.4 | 16 |
| 26.9 | 15 |
| 27.3 | 3 |
| 28.8 | 8 |
| 31.4 | 3 |
| 32.7 | 7 |
| 34.0 | 7 |
| 37.7 | 6. |

11. The crystalline form of claim 1, wherein the crystalline form displays an endothermic event at approximately 177° C.

12. The crystalline form of claim 1, wherein the crystalline form is unsolvated.

13. A pharmaceutical composition comprising:
(a) the crystalline form of claim 1; and
(b) a pharmaceutically acceptable excipient.

14. The pharmaceutical formulation of claim 13, wherein the pharmaceutical formulation is for subcutaneous, intramuscular, intravenous, oral, or inhalation administration.

15. The pharmaceutical formulation of claim 13, wherein the pharmaceutical formulation is for oral administration.

16. A method of treating a coronavirus infection in a human in need thereof, wherein the method comprises administering to the human the crystalline form of claim 1.

17. The method of claim 16, wherein the crystalline form is administered to the human via oral administration.

18. The method of claim 16, wherein the method comprises administering to the human at least one additional therapeutic or prophylactic agent.

19. The method of claim 16, wherein the viral infection is a zoonotic coronavirus infection.

20. The method of claim 16, wherein the viral infection is SARS-CoV-2 infection (COVID-19).

21. The method of claim 16, wherein the viral infection is a SARS-CoV virus infection.

22. The method of claim 16, wherein the viral infection is a MERS-CoV virus infection.

* * * * *

UNITED STATES PATENT AND TRADEMARK OFFICE
CERTIFICATE OF CORRECTION

PATENT NO. : 11,814,406 B2  
APPLICATION NO. : 18/098950  
DATED : November 14, 2023  
INVENTOR(S) : Elaine Bunyan et al.

Page 1 of 1

It is certified that error appears in the above-identified patent and that said Letters Patent is hereby corrected as shown below:

In the Claims

Column 157, Line 52, Claim 9, delete "for" and insert --form--.

Column 158, Line 46, Claim 14, delete "pharmaceutical formulation" and insert --pharmaceutical composition--.

Column 158, Line 47, Claim 14, delete "pharmaceutical formulation" and insert --pharmaceutical composition--.

Column 158, Line 49, Claim 15, delete "pharmaceutical formulation" and insert --pharmaceutical composition--.

Column 158, Line 50, Claim 15, delete "pharmaceutical formulation" and insert --pharmaceutical composition--.

Signed and Sealed this  
Twenty-sixth Day of November, 2024

Katherine Kelly Vidal  
*Director of the United States Patent and Trademark Office*

SEQUENCE LISTING

```
Sequence total quantity: 3
SEQ ID NO: 1            moltype = DNA  length = 20
FEATURE                 Location/Qualifiers
source                  1..20
                        mol_type = genomic DNA
                        organism = Coronavirus
SEQUENCE: 1
ttacaaacat tggccgcaaa                                                20

SEQ ID NO: 2            moltype = DNA  length = 18
FEATURE                 Location/Qualifiers
source                  1..18
                        mol_type = genomic DNA
                        organism = Coronavirus
SEQUENCE: 2
```

```
gcgcgacatt ccgaagaa                                            18

SEQ ID NO: 3           moltype = DNA  length = 23
FEATURE                Location/Qualifiers
source                 1..23
                       mol_type = genomic DNA
                       organism = Coronavirus
SEQUENCE: 3
acaatttgcc cccagcgctt cag                                      23
```